United States Patent
Kawamura et al.

(10) Patent No.: US 9,882,144 B2
(45) Date of Patent: Jan. 30, 2018

(54) ORGANIC ELECTROLUMINESCENT ELEMENT

(71) Applicant: Idemitsu Kosan Co., Ltd., Tokyo (JP)

(72) Inventors: Masahiro Kawamura, Sodegaura (JP); Yumiko Mizuki, Sodegaura (JP); Toshinari Ogiwara, Sodegaura (JP); Hitoshi Kuma, Sodegaura (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 251 days.

(21) Appl. No.: 14/655,612

(22) PCT Filed: Dec. 27, 2013

(86) PCT No.: PCT/JP2013/085228
§ 371 (c)(1),
(2) Date: Jun. 25, 2015

(87) PCT Pub. No.: WO2014/104346
PCT Pub. Date: Jul. 3, 2014

(65) Prior Publication Data
US 2016/0197287 A1    Jul. 7, 2016

(30) Foreign Application Priority Data

Dec. 28, 2012    (JP) .................................. 2012-288983
Jan. 25, 2013    (JP) .................................. 2013-012694

(51) Int. Cl.
*H01L 51/50*    (2006.01)
*H01L 51/00*    (2006.01)
(Continued)

(52) U.S. Cl.
CPC ........ *H01L 51/0067* (2013.01); *C07D 403/10* (2013.01); *C07D 403/14* (2013.01);
(Continued)

(58) Field of Classification Search
None
See application file for complete search history.

(56) References Cited

U.S. PATENT DOCUMENTS

2012/0126208 A1*   5/2012   Kawamura ......... H01L 51/0061
                                                                257/40
2012/0138915 A1    6/2012   Nishimura et al.
(Continued)

FOREIGN PATENT DOCUMENTS

JP       2012-028634 A    2/2012
WO    WO-2011/070963 A1    6/2011
(Continued)

OTHER PUBLICATIONS

Translation of the International Preliminary Report on Patentability and the Written Opinion of the International Searching Authority corresponding to Application No. PCT/JP2013/085228, dated Jun. 30, 2015, 8 pages.
(Continued)

*Primary Examiner* — Gregory D Clark
(74) *Attorney, Agent, or Firm* — Oblon, McClelland, Maier & Neustadt, L.L.P.

(57) ABSTRACT

An organic electroluminescence device includes: an anode; a cathode; and an organic layer interposed between the anode and the cathode, in which the organic layer includes an emitting layer and the emitting layer includes a compound represented by a formula (1) below and a compound represented by a formula (2) below. $Az_1$ of the formula (1) below and $Az_2$ of the formula (2) below are each an azine ring. Cz of the formula (1) below and HAr of the formula (2) below are each a nitrogen-containing heterocyclic ring.

$$\left(\left(Cz\right)_{\overline{m}}L_1\right)_{\overline{n}}L_2\left(L_3\right)_{\overline{o}}Az_1\right)_p \quad (1)$$

(Continued)

-continued

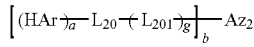
(2)

23 Claims, 3 Drawing Sheets

(51) Int. Cl.
| | |
|---|---|
| *C07D 405/14* | (2006.01) |
| *C07D 403/14* | (2006.01) |
| *C09K 11/06* | (2006.01) |
| *C07D 403/10* | (2006.01) |
| *C07D 409/14* | (2006.01) |
| *C07D 417/10* | (2006.01) |
| *C07D 417/14* | (2006.01) |
| *C07D 471/04* | (2006.01) |
| *C07D 471/06* | (2006.01) |
| *C07D 471/16* | (2006.01) |
| *H05B 33/14* | (2006.01) |
| *H05B 33/20* | (2006.01) |
| *C07D 413/10* | (2006.01) |
| *C07D 491/048* | (2006.01) |
| *C09K 11/02* | (2006.01) |

(52) U.S. Cl.
CPC ......... *C07D 405/14* (2013.01); *C07D 409/14* (2013.01); *C07D 413/10* (2013.01); *C07D 417/10* (2013.01); *C07D 417/14* (2013.01); *C07D 471/04* (2013.01); *C07D 471/06* (2013.01); *C07D 471/16* (2013.01); *C07D 491/048* (2013.01); *C09K 11/025* (2013.01); *C09K 11/06* (2013.01); *H01L 51/0071* (2013.01); *H01L 51/0072* (2013.01); *H01L 51/0073* (2013.01); *H05B 33/14* (2013.01); *H05B 33/20* (2013.01); *C09K 2211/1007* (2013.01); *C09K 2211/1011* (2013.01); *C09K 2211/1029* (2013.01); *C09K 2211/1033* (2013.01); *C09K 2211/1059* (2013.01); *C09K 2211/1074* (2013.01); *H01L 51/5012* (2013.01); *H01L 51/5016* (2013.01); *H01L 2251/308* (2013.01)

(56) References Cited

U.S. PATENT DOCUMENTS

2012/0241732 A1 9/2012 Endo et al.
2012/0248968 A1* 10/2012 Ogiwara ............. H01L 51/5012
                                                              313/504

FOREIGN PATENT DOCUMENTS

WO    WO-2012/124412 A1    9/2012
WO    WO-2012/133188 A1    10/2012

OTHER PUBLICATIONS

Translation of the International Preliminary Report on Patentability and the Written Opinion of the International Searching Authority corresponding to Application No. PCT/JP2013/085151, dated Jun. 30, 2015, 5 pages.
Adachi et al., "Expression of Highly-Efficient Thermally-Activated Delayed-Fluorescence and Application Thereof to OLED," Organic EL Symposium, proceeding for the tenth meeting held on Jun. 17-18, 2010, S2-5, pp. 11-12.
Adachi, C., Device Physics of Organic Semiconductors, pp. 261-262.
International Search Report dated Mar. 25, 2014 issued in Application No. PCT/JP2013/085228.
Tanaka et al., "Efficient green thermally activated delayed fluorescence (TADF) from a phenoxazine-triphenyltriazine (PXZ-TRZ) derivative,"Chem. Commun., 2012, vol. 48, No. 93. pp. 11392-11394.
Tokumaru, K., Organic Photochemical Reaction Theory, Tokyo Kagaku Dojin Co., Ltd., 1973, pp. 79-82.

* cited by examiner

ORGANIC ELECTROLUMINESCENT ELEMENT

CROSS REFERENCE TO RELATED APPLICATIONS

This application is the National Phase of PCT/JP2013/085228, filed Dec. 27, 2013, which claims priority to Japanese Application No. 2012-288983, filed Dec. 28, 2012 and Japanese Application No. 2013-012694, filed Jan. 25, 2013.

TECHNICAL FIELD

The present invention relates to an organic electroluminescence device.

BACKGROUND ART

When voltage is applied on an organic electroluminescence device (hereinafter, occasionally referred to as an organic EL device), holes and electrons are respectively injected into an emitting layer from an anode and a cathode. The injected electrons and holes are recombined in an emitting layer to form excitons. Here, according to the electron spin statistics theory, singlet excitons and triplet excitons are generated at a ratio of 25%:75%. In the classification according to the emission principle, in a fluorescent EL device which uses emission caused by singlet excitons, the limited value of an internal quantum efficiency of the organic EL device is believed to be 25%. On the other hand, in a phosphorescent EL device which uses emission caused by triplet excitons, it has been known that the internal quantum efficiency can be improved up to 100% when intersystem crossing efficiently occurs from the singlet excitons.

A technology for extending a lifetime of a fluorescent organic EL device has recently been improved and applied to a full-color display of a mobile phone, TV and the like. However, an efficiency of a fluorescent EL device is required to be improved.

Based on such a background, a highly efficient fluorescent organic EL device using delayed fluorescence has been proposed and developed. For instance, an organic EL device using TTF (Triplet-Triplet Fusion) mechanism that is one of mechanisms for delayed fluorescence is proposed. The TTF mechanism utilizes a phenomenon in which singlet excitons are generated by collision between two triplet excitons.

By using delayed fluorescence by the TTF mechanism, it is considered that an internal quantum efficiency can be theoretically raised up to 40% even in fluorescent emission. However, as compared with phosphorescent emission, the fluorescent emission is still problematic on improving efficiency. Accordingly, in order to enhance the internal quantum efficiency, an organic EL device using another delayed fluorescence mechanism has been studied.

For instance, TADF (Thermally Activated Delayed Fluorescence) mechanism is used. The TADF mechanism utilizes a phenomenon in which inverse intersystem crossing from triplet excitons to singlet excitons is generated by using a material having a small energy gap ($\Delta ST$) between the singlet energy level and the triplet energy level. Thermally activated delayed fluorescence is described in, for instance, "Device Physics of Organic Semiconductor" Chihaya Adachi, pages 261-262, Mar. 22, 2012, published by Kodansha Company Ltd.

An organic EL device using the TADF mechanism is described in, for instance, non-Patent Literature 1.

Non-Patent Literature 1 describes that green emission by the TADF mechanism can be efficiently obtained by using as a luminescent material a compound (hereinafter, occasionally abbreviated as PXZ-TRZ) having phenoxazine as an electron donating unit and 2,4,6-triphenyl-1,3,5-triazine as an electron acceptor unit. Non-Patent Literature 1 describes that an organic EL device including an emitting layer in which PXZ-TRZ (luminescent material) is doped in CBP (4,4'-Bis(N-carbazolyl)-1,1'-biphenyl)(host material) emits light at an external quantum efficiency (EQE) of up to 12.5%.

CITATION LIST

Non-Patent Literature(s)

Non-Patent Literature 1: Chihaya Adachi et al. "Efficient green thermally activated delayed fluorescence (TADF) from a phenoxazine-triphenylazine (PXZ-TRZ) derivative", Chemical Communications, in 2012, 48, p. 11392-11394

SUMMARY OF THE INVENTION

Problems to be Solved by the Invention

Although the organic EL device described in Non-Patent Literature 1 exhibits the external quantum efficiency of up to 12.5%, voltage reduction in driving the device and further higher efficiency are required for practical use of the device.

An object of the invention is to provide an organic electroluminescence device requiring a low drive voltage and exhibiting an improved luminous efficiency.

Means for Solving the Problems

The inventors focus on a host material in order to reduce a drive voltage and improve a luminous efficiency of an organic EL device that contains a compound having a structure such as a structure of PXZ-TRZ as a luminescent material.

In the organic EL device described in Non-Patent Literature 1, CBP used as the host material has an extremely wide singlet energy gap of 3.51 eV. For this reason, holes and electrons are insufficiently injected to the emitting layer, so that it is speculated that the drive voltage is high and further an amount of generated excitons is small to lead to a low luminous efficiency. The inventors consider that it is necessary to narrow the singlet energy gap of CBP in order to reduce the drive voltage to a practical level and improve the luminous efficiency. In general, when a singlet energy gap of a compound is narrowed, a triplet energy gap is also narrowed. When the triplet energy gap of CBP is extremely narrowed from 2.80 eV, it becomes difficult to cause light emission from a green-emitting material and a yellow-emitting material.

The inventors note that a compound having a specific structure has a small gap between a singlet energy level and a triplet energy level and the singlet energy gap can be narrowed while the triplet energy gap is maintained. The inventors have found that an organic EL device including the emitting layer, in which the above compound is used as the host material and the compound having a structure such as a structure of PXZ-TRZ is used as the luminescent material, requires a low drive voltage and exhibits an improved luminous efficiency and thus has reached the invention.

An organic electroluminescence device according to an aspect of the invention includes: an anode; a cathode; and a single-layer or multi-layer organic layer interposed between the anode and the cathode, in which the organic layer includes the emitting layer, the emitting layer contains a compound represented by a formula (1) below and a compound represented by a formula (2) below, and the emitting layer does not contain a metal complex.

[Formula 1]

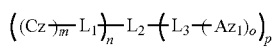
(1)

In the formula (1), Cz is a group derived from a structure represented by a formula (10) below.

[Formula 2]

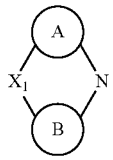
(10)

In the formula (10), $X_1$ represents a single bond, an oxygen atom, a sulfur atom, a carbonyl group, $NR_1$, $CR_2R_3$, $SiR_4R_5$ or $GeR_6R_7$.

A and B each independently represent a substituted or unsubstituted cyclic structure. When at least one of the cyclic structure A and the cyclic structure B has a plurality of substituents, adjacent ones of the substituents may form a ring. When at least one of the cyclic structure A and the cyclic structure B is a substituted or unsubstituted heterocyclic structure, the heterocyclic structure has a partial structure represented by a formula (11) below.

[Formula 3]

(11)

In the formula (1), $L_1$ is a single bond, a substituted or unsubstituted (m+1)-valent aromatic hydrocarbon group or a substituted or unsubstituted (m+1)-valent heterocyclic group.

$L_2$ is a single bond, a substituted or unsubstituted (n+p)-valent aromatic hydrocarbon group or a substituted or unsubstituted (n+p)-valent heterocyclic group.

$L_3$ is a single bond, a substituted or unsubstituted (o+1)-valent aromatic hydrocarbon group or a substituted or unsubstituted (o+1)-valent heterocyclic group.

m is an integer of 1 to 6.
n and p are each independently an integer of 1 to 6.
o is an integer of 1 to 6.
$Az_1$ is represented by a formula (12) below.

[Formula 4]

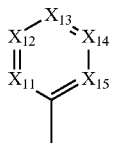
(12)

In the formula (12), $X_{11}$ to $X_{15}$ each independently represent $CR_8$ or a nitrogen atom and at least one of $X_{11}$ to $X_{15}$ is a nitrogen atom. In the formula (12), adjacent ones of $R_8$ may form a ring.

[Formula 5]

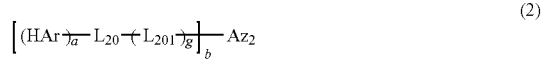
(2)

In the formula (2), $L_{20}$ is a substituted or unsubstituted (a+g)-valent aromatic hydrocarbon group or a substituted or unsubstituted (a+g)-valent heterocyclic group.

$L_{201}$ is a substituted or unsubstituted divalent aromatic hydrocarbon group or a substituted or unsubstituted divalent heterocyclic group.

a is an integer of 1 to 6. b is an integer of 1 to 6. g is an integer of 0 to 2.

HAr is a group derived from a structure represented by a formula (20) below.

[Formula 6]

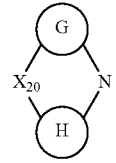
(20)

In the formula (20), $X_{20}$ represents a single bond, an oxygen atom, a sulfur atom, a carbonyl group, $NR_9$, $CR_{10}R_{11}$, $SiR_{12}R_{13}$ or $GeR_{14}R_{15}$.

G and H each independently represent a substituted or unsubstituted cyclic structure. When at least one of the cyclic structure G and the cyclic structure H have a plurality of substituents, adjacent ones of the substituents may form a ring. When at least one of the cyclic structure G and the cyclic structure H is a substituted or unsubstituted heterocyclic structure, the heterocyclic structure has a partial structure represented by a formula (20-2) below.

[Formula 7]

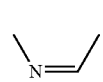
(20-2)

In the formula (2), $Az_2$ is represented by a formula (2d) below.

[Formula 8]

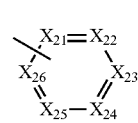
(2d)

In the formula (2d), $X_{21}$ to $X_{26}$ each independently represent $CR_{16}$ or a nitrogen atom. At least one of $X_{21}$ to $X_{26}$ is a nitrogen atom and b of $X_{21}$ to $X_{26}$ is a carbon atom to be bonded to $L_{20}$ or $L_{201}$. In the formula (2d), adjacent ones of $R_{16}$ may form a ring.

$R_1$ to $R_{16}$ are each independently a hydrogen atom, a substituted or unsubstituted aryl group having 6 to 30 carbon atoms forming a ring (hereinafter, referred to as ring carbon atoms), a substituted or unsubstituted heterocyclic group having 5 to 30 ring atoms, a substituted or unsubstituted alkyl group having 1 to 30 carbon atoms, a substituted or unsubstituted alkylsilyl group having 3 to 30 carbon atoms, a substituted or unsubstituted arylsilyl group having 6 to 60 ring carbon atoms, a substituted or unsubstituted alkoxy group having 1 to 30 carbon atoms, a substituted or unsubstituted aryloxy group having 6 to 30 ring carbon atoms, a substituted or unsubstituted alkylamino group having 2 to 30 carbon atoms, a substituted or unsubstituted arylamino group having 6 to 60 ring carbon atoms, a substituted or unsubstituted alkylthio group having 1 to 30 carbon atoms, or a substituted or unsubstituted arylthio group having 6 to 30 ring carbon atoms.

According to the organic EL device in the above aspect of the invention, a drive voltage of the device is reducible and a luminous efficiency thereof is improvable.

DESCRIPTION OF EMBODIMENT(S)

Figure 1:
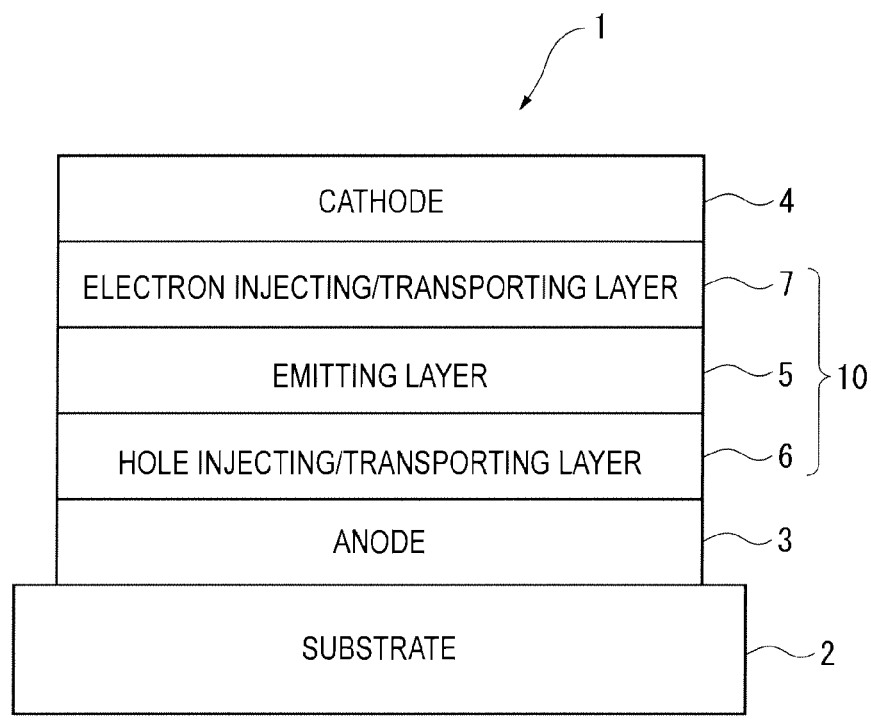
FIG. 1 schematically shows an exemplary arrangement of an organic electroluminescence device according to a first exemplary embodiment of the invention.

An organic EL device according to an exemplary embodiment will be described below.

First Exemplary Embodiment

Arrangement(s) of Organic EL Device

An arrangement of an organic EL device according to a first exemplary embodiment will be described.

The organic EL device according to the first exemplary embodiment includes a pair of electrodes and an organic layer between the pair of electrodes. The organic layer includes one or more layers formed of an organic compound. The organic layer may further include an inorganic compound.

In the organic EL device according to the exemplary embodiment, at least one layer of the organic layer is an emitting layer. Accordingly, the organic layer may be provided by a single emitting layer. Alternatively, the organic layer may be provided by layers employed in an organic EL device such as a hole injecting layer, a hole transporting layer, an electron injecting layer, an electron transporting layer, a hole blocking layer, and an electron blocking layer.

Representative arrangement examples of the organic EL device are as follows:
(a) anode/emitting layer/cathode;
(b) anode/hole injecting•transporting layer/emitting layer/cathode;
(c) anode/emitting layer/electron injecting•transporting layer/cathode;
(d) anode/hole injecting•transporting layer/emitting layer/electron injecting•transporting layer/cathode;
(e) anode/hole injecting•transporting layer/first emitting layer/second emitting layer/electron injecting•transporting layer/cathode; and
(f) anode/hole injecting•transporting layer/emitting layer/blocking layer/electron injecting•transporting layer/cathode.

While the arrangement (d) is preferably used among the above arrangements, the arrangement of the invention is not limited to the above arrangements.

It should be noted that the aforementioned "emitting layer" is an organic compound layer generally employing a doping system and including a first material and a second material. In general, the first material promotes recombination of electrons and holes and transmits excitation energy generated by recombination to the second material. The first material is often referred to as a host material. Accordingly, the first material is referred to as the host material in descriptions hereinafter. In general, the second material receives excitation energy from the host material (the first material) to exhibit a high luminescent performance. The second material is often referred to as a dopant material. Accordingly, the second material is referred to as the dopant material in descriptions hereinafter. The dopant material is preferably a compound having a high quantum efficiency. In the exemplary embodiment, a material emitting delayed fluorescence is used as the dopant material. Particularly, the first exemplary embodiment uses a material emitting delayed fluorescence that significantly exceeds a quantum efficiency of a typical fluorescence, without using a phosphorescence complex.

The "hole injecting/transporting layer (or hole injecting•transporting layer)" means "at least one of a hole injecting layer and a hole transporting layer" while the "electron injecting/transporting layer (or electron injecting•transporting layer)" means "at least one of an electron injecting layer and an electron transporting layer." Herein, when the hole injecting layer and the hole transporting layer are provided, the hole injecting layer is preferably closer to the anode. When the electron injecting layer and the electron transporting layer are provided, the electron injecting layer is preferably closer to the cathode. Moreover, each of the hole injecting layer, hole transporting layer, electron transporting layer and electron injecting layer may be provided by a single layer or a plurality of layers.

In the exemplary embodiment, the electron transporting layer means an organic layer having the highest electron mobility among organic layer(s) providing an electron transporting zone existing between the emitting layer and the cathode. When the electron transporting zone is provided by a single layer, the single layer is the electron transporting layer. Moreover, a blocking layer having an electron mobility that is not always high may be provided as shown in the arrangement (f) between the emitting layer and the electron transporting layer in order to prevent diffusion of excitation energy generated in the emitting layer. Thus, the organic layer adjacent to the emitting layer is not always an electron transporting layer.

FIG. 1 schematically shows an exemplary arrangement of an organic EL device 1 according to the first exemplary embodiment.

An organic electroluminescence device 1 includes a light-transmissive substrate 2, an anode 3, a cathode 4 and an organic layer 10 disposed between the anode 3 and the cathode 4.

The organic layer 10 includes an emitting layer 5 containing a host material and a dopant material. The organic layer 10 also includes a hole injecting•transporting layer 6 between the emitting layer 5 and the anode 3. The organic layer 10 further includes an electron injecting•transporting layer 7 between the emitting layer 5 and the cathode 4.

Emitting Layer

In the organic EL device in the first exemplary embodiment, the emitting layer contains a compound represented by a formula (1) below and a compound represented by a formula (2) below. The emitting layer does not contain a phosphorescent metal complex. The host material and the dopant material contained in the emitting layer have mutually different molecular structures.

Host Material

The host material used in the first exemplary embodiment is represented by the formula (1) below.

[Formula 9]

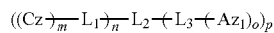
(1)

In the formula (1), Cz is the group derived from the structure represented by the formula (10) below.

[Formula 10]

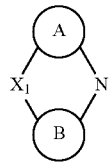
(10)

In the formula (10), $X_1$ represents a single bond, an oxygen atom, a sulfur atom, a carbonyl group, $NR_1$, $CR_2R_3$, $SiR_4R_5$ or $GeR_6R_7$. In other words, the cyclic structure represented by the formula (10) is a cyclic structure selected from the group consisting of cyclic structures represented by formulae (10b) to (10i) below.

[Formula 11]

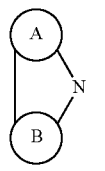
(10b)

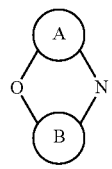
(10c)

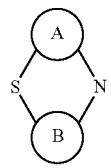
(10d)

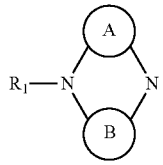
(10e)

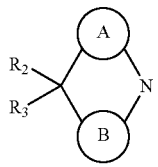
(10f)

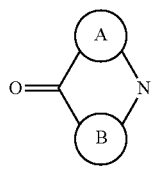
(10g)

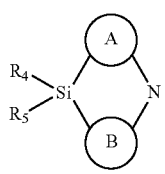
(10h)

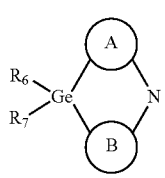
(10i)

In the formulae (10) and (10b) to (10i), A and B each independently represent a substituted or unsubstituted cyclic structure. When at least one of the cyclic structure A and the cyclic structure B has a plurality of substituents, adjacent ones of the substituents may form a ring. The ring to be formed may be either a saturated ring or an unsaturated ring. The substituent at this time is preferably an electron donating substituent. Moreover, adjacent substituents preferably further form an electron donating ring.

When at least one of the cyclic structure A and the cyclic structure B is a substituted or unsubstituted heterocyclic structure in the formulae (10) and (10b) to (10i), the heterocyclic structure has a partial structure represented by a formula (11) below.

[Formula 12]

(11)

The group derived from the structure represented by the formula (10) is preferably a group represented by a formula (10-1) below.

[Formula 13]

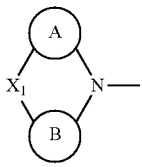
(10-1)

In the formula (10-1), $X_1$ represents the same as $X_1$ of the formula (10). In other words, the group represented by the formula (10-1) is a group selected from the group consisting of groups represented by formulae (10b-1) to (10i-1) below.

[Formula 14]

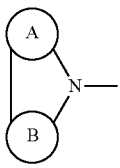
(10b-1)

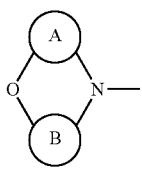
(10c-1)

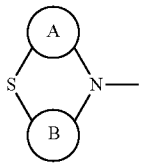
(10d-1)

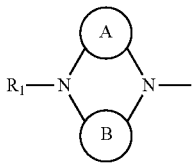
(10e-1)

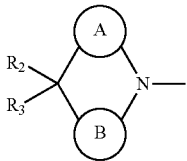
(10f-1)

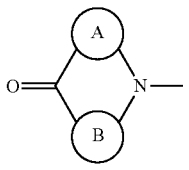
(10g-1)

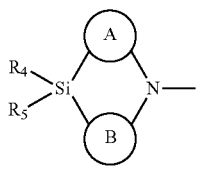
(10h-1)

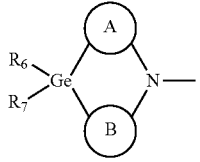
(10i-1)

In the formulae (10b-1) to (10i-1), the cyclic structure A and the cyclic structure B respectively independently represent the same as the cyclic structure A and the cyclic structure B in the formulae (10) and (10b) to (10i).

In the formula (1), $L_1$ represents a single bond, a substituted or unsubstituted (m+1)-valent aromatic hydrocarbon group or a substituted or unsubstituted (m+1)-valent heterocyclic group.

$L_2$ represents a single bond, a substituted or unsubstituted (n+p)-valent aromatic hydrocarbon group or a substituted or unsubstituted (n+p)-valent heterocyclic group.

$L_3$ represents a single bond, a substituted or unsubstituted (o+1)-valent aromatic hydrocarbon group or a substituted or unsubstituted (o+1)-valent heterocyclic group.

In the formula (1), m is an integer of 1 to 6, n and p are each independently an integer of 1 to 6, and o is an integer of 1 to 6. m, n, o and p are each independently an integer of 1 to 3, more preferably 1 or 2.

In the first exemplary embodiment, $L_1$ is a linking group of which a valence is determined depending on a value of m. When m is 1, $L_1$ is a divalent linking group. $L_2$ is a linking group of which a valence is determined depending on values of n and p. When both n and p are 1, $L_2$ is a divalent linking group. The same applies to the following linking groups such as $L_3$.

In the formula (1), $Az_1$ is represented by a formula (12) below.

[Formula 15]

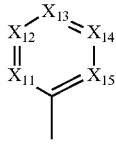
(12)

In the formula (12), $X_{11}$ to $X_{15}$ each independently represent $CR_8$ or a nitrogen atom and at least one of $X_{11}$ to $X_{15}$ is a nitrogen atom. In the formula (12), one to three of $X_{11}$ to $X_{15}$ are preferably nitrogen atom(s). In the formula (12), adjacent ones of $R_8$ may form a ring.

When one nitrogen atom is provided, $X_{11}$ or $X_{15}$ is preferably a nitrogen atom. When two nitrogen atoms are provided, $X_{11}$ and $X_{15}$ are preferably nitrogen atoms. When three nitrogen atoms are provided, $X_{11}$, $X_{13}$ and $X_{15}$ are preferably nitrogen atoms. Among the above arrangements, a triazine ring in which $X_{11}$, $X_{13}$ and $X_{15}$ are nitrogen atoms is more preferable in the formula (12).

In the formulae (1) and (10) to (12), $R_1$ to $R_7$ are each independently a hydrogen atom, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkylsilyl group having 3 to 30 carbon atoms, a substituted or unsubstituted arylsilyl group having 6 to 60 ring carbon atoms, a substituted or unsubstituted alkoxy group having 1 to 30 carbon atoms, a substituted or unsubstituted aryloxy group having 6 to 30 ring carbon atoms, a substituted or unsubstituted alkylamino group having 2 to 30 carbon atoms, a substituted or unsubstituted arylamino group having 6 to 60 ring carbon atoms, a substituted or unsubstituted alkylthio group having 1 to 30 carbon atoms, or a substituted or unsubstituted arylthio group having 6 to 30 ring carbon atoms.

$R_8$ is each independently a hydrogen atom, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkylsilyl group having 3 to 30 carbon atoms, a substituted or unsubstituted arylsilyl group having 6 to 60 ring carbon atoms, a substituted or unsubstituted alkoxy group having 1 to 30 carbon atoms, a substituted or unsubstituted aryloxy group having 6 to 30 ring carbon atoms, a substituted or unsubstituted alkylamino group having 2 to 30 carbon atoms, a substituted or unsubstituted arylamino group having 6 to 60 ring carbon atoms, a substituted or unsubstituted alkylthio group having 1 to 30 carbon atoms, or a substituted or unsubstituted arylthio group having 6 to 30 ring carbon atoms.

In the first exemplary embodiment, the compound represented by the formula (1) is preferably a compound represented by a formula (13) below.

[Formula 16]

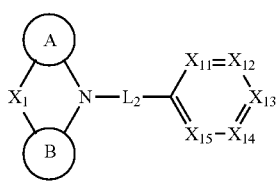

(13)

In the formula (13), $X_1$, a cyclic structure A and a cyclic structure B respectively represent the same as $X_1$, the cyclic structure A and the cyclic structure B of the formula (10).

In the formula (13), $L_2$ represents the same as $L_2$ of the formula (1).

In the formula (13), $X_{11}$ to $X_{15}$ each independently represent the same as $X_{11}$ to $X_{15}$ of the formula (12).

Among the compound represented by the formula (13), compounds represented by formulae (13a) to (13c) below are preferable and the compound represented by the formula (13c) is more preferable.

[Formula 17]

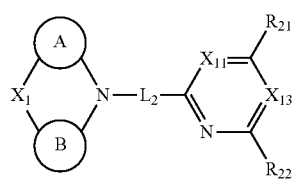

(13a)

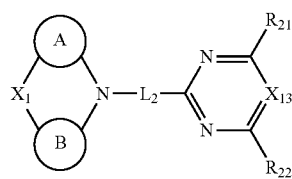

(13b)

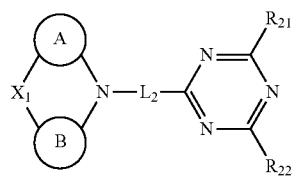

(13c)

In the formulae (13a) to (13c), $X_1$, a cyclic structure A and a cyclic structure B respectively represent the same as $X_1$, the cyclic structure A and the cyclic structure B of the formula (10).

In the formulae (13a) to (13c), $L_2$ represents the same as $L_2$ of the formula (1). In the formula (13a), $X_{11}$ and $X_{13}$ each independently represent the same as $X_{11}$ to $X_{15}$ of the formula (12).

In the formulae (13a) to (13c), $R_{21}$ and $R_{22}$ each independently represent the same as $R_8$ described above.

In the compounds represented by the formulae (1), (13) and (13a) to (13c) or the groups represented by the formulae (10) and (10b) to (10g), the cyclic structure A and the cyclic structure B are a saturated or unsaturated five-membered ring or a saturated or unsaturated six-membered ring. Among the cyclic structures, an aromatic hydrocarbon ring or a heterocycle is preferable, a benzene ring or an azine ring is more preferable, and a benzene ring is further preferable.

In the first exemplary embodiment, both of the cyclic structure A and the cyclic structure B are preferably a substituted or unsubstituted benzene ring. In this arrangement, it is more preferable that at least one of the benzene rings has a substituent. The substituent of the benzene ring is preferably a substituted or unsubstituted aryl group having 6 to 30 ring carbon atoms or a substituted or unsubstituted heterocyclic group having 5 to 30 ring atoms. Further, at least one of the cyclic structure A and the cyclic structure B preferably has a substituent. In this arrangement, the substituent is preferably an electron donating substituent.

In the first exemplary embodiment, Cz of the formula (1) is preferably represented by the formula (10b). Further, both of the cyclic structure A and the cyclic structure B are preferably a substituted or unsubstituted benzene ring. The substituent in this arrangement is the same as described above.

In the formula (10b), when at least one of the cyclic structure A and the cyclic structure B is a heterocycle, the heterocycle preferably has the partial structure represented by the formula (11), specifically, the cyclic structure A and the cyclic structure B in the formula (10b) are preferably a six-membered heterocycle having the partial structure represented by the formula (11).

In the first exemplary embodiment, the compound represented by the formula (1) is preferably a compound represented by a formula (14) below.

[Formula 18]

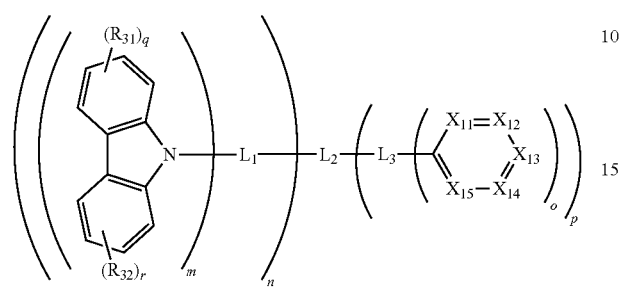

(14)

In the formula (14), $L_1$, $L_2$, $L_3$, m, n, o and p respectively represent the same as $L_1$, $L_2$, $L_3$, m, n, o and p of the formula (1).

In the formula (14), $X_{11}$ to $X_{15}$ each independently represent the same as $X_{11}$ to $X_{15}$ of the formula (12).

In the formula (14), $R_{31}$ and $R_{32}$ each independently represent the same as $R_8$ described above. Adjacent ones of $R_{31}$ may form a ring. Adjacent ones of $R_{32}$ may form a ring.

In the formula (14), q and r are 4.

In the first exemplary embodiment, the compound represented by the formula (1) is preferably a compound represented by a formula (16) below. Specifically, in the compound represented by the formula (14), $L_1$ and $L_3$ are preferably a single bond and n, o and p are preferably 1.

[Formula 19]

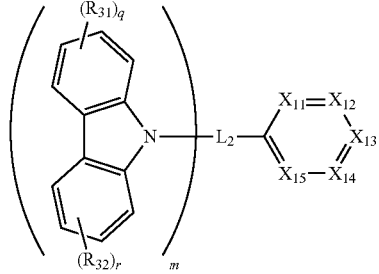

(16)

In the formula (16), $L_2$ and m respectively represents the same as $L_2$ and m of the formula (1).

In the formula (16), $X_{11}$ to $X_{15}$ each independently represent the same as $X_{11}$ to $X_{15}$ of the formula (12).

In the formula (16), $R_{31}$ and $R_{32}$ each independently represent the same as $R_8$ described above. Adjacent ones of $R_{31}$ may form a ring. Adjacent ones of $R_{32}$ may form a ring.

In the formula (16), q and r are 4.

In the first exemplary embodiment, the compound represented by the formula (16) is preferably a compound represented by a formula (17) below. Specifically, in the compound represented by the formula (16), m is preferably 1 and one of four $R_{32}$ is preferably a carbazolyl group.

[Formula 20]

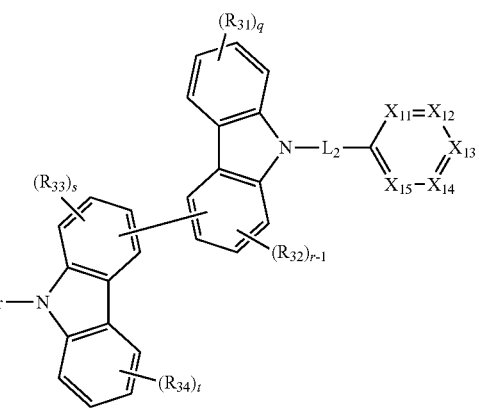

(17)

In the formula (17), $L_2$ represents the same as $L_2$ of the formula (1).

In the formula (17), $X_{11}$ to $X_{15}$ each independently represent the same as $X_{11}$ to $X_{15}$ of the formula (12).

In the formula (17), $R_{31}$ to $R_{34}$ each independently represent the same as $R_8$ described above. Adjacent ones of $R_{31}$ may form a ring. Adjacent ones of $R_{32}$ may form a ring. Adjacent ones of $R_{33}$ may form a ring. Adjacent ones of $R_{34}$ may form a ring.

In the formula (17), q and r are 4, s is 3 and t is 4.

In the formula (17), Ar represents a substituted or unsubstituted aryl group having 6 to 30 ring carbon atoms or a substituted or unsubstituted heterocyclic group having 5 to 30 ring atoms. Ar may be bonded to a nitrogen atom of the carbazole skeleton through a linking group without being directly bonded thereto. The linking group that links Ar with the nitrogen atom of the carbazole skeleton represents the same as $L_1$ described above. Ar is preferably a substituted or unsubstituted aryl group having 6 to 30 ring carbon atoms. Ar is preferably a phenyl group, biphenyl group, terphenyl group, naphthyl group, phenanthryl group, triphenylenyl group, dibenzofuranyl group, dibenzothiophenyl group, carbazolyl group and the like. When Ar is a substituted or unsubstituted aryl group having 6 to 30 ring carbon atoms, Ar is preferably directly bonded to the nitrogen atom of the carbazole skeleton without the linking group.

In the host material used in the first exemplary embodiment, as represented by the formula (17), the electron donating moiety represented by the formula (10) preferably has a biscarbazole structure. When the moiety represented by the formula (10) has a mono-carbazole structure consisting of a single carbazole skeleton, it is speculated that an electron donating performance of the mono-carbazole structure is less than that of the amine structure. In a compound in which an azine ring is bonded to the mono-carbazole structure directly or via a linking group, it is speculated that an electron accepting performance of the azine ring cannot be canceled by the electron donating performance of the mono-carbazole structure. Accordingly, such a compound in which the azine ring is bonded to the mono-carbazole structure directly or via a linking group is an electron accepting compound. On the other hand, in a compound in which a substituent is bonded to the carbazole skeleton, it is considered that the electron donating performance is improved. The above biscarbazole structure is preferable since the electron donating performance is improvable. In the compound represented by the formula (17) in which the azine ring is bonded to the biscarbazole structure via the linking group, it is speculated that the electron accepting performance of the azine ring and the electron donating performance of the biscarbazole structure are balanced with each other, thereby decreasing ΔST.

In the first exemplary embodiment, the compound represented by the formula (17) is preferably a compound represented by a formula (18) below.

[Formula 21]

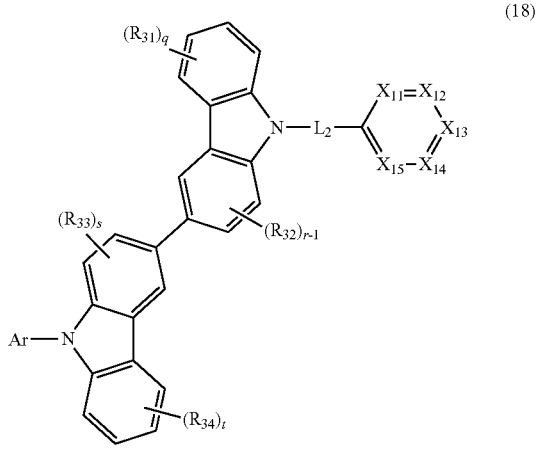

(18)

In the formula (18), $L_2$ represents the same as $L_2$ of the formula (1).

In the formula (18), $X_{11}$ to $X_{15}$ each independently represent the same as $X_{11}$ to $X_{15}$ of the formula (12).

In the formula (18), $R_{31}$ to $R_{34}$ each independently represent the same as $R_8$ described above. Adjacent ones of $R_{31}$ may form a ring. Adjacent ones of $R_{32}$ may form a ring. Adjacent ones of $R_{33}$ may form a ring. Adjacent ones of $R_{34}$ may form a ring.

In the formula (18), q, r, s and t respectively represent the same as q, r, s and t of the formula (17).

In the formula (18), Ar represents the same as Ar of the formula (17).

In the first exemplary embodiment, the compound represented by the formula (17) is preferably a compound represented by a formula (19) below.

[Formula 22]

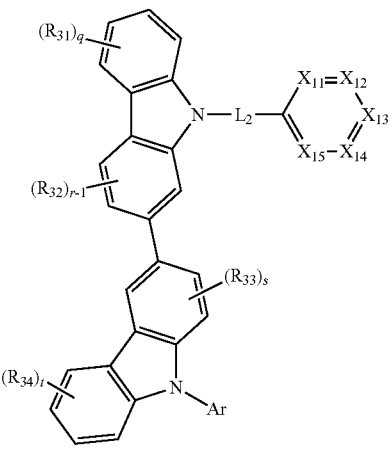

(19)

In the formula (19), $L_2$ represents the same as $L_2$ of the formula (1).

In the formula (19), $X_{11}$ to $X_{15}$ each independently represent the same as $X_{11}$ to $X_{15}$ of the formula (12).

In the formula (19), $R_{31}$ to $R_{34}$ each independently represent the same as $R_8$ described above. Adjacent ones of $R_{31}$ may form a ring. Adjacent ones of $R_{32}$ may form a ring. Adjacent ones of $R_{33}$ may form a ring. Adjacent ones of $R_{34}$ may form a ring.

In the formula (19), q, r, s and t respectively represent the same as q, r, s and t of the formula (17).

In the formula (19), Ar represents the same as Ar of the formula (17).

In the first exemplary embodiment, in the group represented by the formula (10), it is preferable that the cyclic structure A is a substituted or unsubstituted benzene ring and the cyclic structure B is a cyclic structure in which any ones of a plurality of five-membered rings and six-membered rings are mutually fused. In this arrangement, any one of the cyclic structures may have a substituent. In the first exemplary embodiment, the compound represented by the formula (1) is preferably a compound represented by a formula (31) below.

[Formula 23]

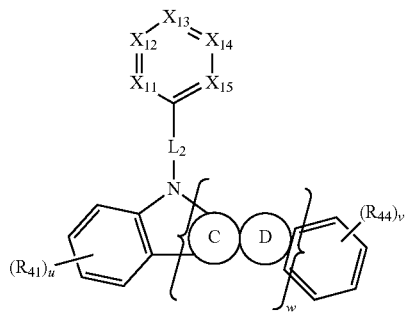

(31)

In the formula (31), $L_2$ represents the same as $L_2$ of the formula (1).

In the formula (31), $X_{11}$ to $X_{15}$ each independently represent the same as $X_{11}$ to $X_{15}$ of the formula (12).

In the formula (31), $R_{41}$ and $R_{44}$ each independently represent the same as $R_8$ described above. Adjacent ones of $R_{41}$ may form a ring. Adjacent ones of $R_{44}$ may form a ring.

In the formula (31), u and v are 4.

In the formula (31), C represents a cyclic structure represented by a formula (32) below and D represents a cyclic structure represented by a formula (33) below. Each of the cyclic structure C and the cyclic structure D is fused to an adjacent cyclic structure at any position.

In the formula (31), w is an integer of 1 to 4. w is a repeating unit of a linking cyclic structure in which the cyclic structure C and the cyclic structure D are fused.

[Formula 24]

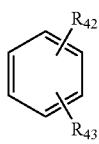
(32)

[Formula 25]

(33)

In the formula (32), $R_{42}$ and $R_{43}$ each independently represent the same as $R_8$ of the formula (1). When $R_{42}$ and $R_{43}$ are substituents at adjacent positions, $R_{42}$ and $R_{43}$ may form a ring.

In the formula (33), $Y_1$ represents $CR_{45}R_{46}$, $NR_{47}$, a sulfur atom, or an oxygen atom. $R_{45}$ to $R_{47}$ each independently represent the same as $R_1$ to $R_7$ in the formula (1).

In the host material used in the first exemplary embodiment, as represented by the formula (31), the electron donating moiety represented by the formula (10) is an indolocarbazole skeleton or a skeleton in which an indole ring is further fused to an indolocarbazole ring. Since the electron accepting moiety represented by the formula (10) is provided by such an electron donating moiety, the electron donating performance of the host material in this arrangement can be improved more than that of the above monocarbazole structure. In the compound represented by the formula (31), it is speculated that the electron accepting performance of the azine ring and the electron donating performance of the electron donating moiety of the indolocarbazole skeleton and the like are balanced with each other, thereby decreasing ΔST.

In the formula (31), w is preferably 1. In this arrangement, the compound represented by the formula (31) is represented by a formula (31a) below.

[Formula 26]

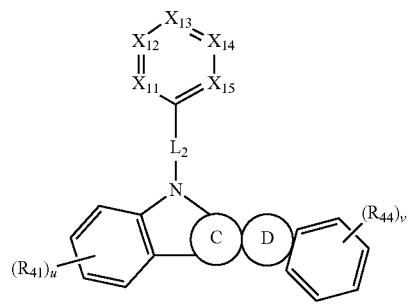
(31a)

In the formula (31a), $L_2$ represents the same as $L_2$ of the formula (1).

In the formula (31a), $X_{11}$ to $X_{15}$ each independently represent the same as $X_{11}$ to $X_{15}$ of the formula (12).

In the formula (31a), $R_{41}$ and $R_{44}$ each independently represent the same as $R_8$ described above. Adjacent ones of $R_{41}$ may form a ring. Adjacent ones of $R_{44}$ may form a ring.

In the formula (31a), u and v are 4.

In the formula (31a), C represents a cyclic structure represented by the formula (32) and D represents a cyclic structure represented by the formula (33). Each of the cyclic structure C and the cyclic structure D is fused to an adjacent cyclic structure at any position.

In the first exemplary embodiment, Cz represented by the formula (1) is preferably a group selected from the group consisting of groups represented by formulae (110) to (115) below.

[Formula 27]

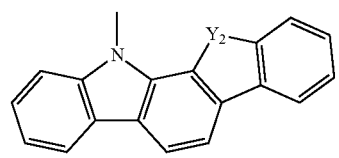
(110)

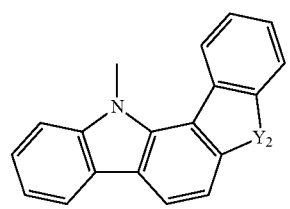
(111)

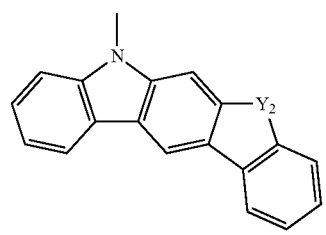
(112)

-continued (113)

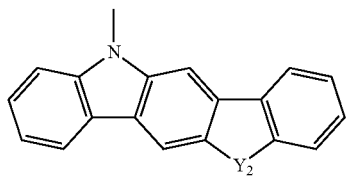

(114)

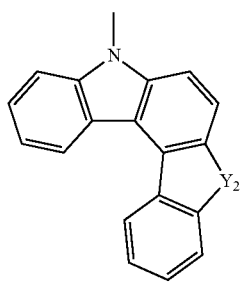

(115)

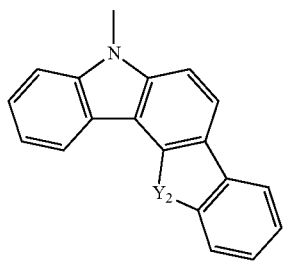

In the formulae (110) to (115), $Y_2$ represents $CR_{48}R_{49}$, $NR_{50}$, a sulfur atom, or an oxygen atom. $R_{48}$ to $R_{50}$ each independently represent the same as $R_1$ to $R_7$ in the formula (1). The groups represented by the formulae (110) to (115) may further have a substituent.

In the formulae (110) to (115), $Y_2$ is preferably an oxygen atom.

The compounds including the groups represented by the formulae (110) to (115) are preferably compounds represented by the formulae (31b) to (31g).

[Formula 28]

(31b)

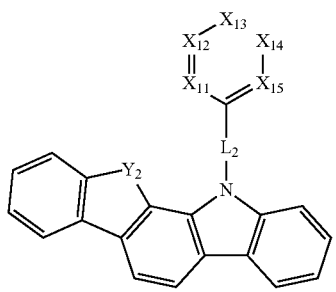

(31c)

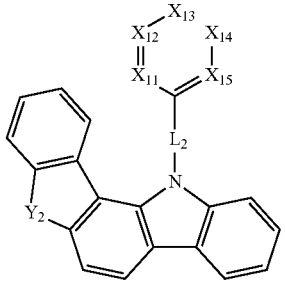

(31d)

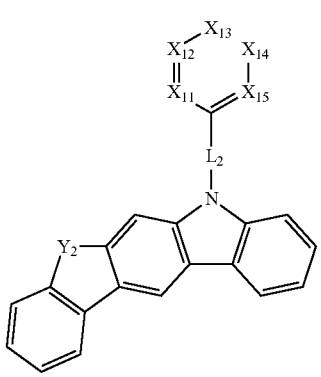

(31e)

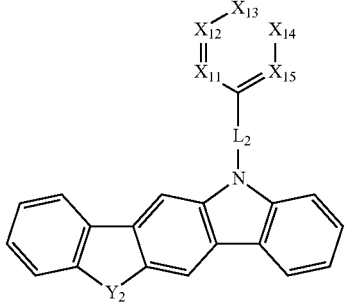

(31f)

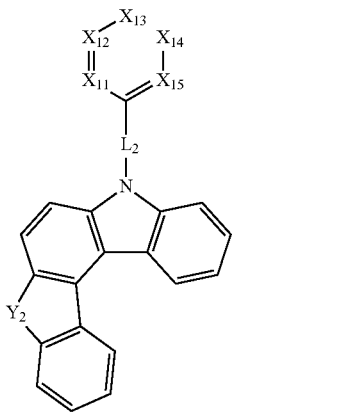

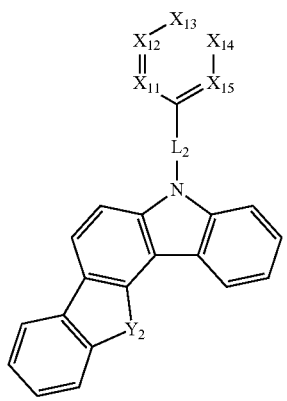
(31g)

In the formulae (31b) to (31g), $L_2$ represents the same as $L_2$ of the formula (1).

In the formulae (31b) to (31g), $X_{11}$ to $X_{15}$ each independently represent the same as $X_{11}$ to $X_{15}$ of the formula (12).

In the formulae (31b) to (31g), $Y_2$ represents $CR_{48}R_{49}$, $NR_{50}$, a sulfur atom, or an oxygen atom. $R_{48}$ to $R_{50}$ each independently represent the same as $R_1$ to $R_7$ in the formula (1).

In the formulae (31b) to (31g), $Y_2$ is preferably an oxygen atom.

In the organic electroluminescence device in the first exemplary embodiment, Cz of the formula (1) may be a group selected from the group consisting of groups derived from structures represented by formulae (116) to (119) below.

[Formula 29]

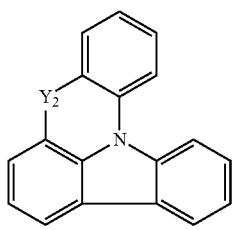
(116)

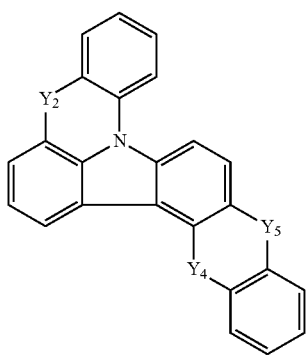
(117)

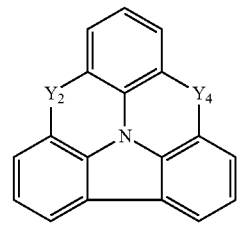
(118)

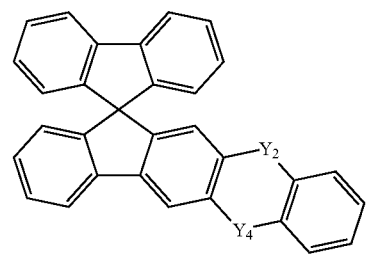
(119)

In the formulae (116) to (119), $Y_2$, $Y_4$ and $Y_5$ each independently represent $CR_{48}R_{49}$, $NR_{50}$, a sulfur atom, or an oxygen atom. $R_{48}$ to $R_{50}$ each independently represent the same as $R_1$ to $R_7$ in the formula (1). The group derived from the structure represented by the formulae (116) to (119) has a hand(s) at any positions and is bonded to $L_2$ in the formula (1). The groups derived from the structures represented by the formulae (116) to (119) may further have a substituent.

In the exemplary embodiment, when $L_2$ is a divalent linking group, $L_2$ is preferably a substituted or unsubstituted divalent aromatic hydrocarbon group.

Moreover, in the exemplary embodiment, when $L_2$ is a divalent linking group, $L_2$ preferably has a divalent six-membered ring structure, more preferably a divalent six-membered ring structure represented by a formula (3), (3a) or (3b) below, further preferably a divalent six-membered ring structure represented by the formula (3) below.

[Formula 30]

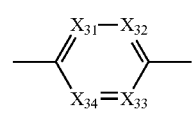
(3)

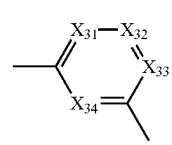
(3a)

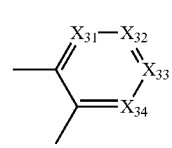
(3b)

In the formulae (3), (3a) and (3b), $X_{31}$ to $X_{34}$ each independently represent $CR_{51}$ or a nitrogen atom. $R_{51}$ each independently represents the same as $R_8$ in the formula (1). In the exemplary embodiment, $X_{31}$ to $X_{34}$ are preferably each independently $CR_{51}$, in which $R_{51}$ is more preferably a hydrogen atom, alkyl group, alkoxy group, aryloxy group, cyano group, halogen atom and silyl group.

Herein, the number of carbon atoms forming a ring (also referred to as ring carbon atoms) means the number of carbon atoms included in atoms forming the ring itself of a compound in which the atoms are bonded to form the ring (e.g., a monocyclic compound, a fused ring compound, a cross-linked compound, a carbocyclic compound, and a heterocyclic compound). When the ring is substituted by a substituent, carbon atom(s) included in the substituent is not counted as the ring carbon atoms. The same applies to the "ring carbon atoms" described below, unless particularly noted. For instance, a benzene ring has 6 ring carbon atoms, a naphthalene ring has 10 ring carbon atoms, a pyridinyl group has 5 ring carbon atoms, and a furanyl group has 4 ring carbon atoms. When a benzene ring or a naphthalene ring is substituted, for instance, by an alkyl group, the carbon atoms of the alkyl group are not counted as the ring carbon atoms. For instance, when a fluorene ring (inclusive of a spirofluorene ring) is bonded as a substituent to a fluorene ring, the carbon atoms of the fluorene ring as a substituent are not counted as the ring carbon atoms.

Herein, the number of atoms forming a ring (also referred to as ring atoms) means the number of atoms forming the ring itself of a compound in which the atoms are bonded to form the ring (e.g., a monocyclic compound, a fused ring compound, a cross-linked compound, a carbocyclic compound, and a heterocyclic compound). Atom(s) not forming the ring (e.g., hydrogen atom(s) for saturating the valence of the atom which forms the ring) and atom(s) in a substituent by which the ring is substituted are not counted as the ring atoms. The same applies to the "ring atoms" described below, unless particularly noted. For instance, a pyridine ring has 6 ring atoms, a quinazoline ring has 10 ring atoms, and a furan ring has 5 ring atoms. Hydrogen atoms respectively bonded to carbon atoms of the pyridine ring or the quinazoline ring and atoms forming a substituent are not counted as the ring atoms. For instance, when a fluorene ring (inclusive of a spirofluorene ring) is bonded as a substituent to a fluorene ring, the atoms of the fluorene ring as a substituent are not included in the ring atoms.

In the exemplary embodiment, examples of the aryl group having 6 to 30 ring carbon atoms include a phenyl group, biphenyl group, terphenyl group, naphthyl group, anthryl group, phenanthryl group, fluorenyl group, pyrenyl group, chrysenyl group, fluoranthenyl group, benzo[a]anthryl group, benzo[c]phenanthryl group, triphenylenyl group, benzo[k]fluoranthenyl group, benzo[g]chrysenyl group, benzo[b]triphenylenyl group, picenyl group, and perylenyl group.

The aryl group in the exemplary embodiment preferably has 6 to 20 ring carbon atoms, more preferably 6 to 12 ring carbon atoms. Among the above aryl group, a phenyl group, biphenyl group, naphthyl group, phenanthryl group, terphenyl group, and fluorenyl group are particularly preferable. A carbon atom at a position 9 of each of 1-fluorenyl group, 2-fluorenyl group, 3-fluorenyl group and 4-fluorenyl group is preferably substituted by a substituted or unsubstituted alkyl group having 1 to 30 carbon atoms later described in the exemplary embodiment.

Examples of the heterocyclic group having 5 to 30 ring atoms in the exemplary embodiment include a pyridyl group, pyrimidinyl group, pyrazinyl group, pyridazinyl group, triazinyl group, quinolyl group, isoquinolinyl group, naphthyridinyl group, phthalazinyl group, quinoxalinyl group, quinazolinyl group, phenanthridinyl group, acridinyl group, phenanthrolinyl group, pyrrolyl group, imidazolyl group, pyrazolyl group, triazolyl group, tetrazolyl group, indolyl group, benzimidazolyl group, indazolyl group, imidazopyridinyl group, benzotriazolyl group, carbazolyl group, furyl group, thienyl group, oxazolyl group, thiazolyl group, isoxazolyl group, isothiazolyl group, oxadiazolyl group, thiadiazole group, benzofuranyl group, benzothiophenyl group, benzoxazolyl group, benzothiazolyl group, benzisoxazolyl group, benzisothiazolyl group, benzoxadiazolyl group, benzothiadiazolyl group, dibenzofuranyl group, dibenzothiophenyl group, piperidinyl group, pyrrolidinyl group, piperazinyl group, morpholyl group, phenazinyl group, phenothiazinyl group, and phenoxazinyl group.

The heterocyclic group in the exemplary embodiment preferably has 5 to 20 ring atoms, more preferably 5 to 14 ring atoms. Among the above heterocyclic group, a 1-dibenzofuranyl group, 2-dibenzofuranyl group, 3-dibenzofuranyl group, 4-dibenzofuranyl group, 1-dibenzothiophenyl group, 2-dibenzothiophenyl group, 3-dibenzothiophenyl group, 4-dibenzothiophenyl group, 1-carbazolyl group, 2-carbazolyl group, 3-carbazolyl group, 4-carbazolyl group, and 9-carbazolyl group are particularly preferable. A nitrogen atom at a position 9 of each of 1-carbazolyl group, 2-carbazolyl group, 3-carbazolyl group and 4-carbazolyl group is preferably substituted by a substituted or unsubstituted aryl group having 6 to 30 ring carbon atoms or a substituted or unsubstituted heterocyclic group having 5 to 30 ring atoms in the exemplary embodiment.

The alkyl group having 1 to 30 carbon atoms in the exemplary embodiment is preferably linear, branched or cyclic. Examples of the linear or branched alkyl group include: a methyl group, ethyl group, n-propyl group, isopropyl group, n-butyl group, s-butyl group, isobutyl group, t-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, neopentyl group, amyl group, isoamyl group, 1-methylpentyl group, 2-methylpentyl group, 1-pentylhexyl group, 1-butylpentyl group, 1-heptyloctyl group, and 3-methylpentyl group.

The linear or branched alkyl group in the exemplary embodiment preferably has 1 to 10 carbon atoms, more preferably 1 to 6 carbon atoms. Among the linear or branched alkyl group, a methyl group, ethyl group, propyl group, isopropyl group, n-butyl group, s-butyl group, isobutyl group, t-butyl group, n-pentyl group, n-hexyl group, amyl group, isoamyl group, and neopentyl group are particularly preferable.

Examples of the cycloalkyl group in the exemplary embodiment include a cyclopropyl group, cyclobutyl group, cyclopentyl group, cyclohexyl group, 4-methylcyclohexyl group, adamantyl group and norbornyl group. The cycloalkyl group preferably has 3 to 10 ring carbon atoms, more preferably 5 to 8 ring carbon atoms. Among the above cycloalkyl group, a cyclopentyl group and a cyclohexyl group are particularly preferable.

The halogenated alkyl group provided by substituting the alkyl group with a halogen atom is exemplified by a halogenated alkyl group obtained by substituting the alkyl group having 1 to 30 carbon atoms with one or more halogen atoms. Specific examples of the halogenated alkyl group includes a fluoromethyl group, difluoromethyl group, trifluoromethyl group, fluoroethyl group, trifluoromethylmethyl group, trifluoroethyl group, and pentafluoroethyl group.

The alkylsilyl group having 3 to 30 carbon atoms in the exemplary embodiment is exemplified by a trialkylsilyl group having the above alkyl group having 1 to 30 carbon atoms. Specific examples of the trialkylsilyl group include a trimethylsilyl group, triethylsilyl group, tri-n-butylsilyl group, tri-n-octylsilyl group, triisobutylsilyl group, dimethylethylsilyl group, dimethylisopropylsilyl group, dimethyl-n-propylsilyl group, dimethyl-n-butylsilyl group, dimethyl-t-butylsilyl group, diethylisopropylsilyl group, vinyldimethylsilyl group, propyldimethylsilyl group and triisopropylsilyl group. Three alkyl groups in the trialkylsilyl group may be mutually the same or different.

Examples of the arylsilyl group having 6 to 30 ring carbon atoms in the exemplary embodiment include a dialkylarylsilyl group, alkyldiarylsilyl group and triarylsilyl group.

The dialkylarylsilyl group is exemplified by a dialkylarylsilyl group including two of the alkyl group listed as the examples of the alkyl group having 1 to 30 carbon atoms and one of the aryl group listed as the examples of the aryl group having 6 to 30 ring carbon atoms. The dialkylarylsilyl group preferably has 8 to 30 carbon atoms.

The alkyldiarylsilyl group is exemplified by an alkyldiarylsilyl group including one of the alkyl group listed as the examples of the alkyl group having 1 to 30 carbon atoms and two of the aryl group listed as the examples of the aryl group having 6 to 30 ring carbon atoms. The alkyldiarylsilyl group preferably has 13 to 30 carbon atoms.

The triarylsilyl group is exemplified by a triarylsilyl group having three of the above aryl group having 6 to 30 ring carbon atoms. The triarylsilyl group preferably has 18 to 30 carbon atoms.

The alkoxy group having 1 to 30 carbon atoms in the exemplary embodiment is represented by —$OZ_1$. —$OZ_1$ is exemplified by the above alkyl group having 1 to 30 carbon atoms. Examples of the alkoxy group include a methoxy group, ethoxy group, propoxy group, butoxy group, pentyloxy group and hexyloxy group.

The halogenated alkoxy group provided by substituting the alkoxy group with a halogen atom is exemplified by a halogenated alkoxy group obtained by substituting the alkoxy group having 1 to 30 carbon atoms with one or more halogen atoms.

The aryloxy group having 6 to 30 ring carbon atoms in the exemplary embodiment is represented by —$OZ_2$. $Z_2$ is exemplified by the examples of the aryl group having 6 to 30 ring carbon atoms or later-described monocyclic group and fused cyclic group. The aryloxy group is exemplified by a phenoxy group.

The alkylamino group having 2 to 30 carbon atoms is represented by —$NHR_V$ or —$N(R_V)_2$. $R_V$ is exemplified by the above alkyl group having 1 to 30 carbon atoms.

The arylamino group having 6 to 60 ring carbon atoms is represented by —$NHR_W$ or —$N(R_W)_2$. $R_W$ is exemplified by the above aryl group having 6 to 30 ring carbon atoms.

The alkylthio group having 1 to 30 carbon atoms is represented by —$SR_V$. $R_V$ is exemplified by the above alkyl group having 1 to 30 carbon atoms.

The arylthio group having 6 to 30 ring carbon atoms is represented by —$SR_W$. $R_W$ is exemplified by the above aryl group having 6 to 30 ring carbon atoms.

In the invention, "carbon atoms forming a ring (ring carbon atoms)" mean carbon atoms forming a saturated ring, an unsaturated ring, or an aromatic ring. "Atoms forming a ring (ring atoms)" mean carbon atoms and hetero atoms forming a hetero ring including a saturated ring, unsaturated ring, or aromatic ring.

In the invention, a hydrogen atom includes isotope having different numbers of neutrons, specifically, protium, deuterium and tritium.

In the exemplary embodiment, examples of the substituent meant by "substituted or unsubstituted" and the substituent in the cyclic structures A and B are an alkenyl group, alkynyl group, aralkyl group, halogen atom, cyano group, hydroxyl group, nitro group and carboxy group, in addition to the above-described aryl group, heterocyclic group, alkyl group (linear or branched alkyl group, cycloalkyl group and haloalkyl group), alkylsilyl group, arylsilyl group, alkoxy group, aryloxy group, alkylamino group, arylamino group, alkylthio group, and arylthio group.

Among the above substituents, an aryl group, heterocyclic group, alkyl group, halogen atom, alkylsilyl group, arylsilyl group and cyano group are preferable. More preferable substituents are the preferable substituents specifically described for each substituent.

In the exemplary embodiment, the aromatic hydrocarbon group is preferably an aryl group having 6 to 30 ring carbon atoms and the heterocyclic group is preferably a heterocyclic group having 5 to 30 ring atoms.

The alkenyl group is preferably an alkenyl group having 2 to 30 carbon atoms, which may be linear, branched or cyclic. Examples of the alkenyl group include a vinyl group, propenyl group, butenyl group, oleyl group, eicosapentaenyl group, docosahexaenyl group, styryl group, 2,2-diphenylvinyl group, 1,2,2-triphenylvinyl group, 2-phenyl-2-propenyl group, cyclopentadienyl group, cyclopentenyl group, cyclohexenyl group, and cyclohexadienyl group.

The alkynyl group is preferably an alkynyl group having 2 to 30 carbon atoms, which may be linear, branched or cyclic. Examples of the alkynyl group include ethynyl, propynyl, and 2-phenylethynyl.

The aralkyl group is preferably an aralkyl group having 6 to 30 ring carbon atoms and is represented by —$Z_3$—$Z_4$. $Z_3$ is exemplified by an alkylene group derived from the above alkyl group having 1 to 30 carbon atoms. $Z_4$ is exemplified by the above aryl group having 6 to 30 ring carbon atoms. This aralkyl group is preferably an aralkyl group having 7 to 30 carbon atoms, in which an aryl moiety has 6 to 30 carbon atoms, preferably 6 to 20 carbon atoms, more preferably 6 to 12 carbon atoms and an alkyl moiety has 1 to 30 carbon atoms, preferably 1 to 20 carbon atoms, more preferably 1 to 10 carbon atoms, further preferably 1 to 6 carbon atoms. Examples of the aralkyl group include a benzyl group, 2-phenylpropane-2-yl group, 1-phenylethyl group, 2-phenylethyl group, 1-phenylisopropyl group, 2-phenylisopropyl group, phenyl-t-butyl group, α-naphthylmethyl group, 1-α-naphthylethyl group, 2-α-naphthylethyl group, 1-α-naphthylisopropyl group, 2-α-naphthylisopropyl group, β-naphthylmethyl group, 1-β-naphthylethyl group, 2-β-naphthylethyl group, 1-β-naphthylisopropyl group, and 2-β-naphthylisopropyl group.

Examples of the halogen atom are fluorine, chlorine, bromine and iodine, among which a fluorine atom is preferable.

"Unsubstituted" in "substituted or unsubstituted" herein means that a group is not substituted by the above-described substituents but bonded with a hydrogen atom.

Herein, "XX to YY carbon atoms" in the description of "substituted or unsubstituted ZZ group having XX to YY carbon atoms" represent carbon atoms of an unsubstituted ZZ group and do not include carbon atoms of a substituent(s) of the substituted ZZ group. "YY" is larger than "XX" and each of "XX" and "YY" represents an integer of 1 or more.

Herein, "XX to YY atoms" in the description of "substituted or unsubstituted ZZ group having XX to YY atoms" represent atoms of an unsubstituted ZZ group and does not include atoms of a substituent(s) of the substituted ZZ group. "YY" is larger than "XX" and each of "XX" and "YY" represents an integer of 1 or more.

The same description as the above applies to "substituted or unsubstituted" in the following compound or a partial structure thereof.
Specific examples of the compound represented by the formula (1) are shown below, but the invention is not limited thereto.
[Formula 31]
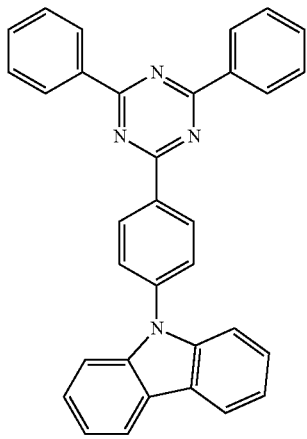
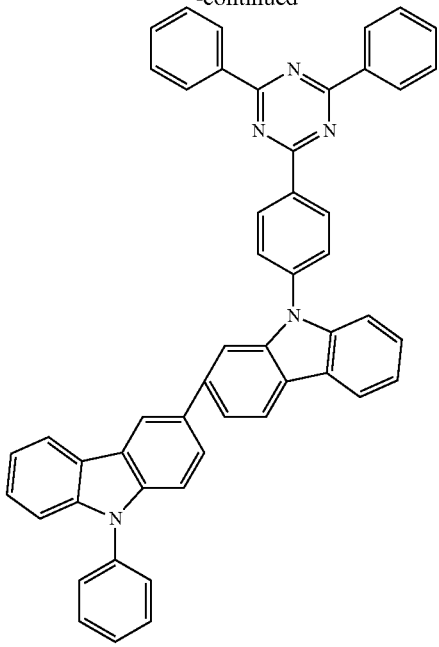
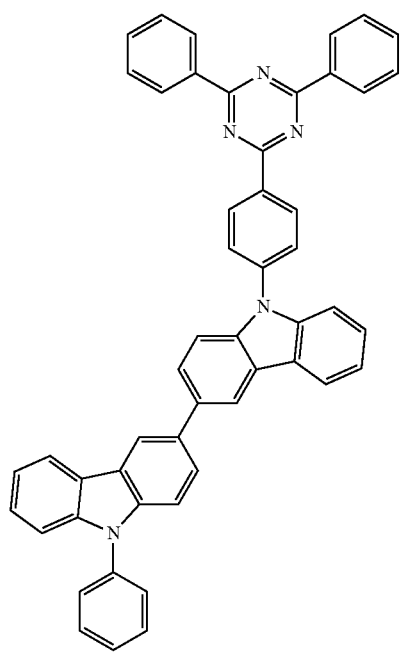
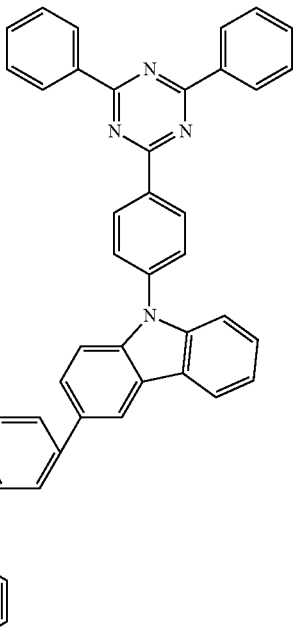

-continued
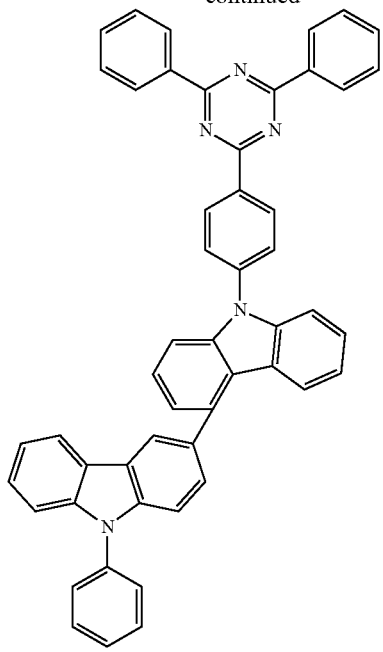
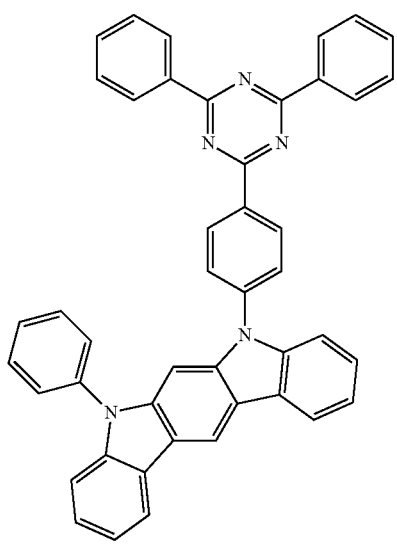
-continued
[Formula 32]
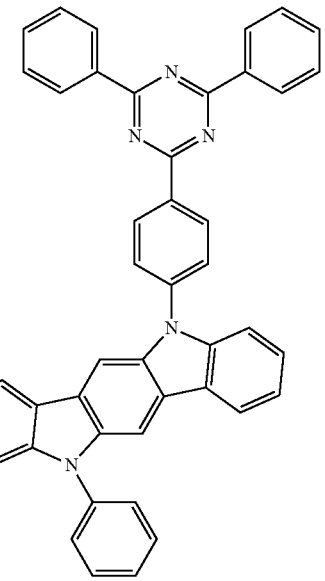
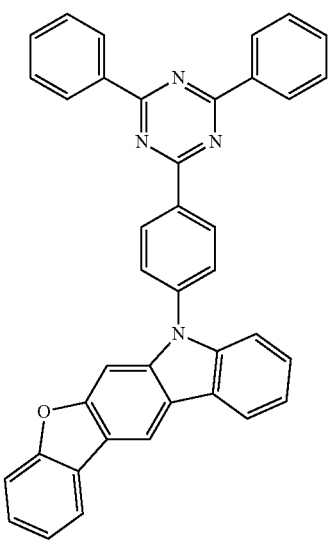
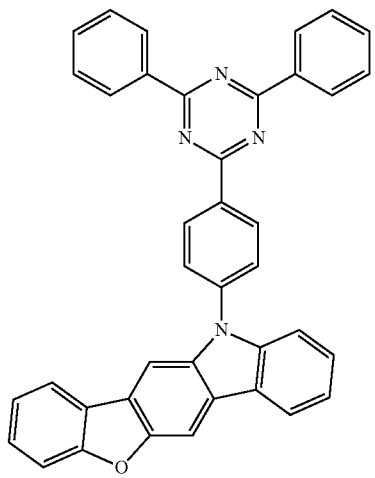

31
-continued
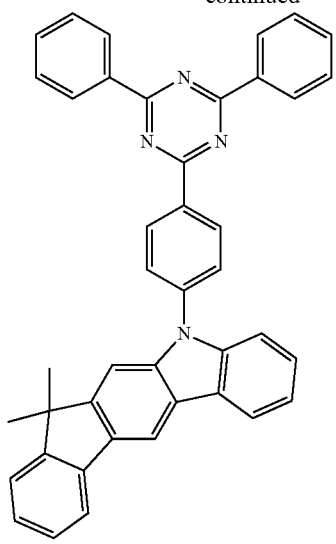
[Formula 33]
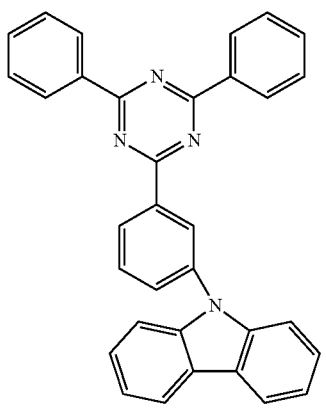
32
-continued
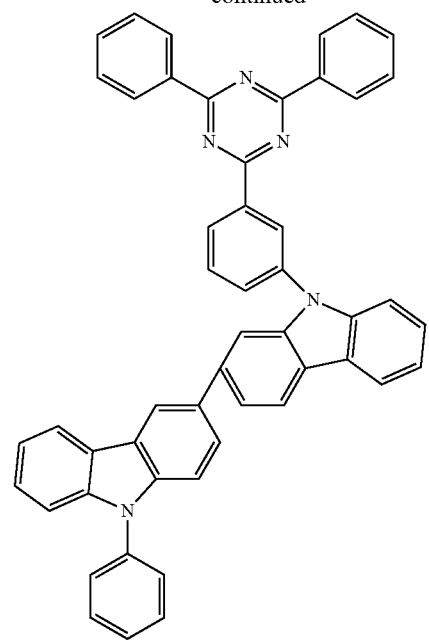
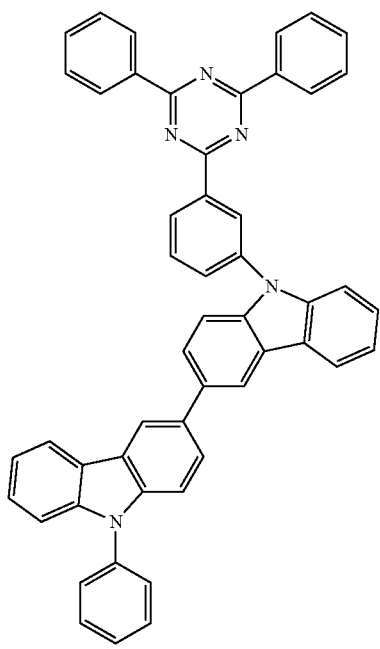
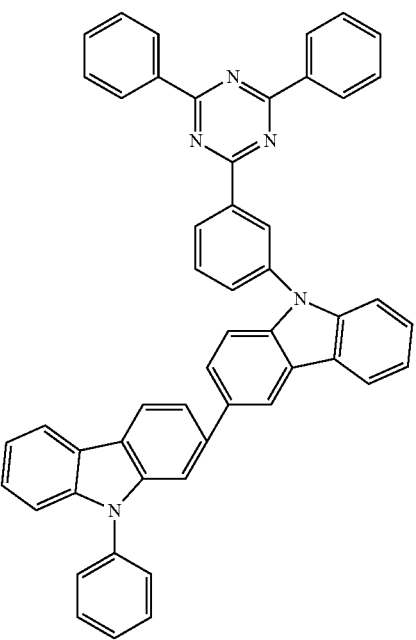

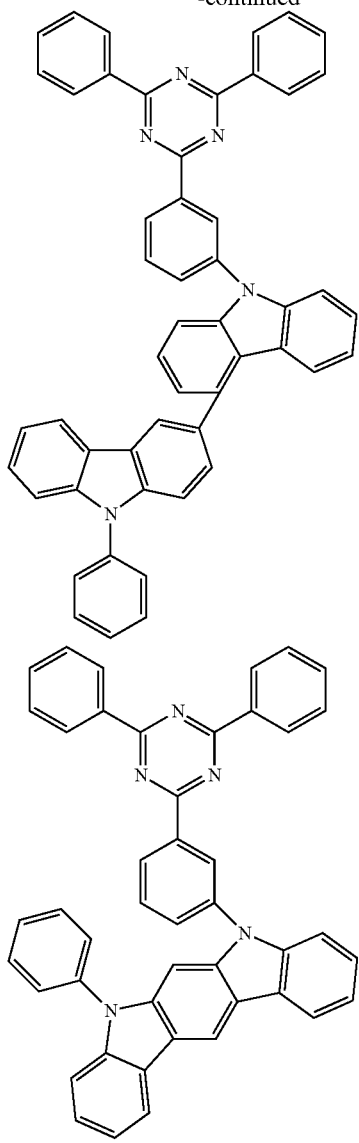
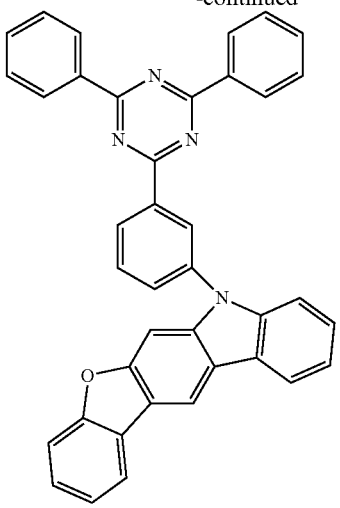
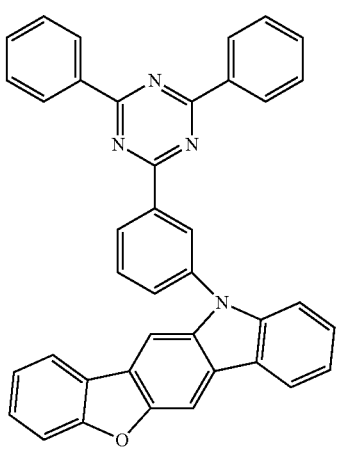
[Formula 34]
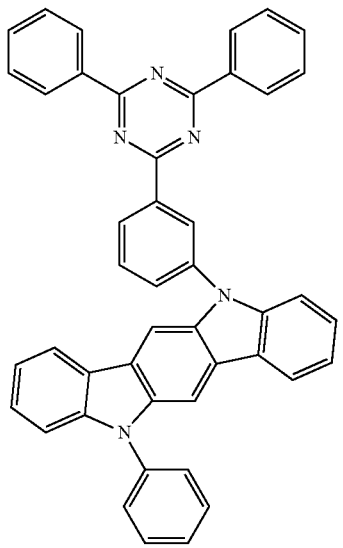
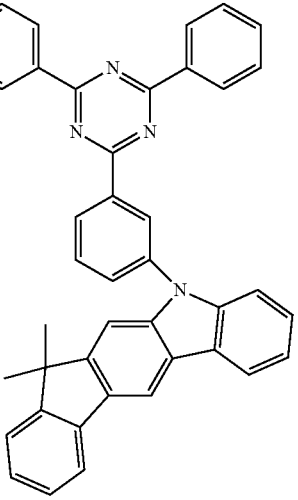

35
-continued
[Formula 35]
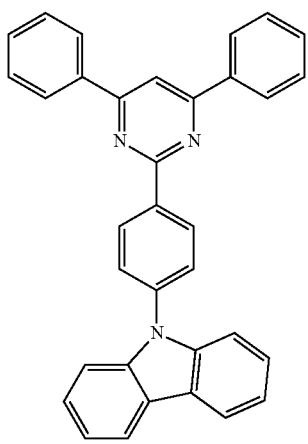
36
-continued
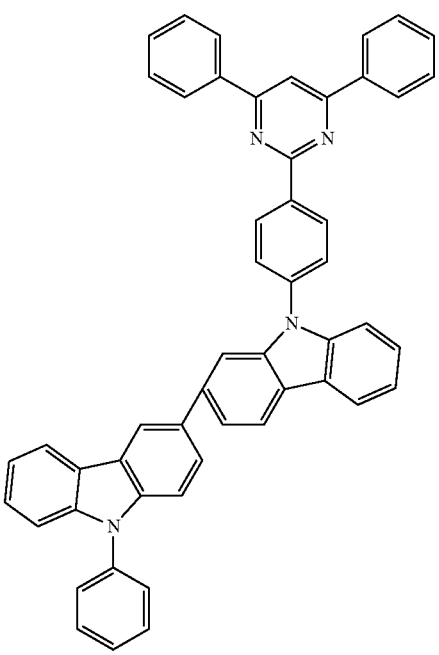
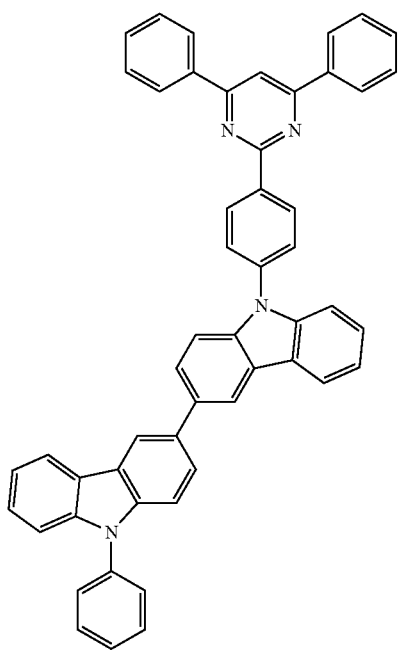
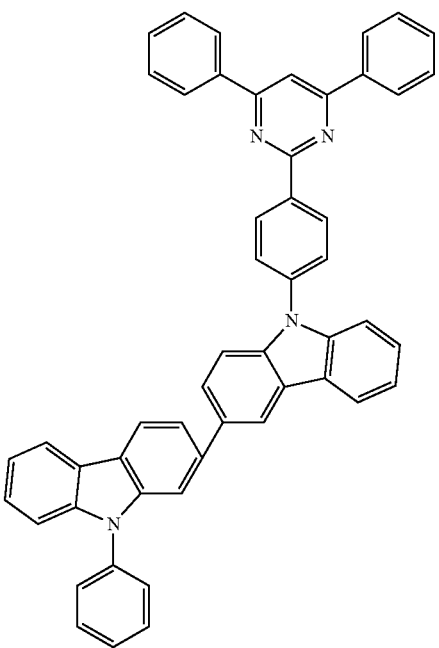

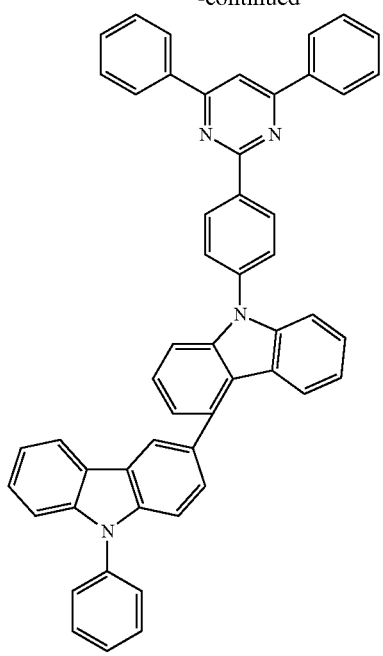
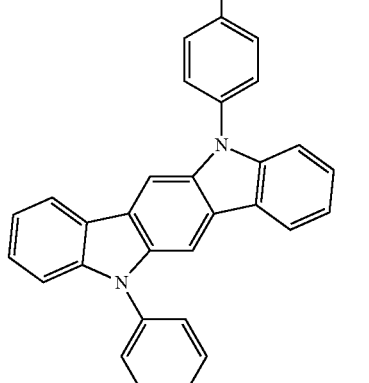
[Formula 36]
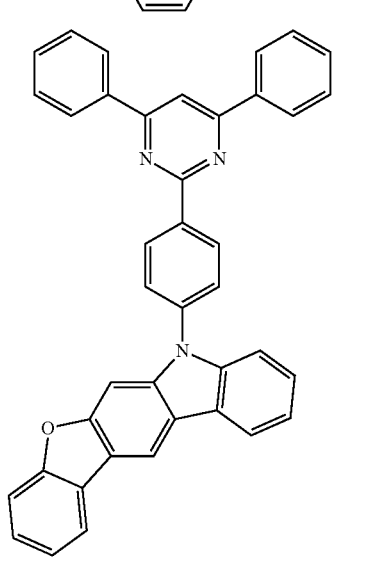
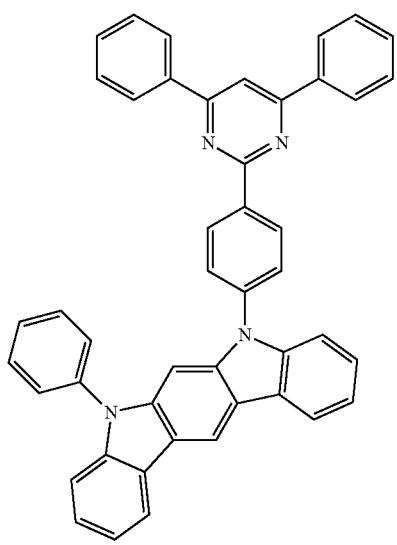
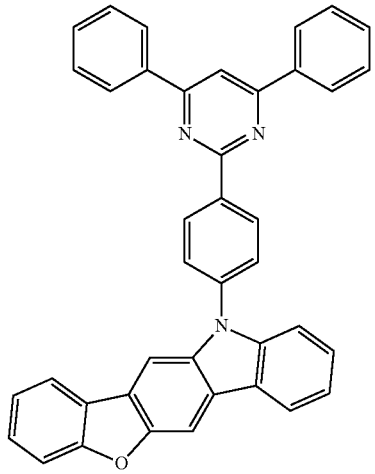

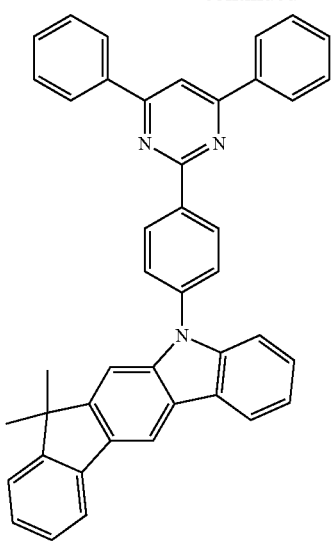
[Formula 37]
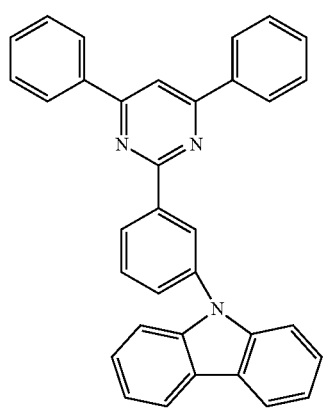
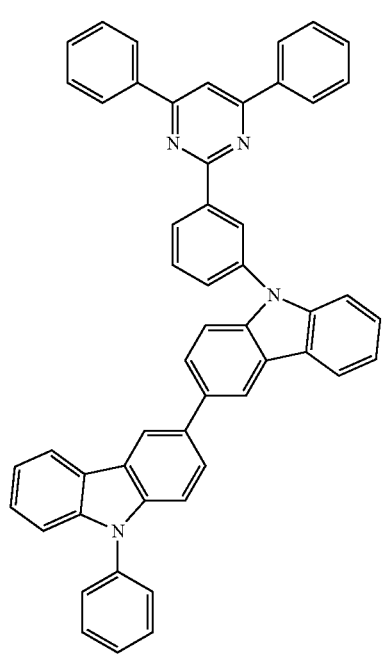
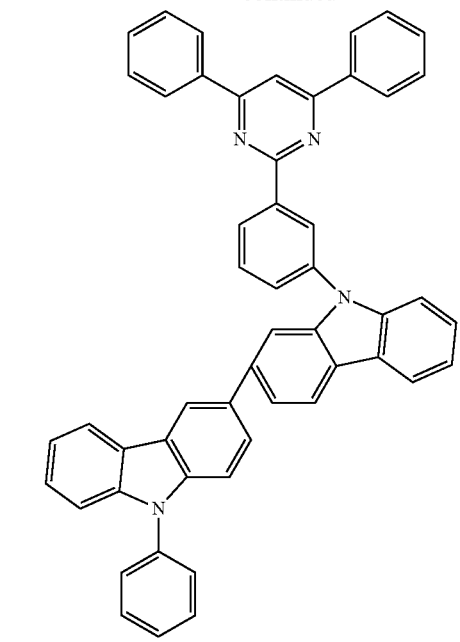
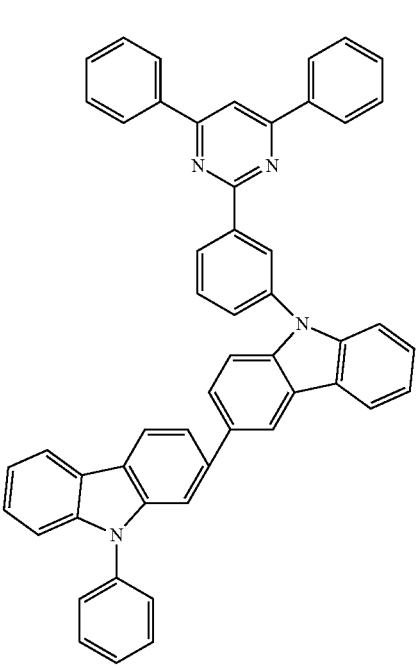

-continued
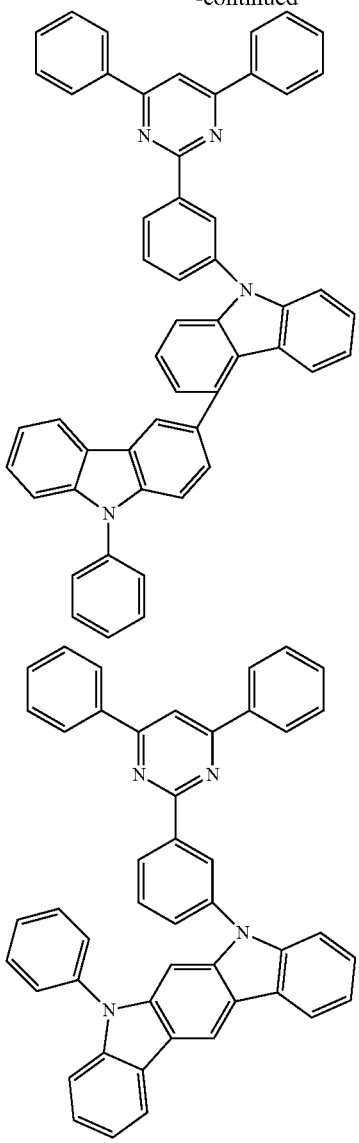
[Formula 38]
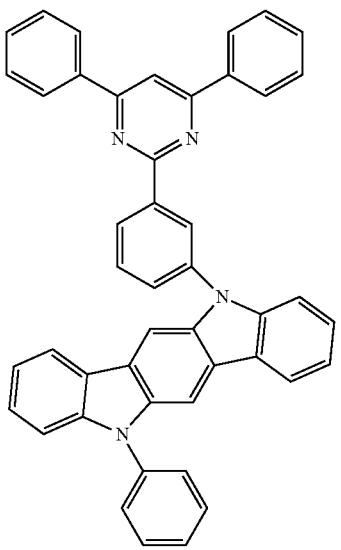
-continued

[Formula 39]
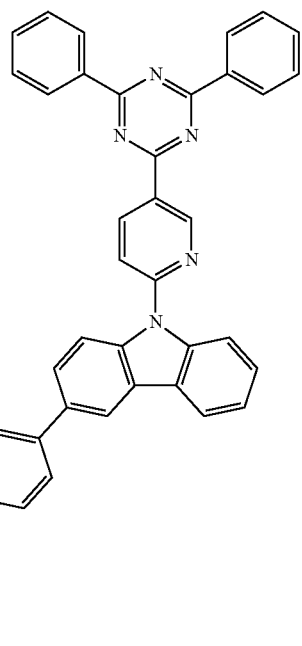
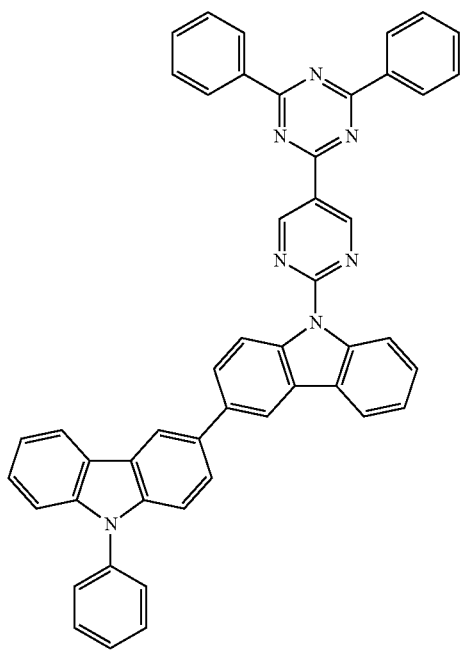
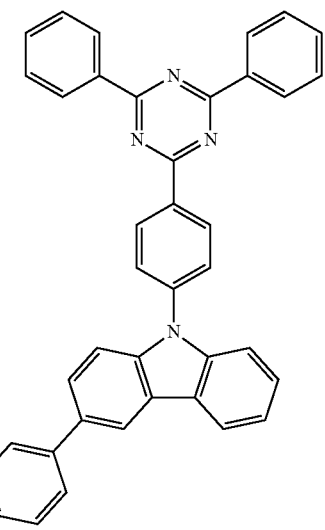
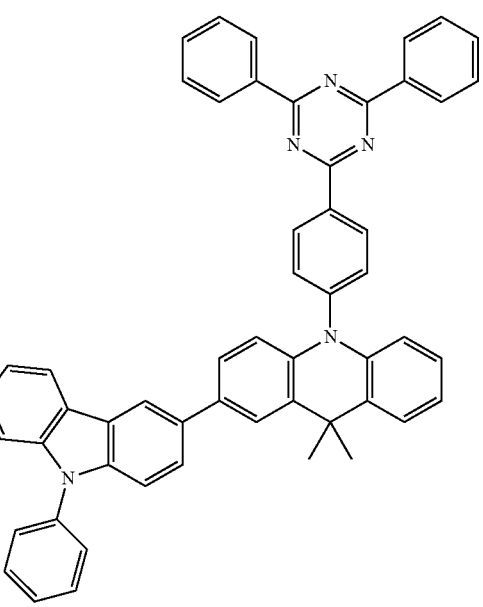
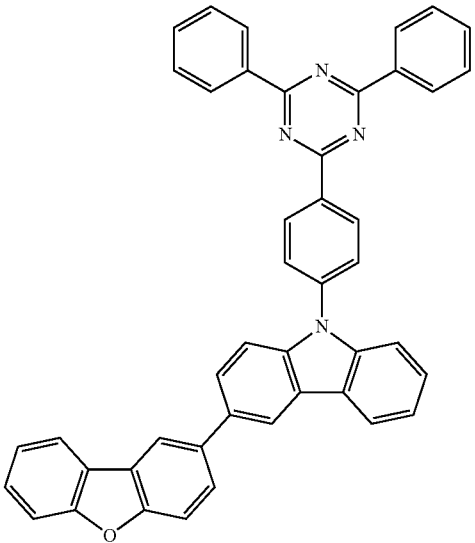

-continued
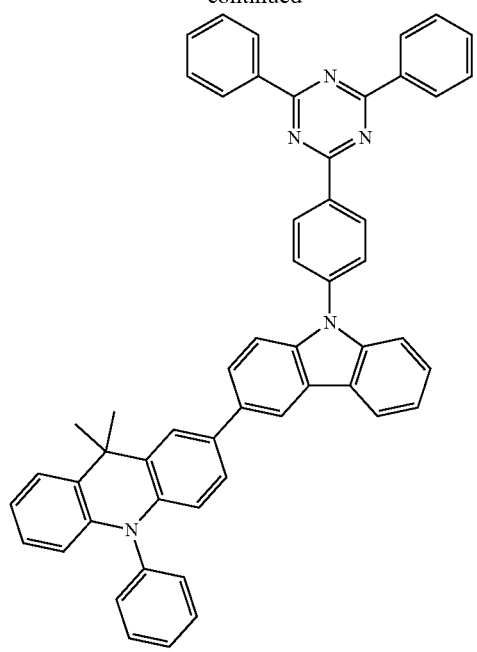
[Formula 40]
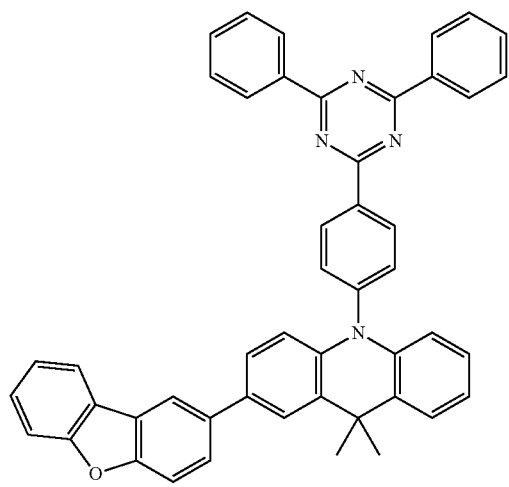
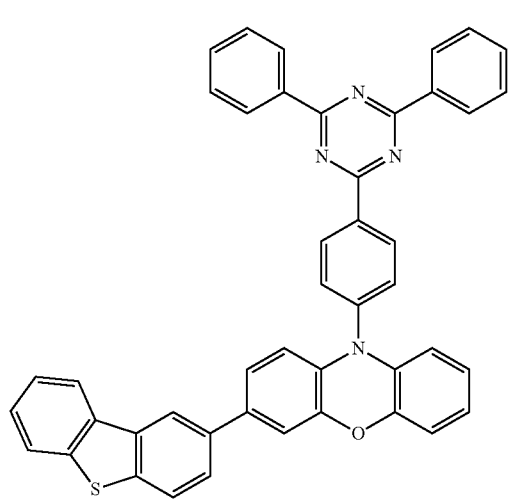
-continued
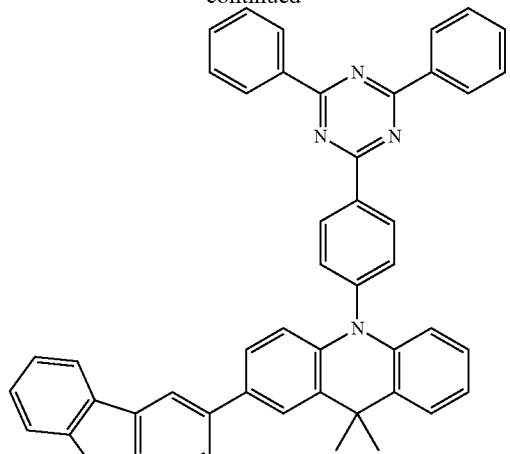
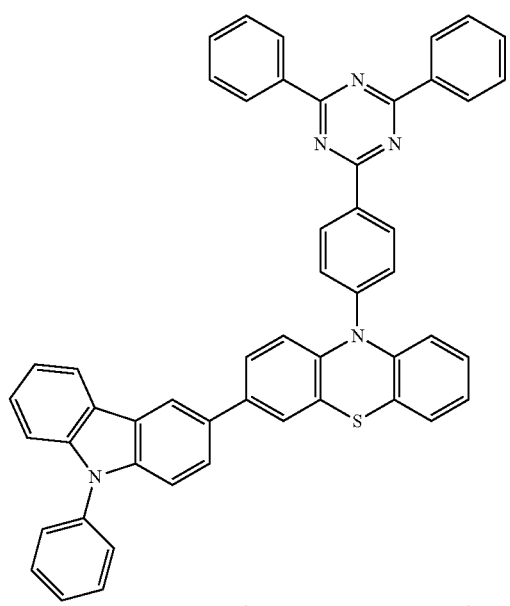
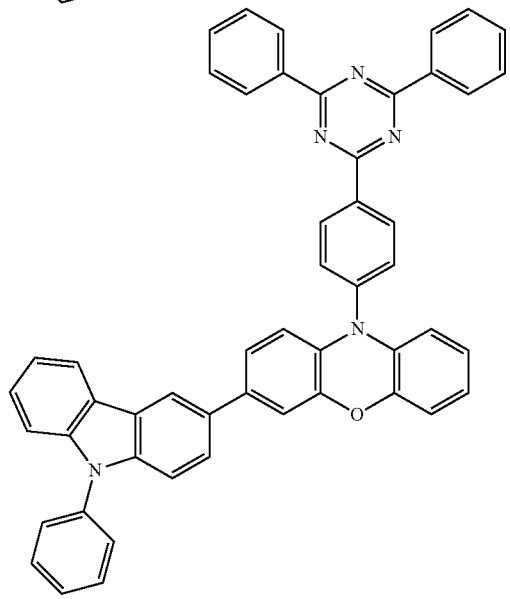

-continued
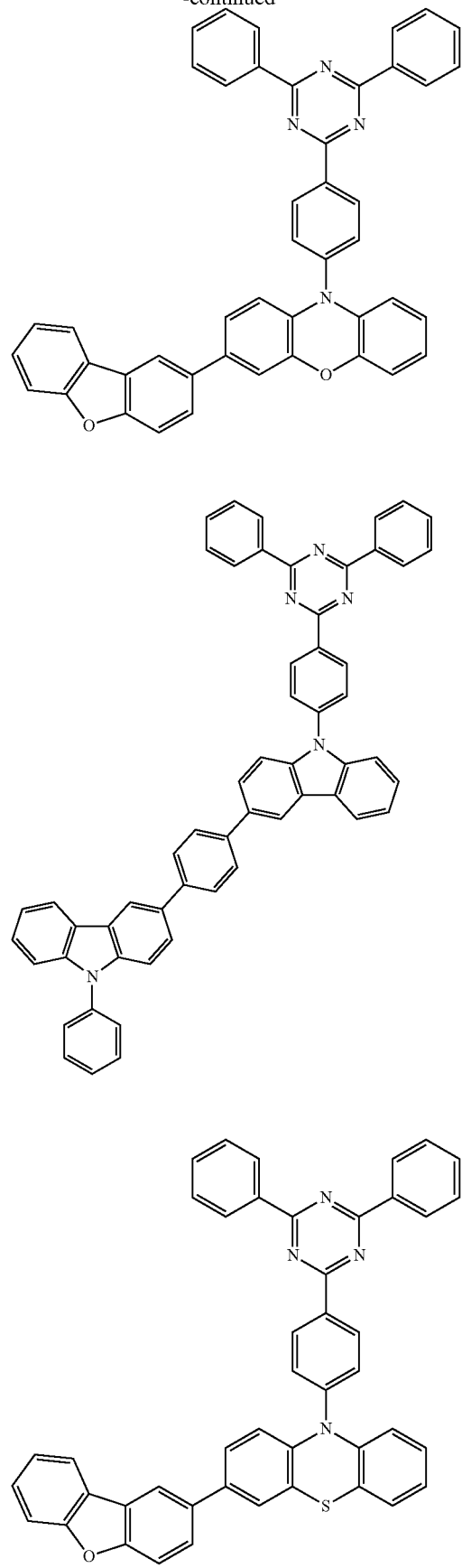
-continued
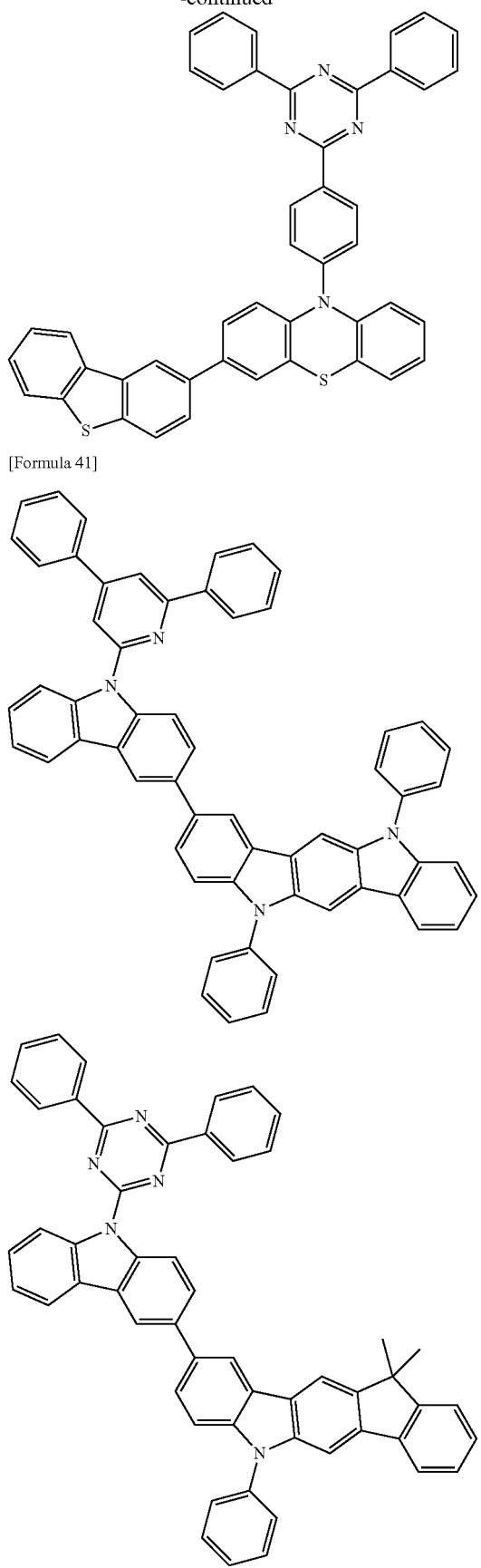
[Formula 41]

49
-continued
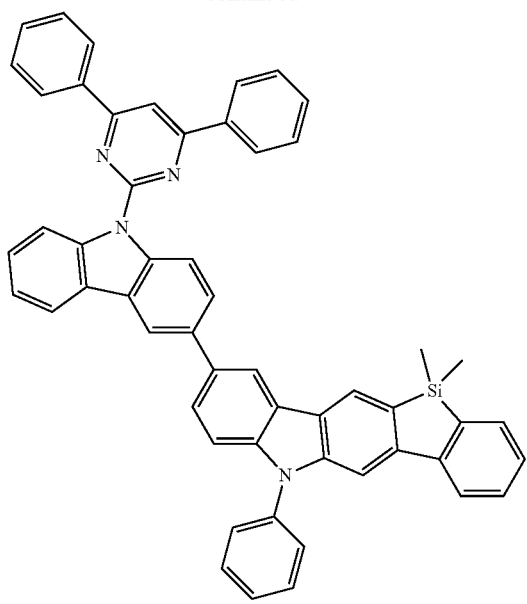
50
-continued
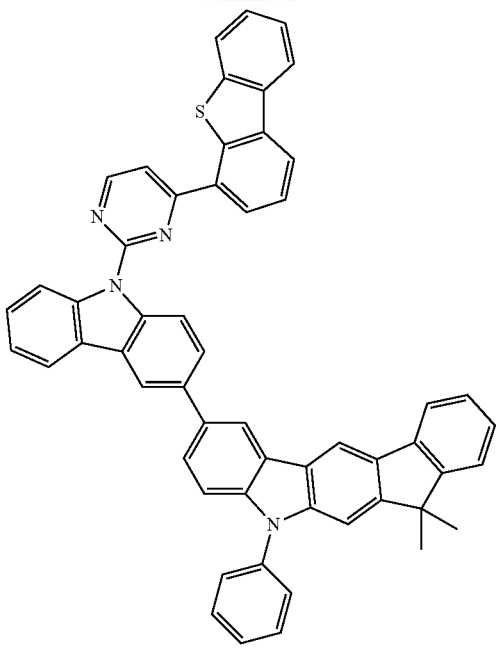
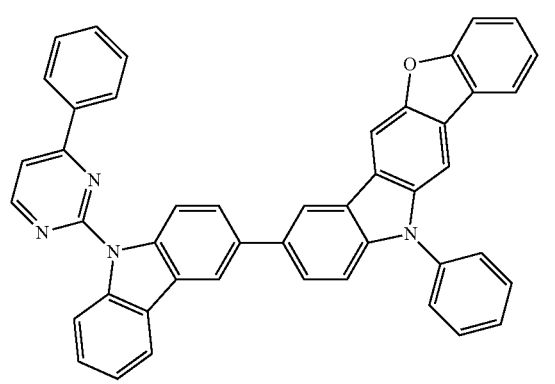
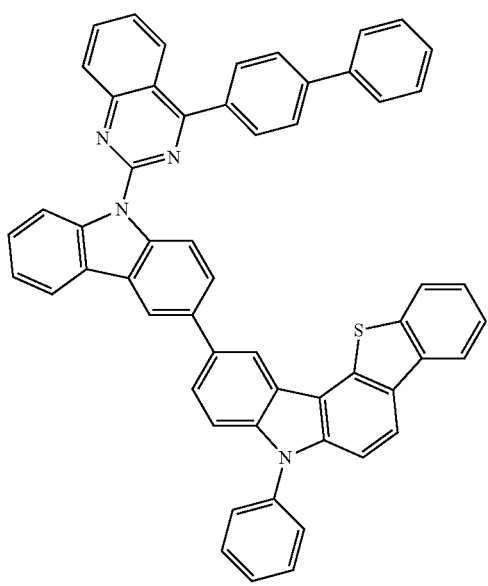
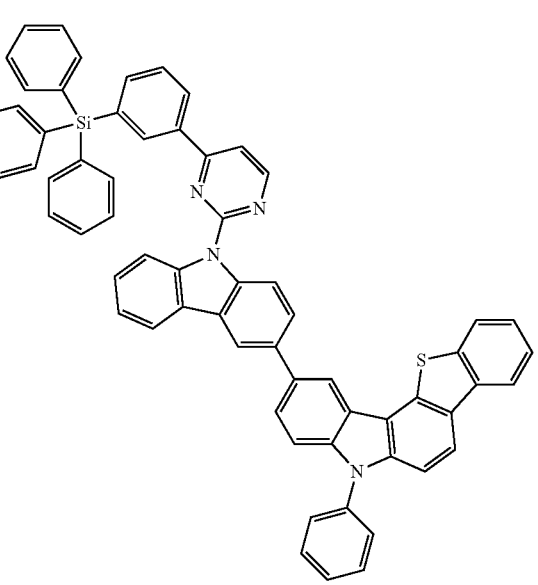

[Formula 42]
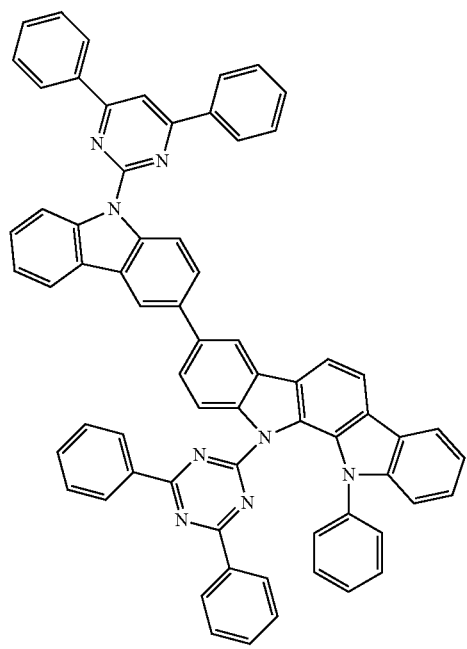
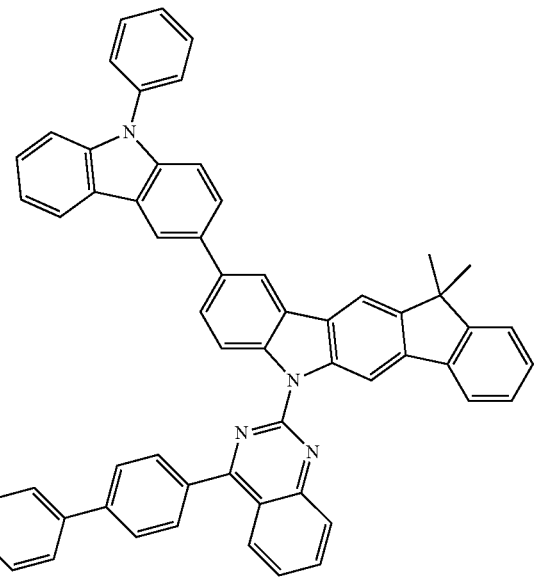
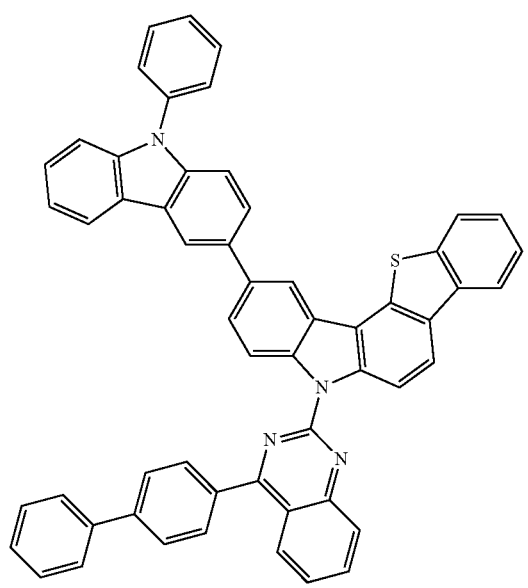
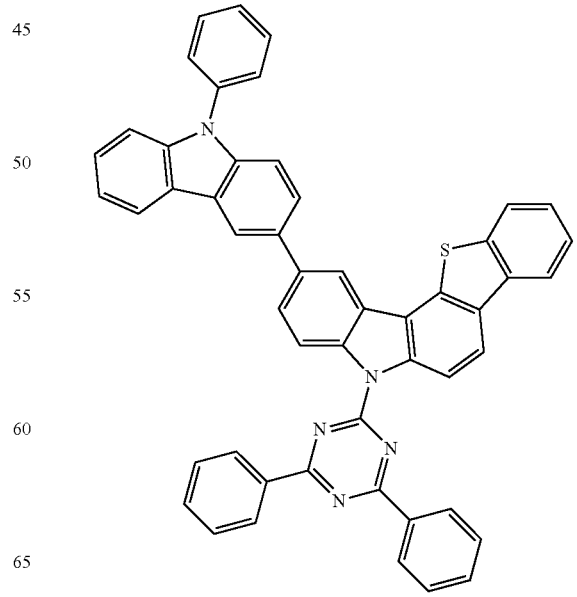

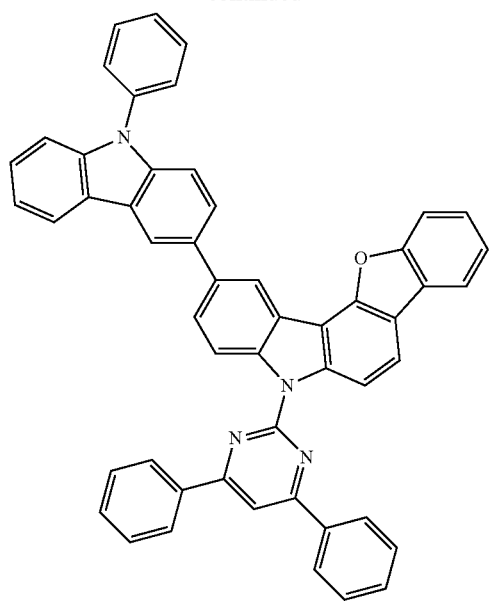
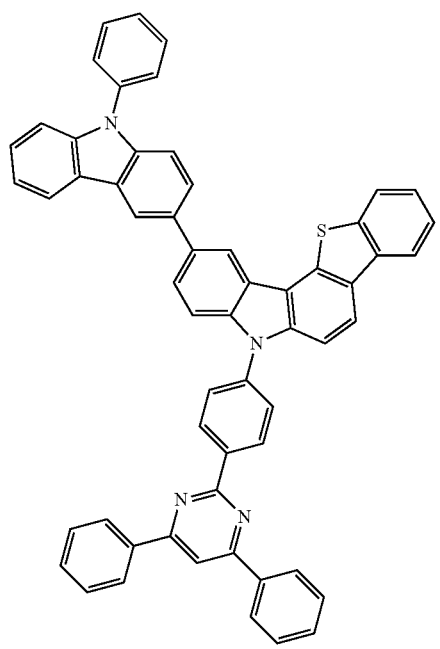
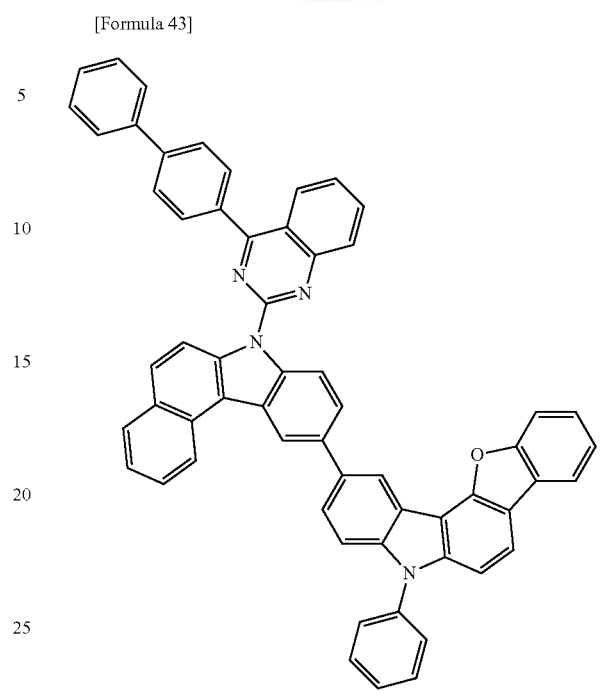
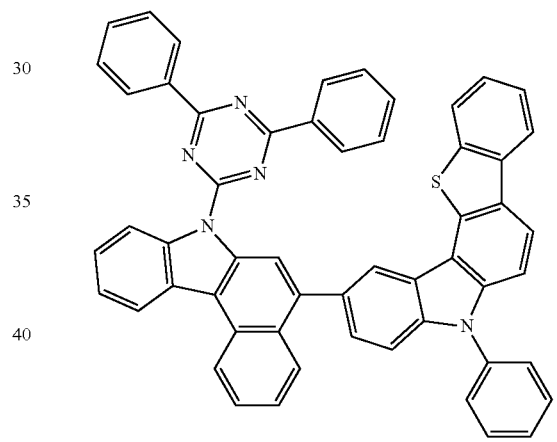
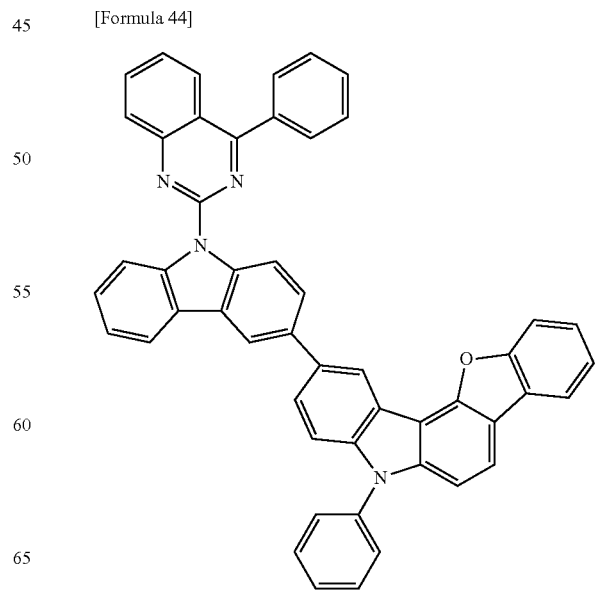

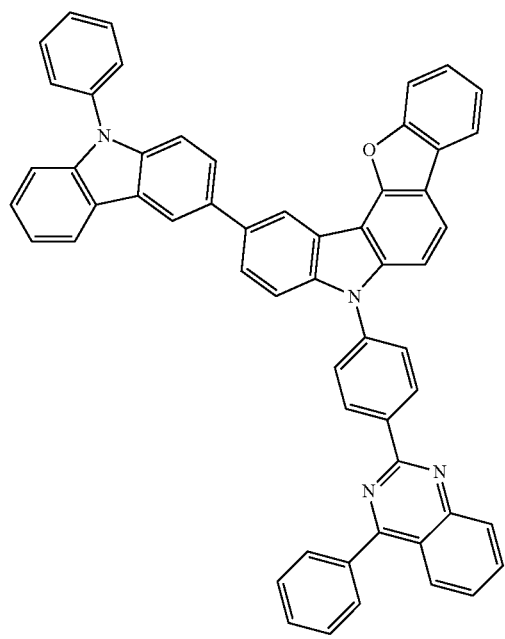
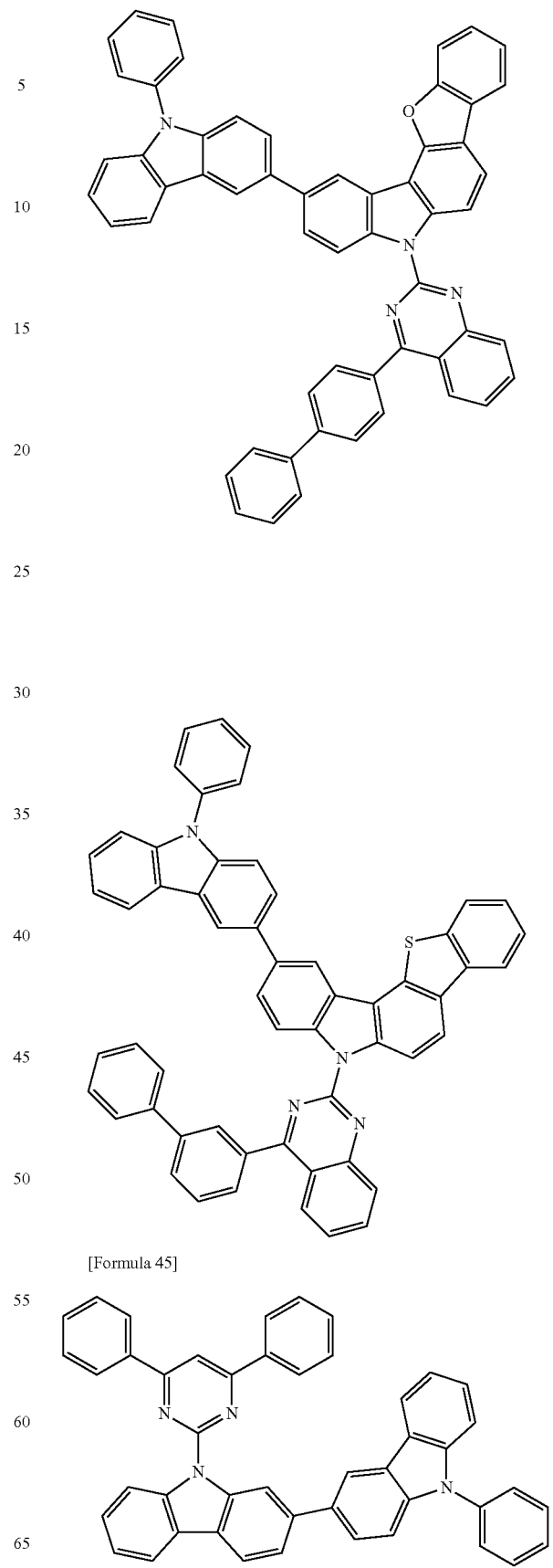
[Formula 45]

[Formula 46]
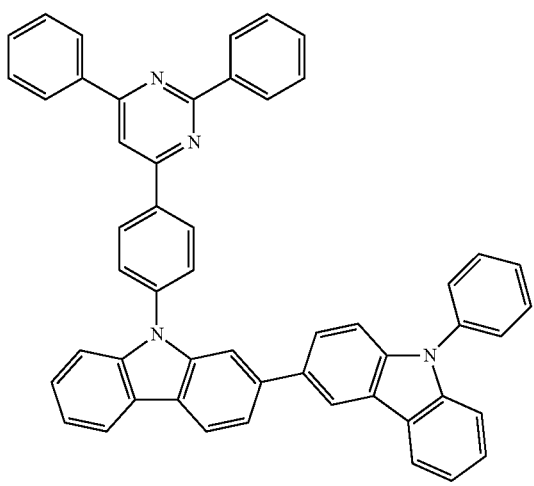
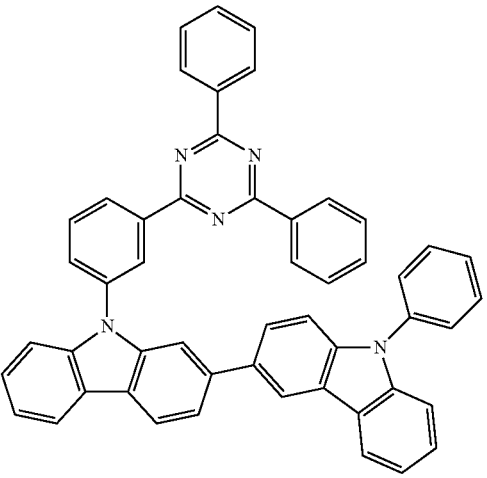
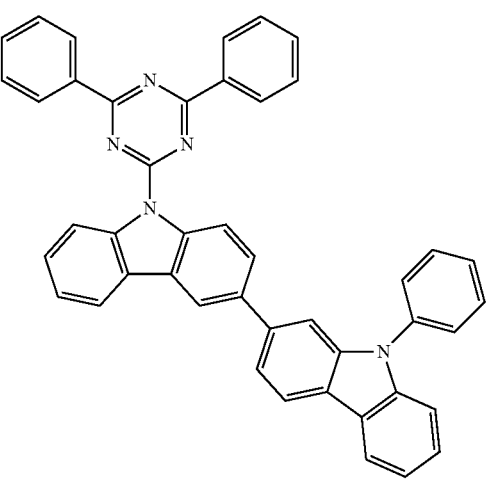
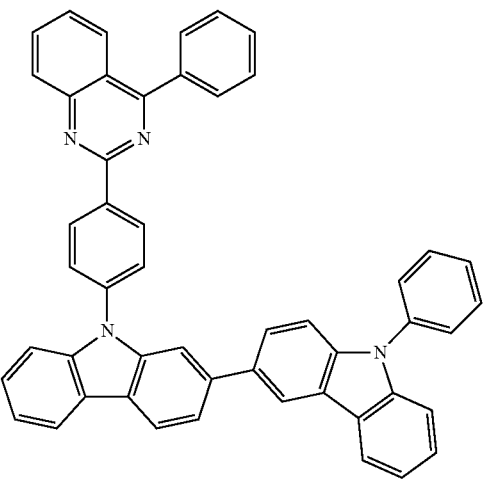

[Formula 47]
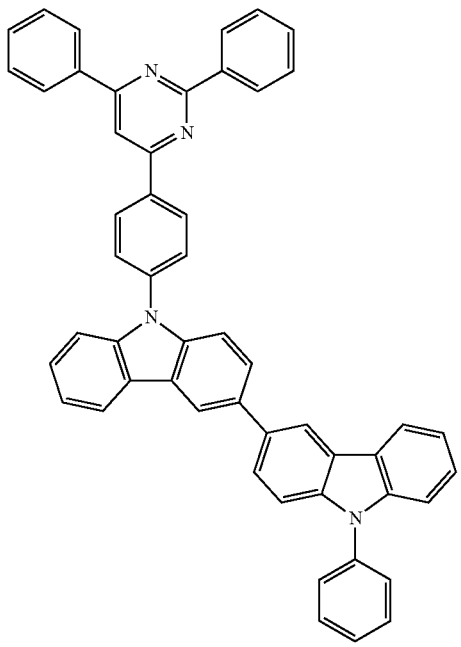
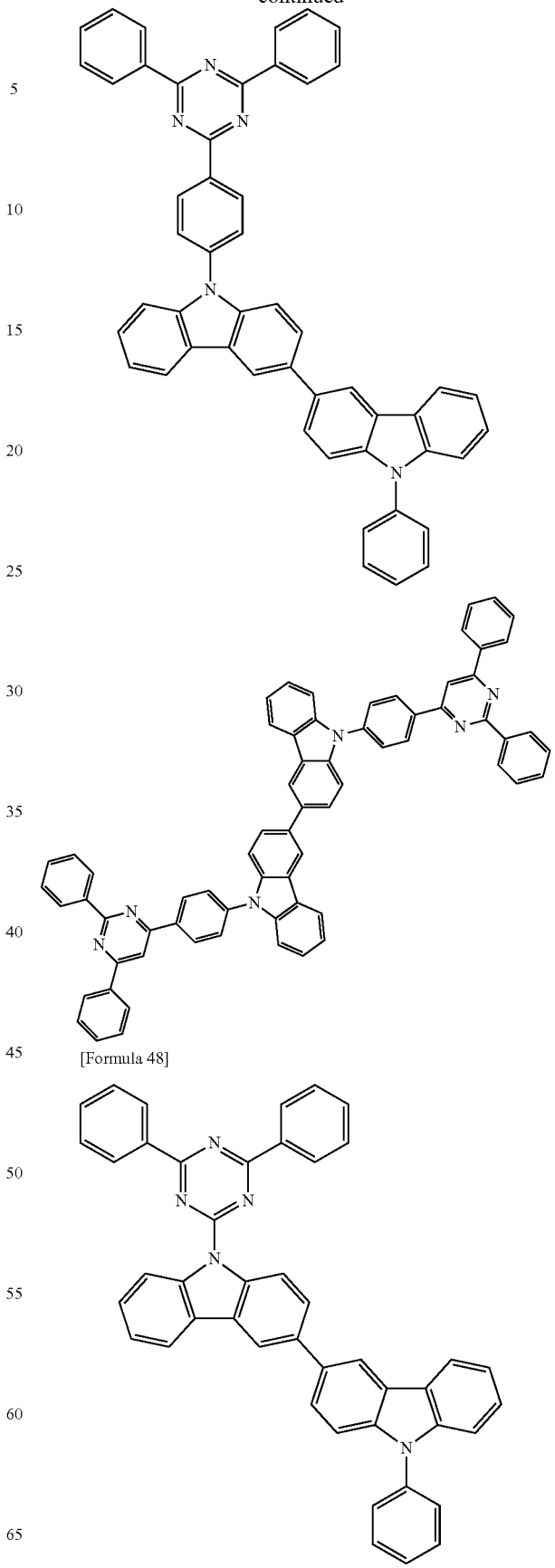
[Formula 48]

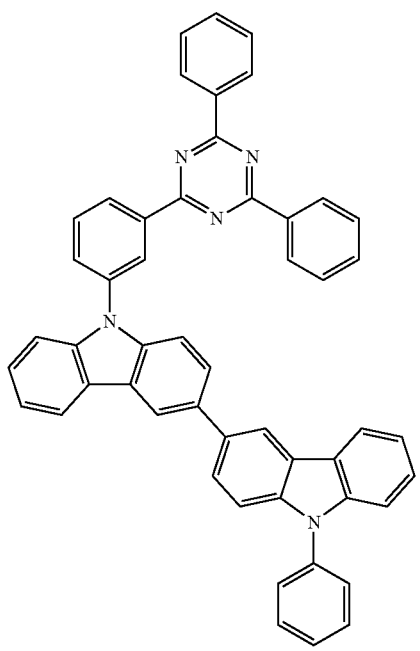
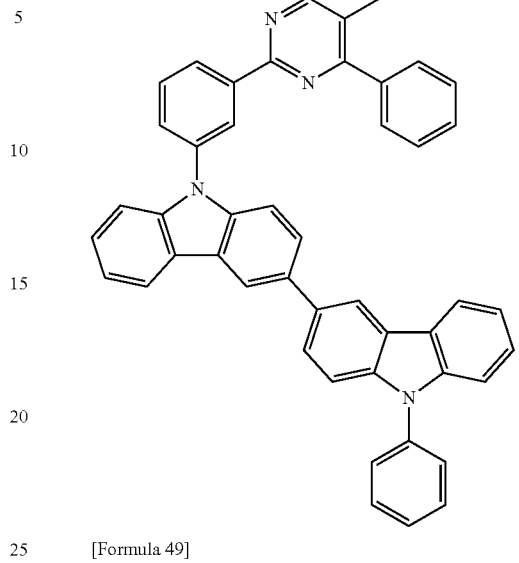
[Formula 49]
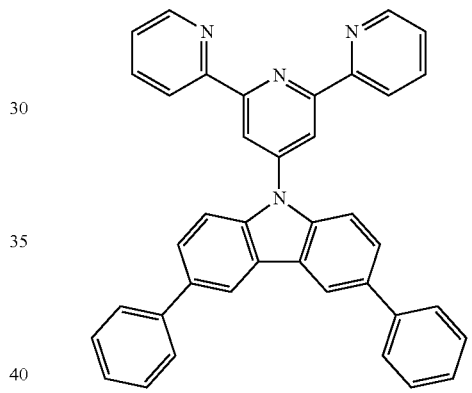
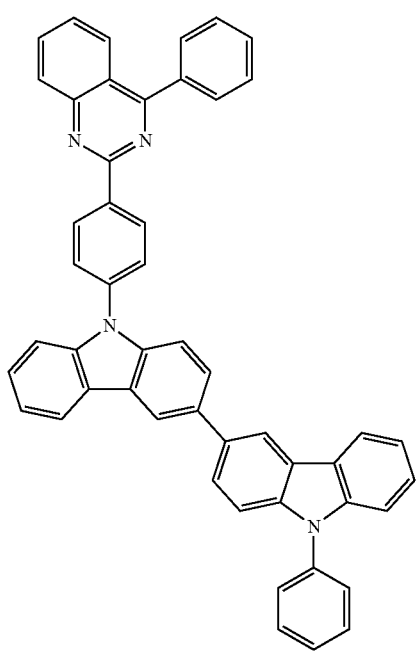
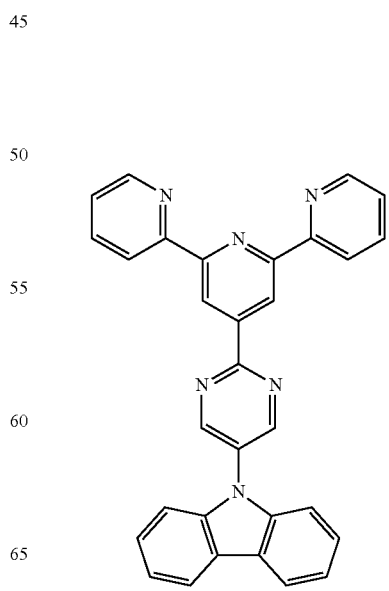

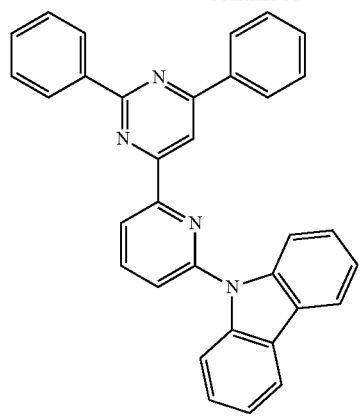
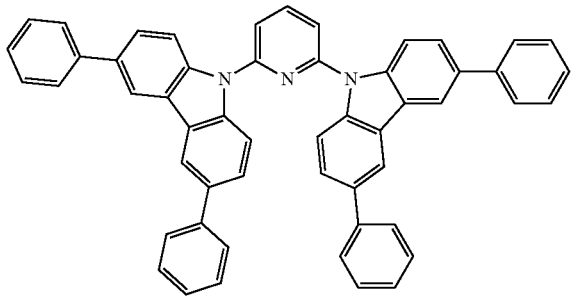
[Formula 50]
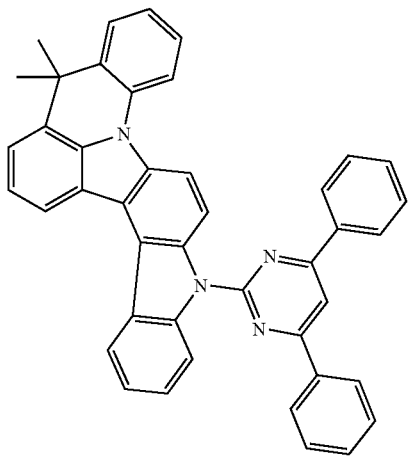
[Formula 51]
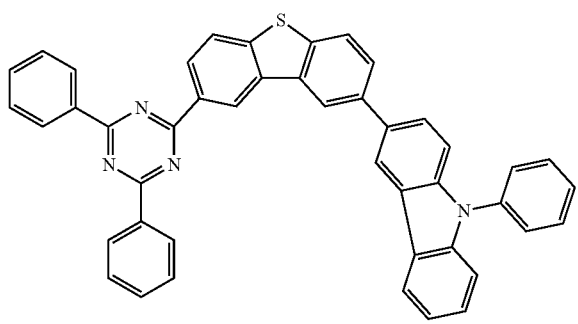
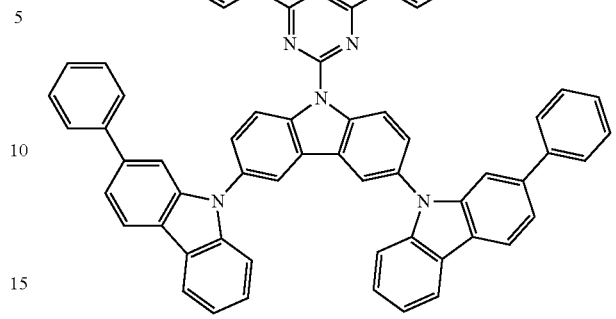
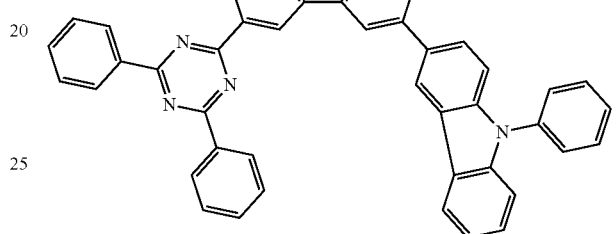
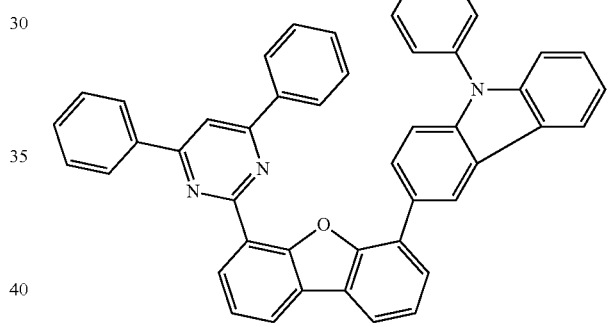
[Formula 52]
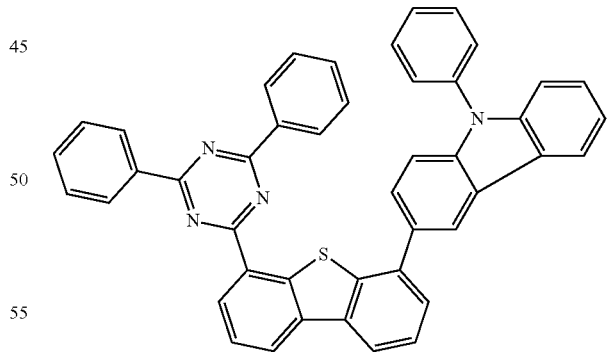
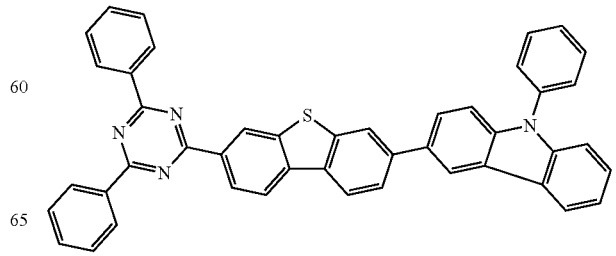

65
-continued
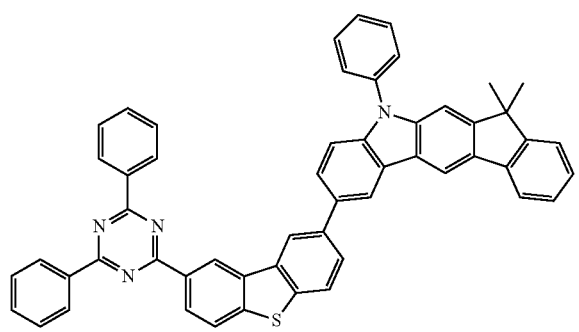
[Formula 53]
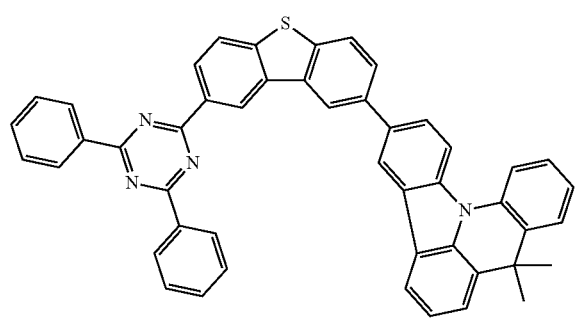
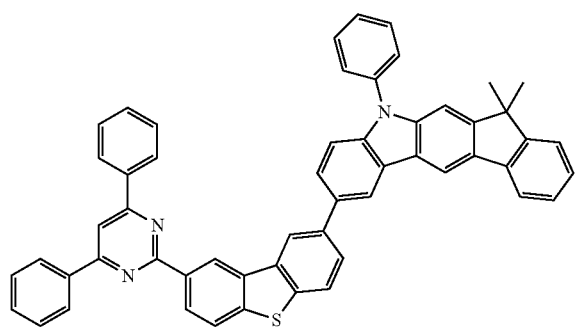
66
-continued
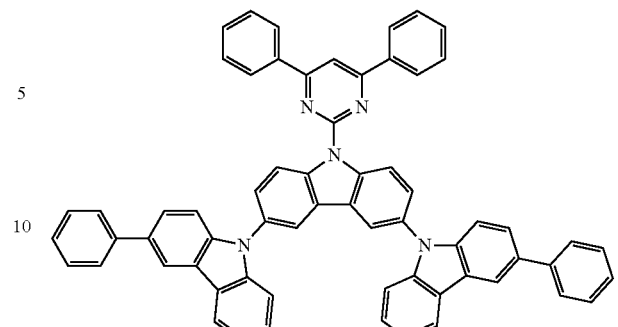
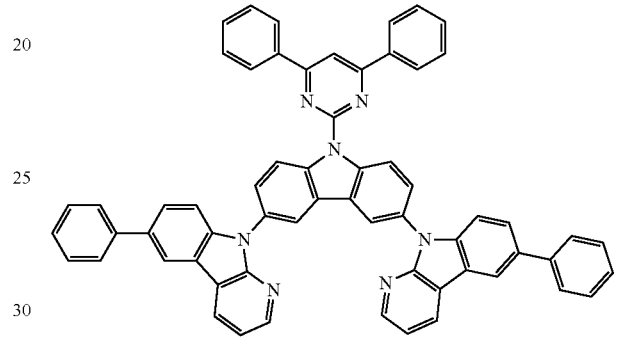
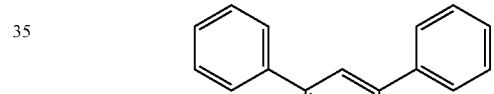
[Formula 54]
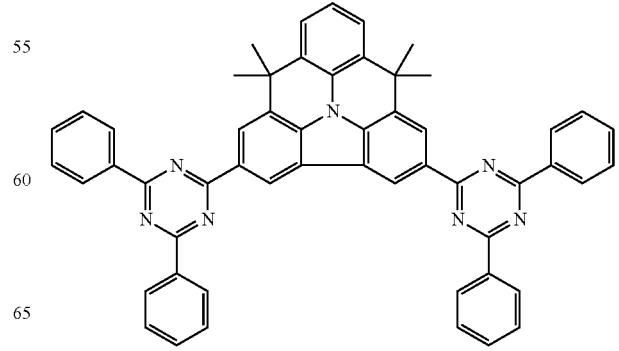
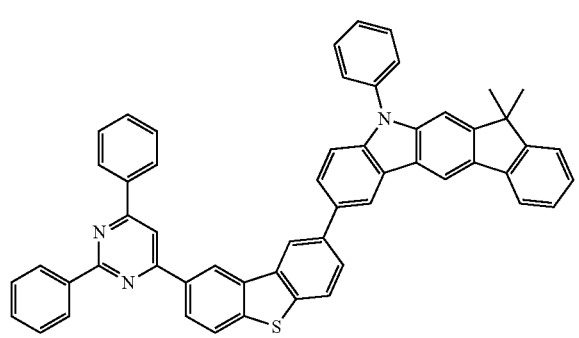

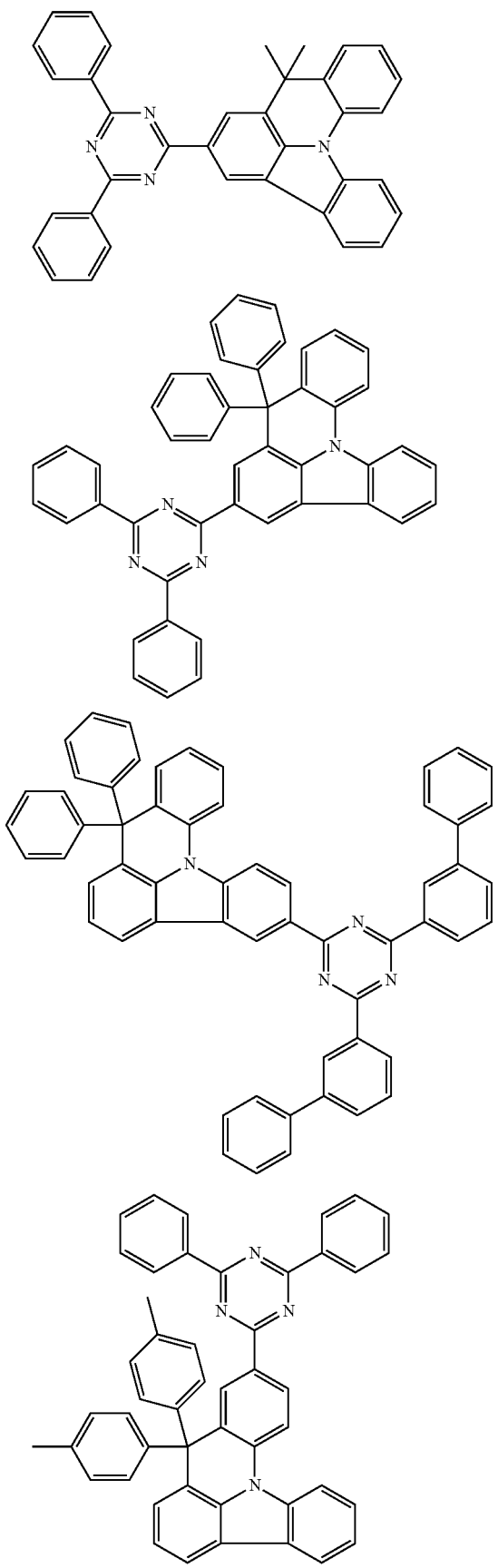
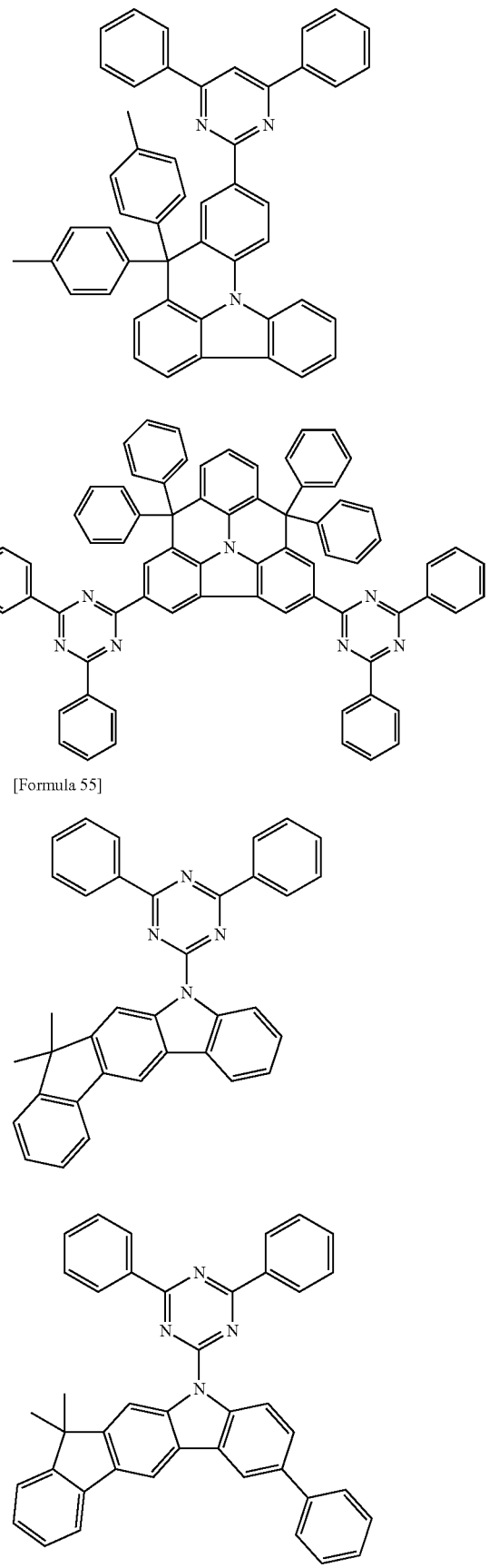
[Formula 55]

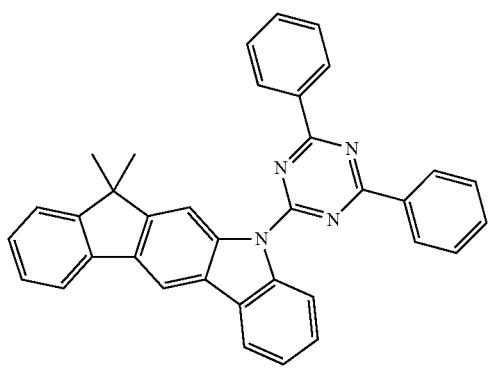
[Formula 56]
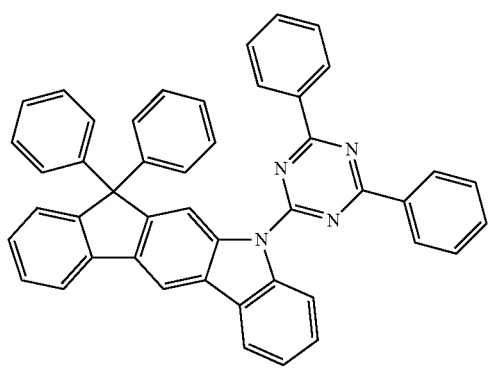
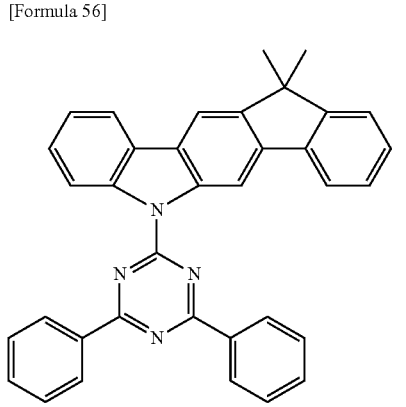
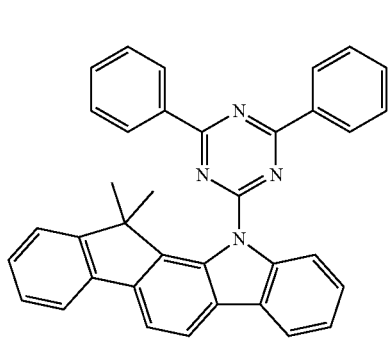
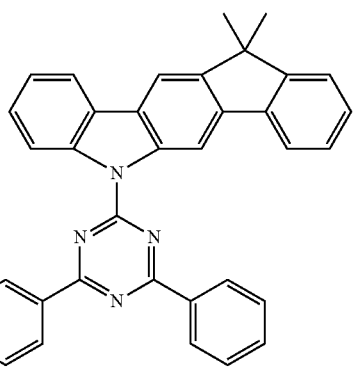
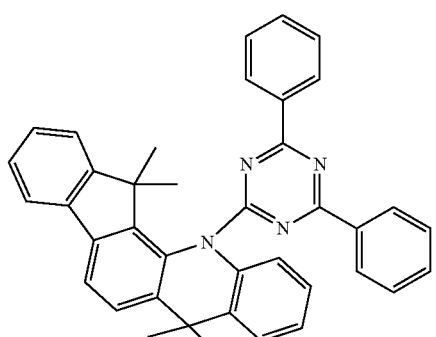
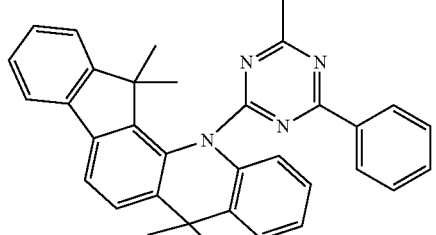
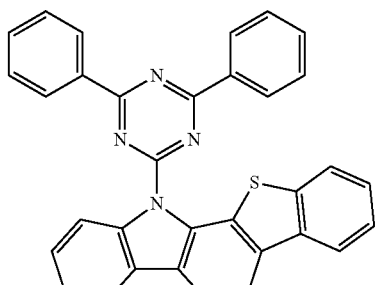
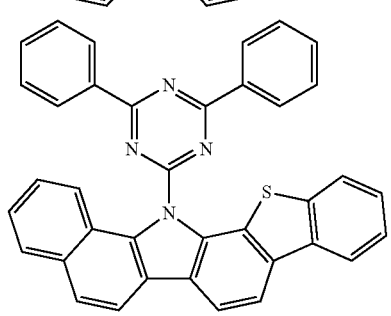
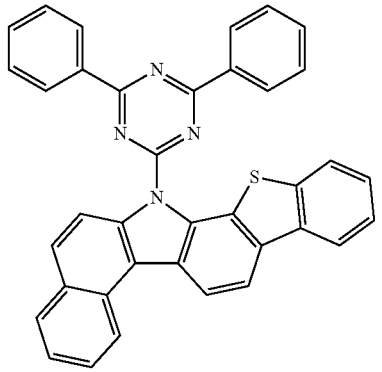

-continued
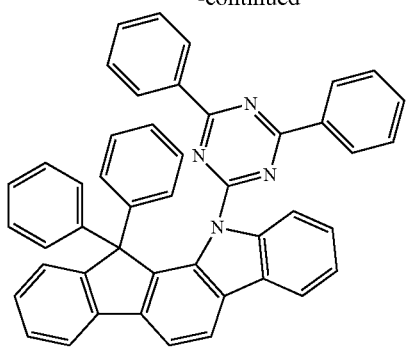
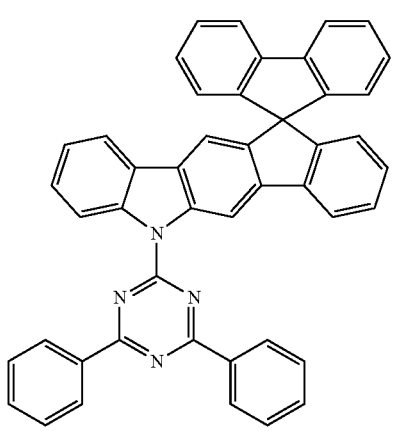
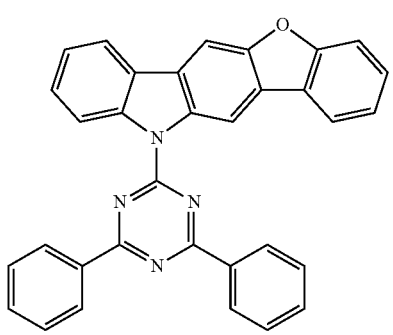
-continued
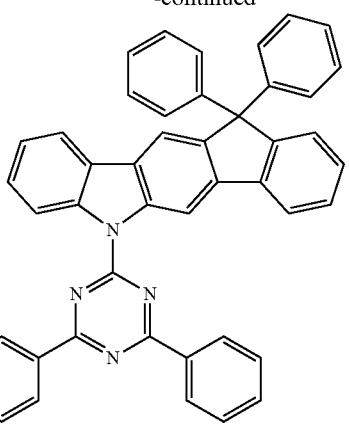
[Formula 57]
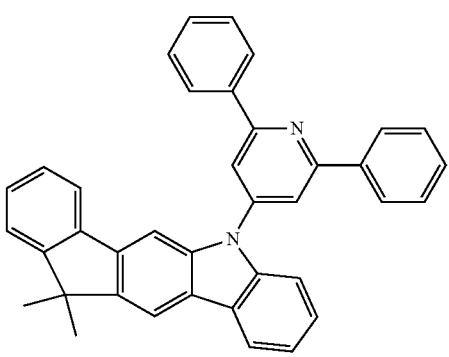
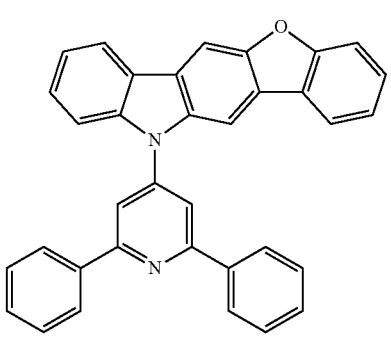
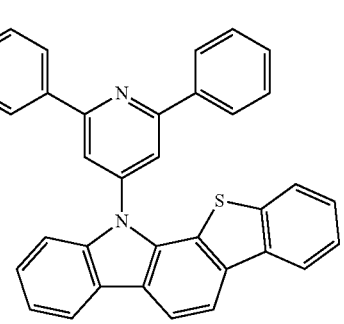

-continued
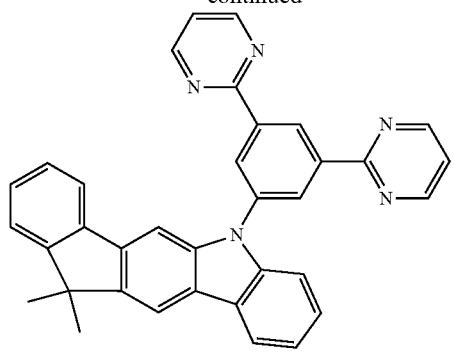
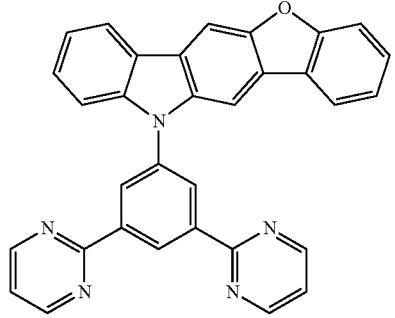
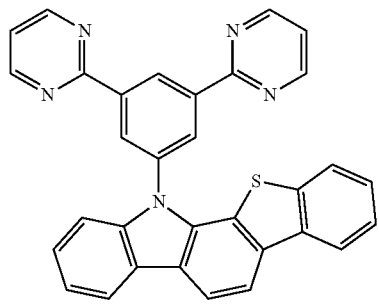
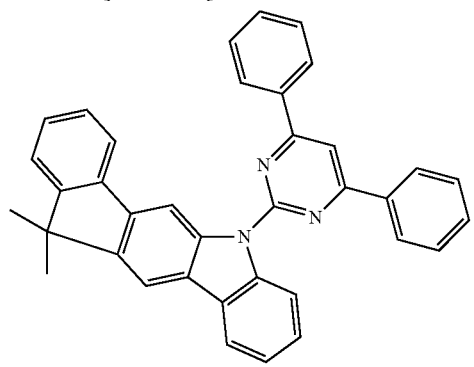
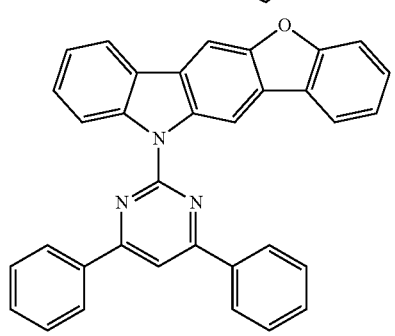
-continued
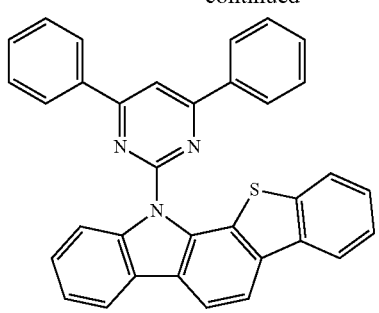
[Formula 58]
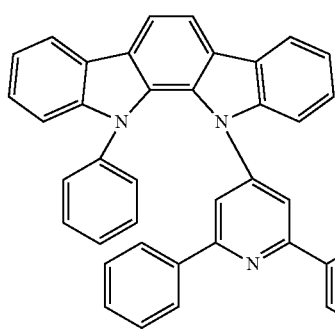
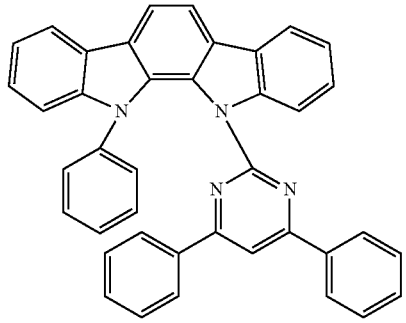
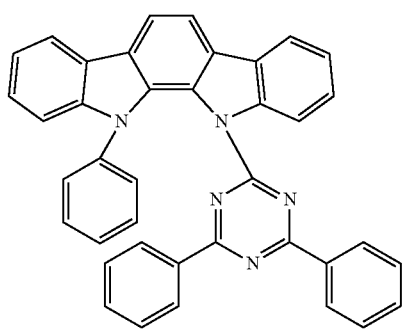

75
-continued
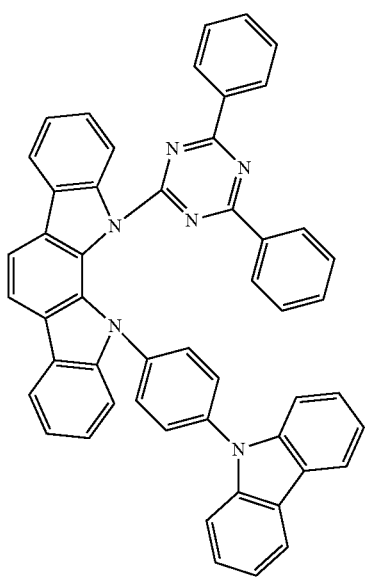
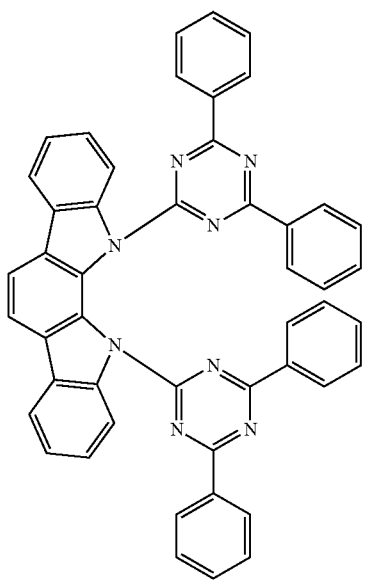
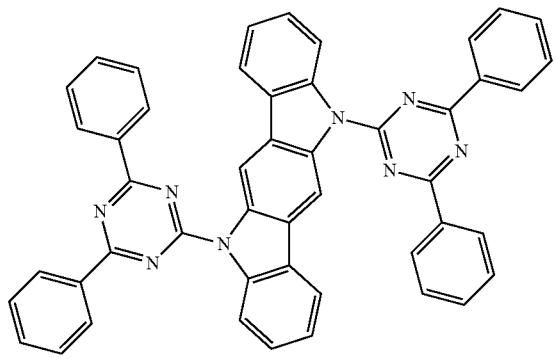
76
-continued
[Formula 59]
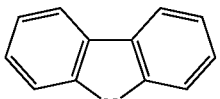
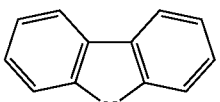
[Formula 60]

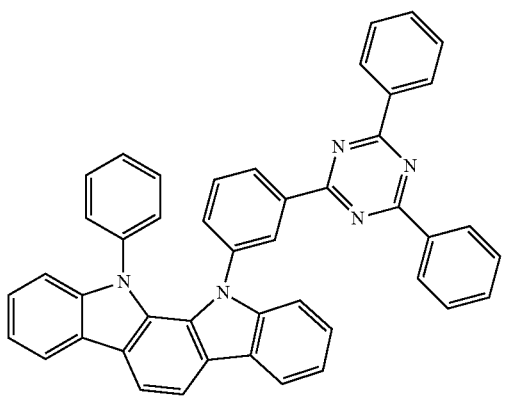

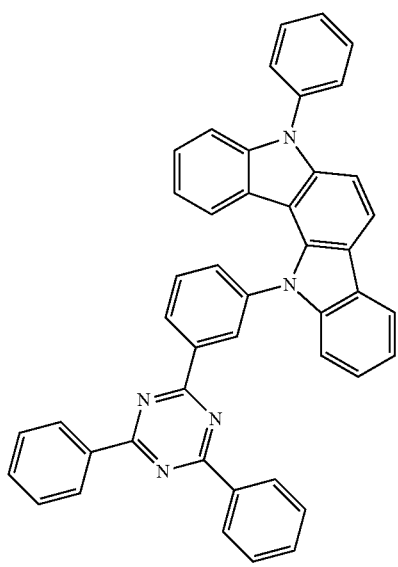

[Formula 61]

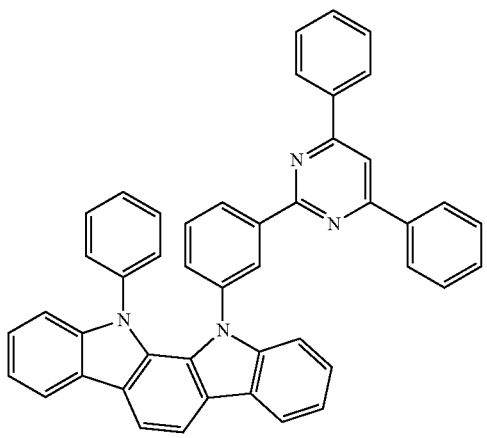

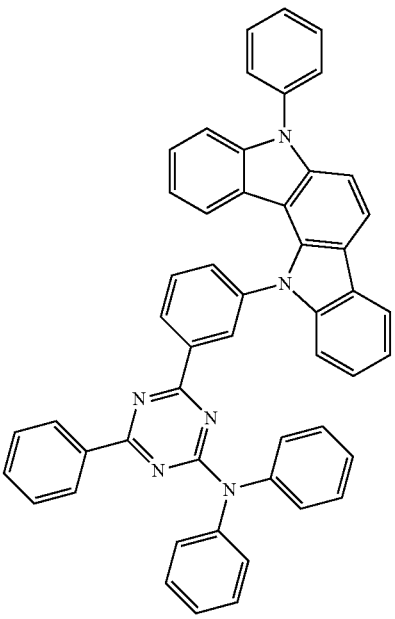 [SMILES: c1ccc(-c2nc(-c3cccc(-n4c5ccccc5c5ccc6c(c7ccccc7n6-c6ccccc6)c54)c3)nc(N(c3ccccc3)c3ccccc3)n2)cc1]

Dopant Material

The dopant material used in the first exemplary embodiment is represented by the above formula (2a) or a formula (2) below. Since the compound represented by the formula (2a) and a compound represented by the formula (2) below are substantially the same, the compound represented by the formula (2a) is described below as the compound represented by the formula (2).

The dopant material in the exemplary embodiment is preferably a compound emitting delayed fluorescence. The emission from the dopant material is preferably the maximum emission from the organic EL device.

[Formula 62]

$$[(HAr)_a\!-\!L_{20}\!-\!(L_{201})_g]_b\!-\!Az_2 \quad (2)$$

In the formula (2), $L_{20}$ is a substituted or unsubstituted (a+g)-valent aromatic hydrocarbon group or a substituted or unsubstituted (a+g)-valent heterocyclic group.

In the formula (2), $L_{201}$ is a substituted or unsubstituted divalent aromatic hydrocarbon group or a substituted or unsubstituted divalent heterocyclic group.

In the formula (2), a is an integer of 1 to 6 and b is an integer of 1 to 6. a and b are each independently preferably an integer of 1 to 3, more preferably 1 or 2. When a is 2 or more, HAr bonded to $L_{20}$ is 2 or more and may be mutually the same or different.

In the formula (2), g is an integer of 0 to 2, preferably 0 or 1. When g is from 1 to 2, $L_{20}$ and $L_{201}$ may independently be the same or different. When g is 2, two $L_{201}$ may independently be the same or different.

In the formula (2), HAr is a group derived from a structure represented by a formula (20) below.

[Formula 63]

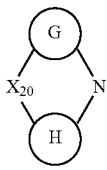
(20)

In the formula (20), $X_{20}$ represents a single bond, an oxygen atom, a sulfur atom, a carbonyl group, $NR_9$, $CR_{10}R_{11}$, $SiR_{12}R_{13}$ or $GeR_{14}R_{15}$. $R_9$ to $R_{15}$ each independently represent the same as $R_1$ to $R_7$ described above. In the formula (20), $X_{20}$ is preferably an oxygen atom, a sulfur atom, a carbonyl group, $NR_9$, $CR_{10}R_{11}$, $SiR_{12}R_{13}$ or $GeR_{14}R_{15}$.

The cyclic structure represented by the formula (20) is a cyclic structure selected from the group consisting of cyclic structures represented by formulae (20b) to (20i) below.

[Formula 64]

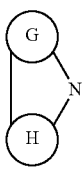
(20b)

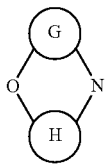
(20c)

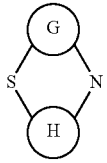
(20d)

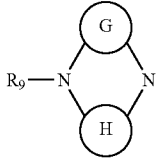
(20e)

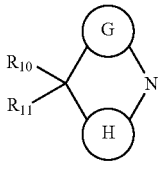
(20f)

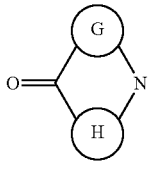
(20g)

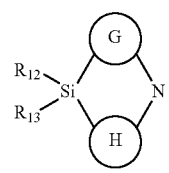
(20h)

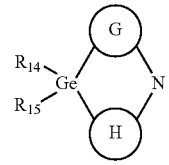
(20i)

In the formulae (20), (20b) to (20i), G and H each independently represent a substituted or unsubstituted cyclic structure. When at least one of the cyclic structure G and the cyclic structure H have a plurality of substituents, adjacent ones of the substituents may form a ring. The ring to be formed may be either a saturated ring or an unsaturated ring. The substituent at this time is preferably an electron donating substituent. Moreover, adjacent substituents preferably further form an electron donating ring. Among the cyclic structures, the cyclic structure selected from the group consisting of cyclic structures represented by the formulae (20c) to (20i) is preferable.

When at least one of the cyclic structure A and the cyclic structure B is a substituted or unsubstituted heterocyclic structure in the formulae (20) and (20b) to (20i), the heterocyclic structure has a partial structure represented by a formula (20-2) below.

[Formula 65]

\N=/
(20-2)

The group derived from the structure represented by the formula (20) is preferably a group represented by a formula (20-1) below.

[Formula 66]

(20-1)

In the formula (20-1), $X_{20}$ represents the same as $X_{20}$ of the formula (20). In other words, the group represented by the formula (20-1) is a group selected from the group consisting of groups represented by formulae (20b-1) to (20i-1) below.

[Formula 67]

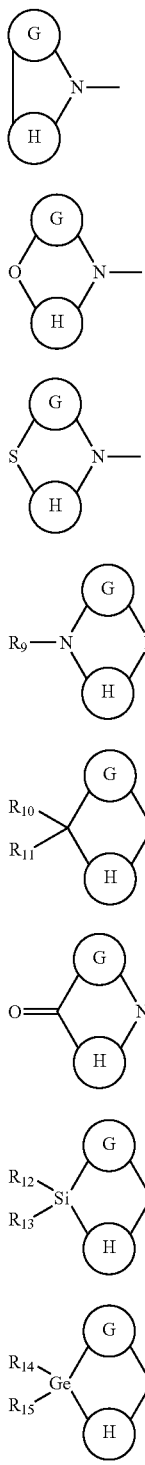

(20b-1)
(20c-1)
(20d-1)
(20e-1)
(20f-1)
(20g-1)
(20h-1)
(20i-1)

In the formulae (20b-1) to (20i-1), the cyclic structure G and the cyclic structure H respectively represent the same as the cyclic structure G and the cyclic structure H in the formulae (20) and (20b) to (20i). Among the above groups, the group selected from the group consisting of the groups represented by the formulae (20c-1) to (20i-1) is preferable as HAr of the formula (2).

In the exemplary embodiment, HAr of the formula (2) is preferably a group derived from a structure represented by a formula (2B) below.

[Formula 68]

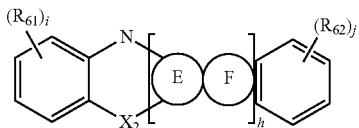

(2B)

In the formula (2B), $X_2$ represents the same as $X_{20}$ of the formula (20). $X_2$ is preferably an oxygen atom, a sulfur atom, a carbonyl group, $NR_9$, $CR_{10}R_{11}$, $SiR_{12}R_{13}$ or $GeR_{14}R_{15}$.

In the formula (2B), $R_{61}$ and $R_{62}$ each independently represent the same as $R_8$ described above. Adjacent ones of $R_{61}$ may form a ring. Adjacent ones of $R_{62}$ may form a ring.

In the formula (2B), i and j are 4.

In the formula (2B), E represents a cyclic structure represented by a formula (2h) below and F represents a cyclic structure represented by a formula (2i) or (2j) below. Each of the cyclic structure E and the cyclic structure F is fused to an adjacent cyclic structure at any position. In the formula (2B), h is an integer of 0 to 4. h is a repeating unit of a linking cyclic structure in which the cyclic structure E and the cyclic structure F are fused to each other. When h is 2 or more, a plurality of cyclic structures F may be the same or different.

[Formula 69]

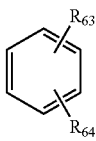

(2h)

[Formula 70]

(2i)

(2j)

In the formula (2h), when $R_{63}$ and $R_{64}$ are substituents at adjacent positions, $R_{63}$ and $R_{64}$ may form a ring.

$Y_3$ in the formula (2i) represents $CR_{65}R_{66}$, $NR_{67}$, a sulfur atom, an oxygen atom or a nitrogen atom to be bonded to $L_{20}$. $Y_6$ in the formula (2j) represents $CR_{65}R_{66}$, $NR_{67}$, or a nitrogen atom to be bonded to $L_{20}$.

$X_4$ in the formula (2j) represents $NR_9$ or $CR_{10}R_{11}$ in which $R_9$ to $R_{11}$ each independently represent the same as $R_1$ to $R_7$ described above. $R_{63}$ and $R_{64}$ each independently represent the same as $R_8$ described above. $R_{65}$ to $R_{67}$ each independently represent the same as $R_1$ to $R_7$ described above.

In the exemplary embodiment, h in the formula (2B) is preferably 0 or 1.

In the formula (2B), when h is 0, HAr is preferably a group represented by a formula (2b) or (2bx) below.

[Formula 71]

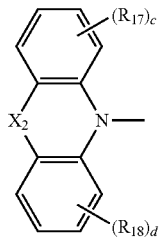
(2b)

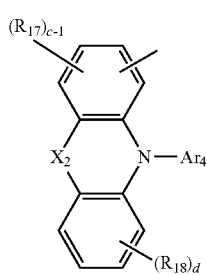
(2bx)

In the formulae (2b) and (2bx), $X_2$ represents a single bond, an oxygen atom, a sulfur atom, a carbonyl group, $NR_9$, $CR_{10}R_{11}$, $SiR_{12}R_{13}$ or $GeR_{14}R_{15}$. In other words, the group represented by the formula (2b) is a group selected from the group consisting of groups represented by formulae (2b-1) to (2b-8) below.

[Formula 72]

(2b-1)

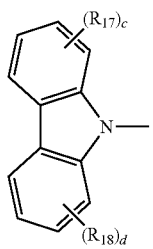

(2b-2)

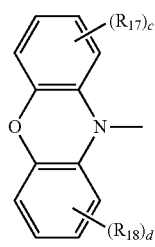

(2b-3)

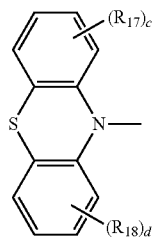

-continued (2b-4)

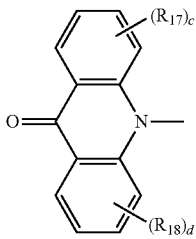

(2b-5)

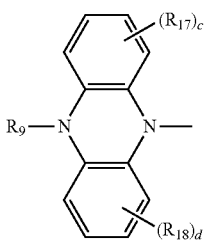

(2b-6)

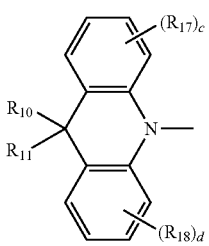

(2b-7)

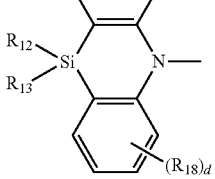

(2b-8)

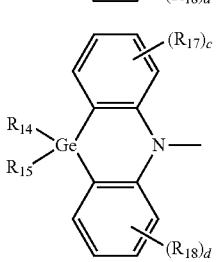

In the formulae (2b), (2bx) and (2b-1) to (2b-8), c and d are 4. Among the above groups, the group selected from the group consisting of the groups represented by the formulae (2b-2) to (2b-8) is preferable as HAr of the formula (2).

In the formulae (2b), (2bx) and (2b-1) to (2b-8), $R_9$ to $R_{15}$ each independently represent the same as $R_1$ to $R_7$ described above. $R_{17}$ and $R_{18}$ each independently represent the same as $R_8$ described above. Adjacent ones of $R_{17}$ may form a ring. Adjacent ones of $R_{18}$ may form a ring.

In the formula (2bx), $Ar_4$ represents the same as $R_1$ to $R_8$ described above. $Ar_4$ is preferably a substituted or unsubstituted aryl group having 6 to 30 ring carbon atoms or a substituted or unsubstituted heterocyclic group having 5 to 30 ring atoms, more preferably a substituted or unsubstituted aryl group having 6 to 30 ring carbon atoms. $Ar_4$ is preferably a phenyl group, biphenyl group, terphenyl group, naphthyl group, phenanthryl group, triphenylenyl group, dibenzofuranyl group, dibenzothiophenyl group, carbazolyl group and the like.

In the formula (2), $Az_2$ is represented by a formula (2d) below.

[Formula 73]

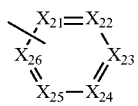

(2d)

In the formula (2d), $X_{21}$ to $X_{26}$ each independently represent $CR_{16}$ or a nitrogen atom. At least one of $X_{21}$ to $X_{26}$ is a nitrogen atom and b of $X_{21}$ to $X_{26}$ is a carbon atom to be bonded to $L_{20}$ or $L_{201}$. Since b is an integer of 1 to 3 as described above, one to three of $X_{21}$ to $X_{26}$ are carbon atom(s) to be bonded to $L_{20}$. $R_{16}$ represents the same as $R_8$ described above.

In the formula (21), one to three of $X_{21}$ to $X_{26}$ are preferably nitrogen atom(s). For instance, when $X_{26}$ is a carbon atom bonded to $L_{20}$ and one of $X_{21}$ to $X_{25}$ is a nitrogen atom, $X_{21}$ or $X_2$ is preferably a nitrogen atom. When two of $X_{21}$ to $X_{25}$ are nitrogen atoms, $X_{21}$ and $X_{25}$ are preferably nitrogen atoms. When three of $X_{21}$ to $X_{25}$ are nitrogen atoms, $X_{21}$, $X_{23}$ and $X_{25}$ are preferably nitrogen atoms. A triazine ring in which $X_{21}$, $X_{23}$ and $X_{25}$ are nitrogen atoms is preferable in the formula (2d).

In the exemplary embodiment, it is preferable that a and b are 1 and g is 0 in the formula (2) and $X_{26}$ is a carbon atom to be bonded to $L_{20}$ in formula (2d). In other words, the compound represented by the formula (2) is preferably a compound represented by a formula (21) below.

[Formula 74]

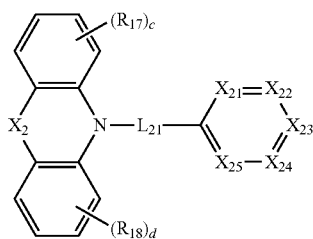

(21)

In the formula (21), $X_2$ represents the same as $X_2$ of the formula (2b).

In the formula (21), $L_{21}$ is a substituted or unsubstituted divalent aromatic hydrocarbon group or a substituted or unsubstituted divalent heterocyclic group.

In the formula (21), $X_{21}$ to $X_{25}$ each independently represent $CR_{16}$ or a nitrogen atom and at least one of $X_{21}$ to $X_{25}$ is a nitrogen atom. When one of $X_{21}$ to $X_{25}$ is a nitrogen atom, $X_{21}$ or $X_{25}$ is preferably a nitrogen atom. When two of $X_{21}$ to $X_{25}$ are nitrogen atoms, $X_{21}$ and $X_{25}$ are preferably nitrogen atoms. When three of $X_{21}$ to $X_{25}$ are nitrogen atoms, $X_{21}$, $X_{23}$ and $X_{25}$ are preferably nitrogen atoms.

In the formula (21), c and d are 4 and $R_{17}$ and $R_{18}$ each independently represent the same as $R_8$ described above. A plurality of $R_{17}$ may be mutually the same or different. A plurality of $R_{18}$ may be mutually the same or different.

In the exemplary embodiment, the compound represented by the formula (2) is preferably the compound represented by the formula (21), in which $X_2$ is preferably an oxygen atom.

In the exemplary embodiment, it is preferable that a is 2 and b is 1 in the formula (2) and $X_{26}$ is a carbon atom to be bonded to $L_{20}$ in formula (2d). In other words, the compound represented by the formula (2) is preferably a compound represented by a formula (22) below.

[Formula 75]

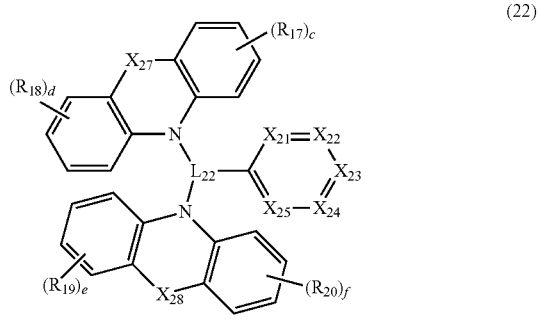

(22)

In the formula (22), $X_{27}$ and $X_{28}$ each independently represent the same as $X_2$ of the formula (2b), in which $X_{27}$ and $X_{28}$ may be mutually the same or different.

In the formula (22), $L_{22}$ is a substituted or unsubstituted trivalent aromatic hydrocarbon group or a substituted or unsubstituted trivalent heterocyclic group.

In the formula (22), $X_{21}$ to $X_{25}$ each independently represent $CR_{16}$ or a nitrogen atom and at least one of $X_{21}$ to $X_{25}$ is a nitrogen atom. When one of $X_{21}$ to $X_{25}$ is a nitrogen atom, $X_{21}$ or $X_{25}$ is preferably a nitrogen atom. When two of $X_{21}$ to $X_{25}$ are nitrogen atoms, $X_{21}$ and $X_{25}$ are preferably nitrogen atoms. When three of $X_{21}$ to $X_{25}$ are nitrogen atoms, $X_{21}$, $X_{23}$ and $X_{25}$ are preferably nitrogen atoms.

In the formula (22), c, d, e and f are each 4 and $R_{17}$ to $R_{20}$ each independently represent the same as $R_8$ described above. Adjacent ones of $R_{17}$ may form a ring. Adjacent ones of $R_{18}$ may form a ring.

In the first exemplary embodiment, the compound represented by the formula (2) is preferably the compound represented by the formula (22), in which $X_{27}$ and $X_{28}$ are preferably oxygen atoms.

In the exemplary embodiment, it is preferable that a is 1, b is 2, and g is 0 in the formula (2) and $X_{24}$ and $X_{26}$ are carbon atoms to be bonded to $L_{20}$ and $X_{21}$, $X_{23}$ and $X_{25}$ are nitrogen atoms in formula (2d). In other words, the compound represented by the formula (2) is preferably a compound represented by a formula (23) below.

[Formula 76]

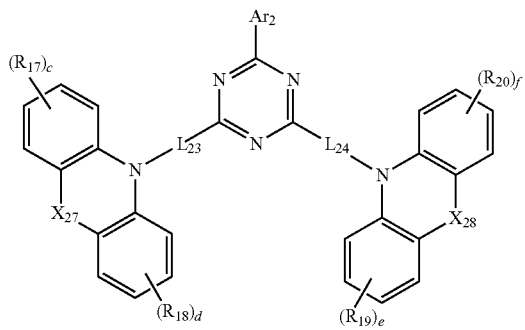

(23)

[Formula 77]

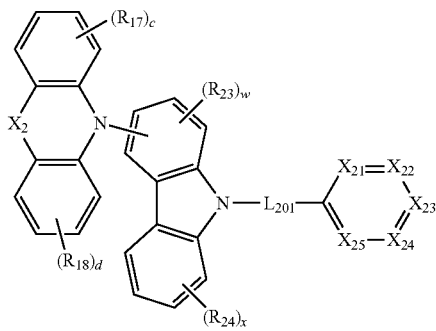

(24)

In the formula (23), $X_{27}$ and $X_{28}$ represent the same as $X_2$ of the formula (2b) and $X_{27}$ and $X_{28}$ may be mutually the same or different.

In the formula (23), $L_{23}$ and $L_{24}$ each independently represent a substituted or unsubstituted divalent aromatic hydrocarbon group or a substituted or unsubstituted divalent heterocyclic group.

In the formula (23), $Ar_2$ represents the same as $R_1$ to $R_8$ described above. $Ar_2$ is preferably a substituted or unsubstituted aryl group having 6 to 30 ring carbon atoms or a substituted or unsubstituted heterocyclic group having 5 to 30 ring atoms, more preferably a substituted or unsubstituted aryl group having 6 to 30 ring carbon atoms. $Ar_2$ is preferably a phenyl group, biphenyl group, terphenyl group, naphthyl group, phenanthryl group, triphenylenyl group, dibenzofuranyl group, dibenzothiophenyl group, carbazolyl group and the like.

In the formula (23), c, d, e and f are each 4 and $R_{17}$ to $R_{20}$ each independently represent the same as $R_8$ described above. Adjacent ones of $R_{17}$ may form a ring. Adjacent ones of $R_{18}$ may form a ring.

In the first exemplary embodiment, the compound represented by the formula (2) is preferably the compound represented by the formula (23), in which $X_{27}$ and $X_{28}$ are preferably oxygen atoms.

In the first exemplary embodiment, in the compound represented by the formula (2), it is preferable that HAr is the group represented by the formula (2b), $L_{20}$ is a substituted or unsubstituted divalent heterocyclic group, and g is 1. In this arrangement, $L_{20}$ is more preferably a substituted or unsubstituted divalent carbazolyl group. Further, the compound represented by the formula (2) is preferably a compound represented by a formula (24) below.

In the formula (24), $X_{21}$ to $X_{25}$ represent the same as $X_{21}$ to $X_{25}$ of the formula (21).

In the formula (24), $R_{17}$ to $R_{18}$ and $R_{23}$ to $R_{24}$ each independently represent the same as $R_8$ described above. Adjacent ones of $R_{17}$ may form a ring. Adjacent ones of $R_{18}$ may form a ring. Adjacent ones of $R_{23}$ may form a ring. Adjacent ones of $R_{24}$ may form a ring.

In the formula (24), $L_{201}$ represents the same as $L_{201}$ of the formula (2). In the formula (24), c, d and x are 4 and w is 3.

In the formula (2B), when h is 1 and the cyclic structure F is represented by the formula (2i), the structure of the formula (2B) is represented by any one of formulae (2B-1) to (2B-6) below.

[Formula 78]

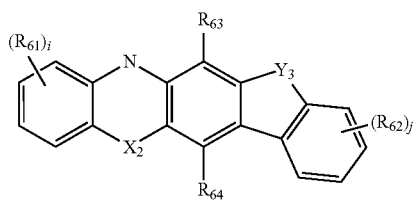

(2B-1)

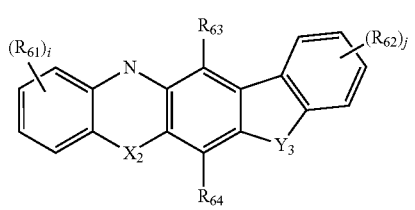

(2B-2)

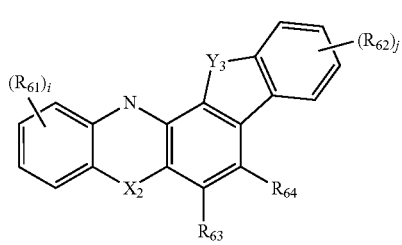

(2B-3)

(2B-4)
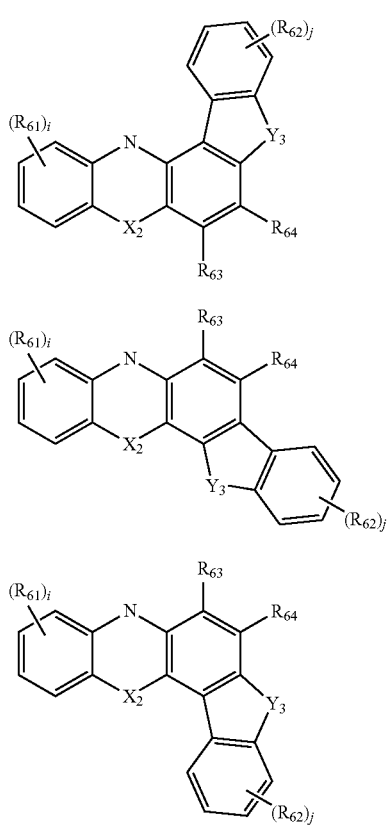

(2B-5)

(2B-6)

In the formulae (2B-1) to (2B-6), X₂ represents the same as X₂ of the formula (2b).

In the formulae (2B-1) to (2B-6), $R_{61}$ to $R_{64}$ each independently represent the same as $R_8$ described above. Adjacent ones of $R_{61}$ may form a ring. Adjacent ones of $R_{62}$ may form a ring. Adjacent $R_{63}$ and $R_{64}$ may form a ring.

In the formulae (2B-1) to (2B-6), $Y_3$ represents the same as $Y_3$ of the formula (2i).

In the formulae (2B-1) to (2B-6), i and j are 4.

Groups derived from the structure represented by the formulae (2B-1) to (2B-6) are preferably groups represented by formulae (2B-7) to (2B-18) below.

[Formula 79]

(2B-7)
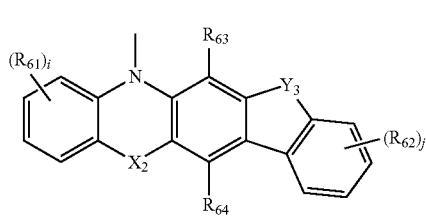

(2B-8)
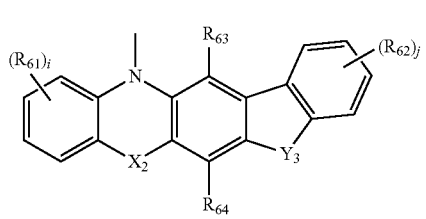

(2B-9)
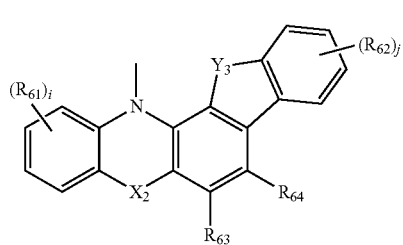

(2B-10)
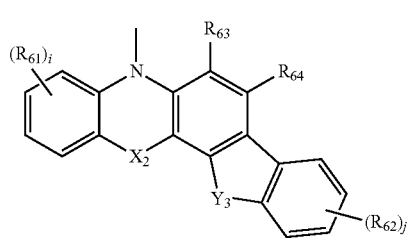

(2B-11)
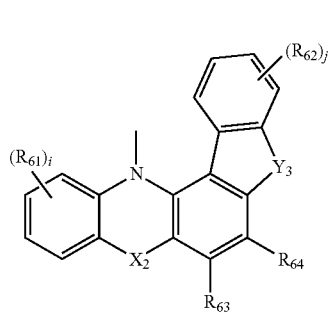

(2B-12)
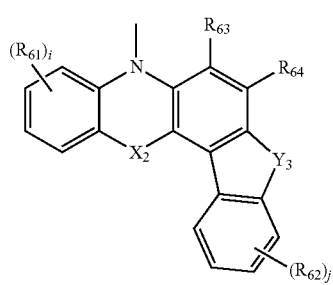

[Formula 80]

(SB-13)
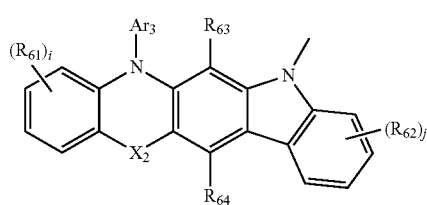

(SB-14)
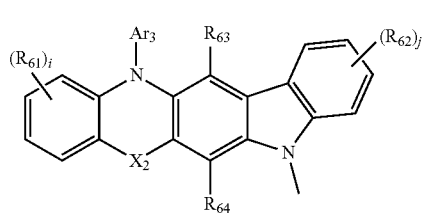

(SB-15)

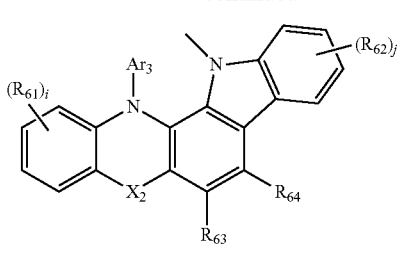

(SB-16)

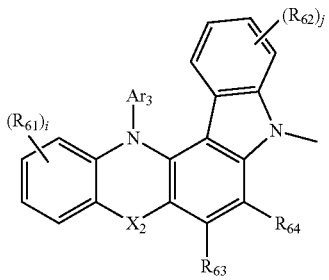

(SB-17)

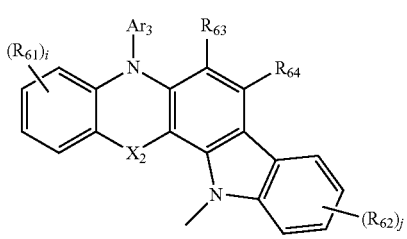

(SB-18)

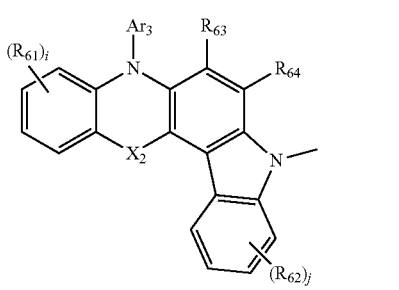

In the formulae (2B-7) to (2B-12), $X_2$ represents the same as $X_2$ of the formula (2b), in which $X_2$ is preferably an oxygen atom.

In the formulae (2B-7) to (2B-12), $R_{61}$ to $R_{64}$ each independently represent the same as $R_8$ described above. Adjacent ones of $R_{61}$ may form a ring. Adjacent ones of $R_{62}$ may form a ring. Adjacent $R_{63}$ and $R_{64}$ may form a ring.

In the formulae (2B-7) to (2B-12), $Y_3$ represents the same as $Y_3$ of the formula (2i), among which $Y_3$ is preferably $NR_{67}$. $R_{67}$ represents the same as $R_1$ to $R_7$ described above and is preferably a substituted or unsubstituted aryl group having 6 to 30 ring carbon atoms.

In the formulae (2B-7) to (2B-12), i and j are 4.

In the formulae (2B-13) to (2B-18), $X_2$ represents the same as $X_2$ of the formula (2b), among which $X_2$ is preferably an oxygen atom.

In the formulae (2B-13) to (2B-18), $R_{61}$ to $R_{64}$ each independently represent the same as $R_8$ described above. Adjacent ones of $R_{61}$ may form a ring. Adjacent ones of $R_{62}$ may form a ring. Adjacent $R_{63}$ and $R_{64}$ may form a ring.

In the formulae (2B-13) to (2B-18), $Ar_3$ represents the same as $R_1$ to $R_7$ described above. $Ar_3$ is preferably a substituted or unsubstituted aryl group having 6 to 30 ring carbon atoms or a substituted or unsubstituted heterocyclic group having 5 to 30 ring atoms, more preferably a substituted or unsubstituted aryl group having 6 to 30 ring carbon atoms. $Ar_3$ is preferably a phenyl group, biphenyl group, terphenyl group, naphthyl group, phenanthryl group, triphenylenyl group, dibenzofuranyl group, dibenzothiophenyl group, carbazolyl group and the like.

In the formulae (2B-13) to (2B-18), i and j are 4.

In the formula (2B), when h is 1 and the cyclic structure F is represented by the formula (2j), the structure of the formula (2B) is represented by any one of formulae (2B-19) to (2B-20) below.

[Formula 81]

(2B-19)

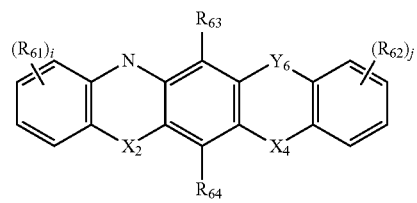

(2B-20)

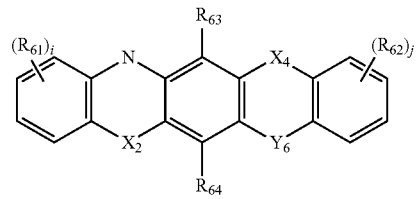

In the formulae (2B-19) to (2B-20), $X_2$ and $X_4$ represent the same as $X_2$ of the formula (2b) and $X_4$ represents the same as $X_4$ of the formula (2j).

In the formulae (2B-19) to (2B-20), $R_{61}$ to $R_{64}$ each independently represent the same as $R_8$ described above. Adjacent ones of $R_{61}$ may form a ring. Adjacent ones of $R_{62}$ may form a ring. Adjacent $R_{63}$ and $R_{64}$ may form a ring.

In the formulae (2B-19) to (2B-20), $Y_6$ represents the same as $Y_3$ of the formula (2i).

In the formulae (2B-19) to (2B-20), i and j are 4.

Groups derived from the structure represented by the formulae (2B-19) to (2B-20) are preferably groups represented by formulae (2B-21) to (2B-22) below.

[Formula 82]

(2B-21)

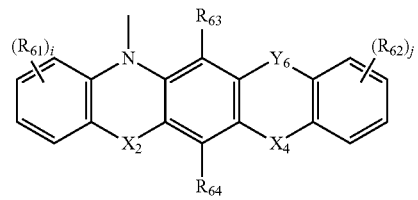

(2B-22)

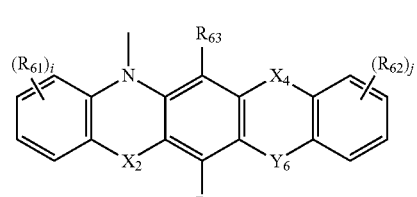

In the formulae (2B-21) to (2B-22), $X_2$, $X_4$, $R_{61}$ to $R_{64}$, $Y_6$, i and j respectively represent the same as $X_2$, $X_4$, $R_{61}$ to $R_{64}$, $Y_6$, i and j of the formulae (2B-19) to (2B-20).

In the exemplary embodiment, when $L_{20}$ to $L_{24}$ and $L_{201}$ are divalent linking groups to be bonded to $Az_2$, $L_{20}$ to $L_{24}$ and $L_{201}$ are each preferably a substituted or unsubstituted divalent aromatic hydrocarbon group. When g is 1 or more in the formula (2), not $L_{20}$ but $L_{201}$ is a divalent linking group to be bonded to $Az_2$.

Moreover, in the exemplary embodiment, when $L_{20}$ to $L_{24}$ and $L_{201}$ are divalent linking groups to be bonded to $Az_2$, $L_{20}$ to $L_{24}$ and $L_{201}$ each preferably have a divalent six-membered ring structure, more preferably a divalent six-membered ring structure represented by a formula (2e), (2f) or (2g) below, further preferably a divalent six-membered ring structure represented by the formula (2e) below.

[Formula 83]

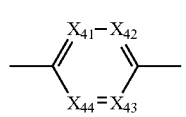 (2e)

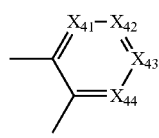 (2f)

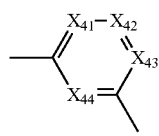 (2g)

In the formulae (2e) to (2g), $X_{41}$ to $X_{44}$ each independently represent $CR_{52}$ or a nitrogen atom, in which $R_{52}$ each independently represents the same as $R_8$ in the formula (1).

In the exemplary embodiment, $X_{41}$ to $X_{44}$ of the formulae (2e) to (2g) are each independently preferably $CR_{52}$, in which $R_{52}$ is more preferably a hydrogen atom, alkyl group, alkoxy group, aryloxy group, cyano group, halogen atom and silyl group.

When g is 1 in the formula (2), $L_{201}$ preferably has a divalent six-membered ring structure represented by the formula (2e) and $L_{20}$ is preferably a heterocyclic group having 5 to 30 ring atoms. In this arrangement, the heterocyclic group is preferably a carbazolyl group, in which a nitrogen atom at a position 9 of the carbazolyl group is preferably bonded to $L_{201}$. Further preferably, at least one of the structures represented by the formulae (2b) and (2bx) is bonded to the carbazolyl group.

Moreover, $L_{21}$ of the formula (21), $L_{22}$ of the formula (22), $L_{23}$ and $L_{24}$ of the formula (23) and $L_{201}$ of the formula (24) each preferably have a divalent six-membered ring structure represented by the formula (2e).

Specific examples of the compound represented by the formula (2) are shown below, but the invention is not limited thereto.

[Formula 84]

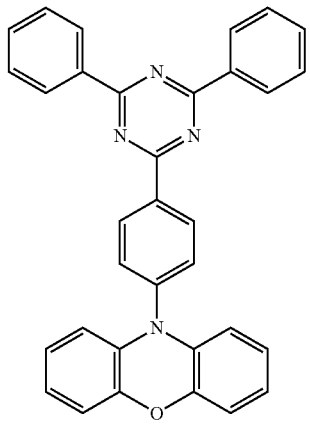

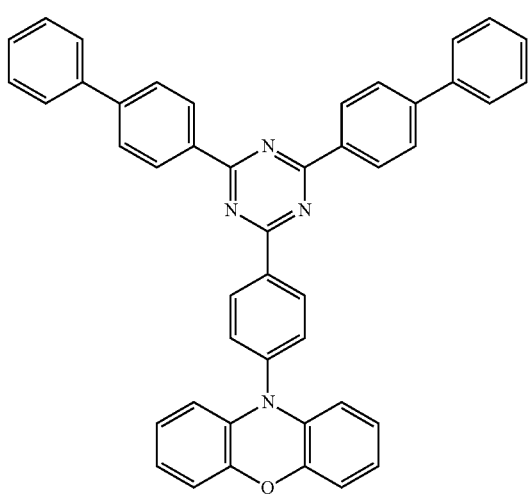

95
-continued
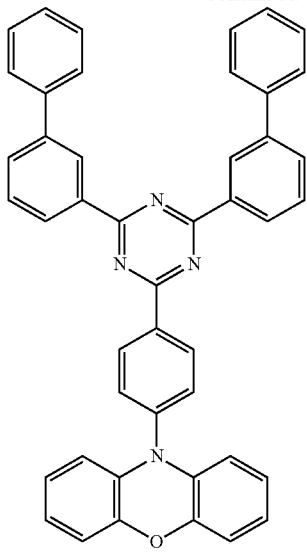
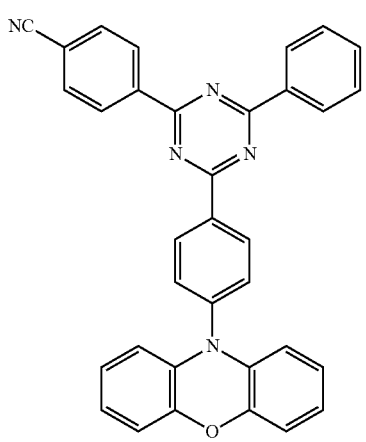
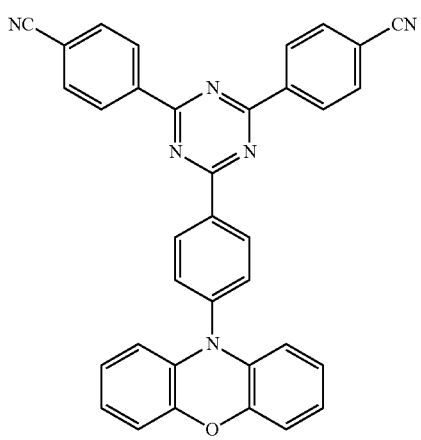
96
-continued
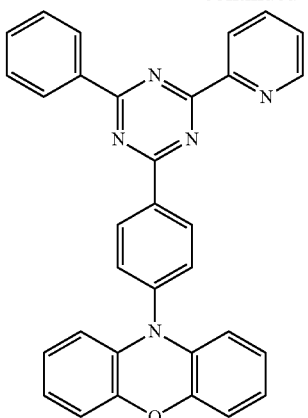
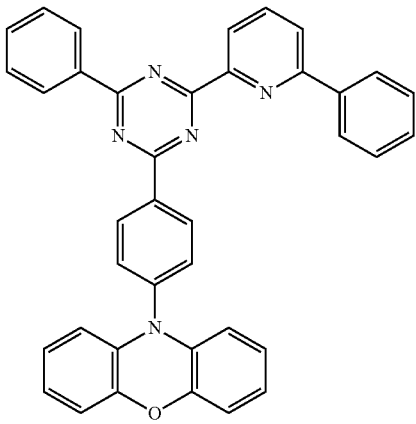
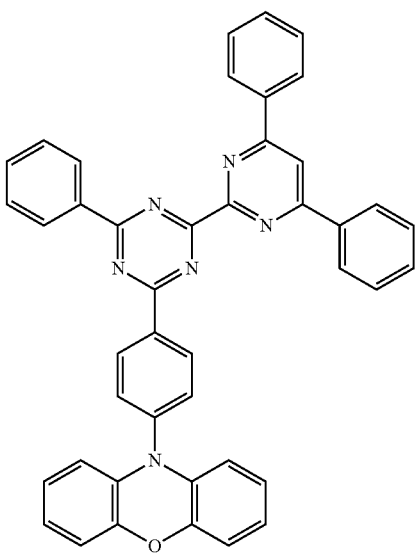

97
-continued
[Formula 85]
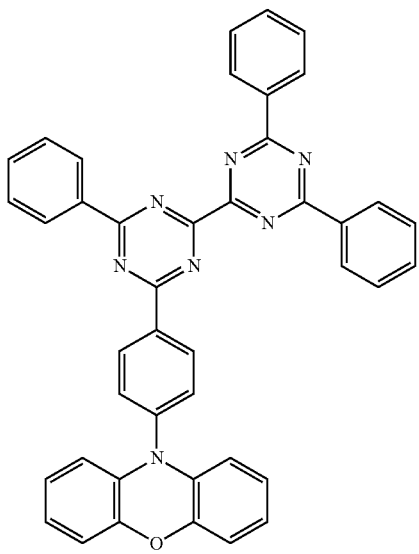
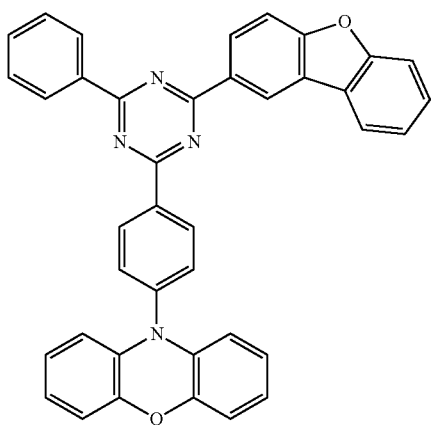
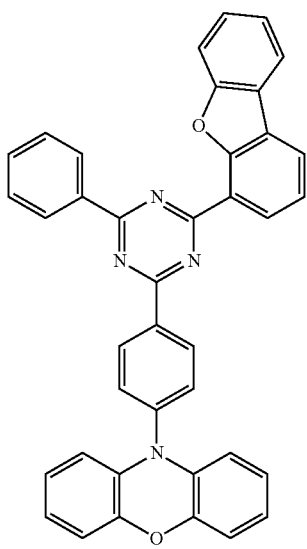
98
-continued
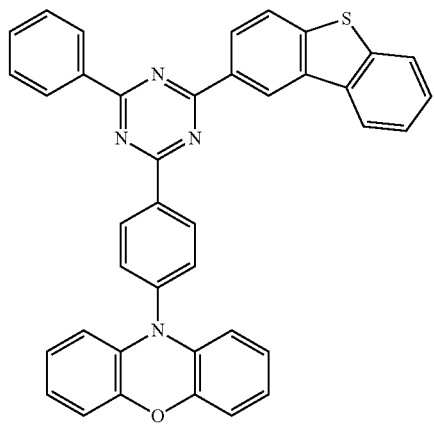
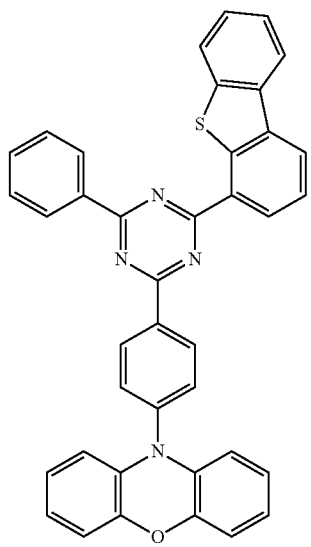
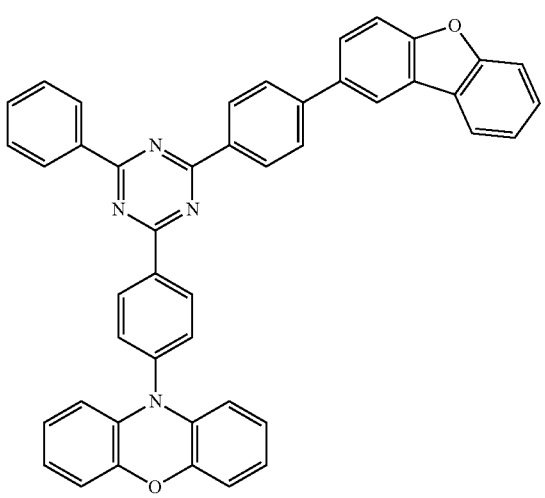

99
-continued
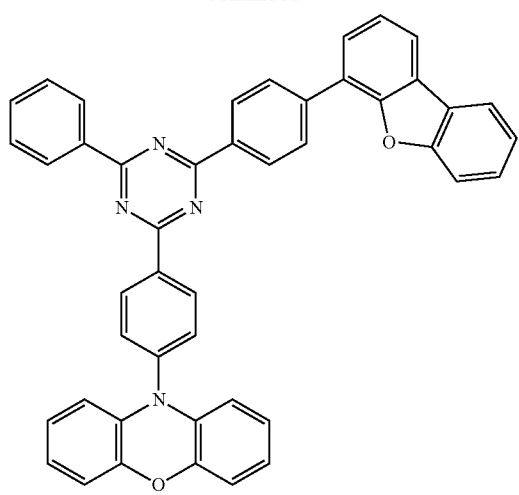
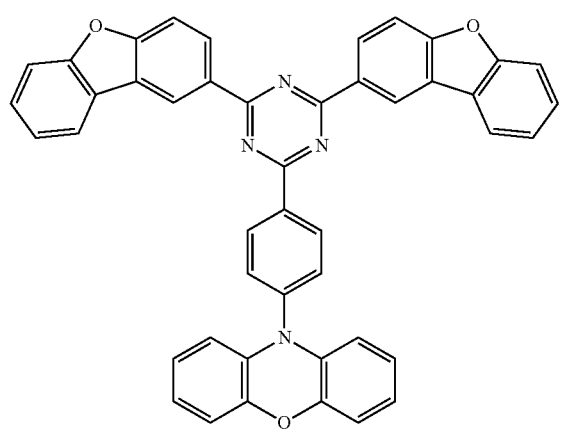
[Formula 86]
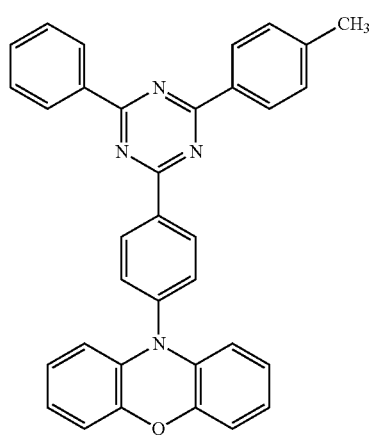
100
-continued
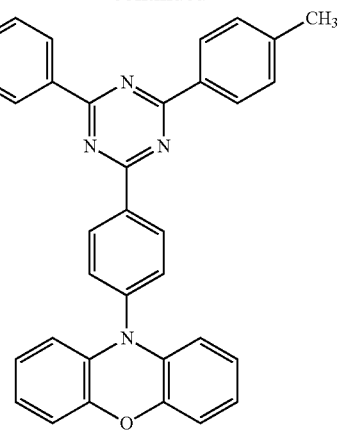
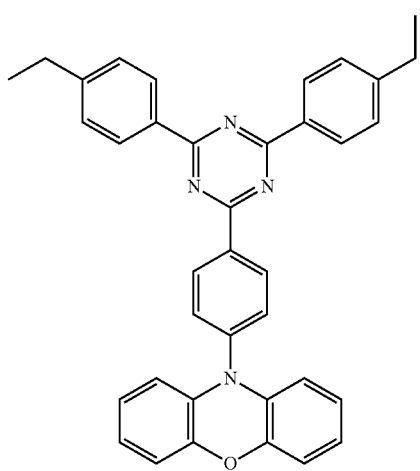

101
-continued
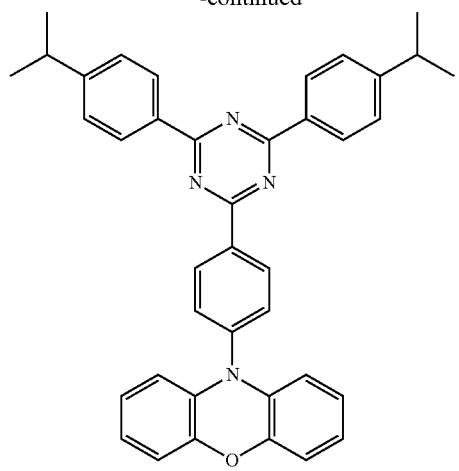
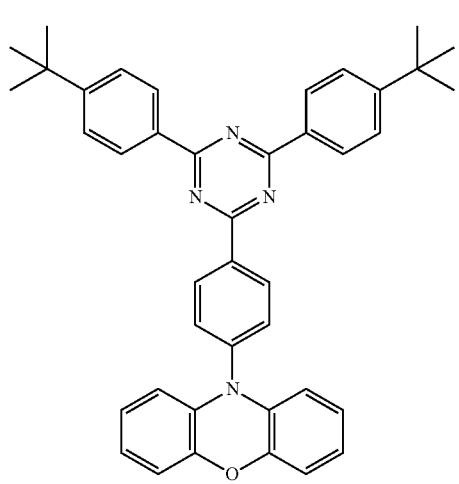
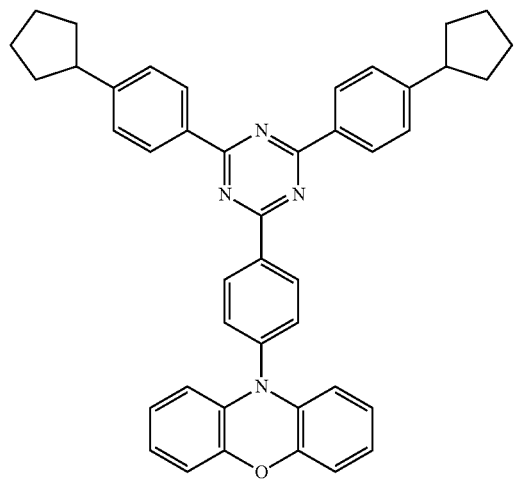
102
-continued
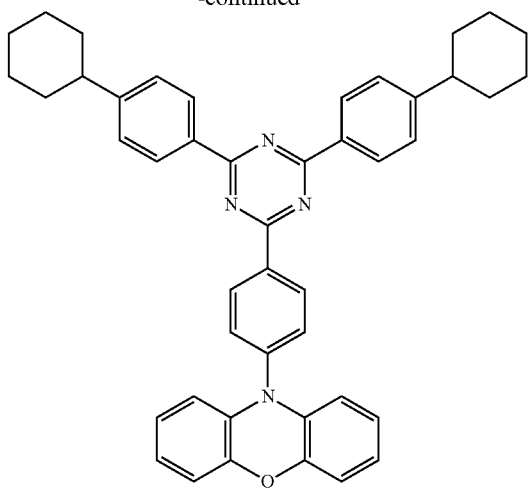
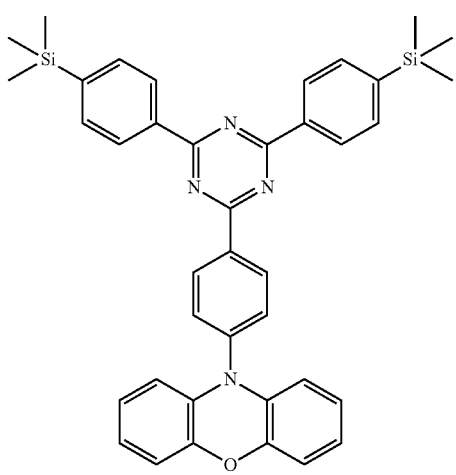
[Formula 87]
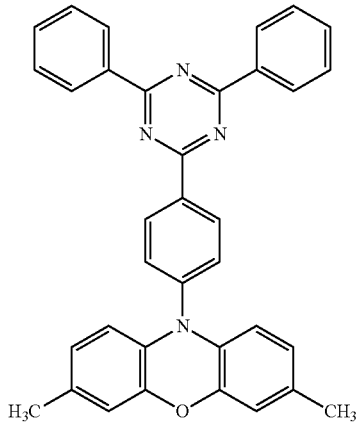

103
-continued
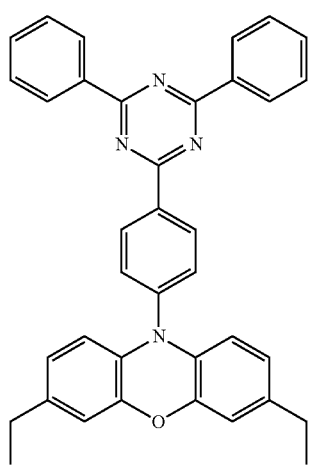
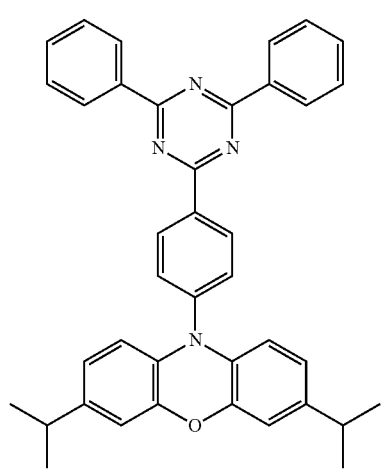
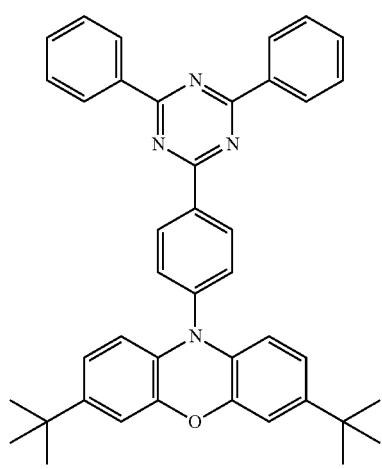
104
-continued
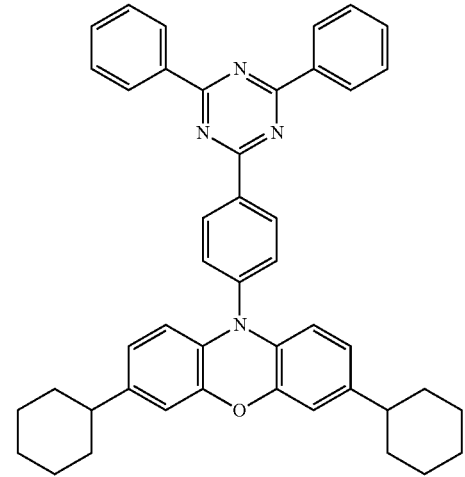
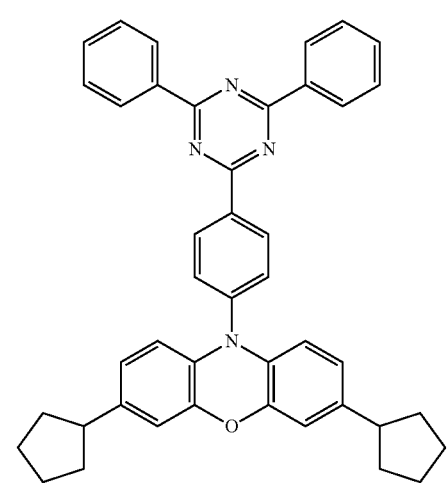
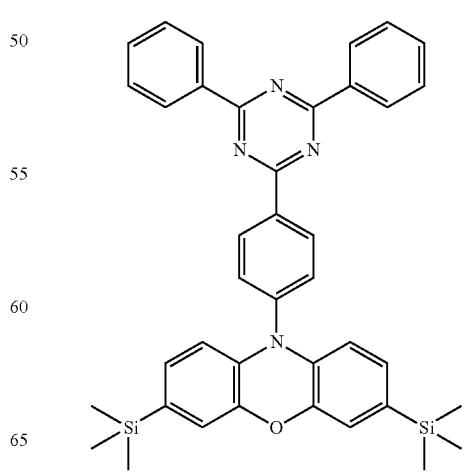

105
-continued
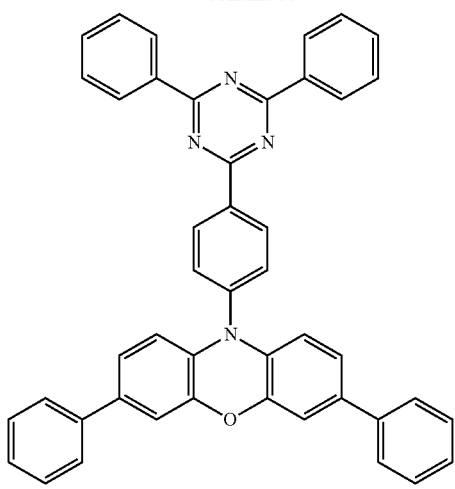
[Formula 88]
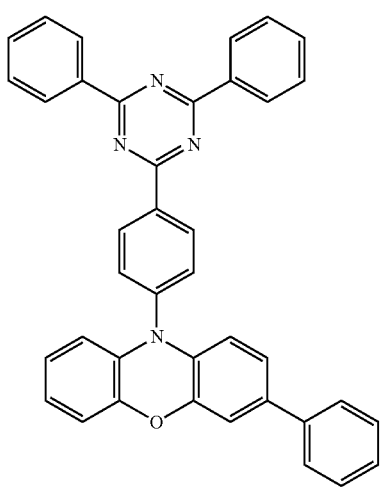
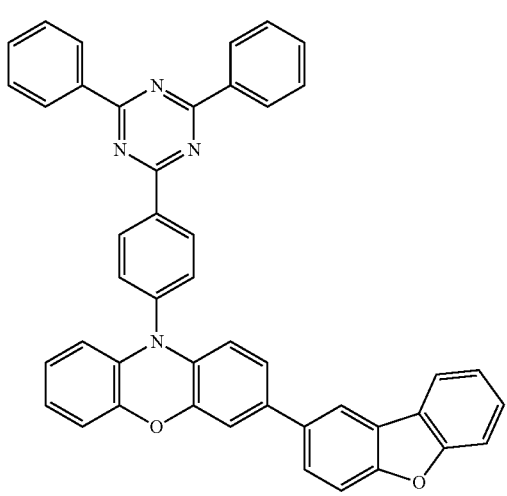
106
-continued
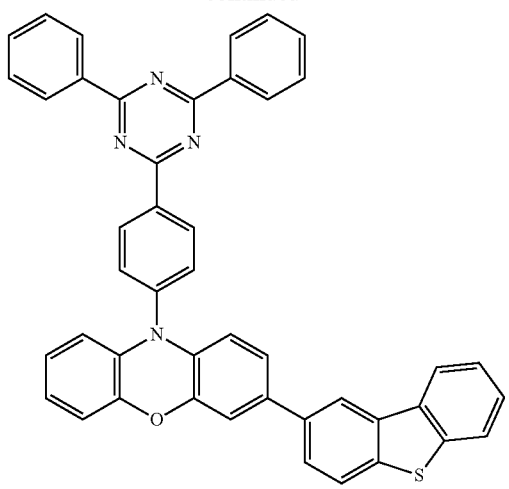
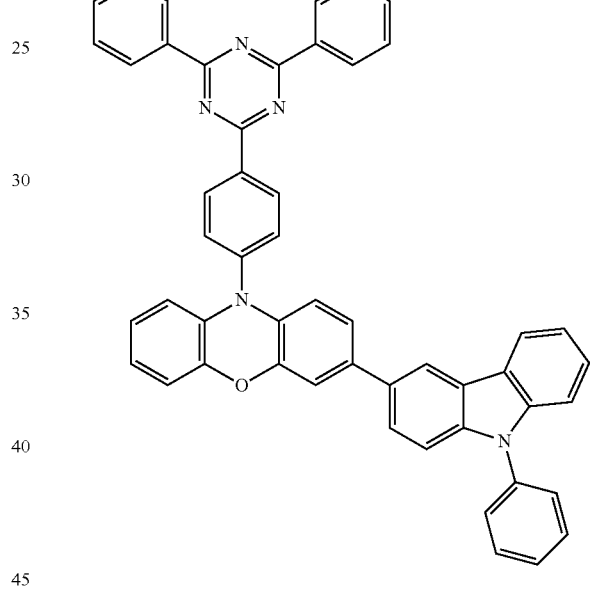
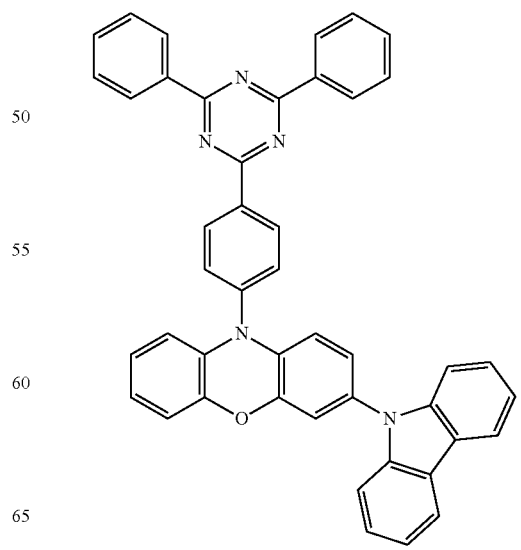

107
-continued
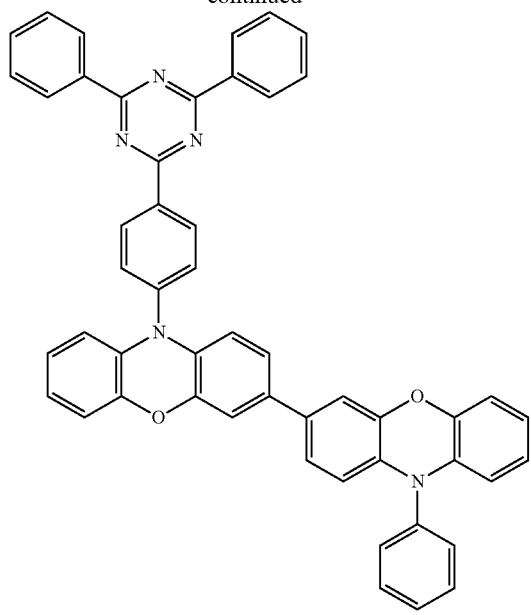
108
-continued
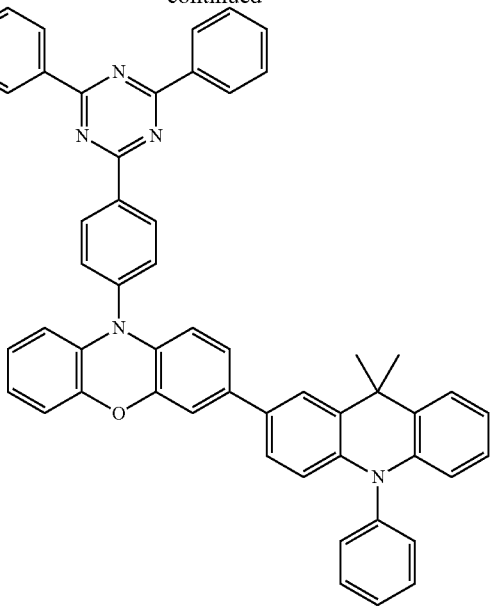
[Formula 89]
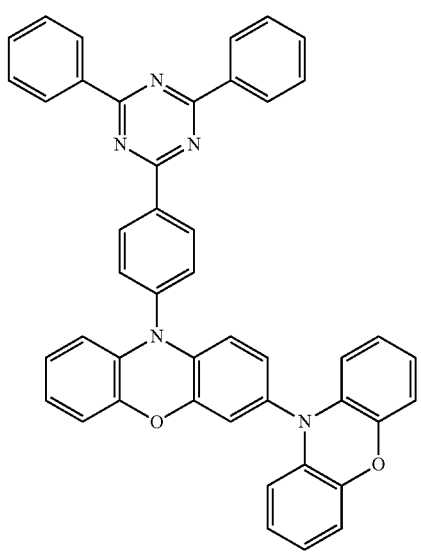
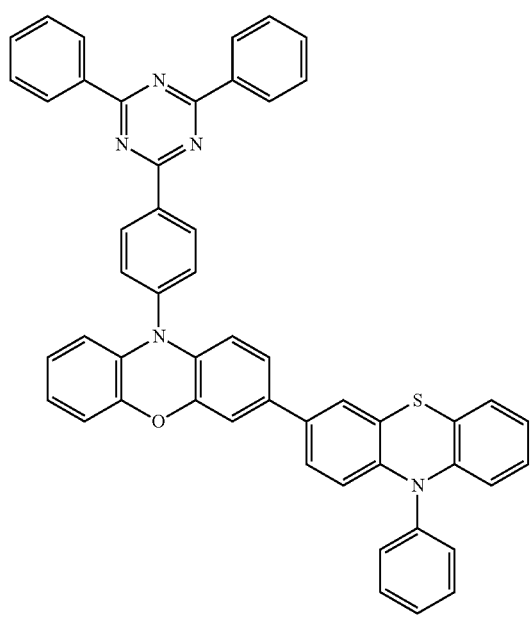
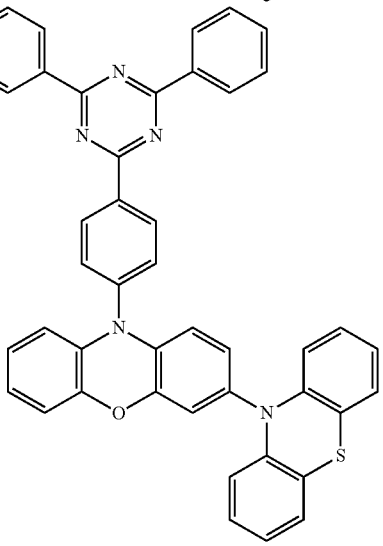

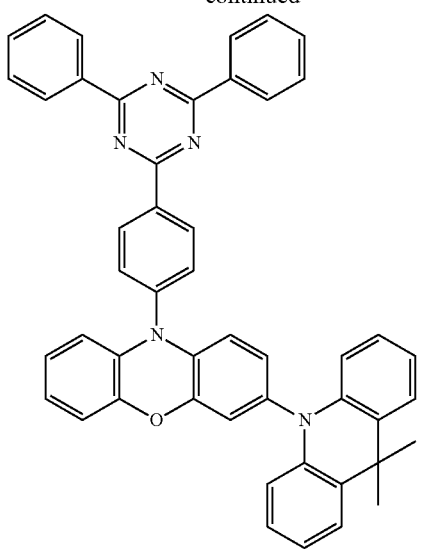
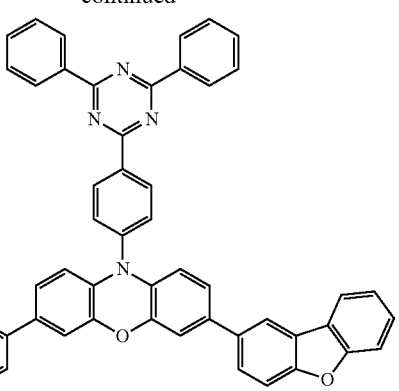
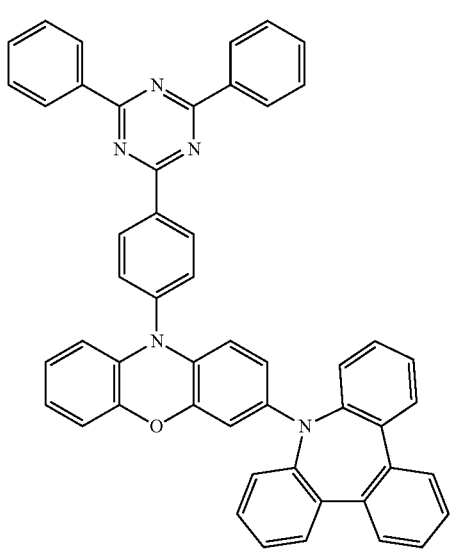
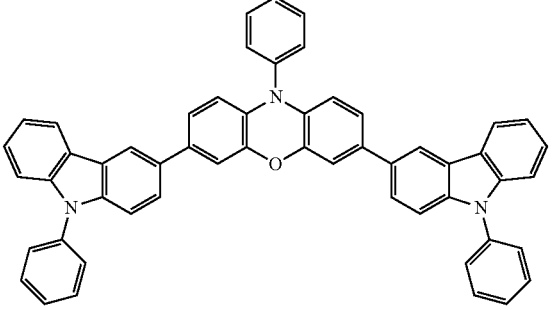
[Formula 90]
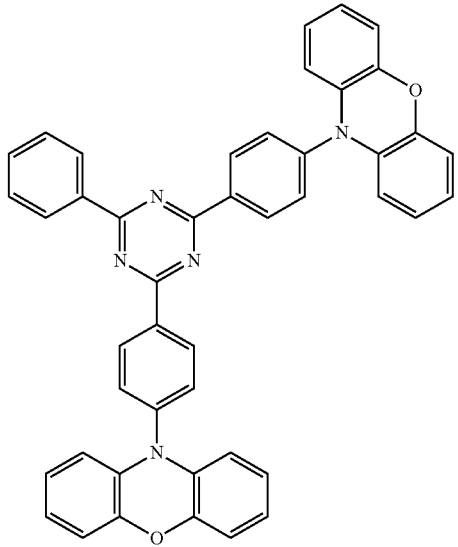

111
-continued
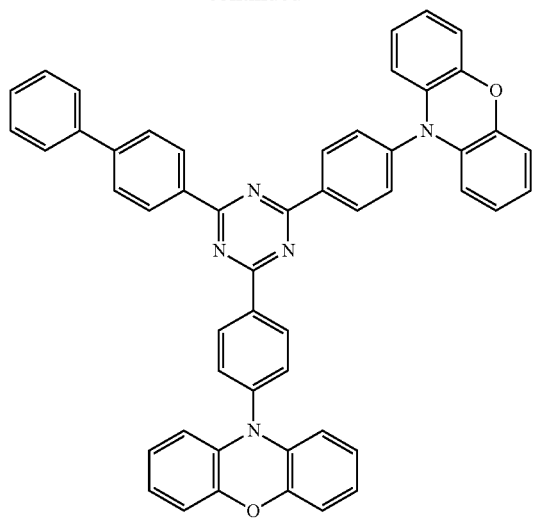
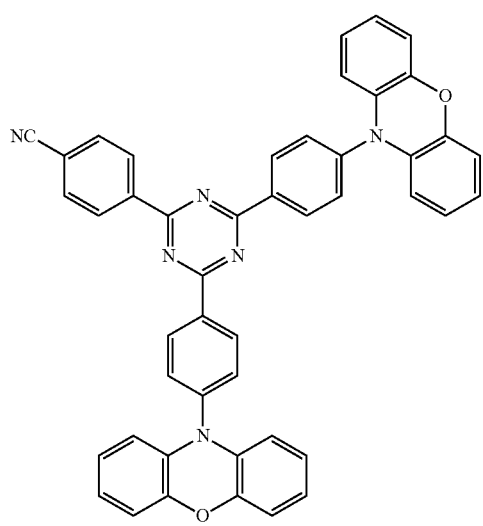
[Formula 91]
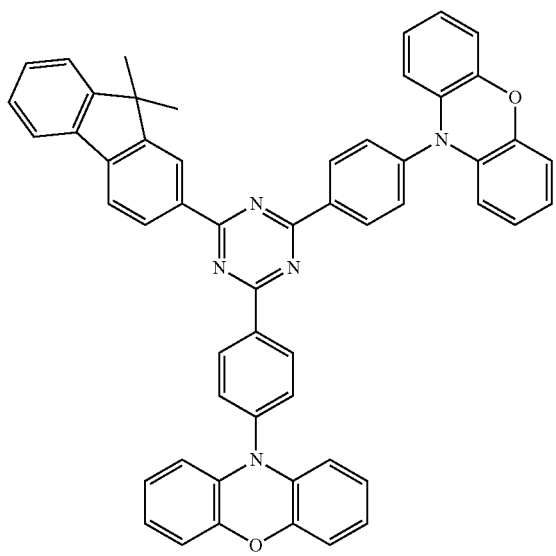
112
-continued
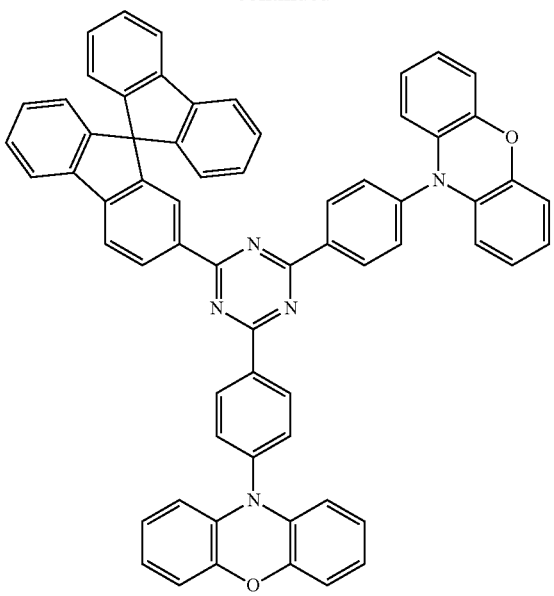
[Formula 92]
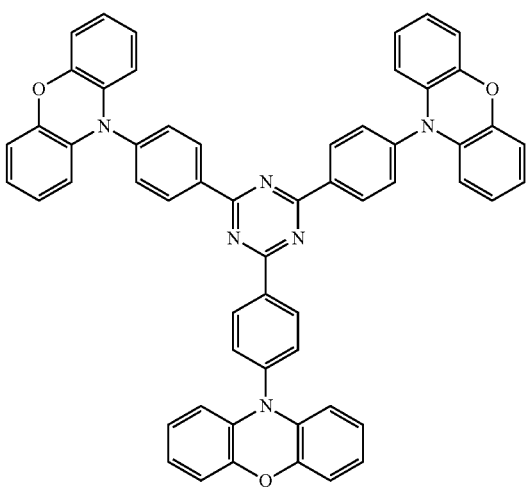
[Formula 93]
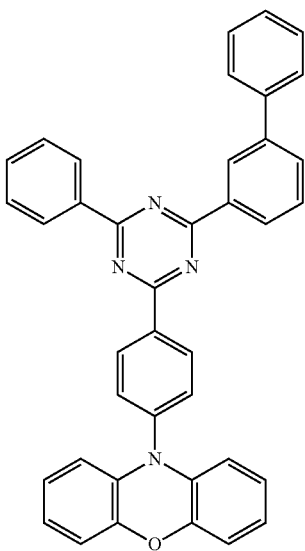

113
-continued
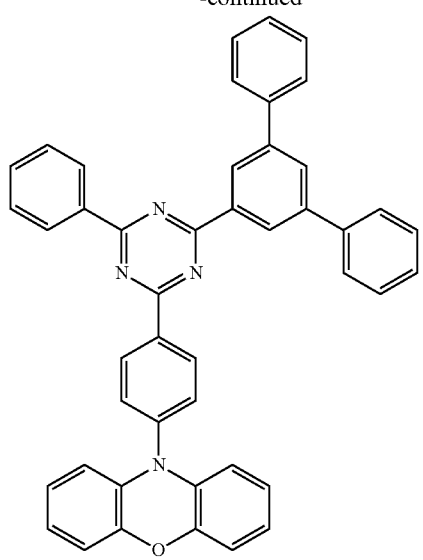
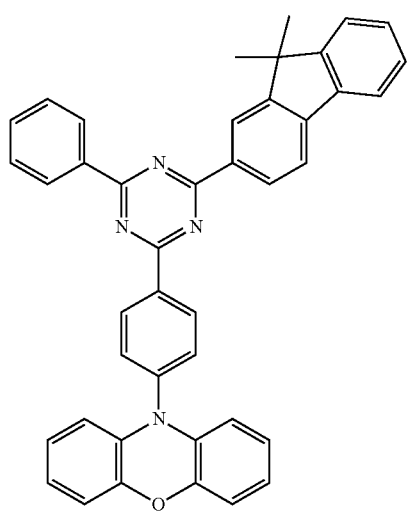
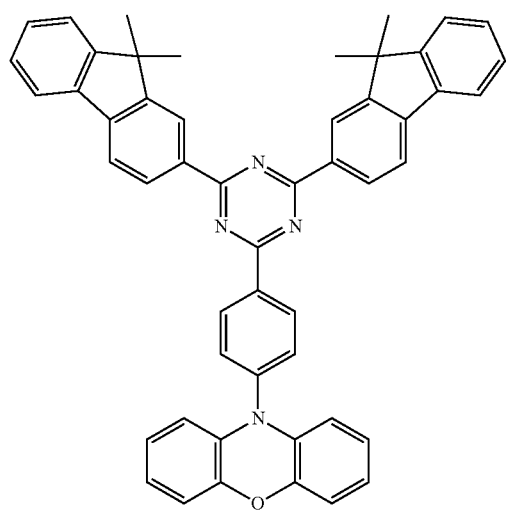
114
-continued
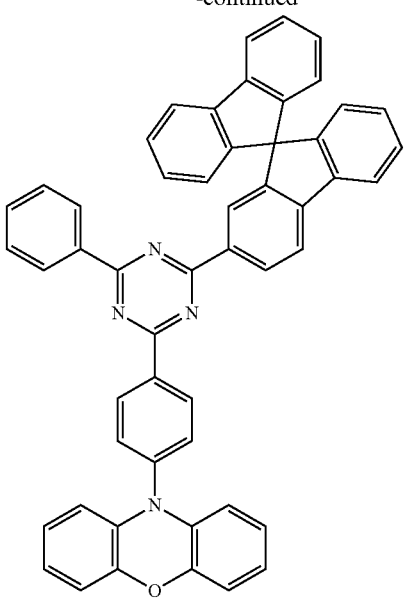
[Formula 94]
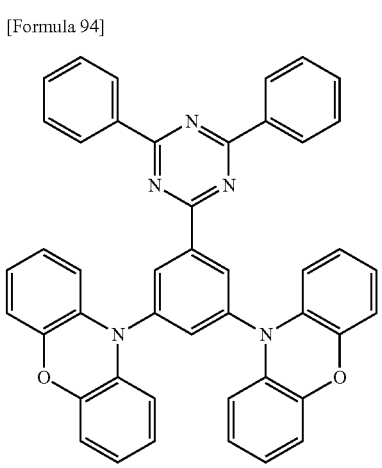
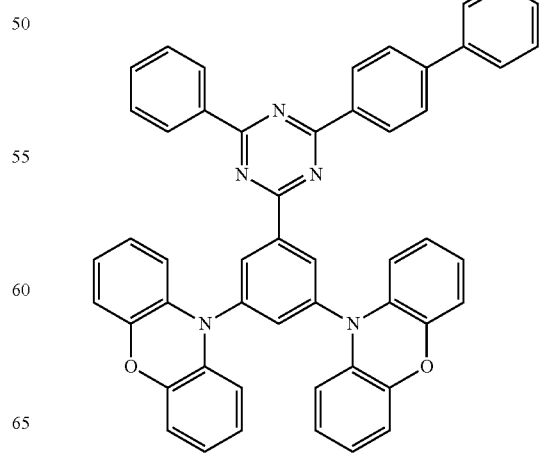

115
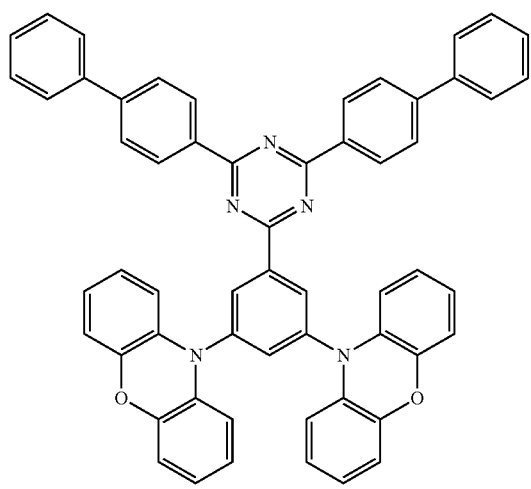
116
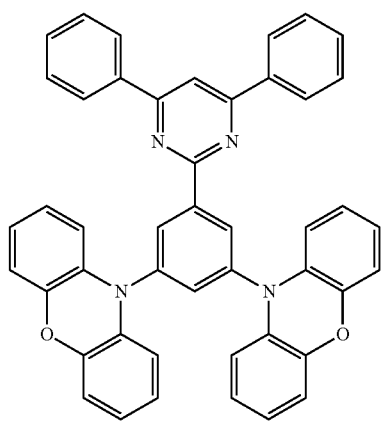
[Formula 95]
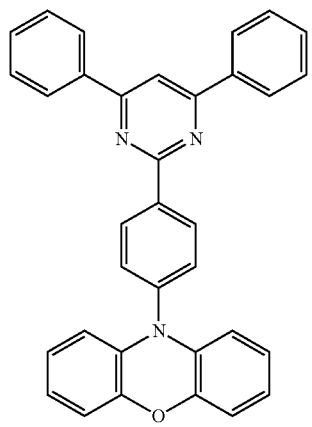
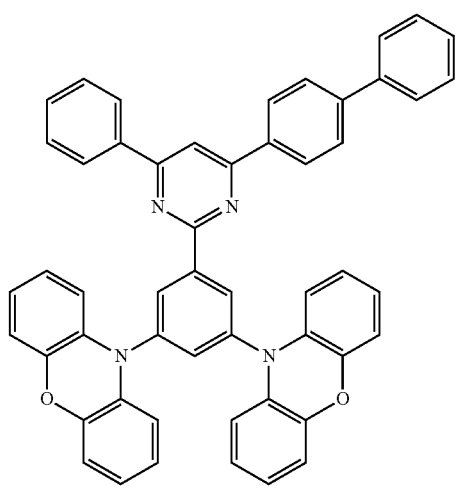
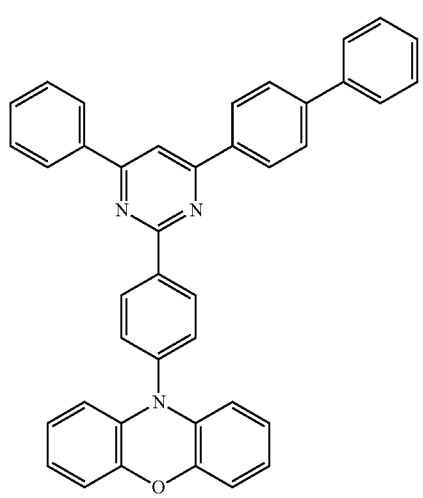
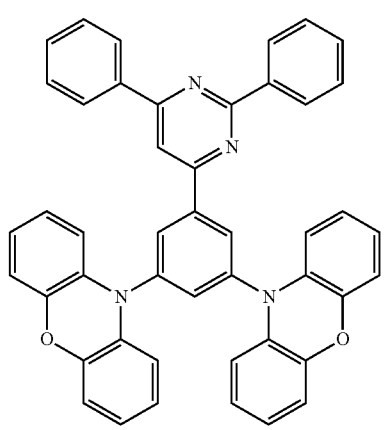

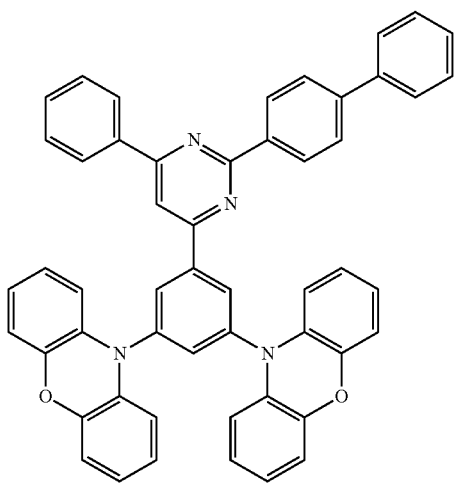
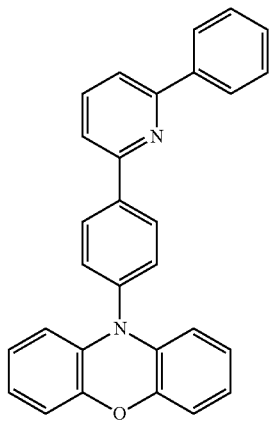
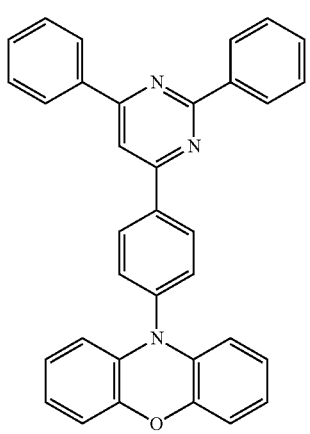
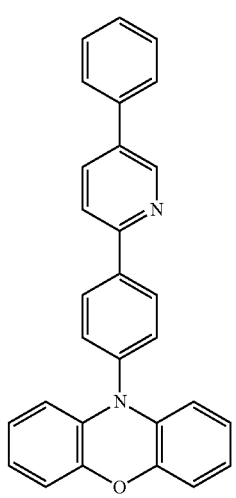
[Formula 96]
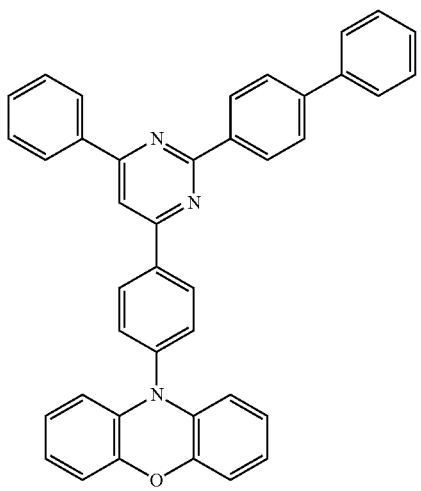
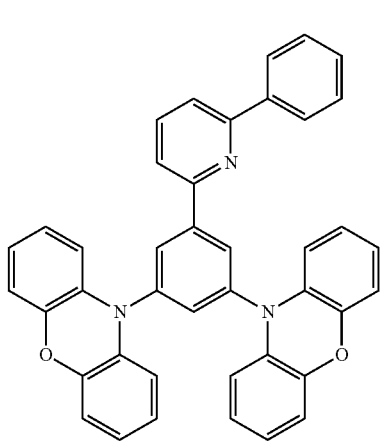

119
-continued
[Formula 97]
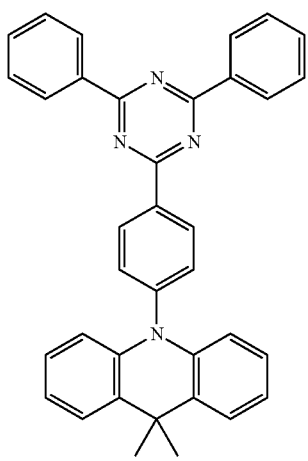
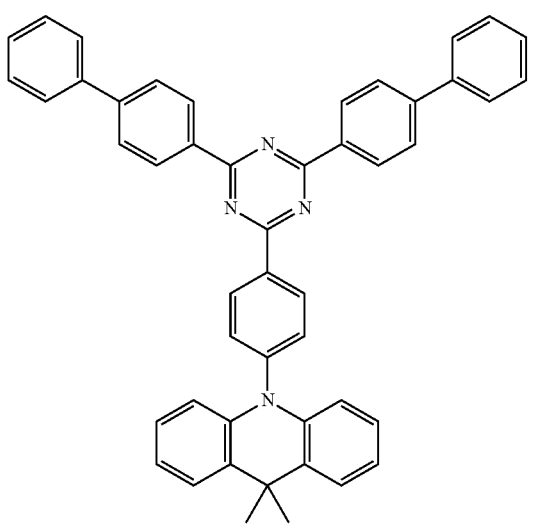
120
-continued
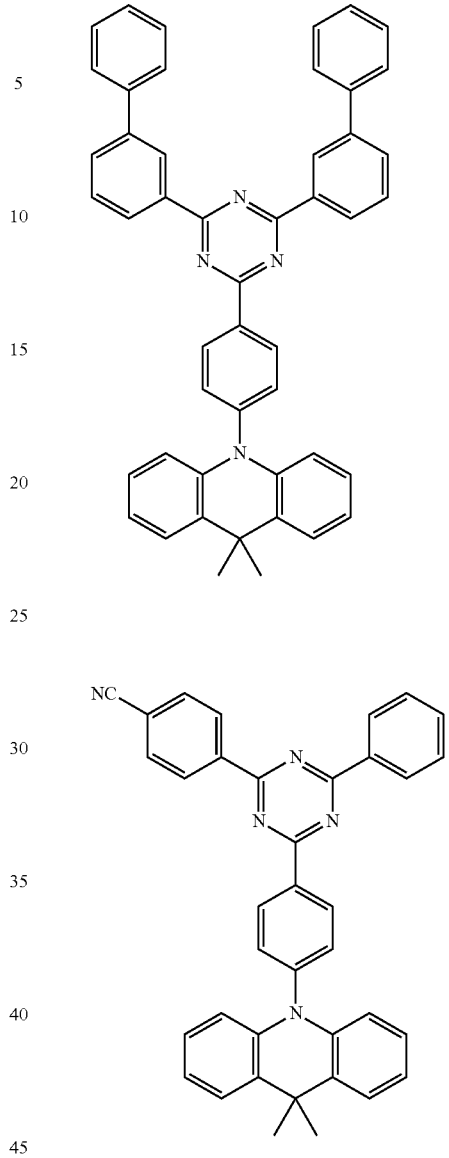
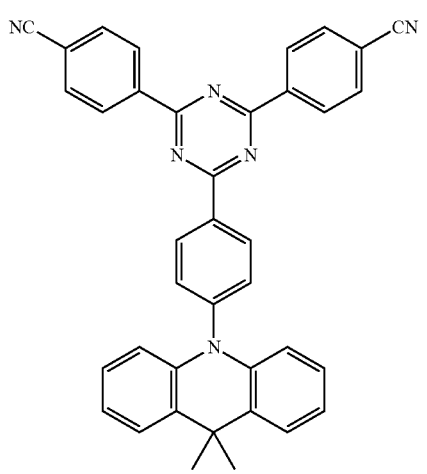

121
-continued
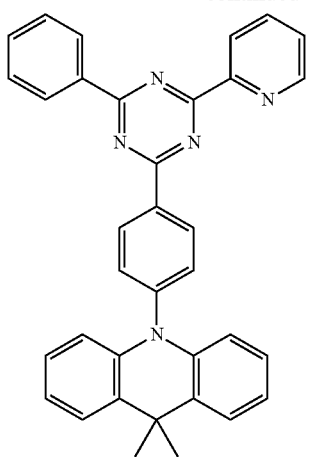
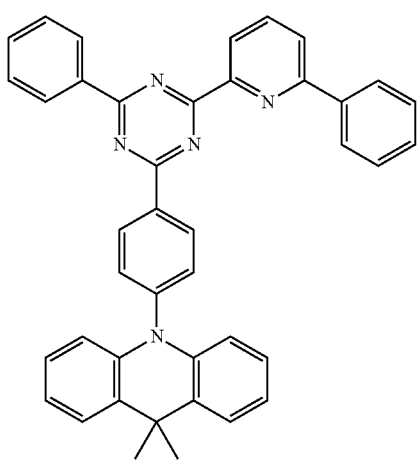
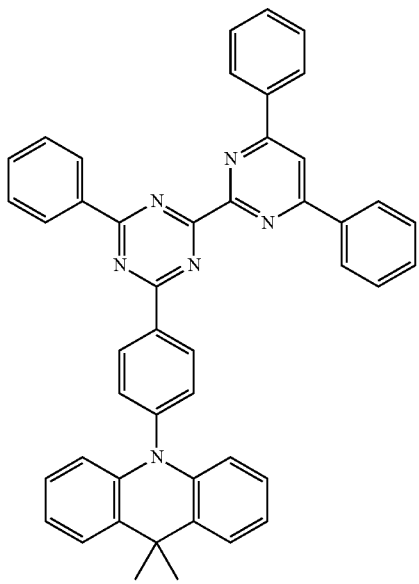
122
-continued
[Formula 98]
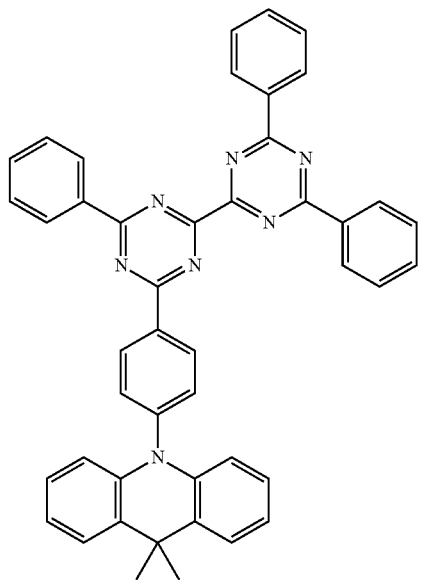
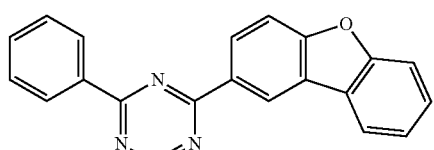
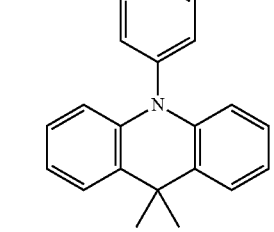
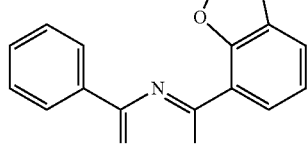
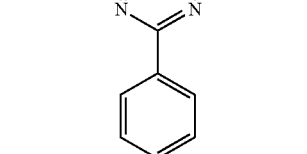
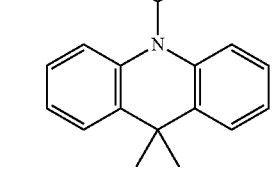

123
-continued
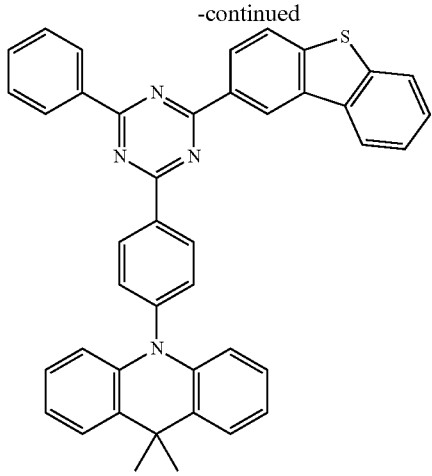
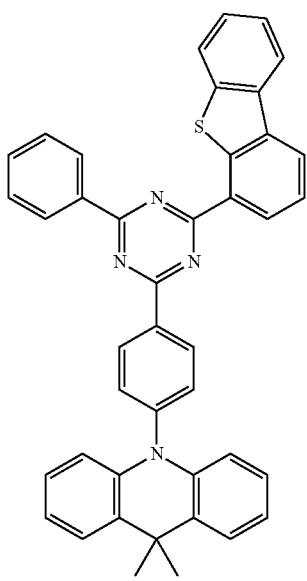
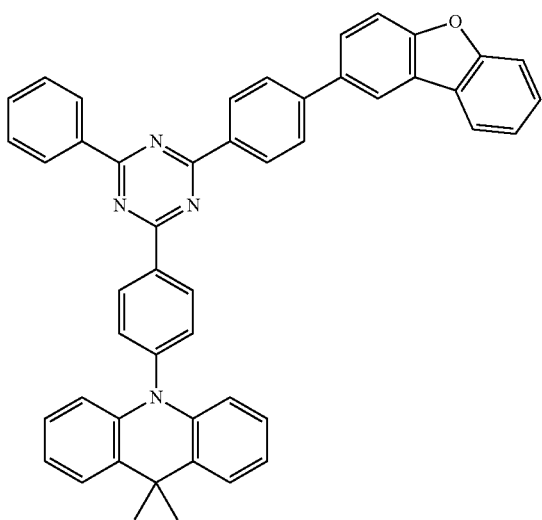
124
-continued
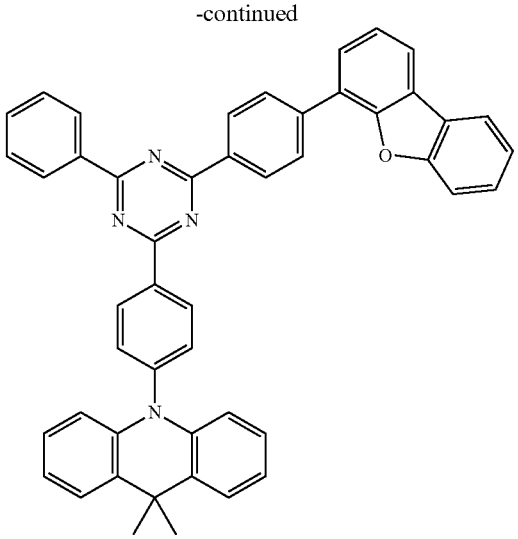
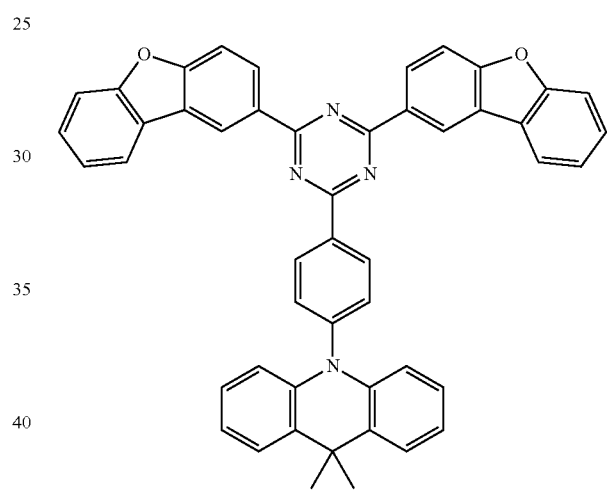
[Formula 99]
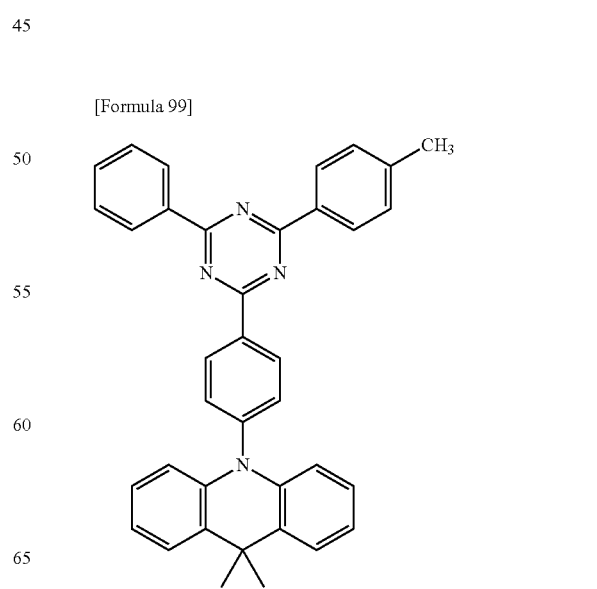

125
-continued
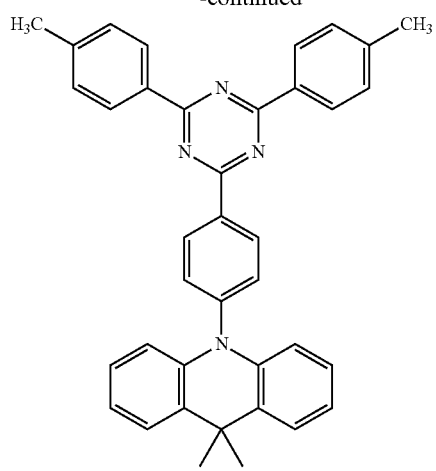
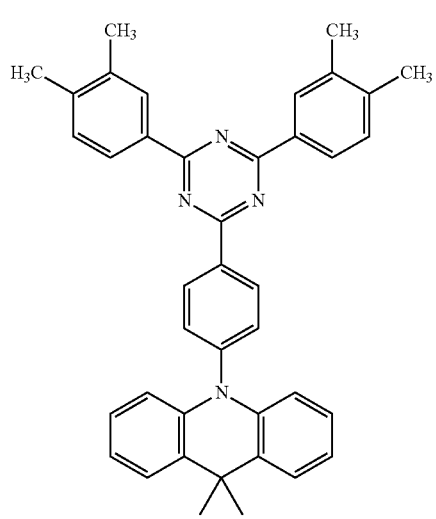
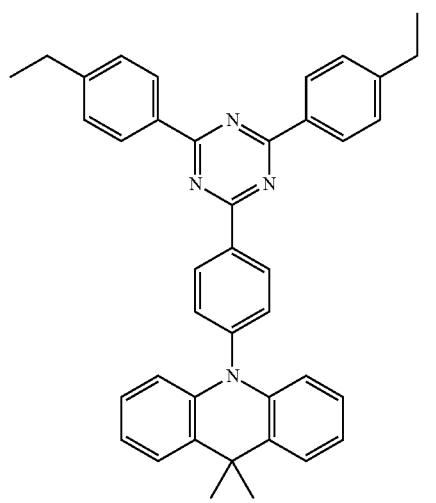
126
-continued
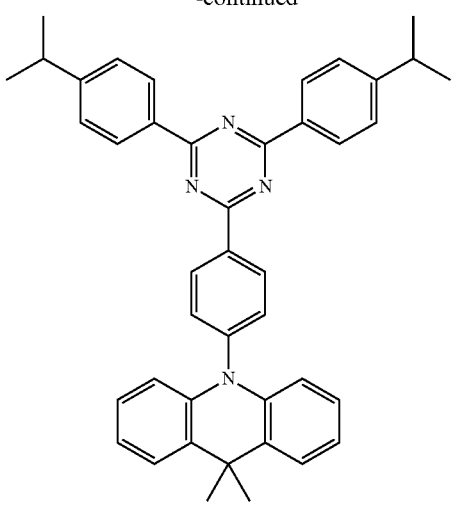
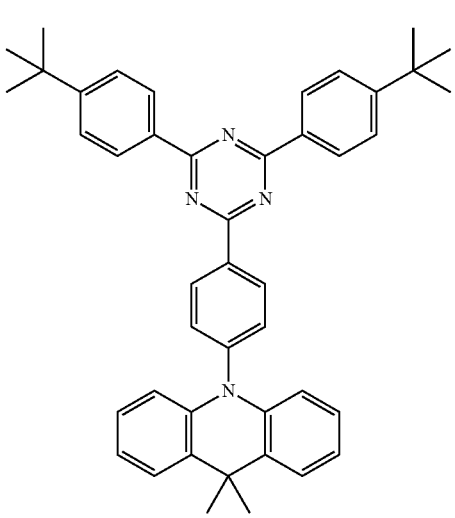
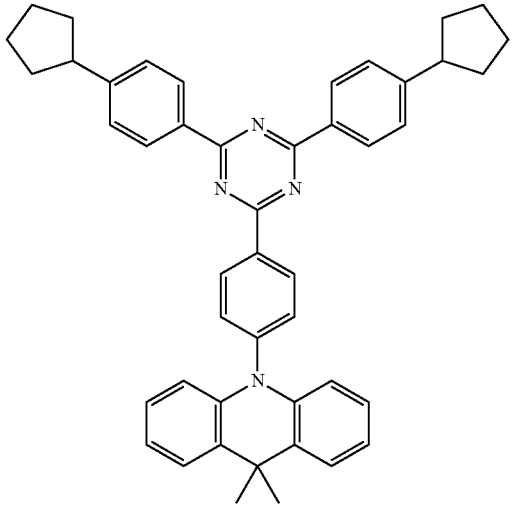

127
-continued
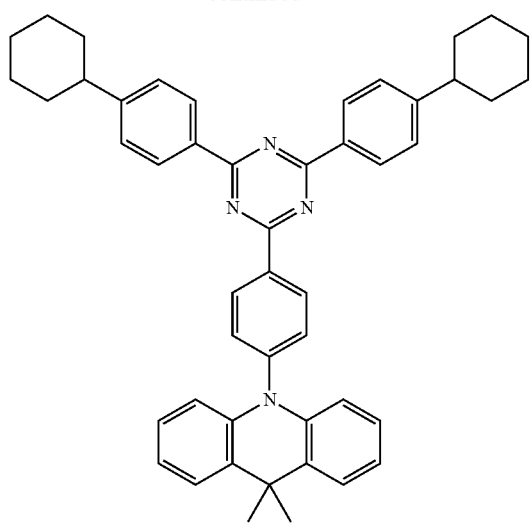
128
-continued
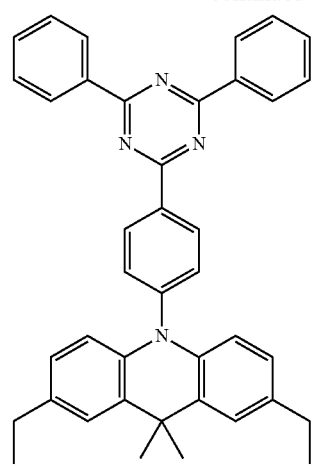
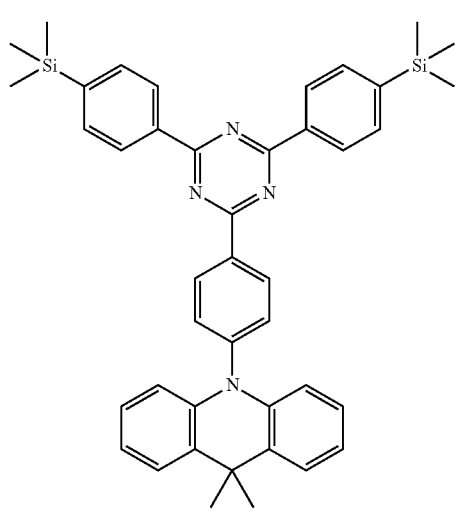
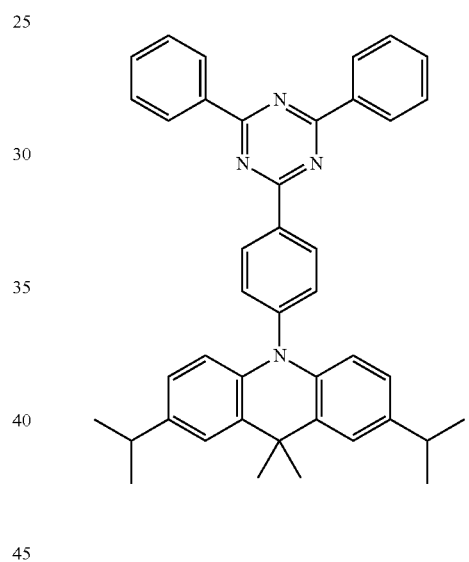
[Formula 100]
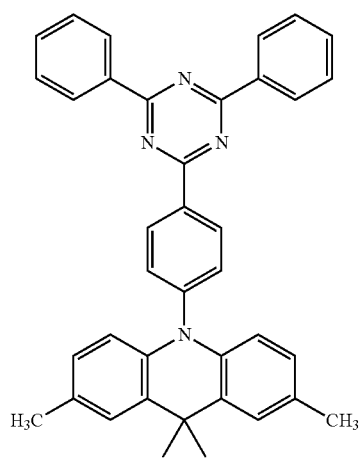
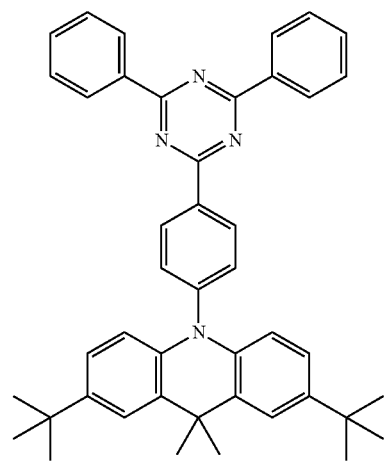

129
-continued
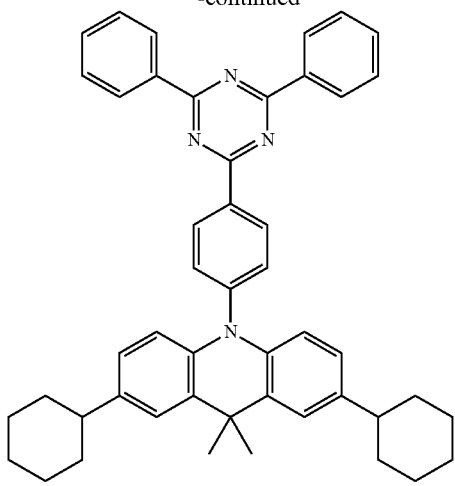
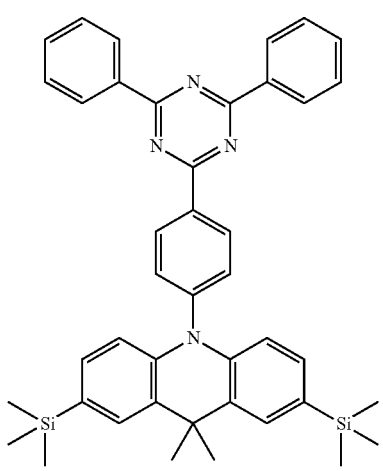
130
-continued
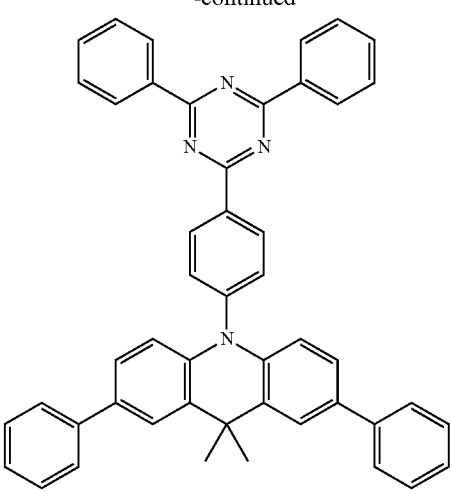
[Formula 101]
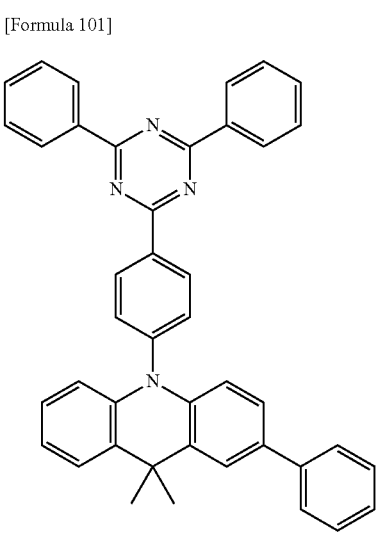
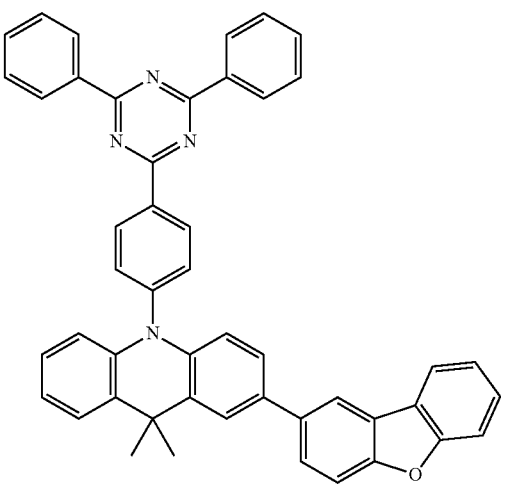

131
-continued
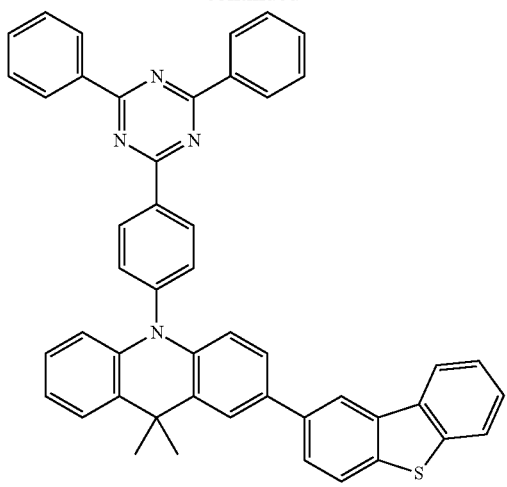
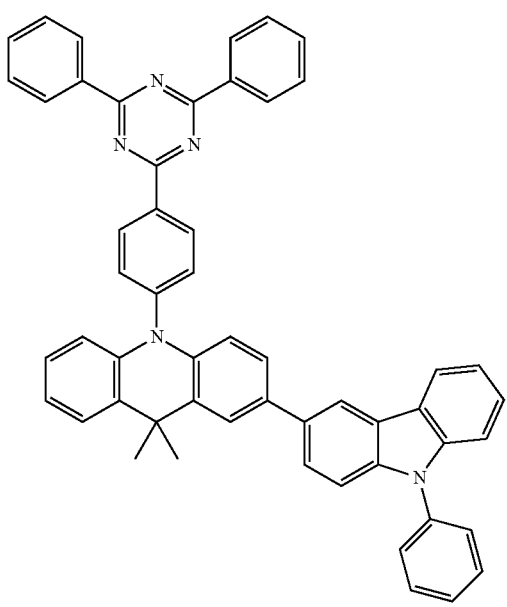
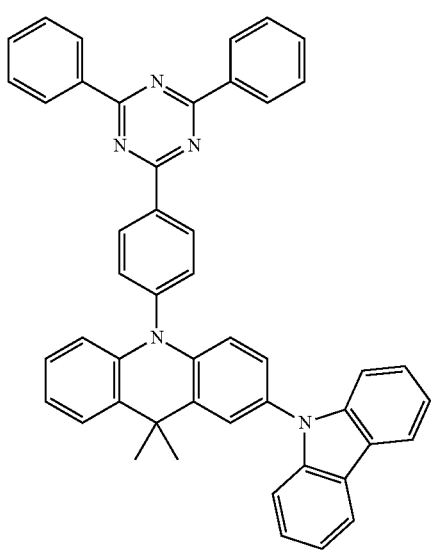
132
-continued
[Formula 102]
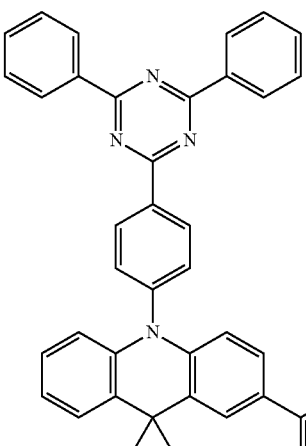
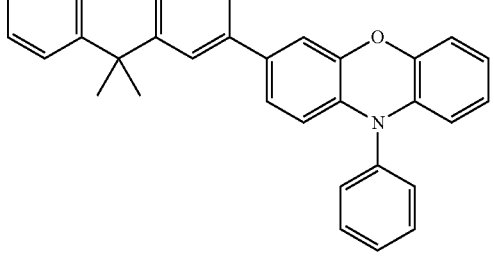
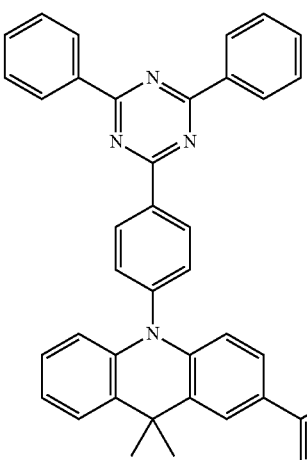
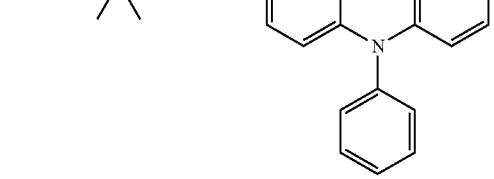

133
-continued
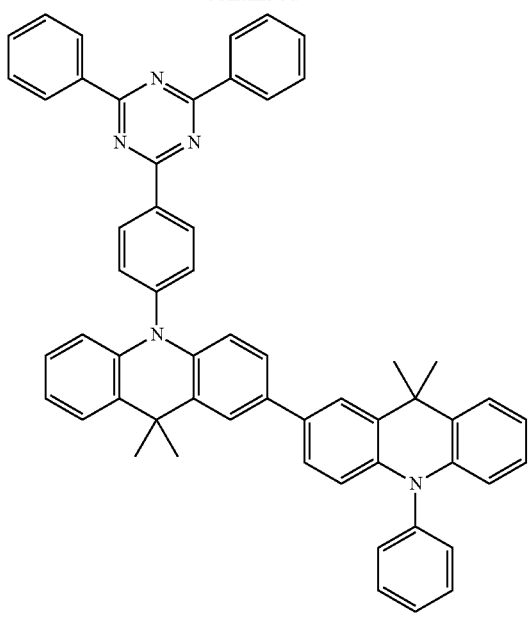
134
-continued
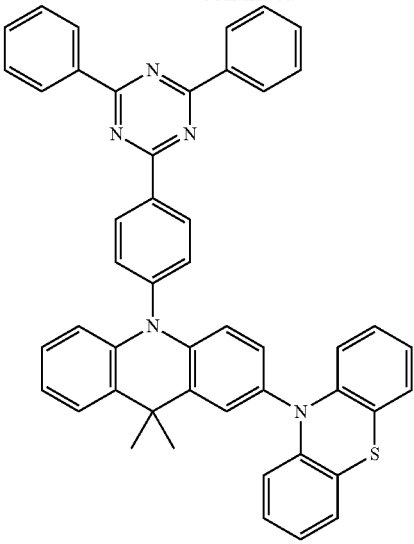
[Formula 103]
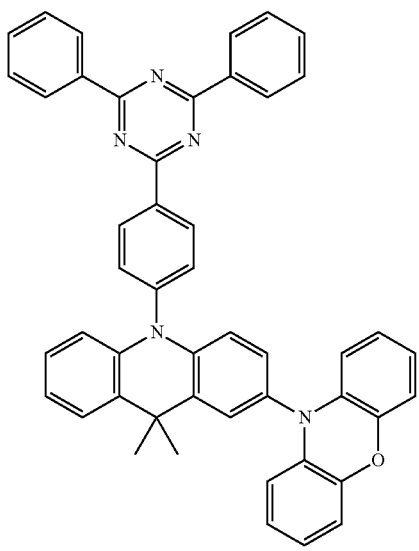
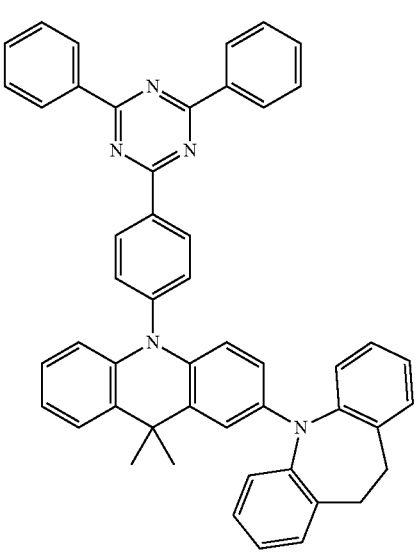

135
-continued
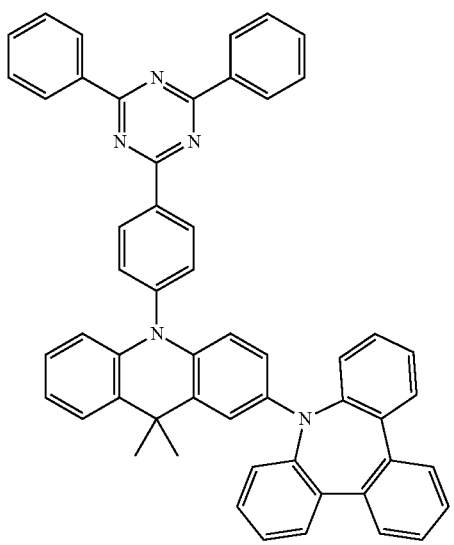
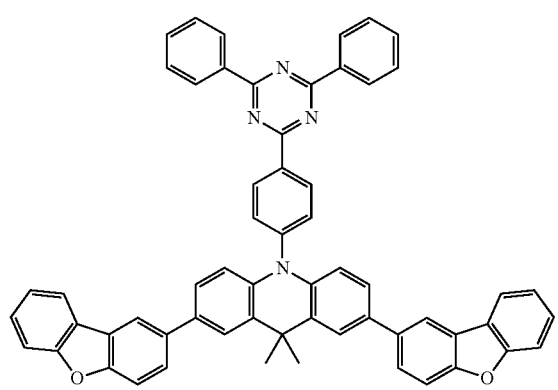
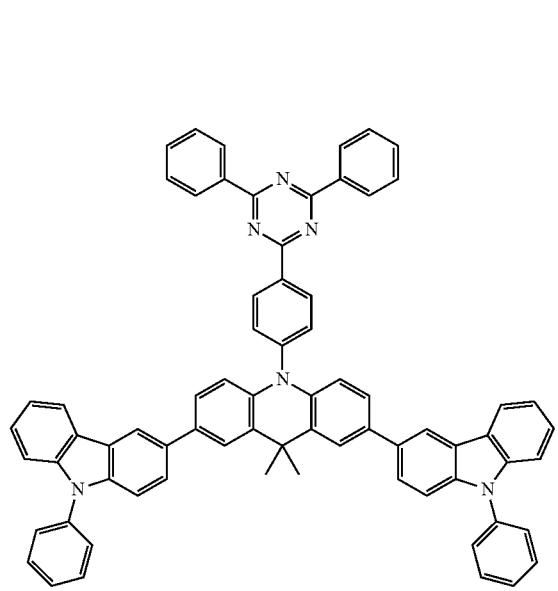
136
-continued
[Formula 104]
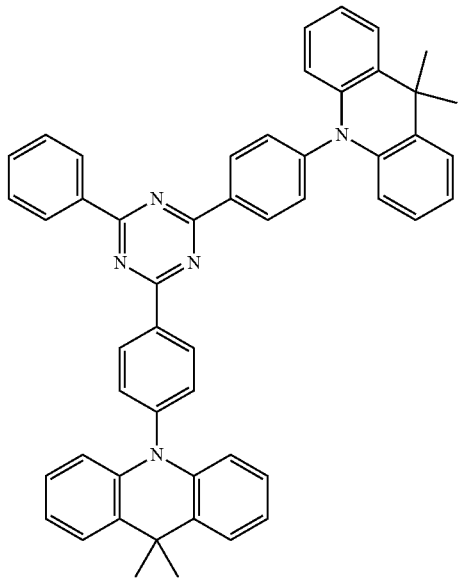
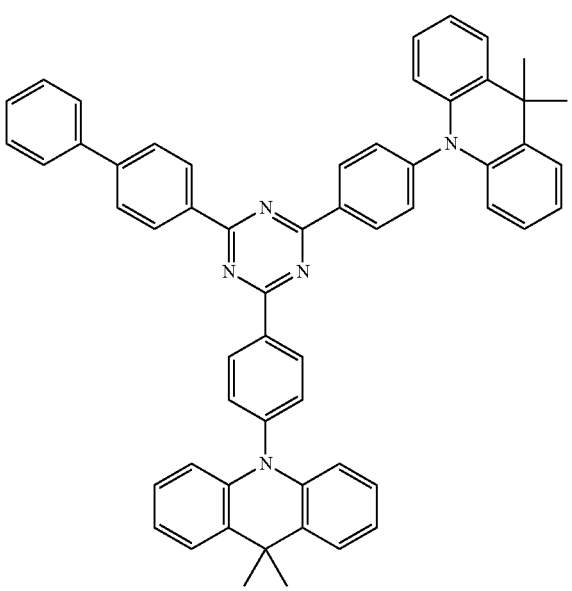

137
-continued
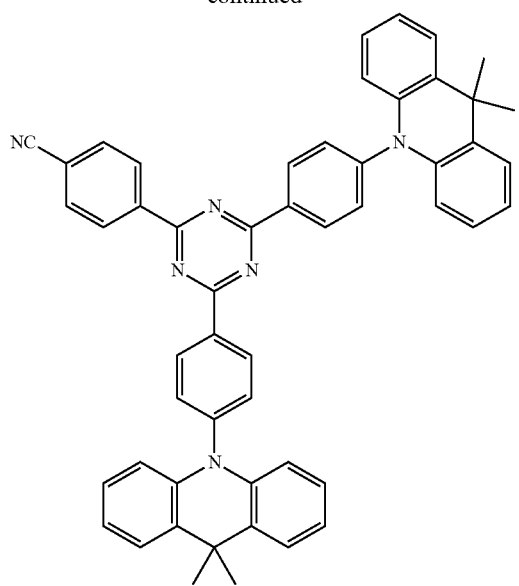
138
-continued
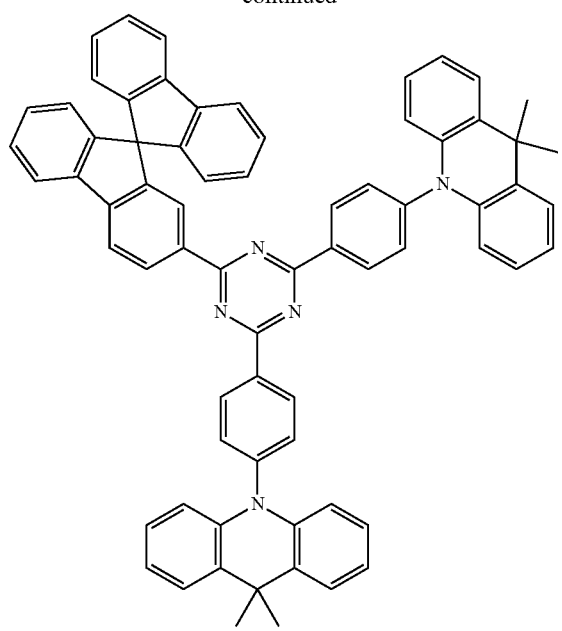
[Formula 105]
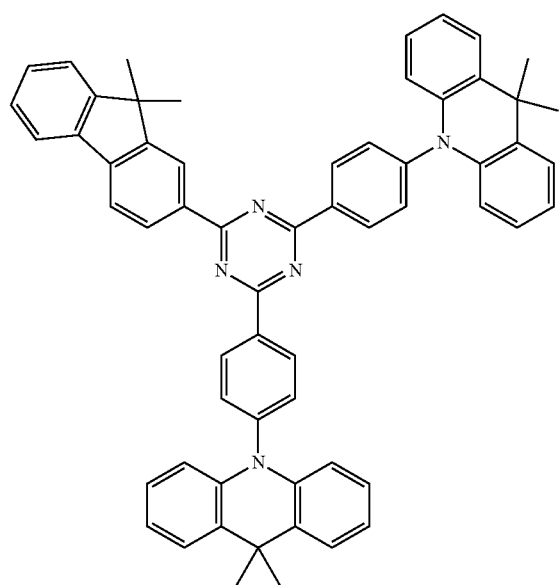
[Formula 106]
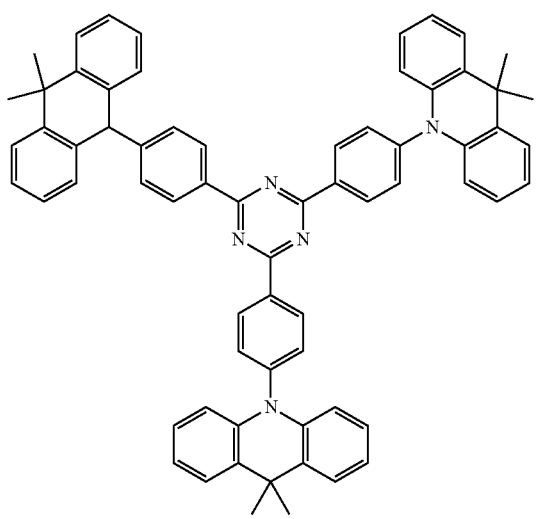

139
-continued
[Formula 107]
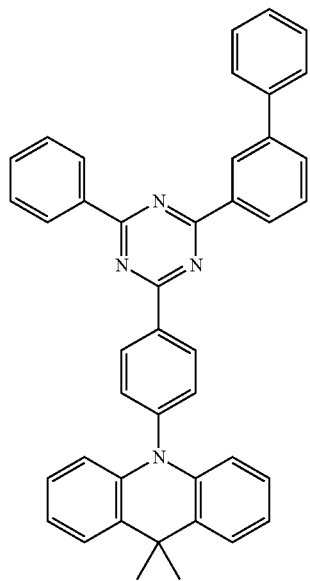
140
-continued
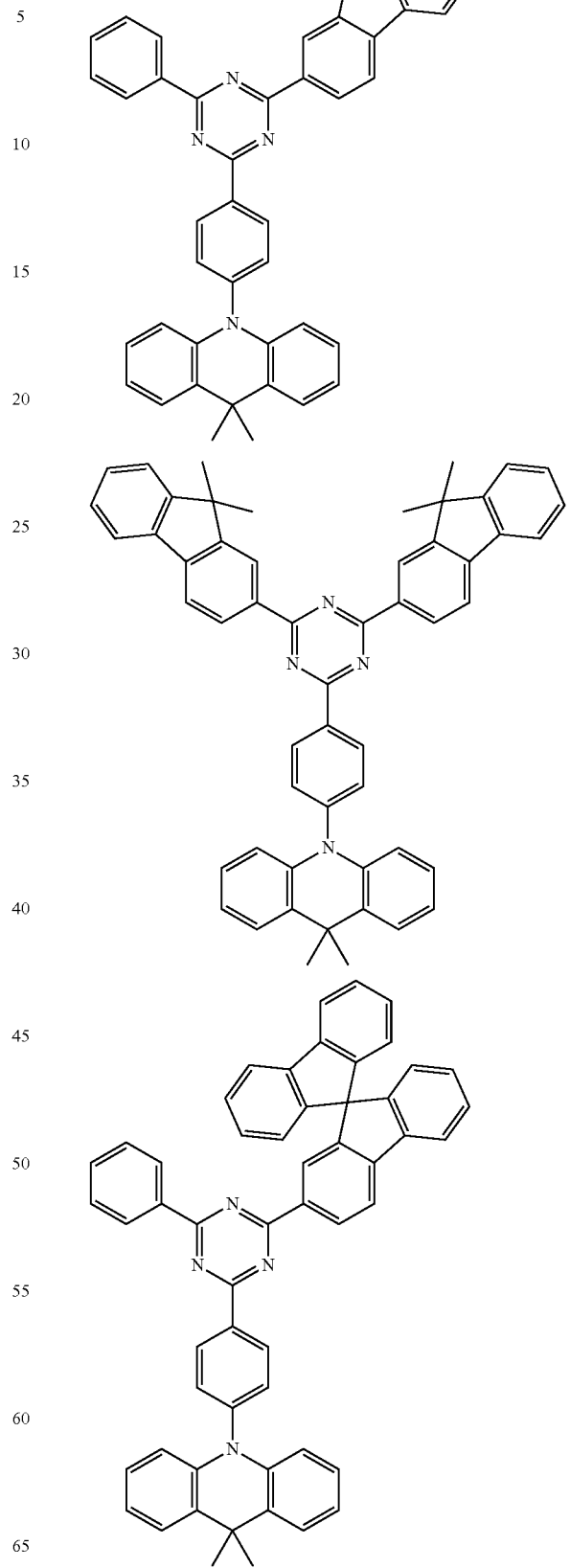

141
-continued
[Formula 108]
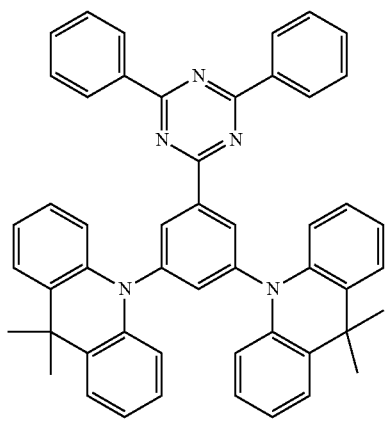
[Formula 109]
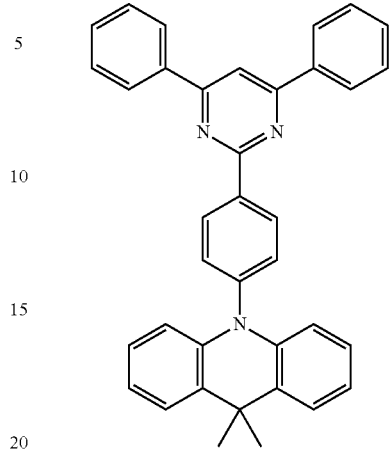
142
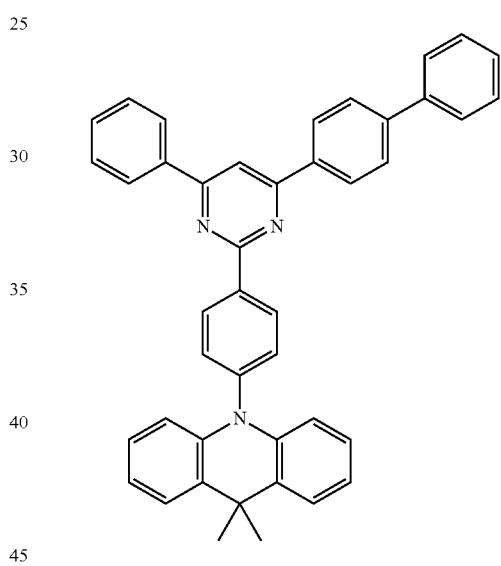
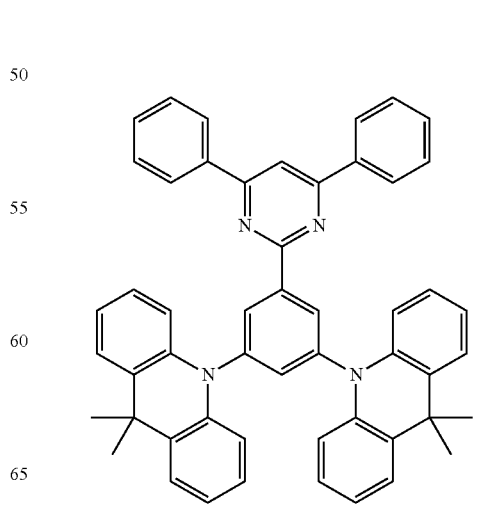

-continued
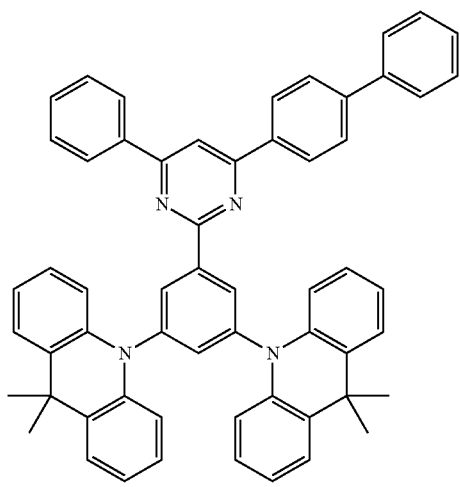
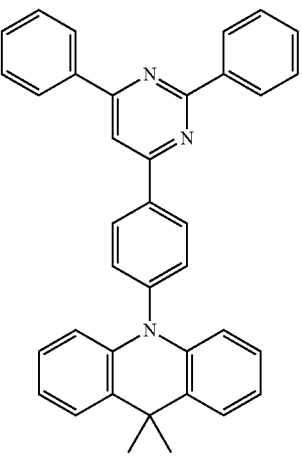
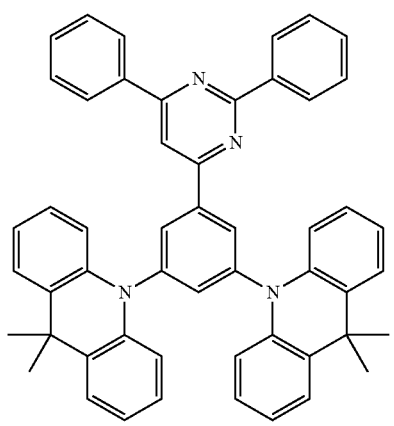
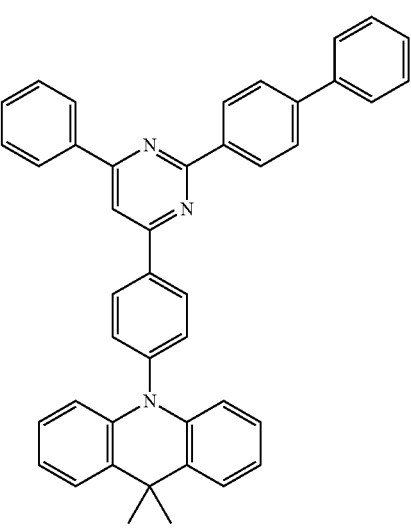
[Formula 110]
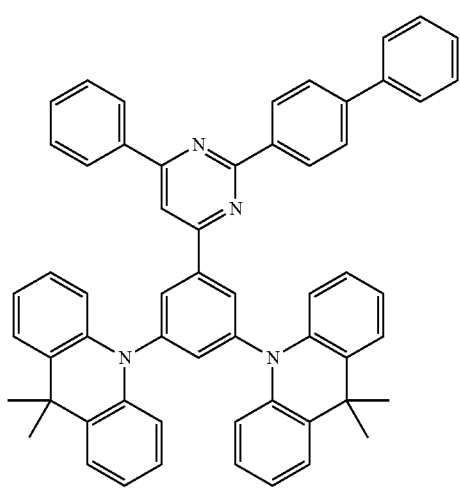
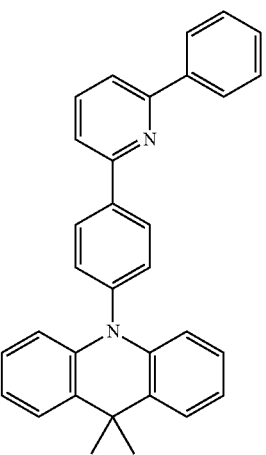

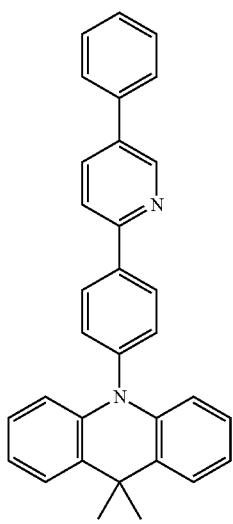
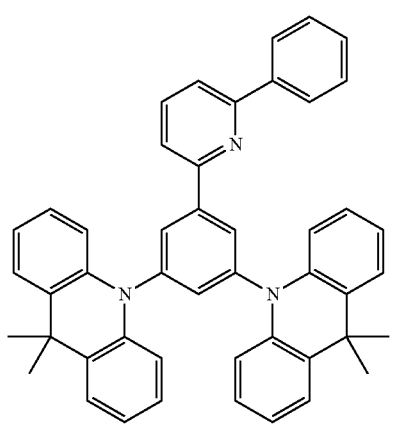
[Formula 111]
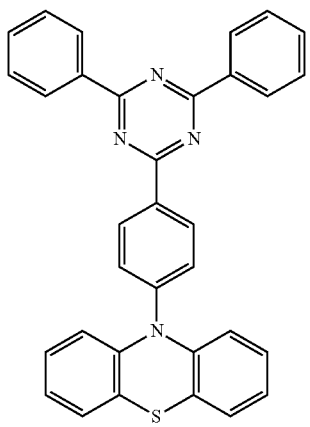
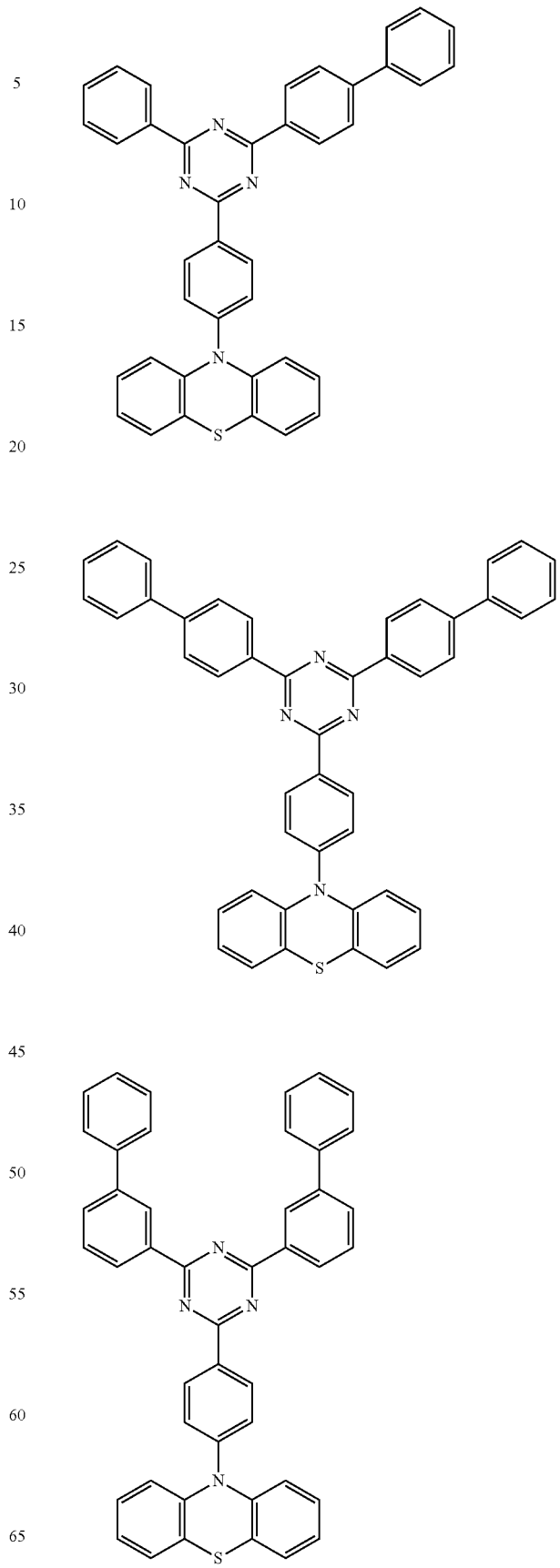

147
-continued
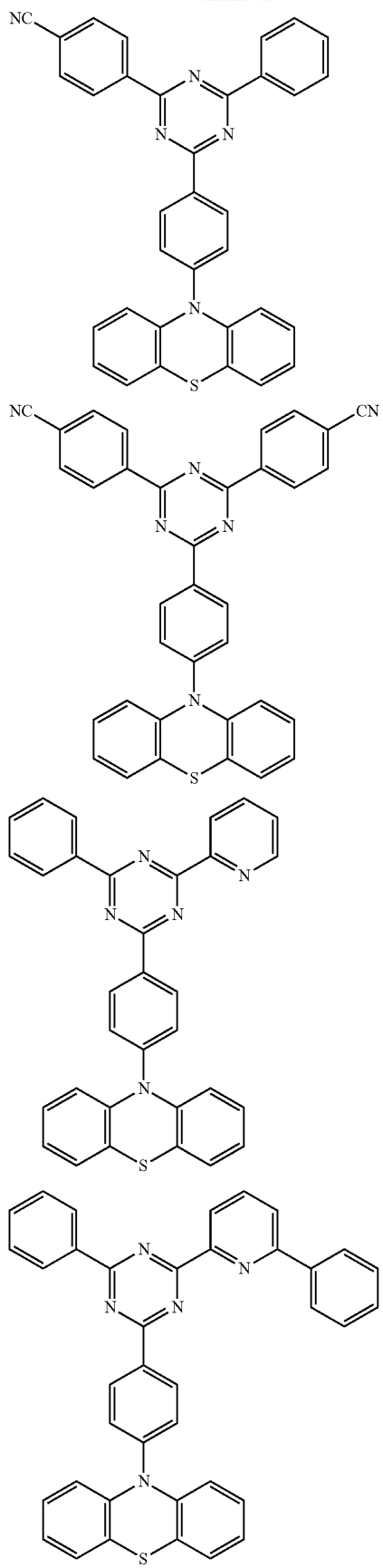
148
-continued
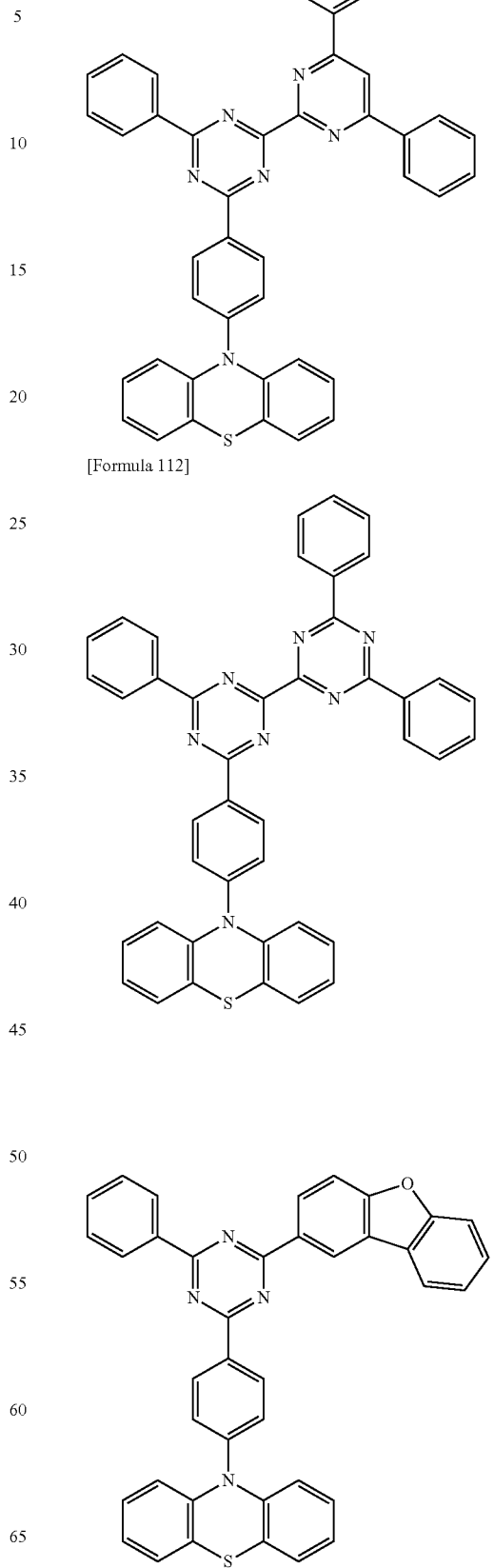
[Formula 112]

149
-continued
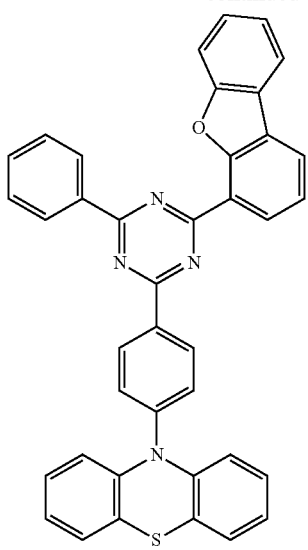
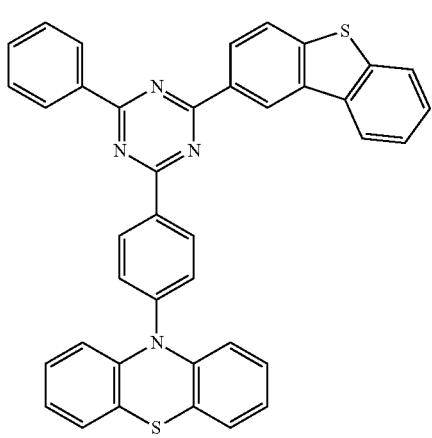
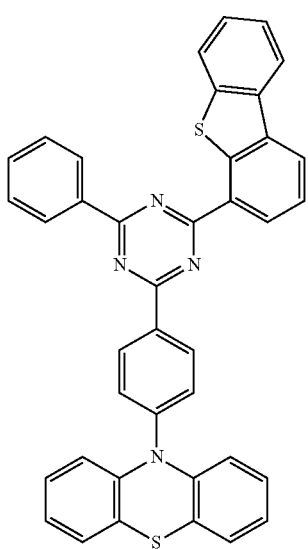
150
-continued
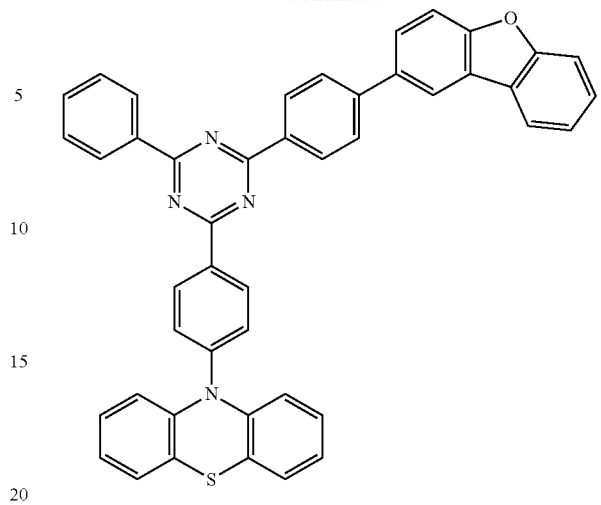
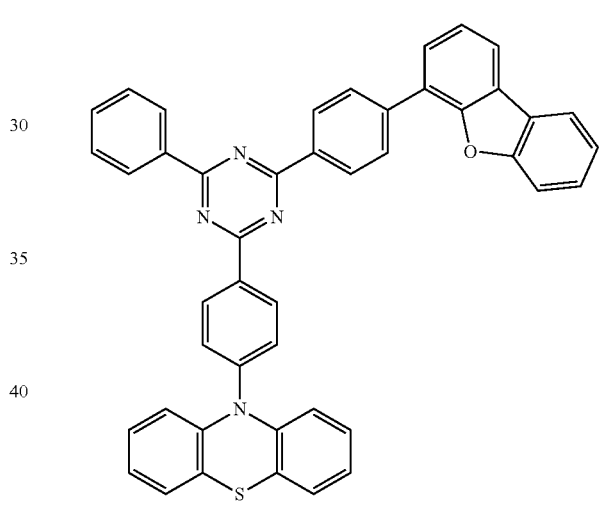
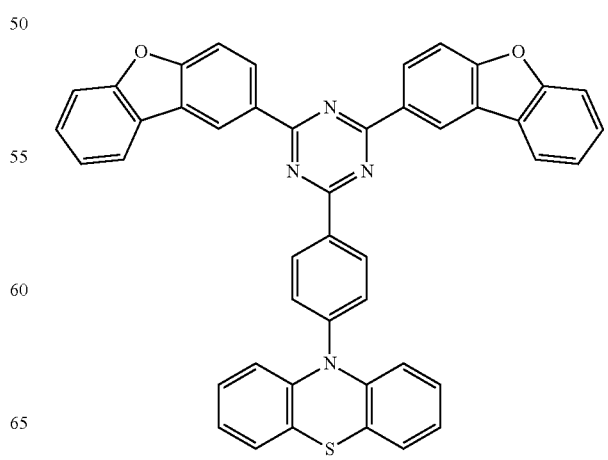

151
-continued
[Formula 113]
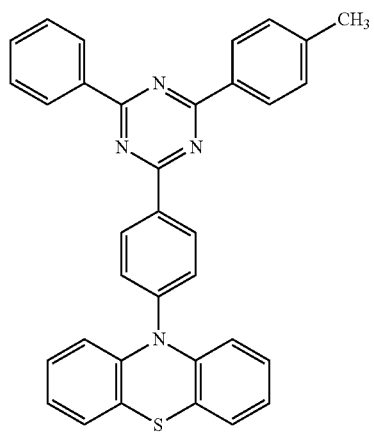
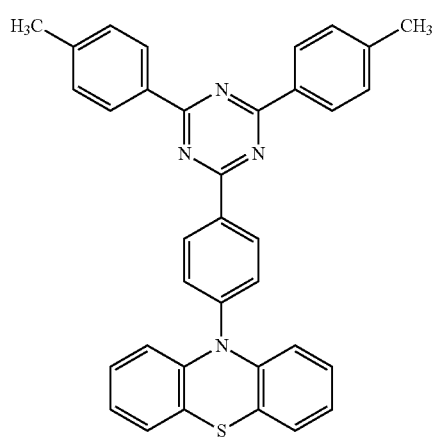
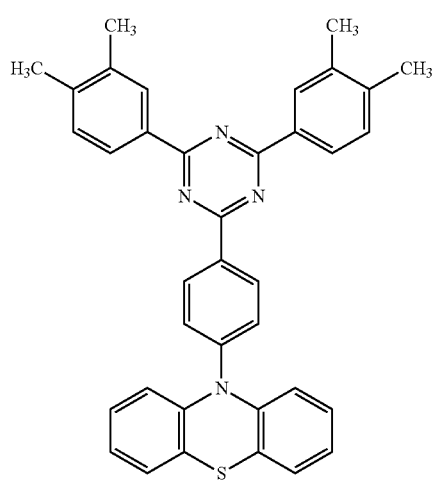
152
-continued
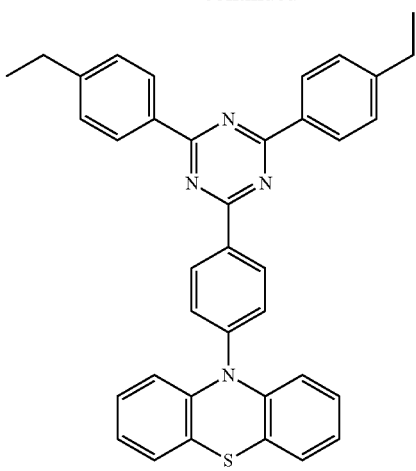
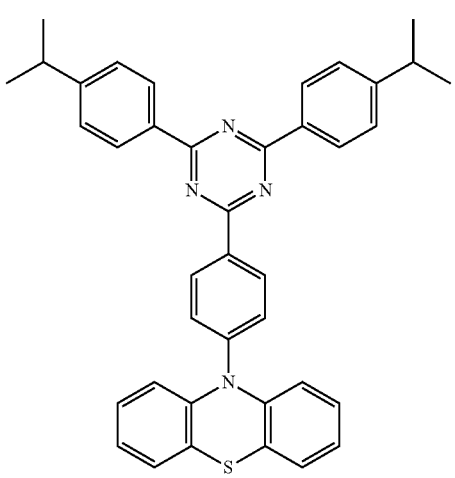
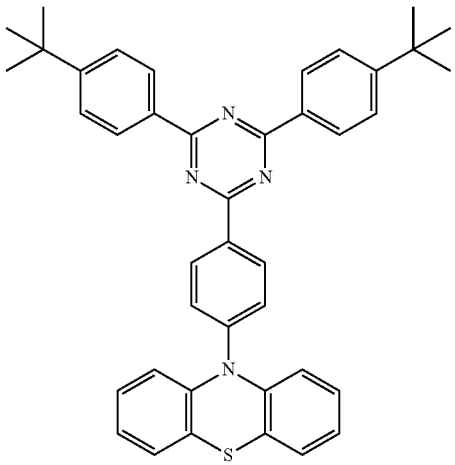

153
-continued
[Formula 114]
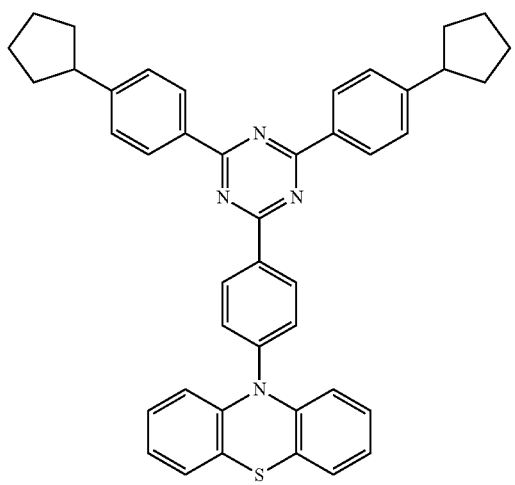
154
-continued
[Formula 115]
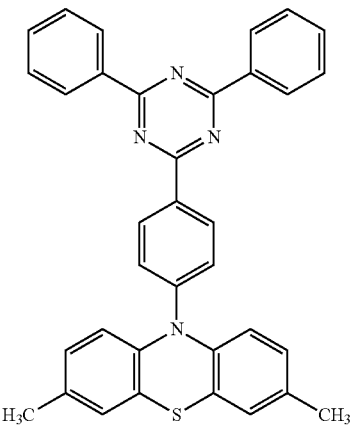
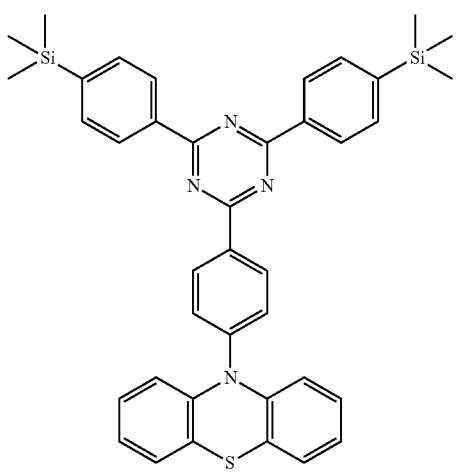
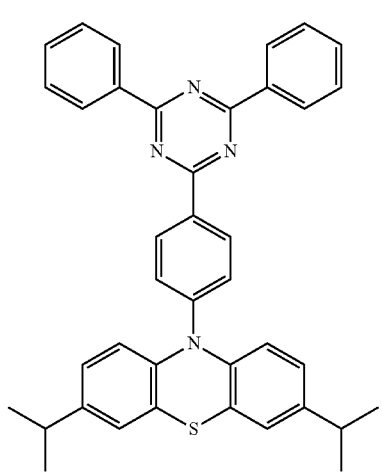

155
-continued
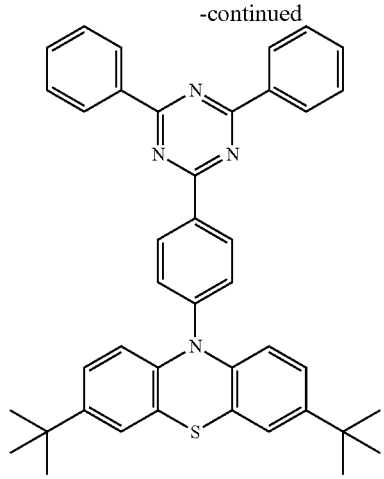
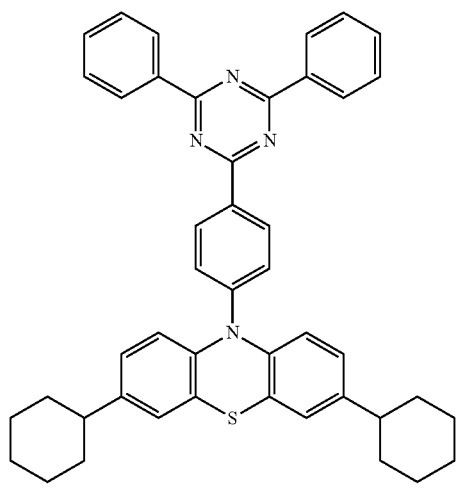
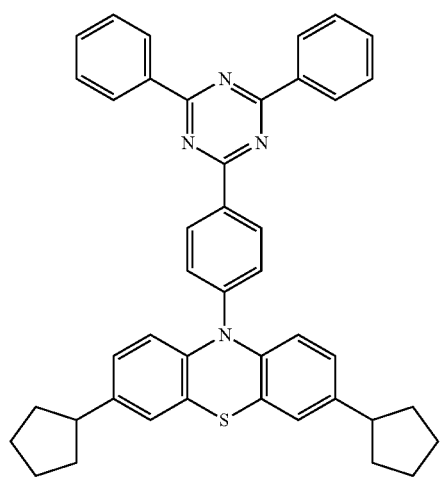
156
-continued
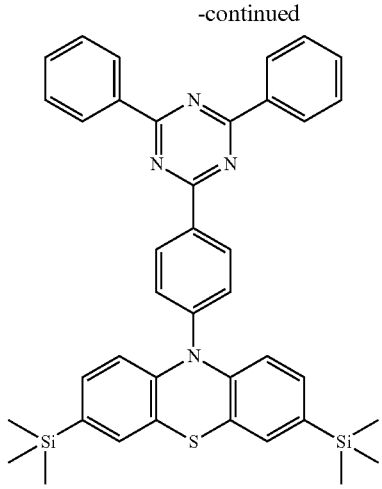
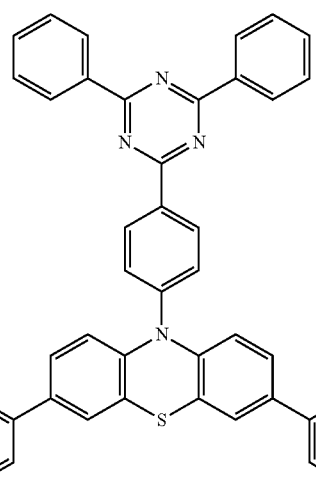
[Formula 116]
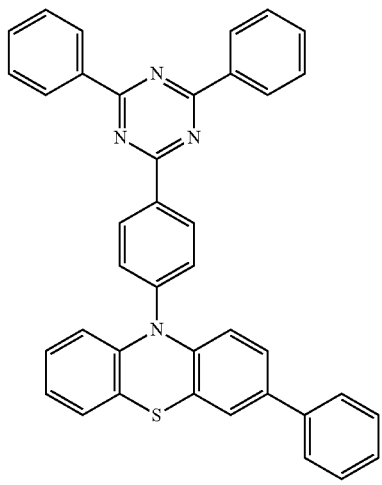

157
-continued
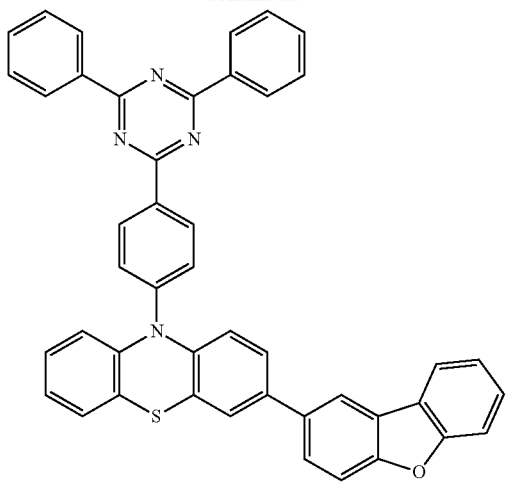
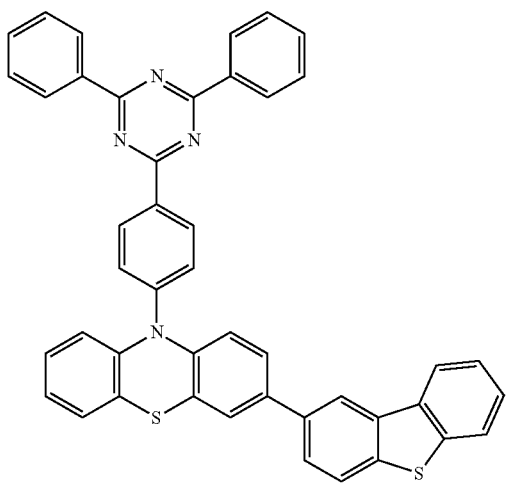
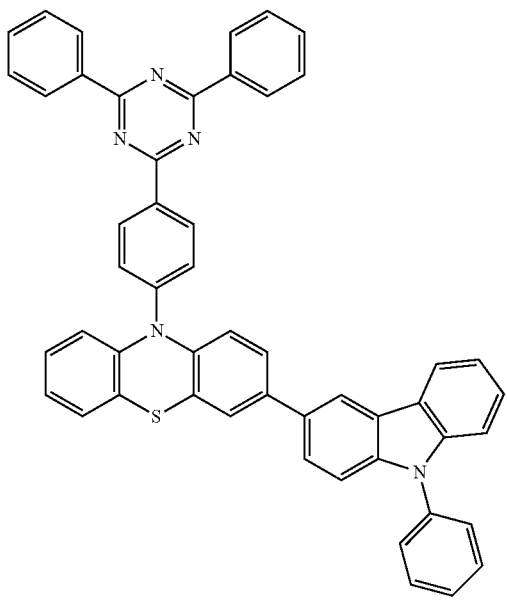
158
-continued
[Formula 117]
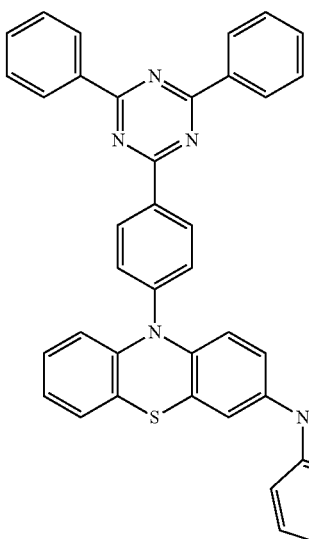
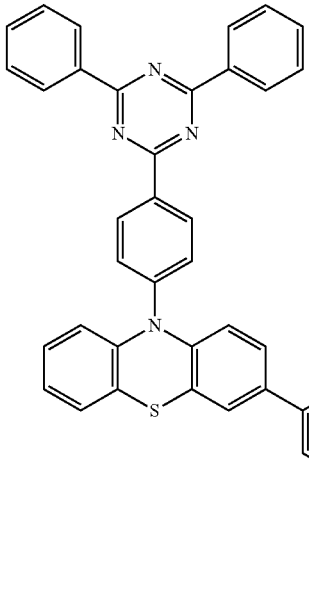

159
-continued
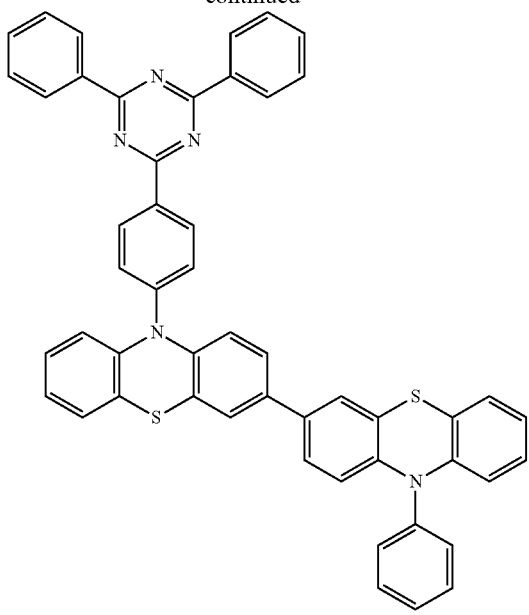
160
-continued
[Formula 118]
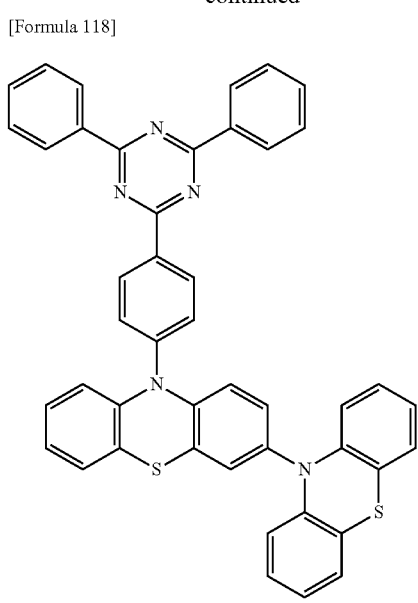
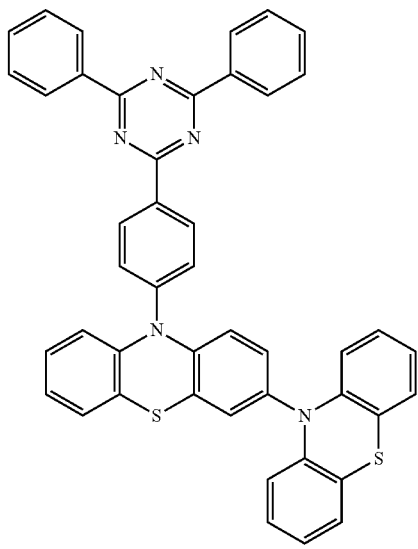
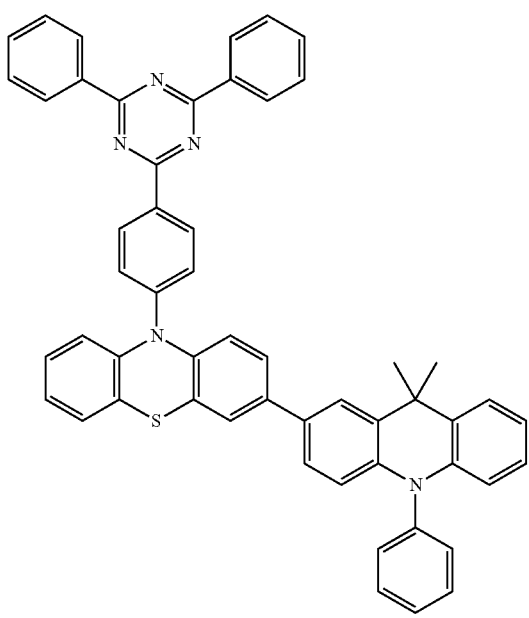
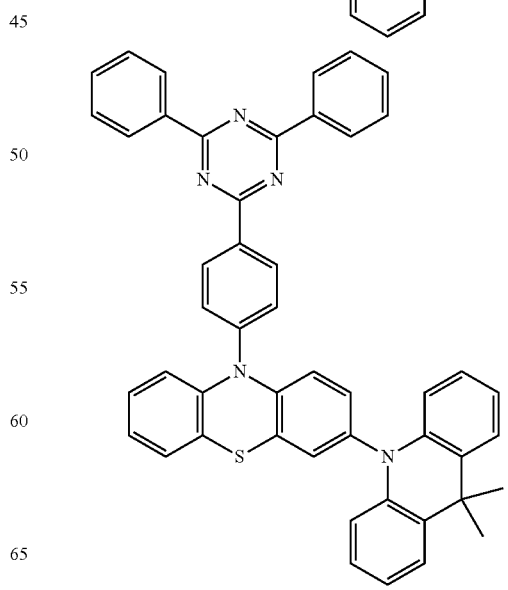

161
-continued
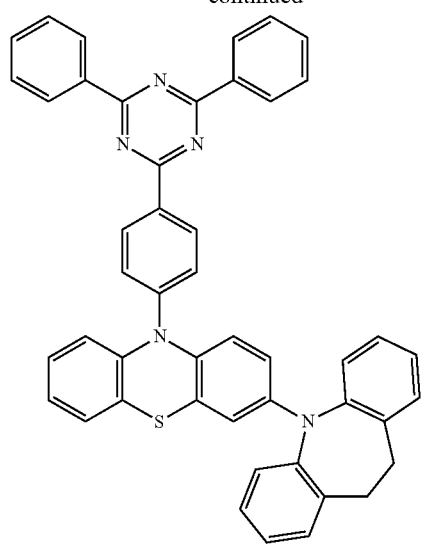
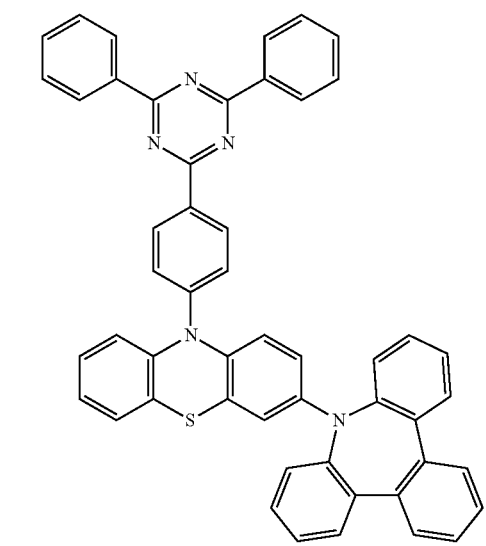
162
-continued
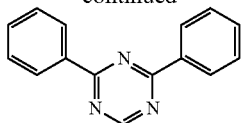
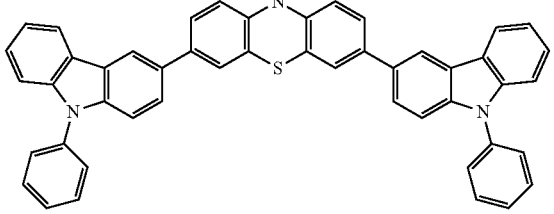
[Formula 119]
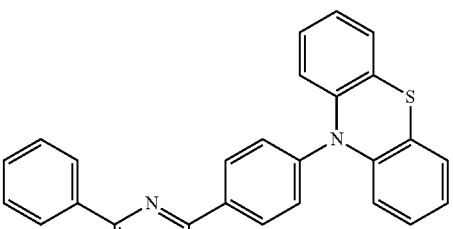
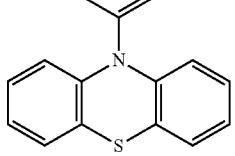
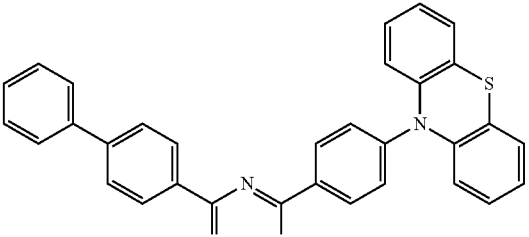
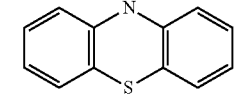

163
-continued
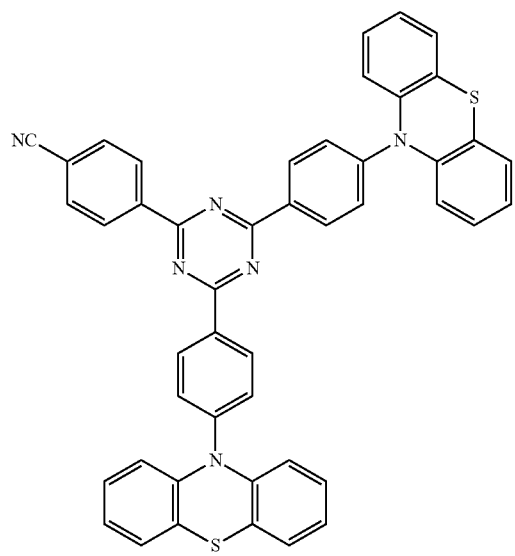
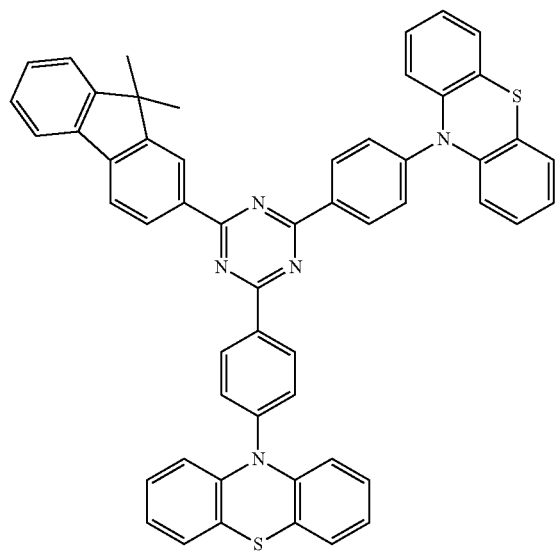
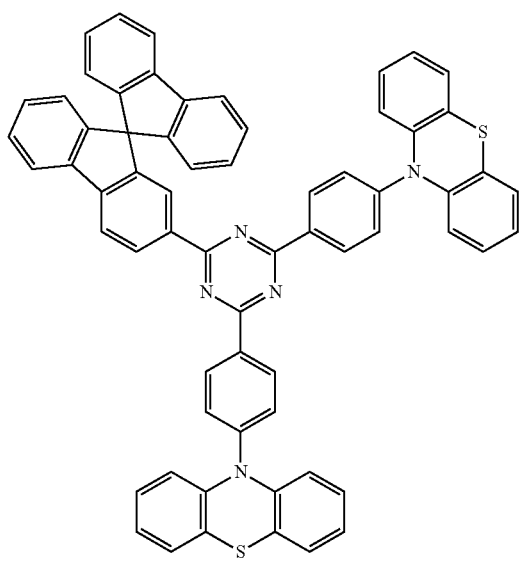
164
-continued
[Formula 120]
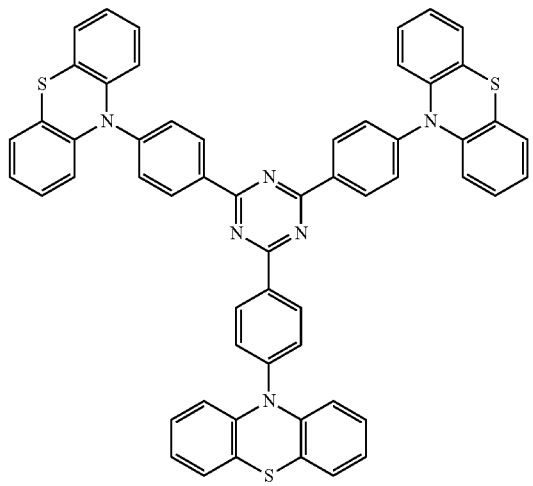
[Formula 121]
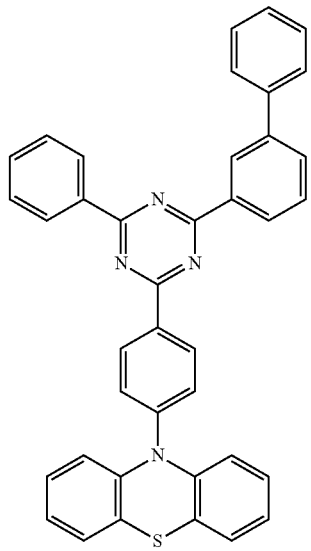
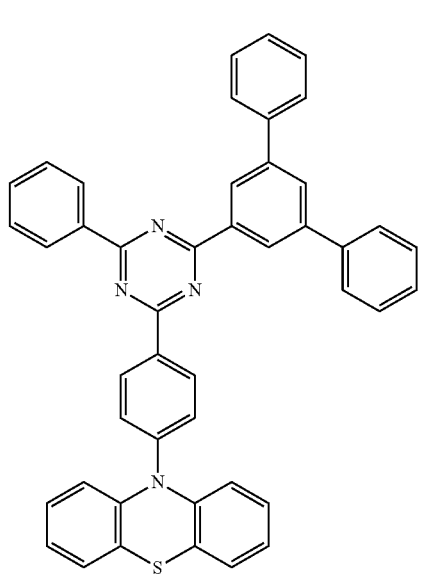

-continued
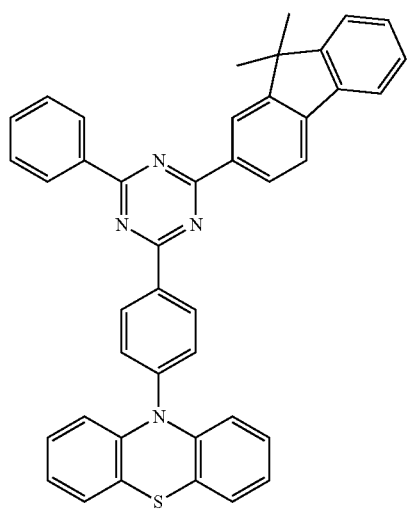
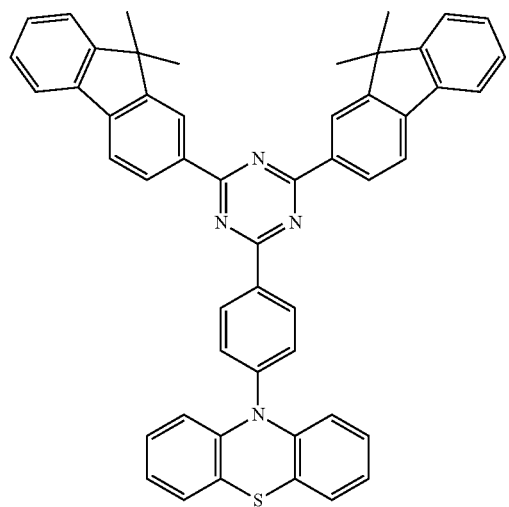
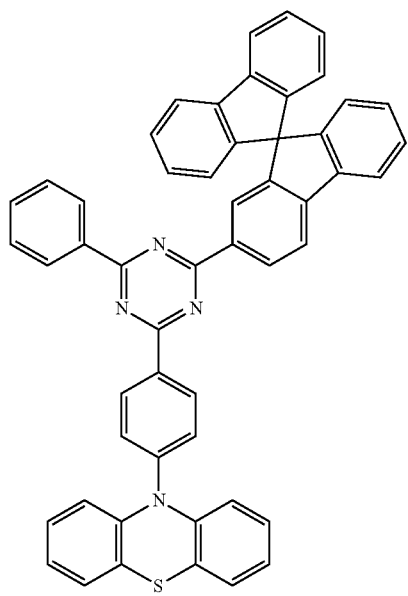
-continued
[Formula 122]
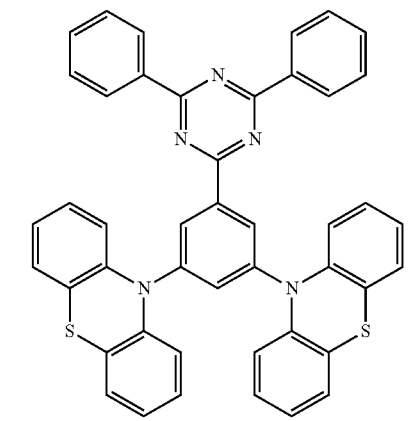
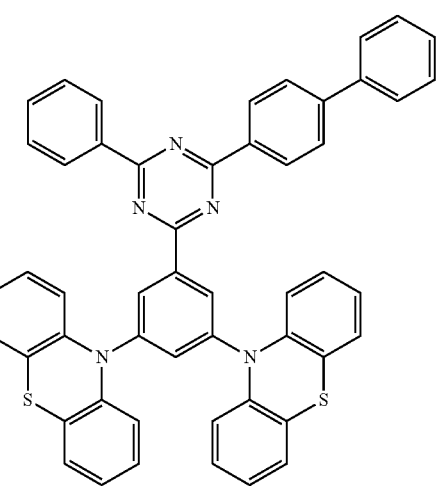
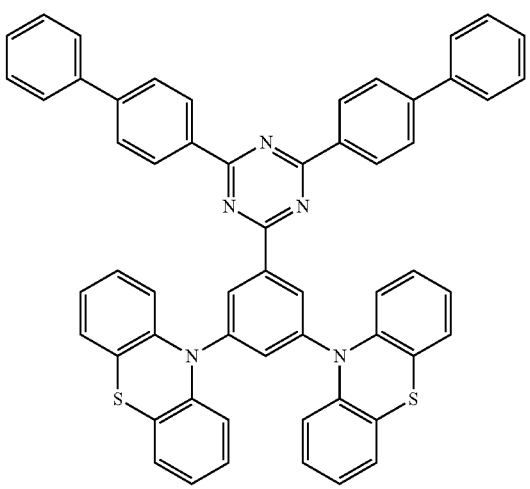

167
-continued
[Formula 123]
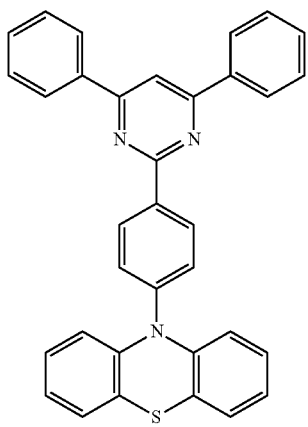
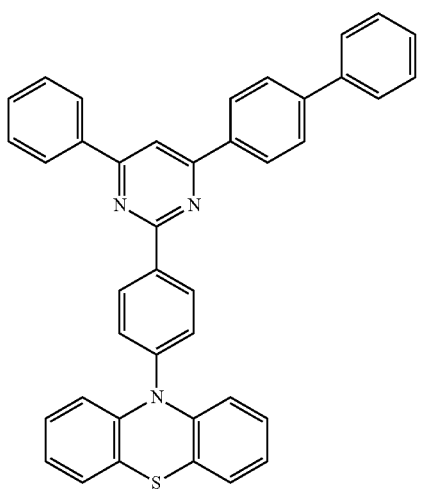
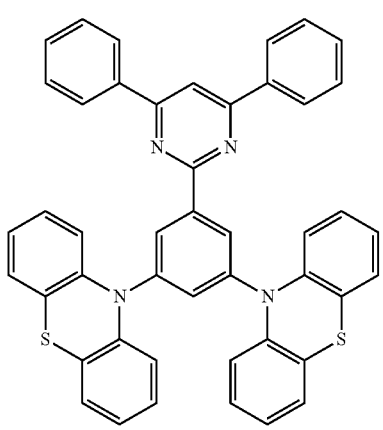
168
-continued
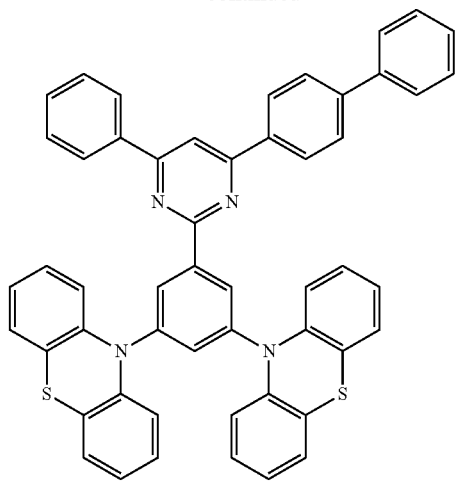
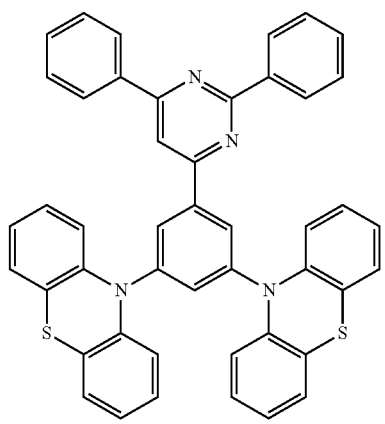
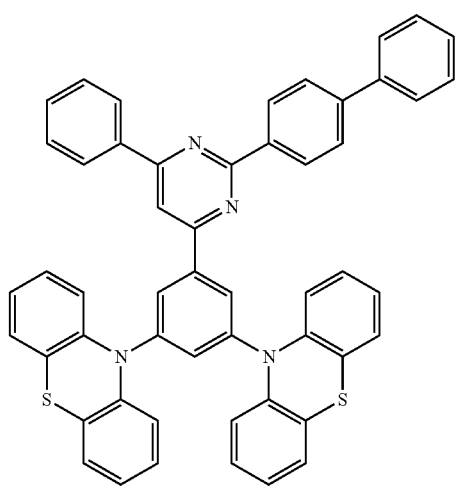

169
-continued
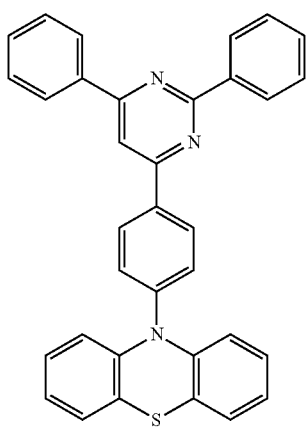
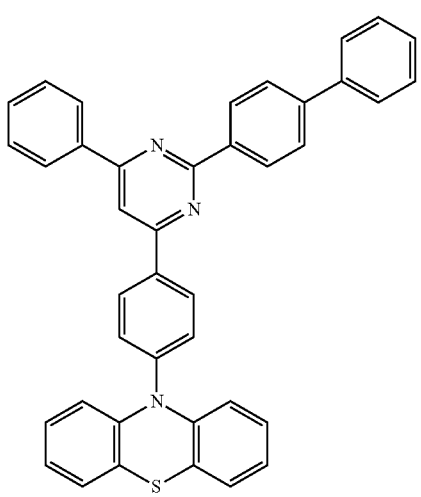
[Formula 124]
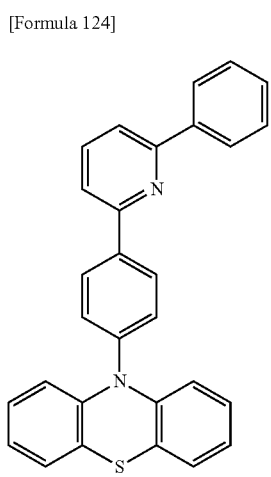
170
-continued
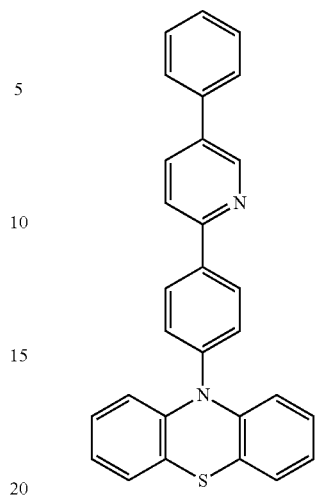
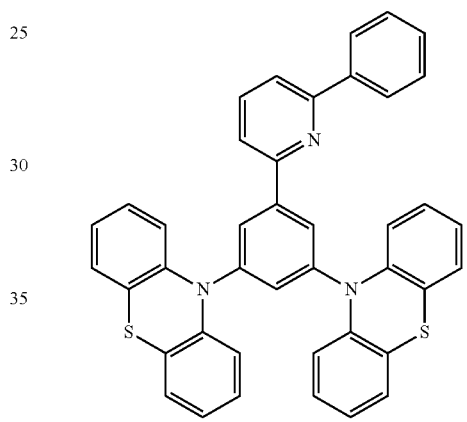
[Formula 125]
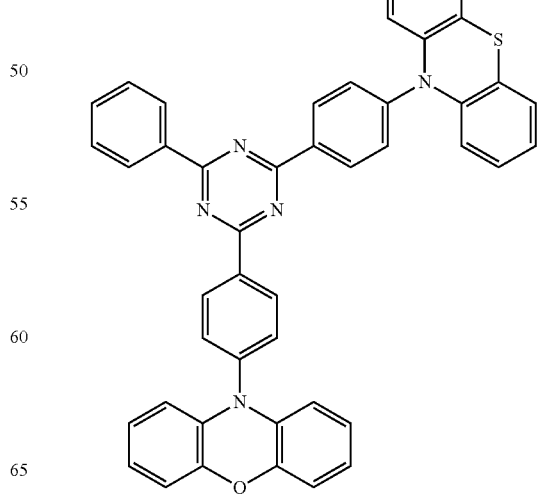

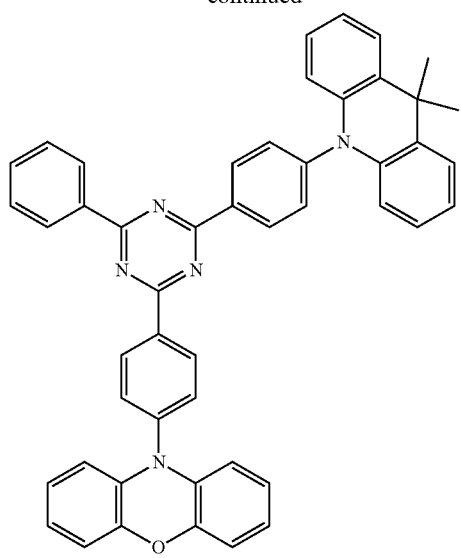
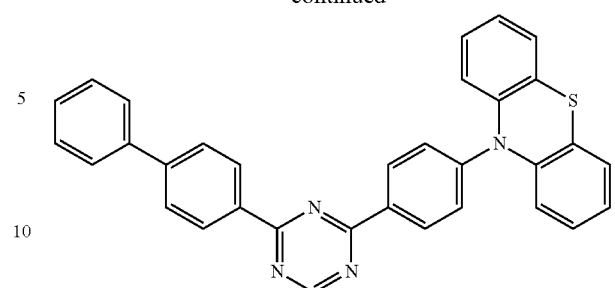
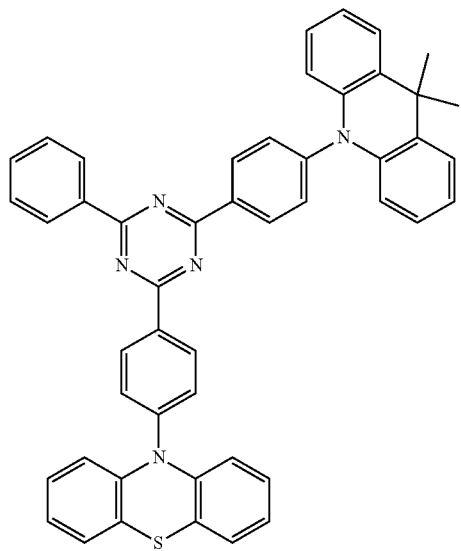
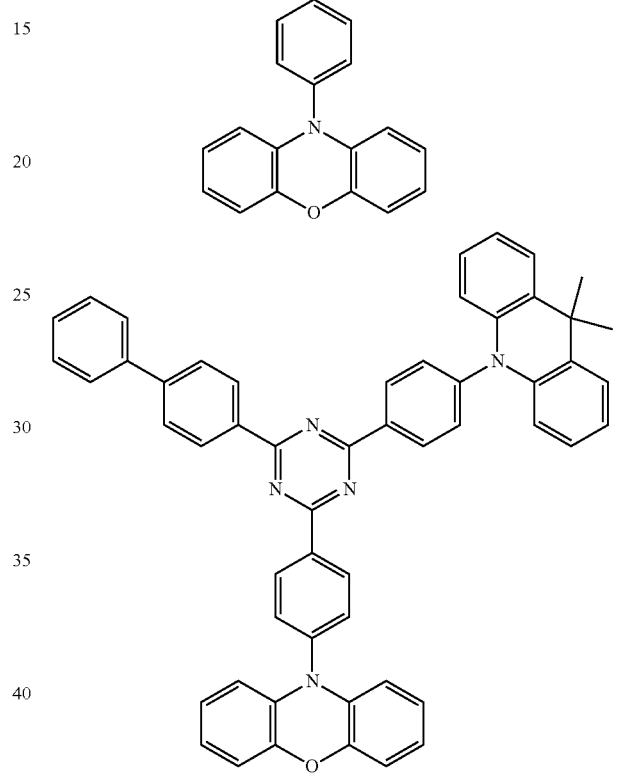
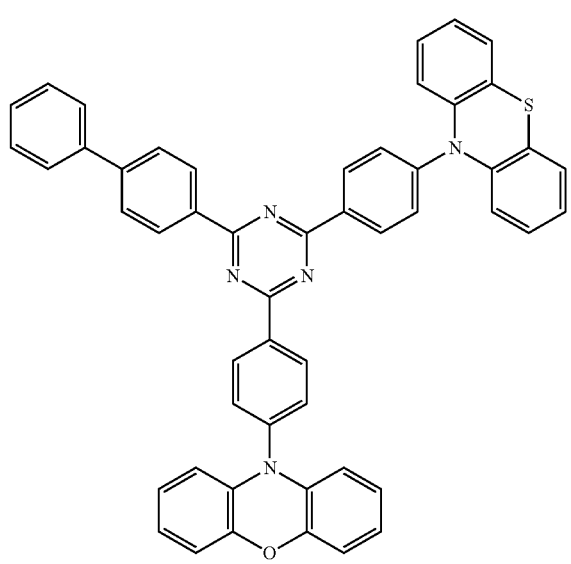
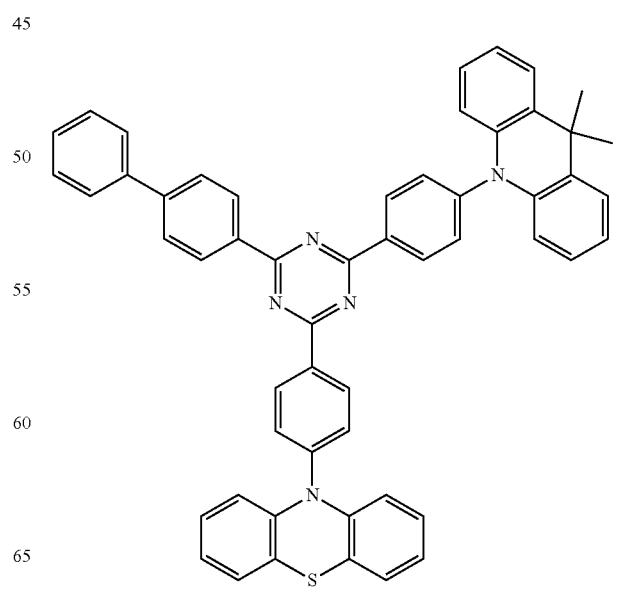

[Formula 126]
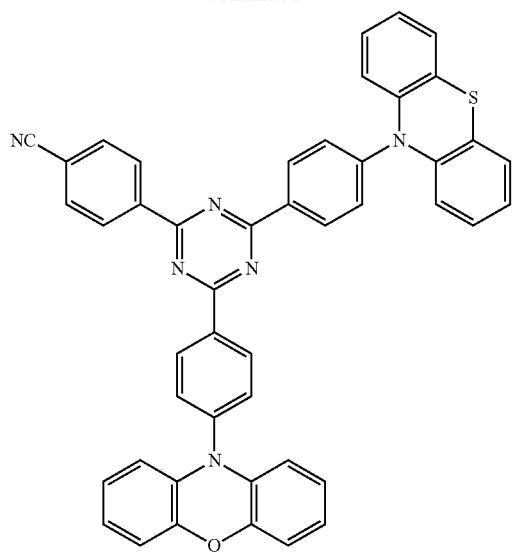
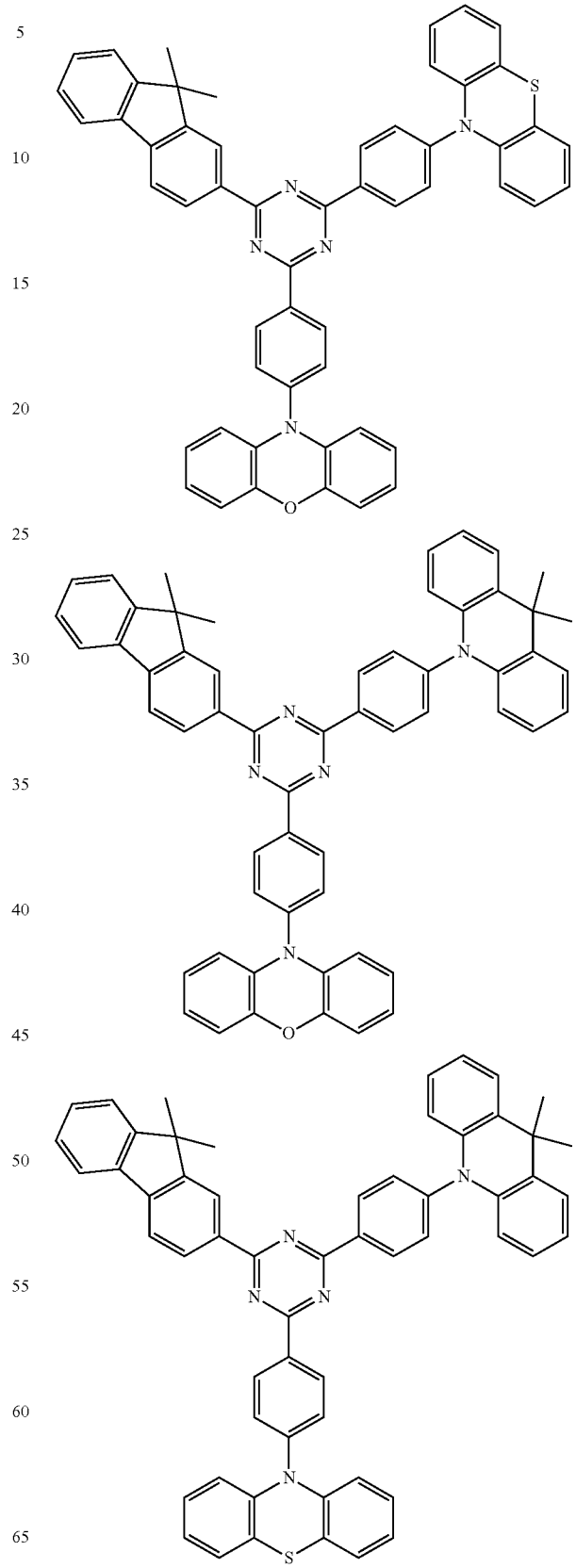

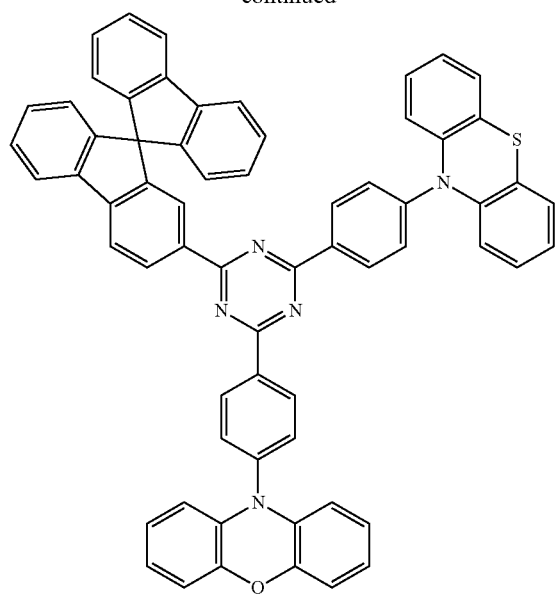
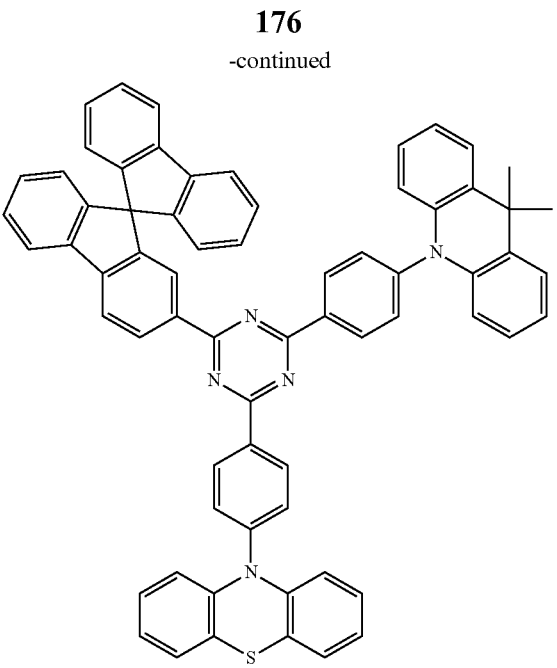
[Formula 127]
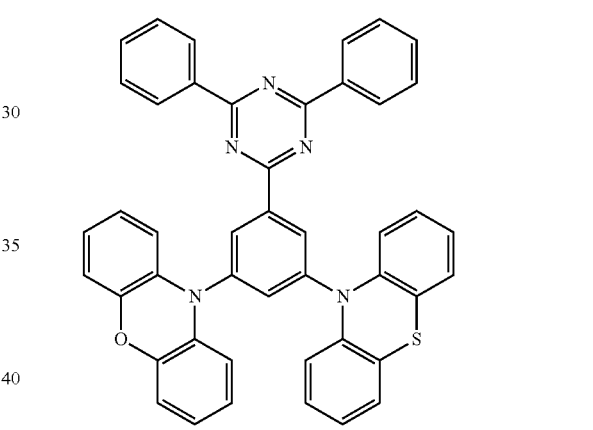
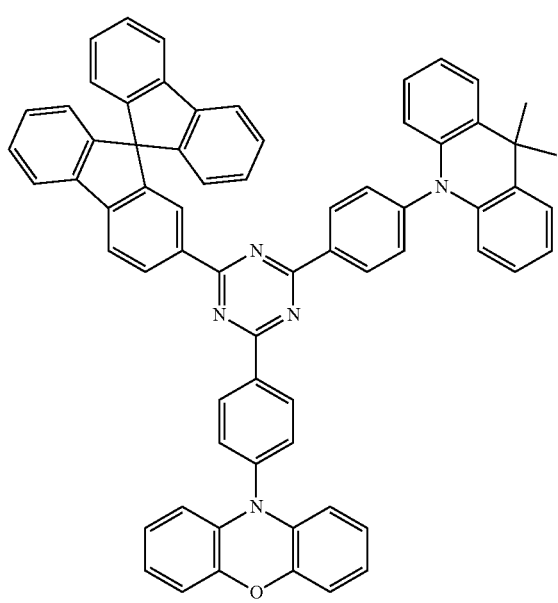
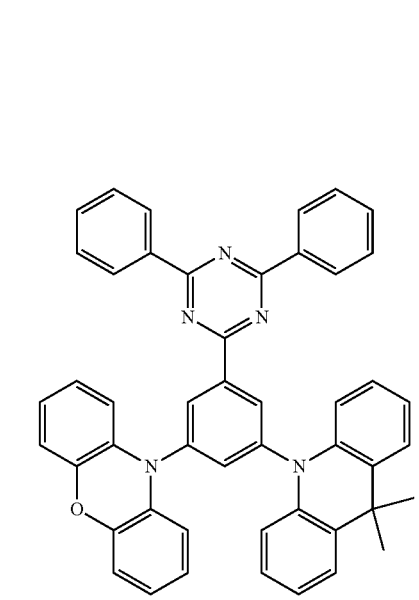

177
-continued
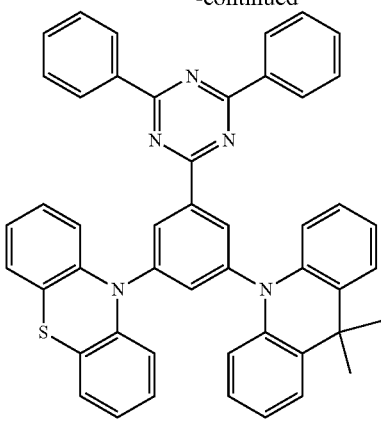
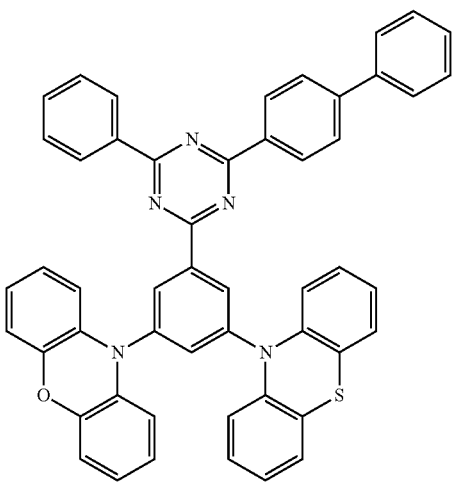
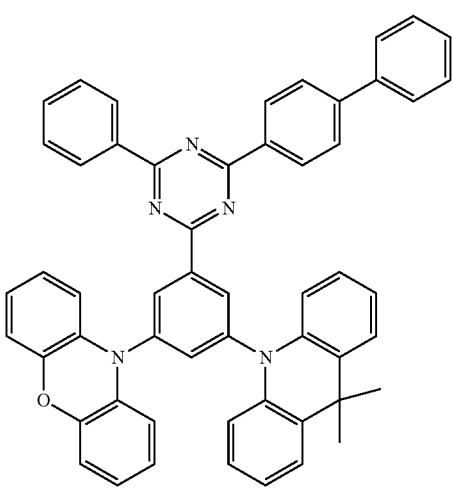
178
-continued
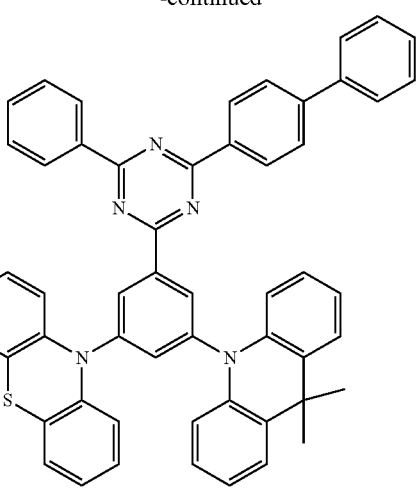
[Formula 128]
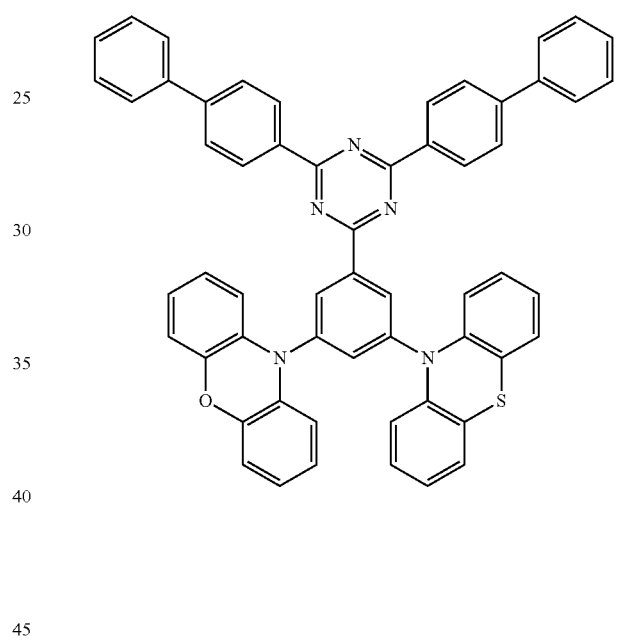
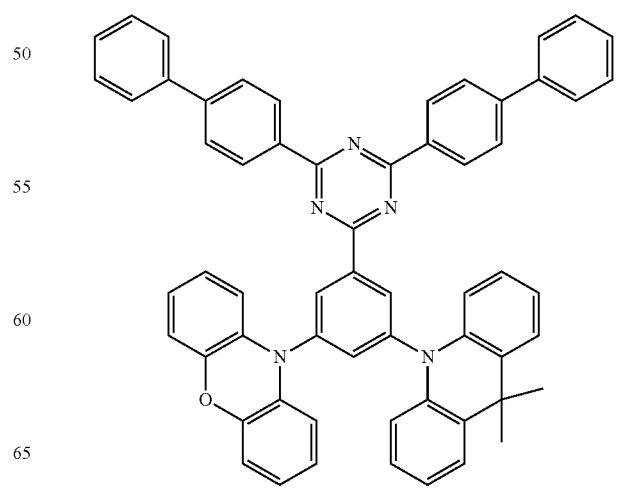

179
-continued
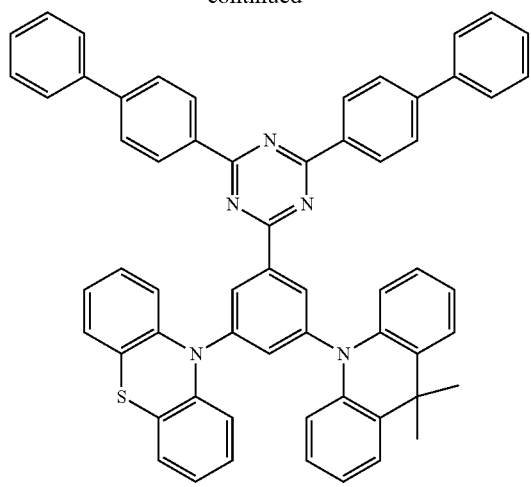
[Formula 129]
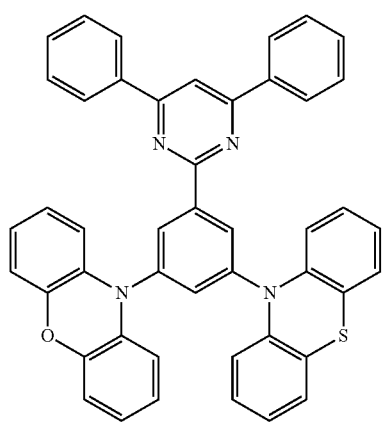
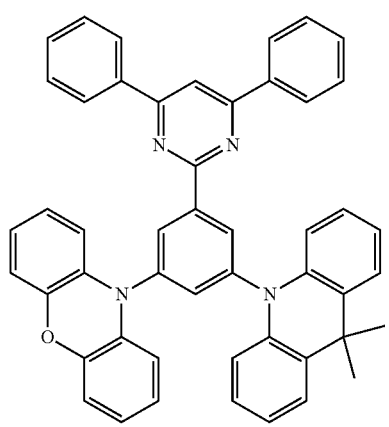
180
-continued
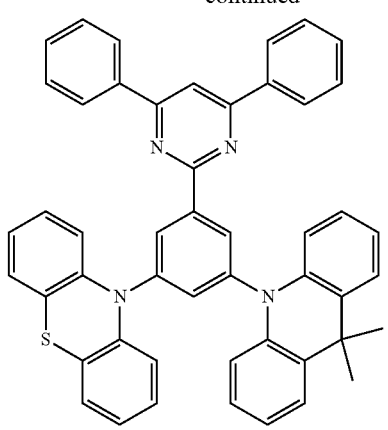
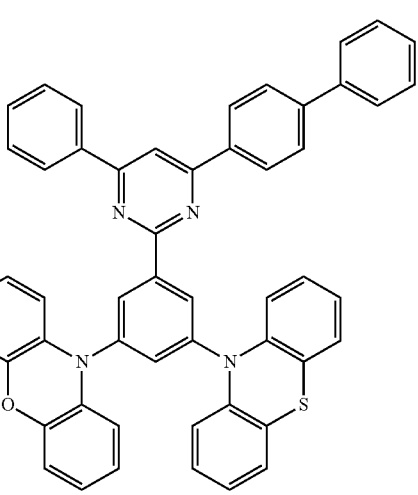
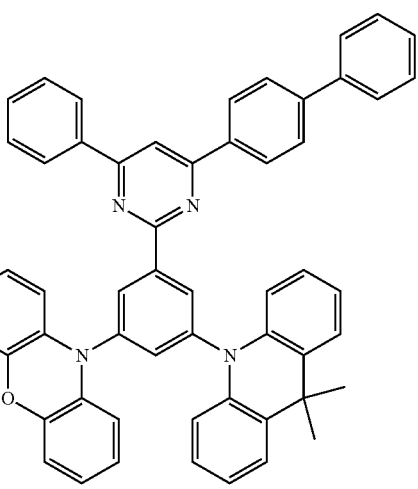

181
-continued
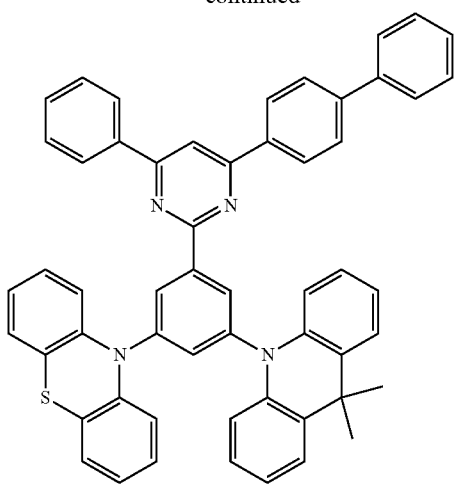
[Formula 130]
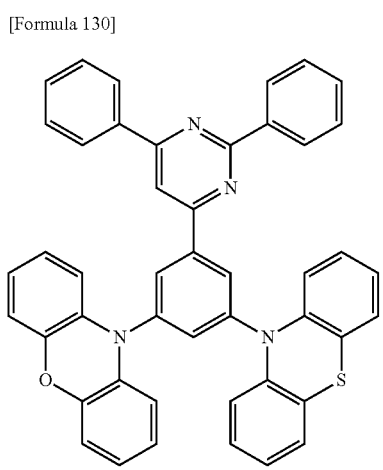
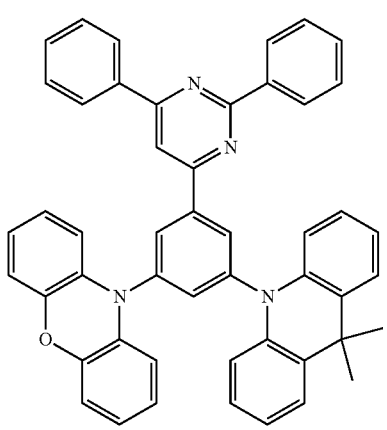
182
-continued
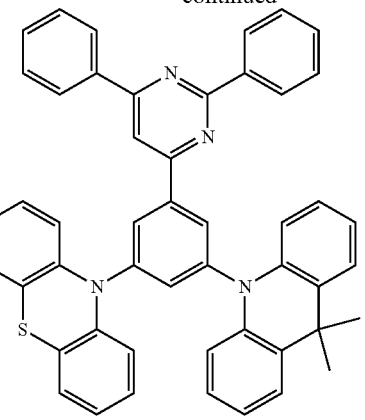
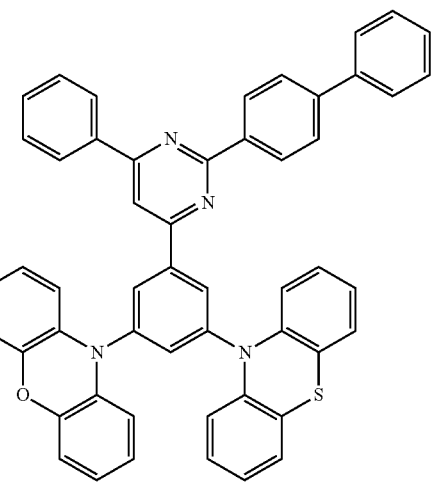
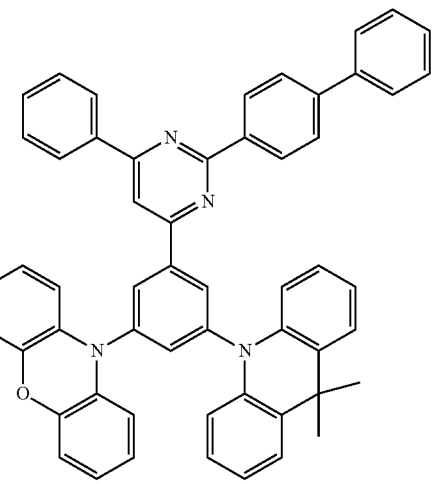

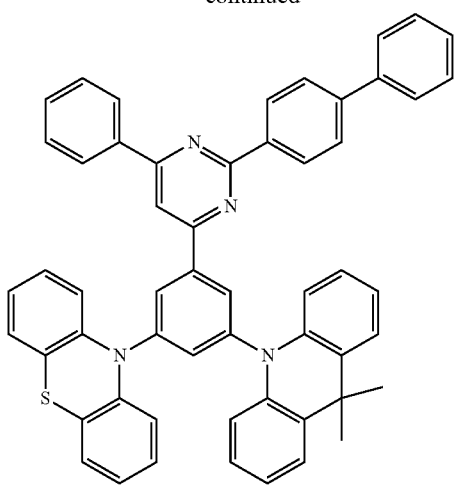
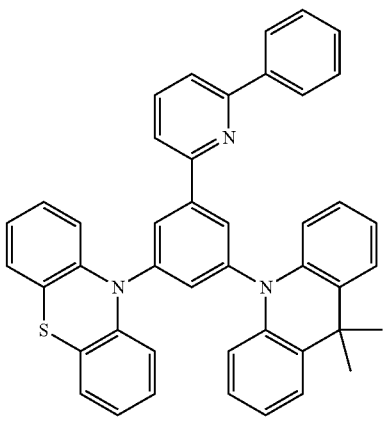
[Formula 131]
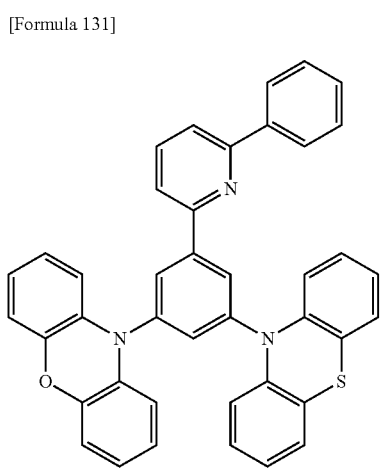
[Formula 132]
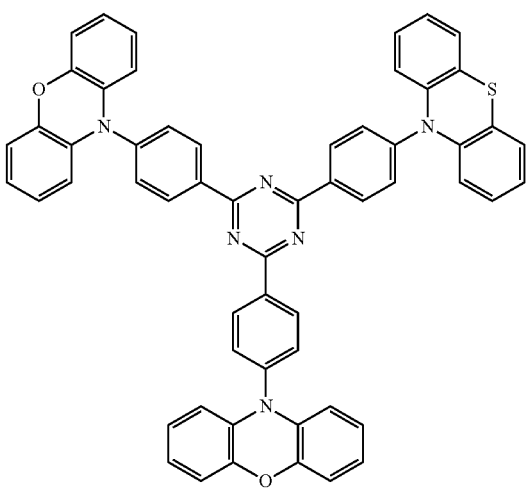
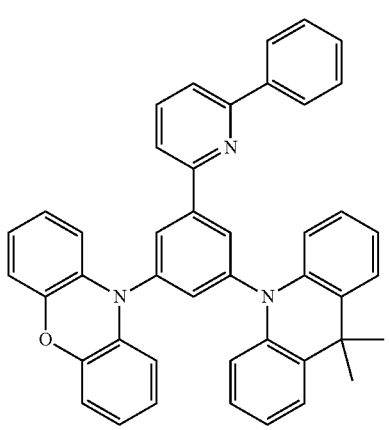
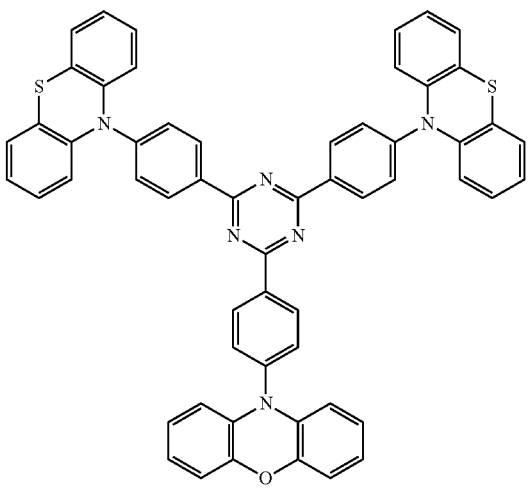

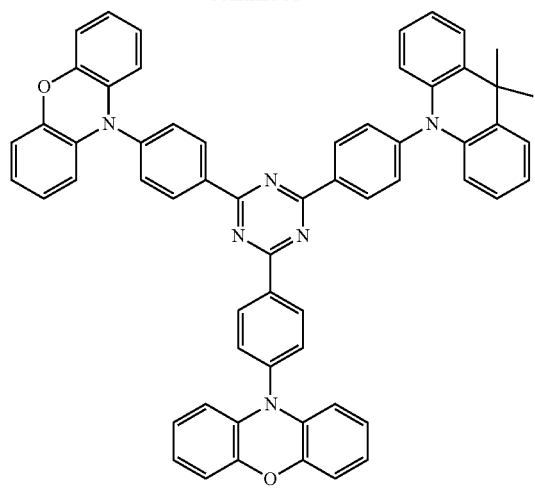
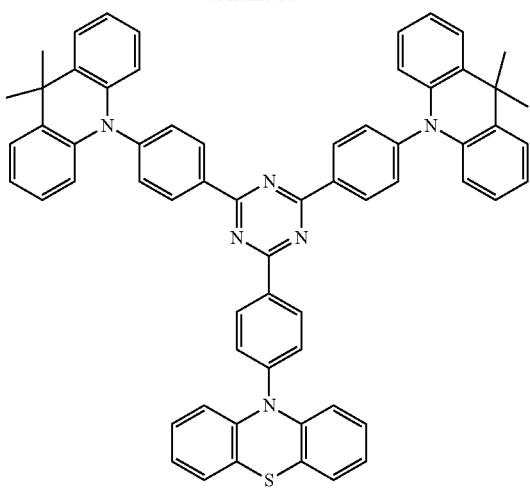
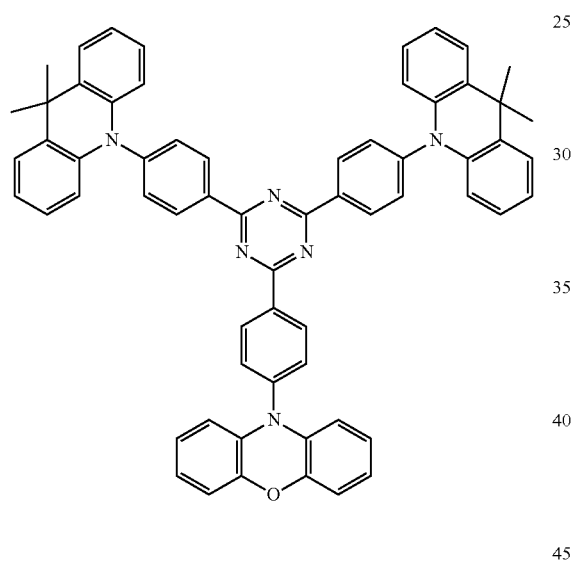
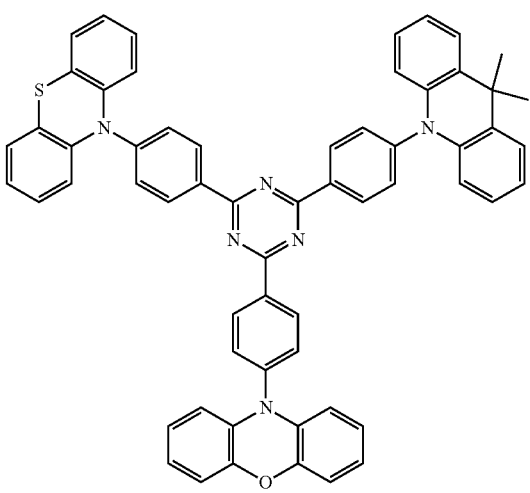
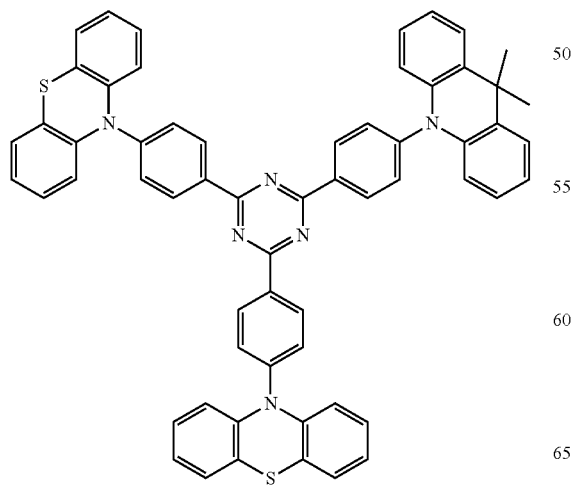
[Formula 133]
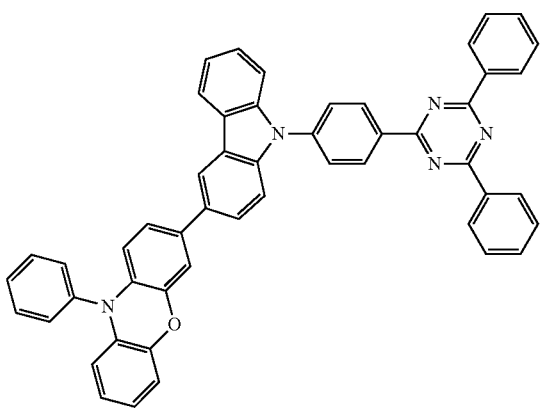

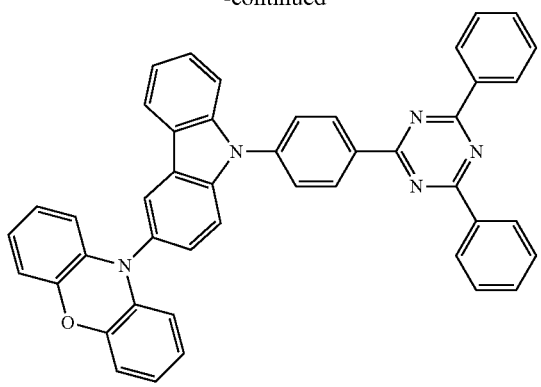
[Formula 134]
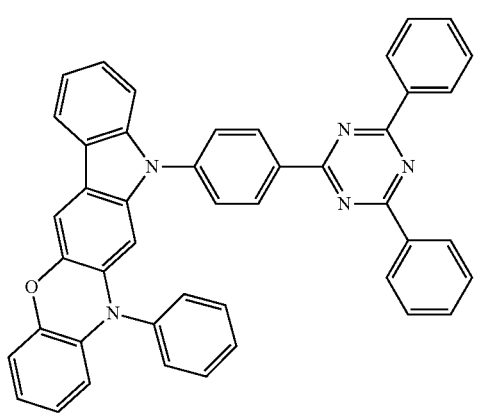
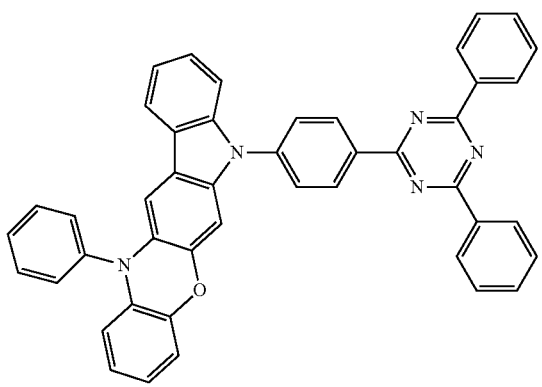
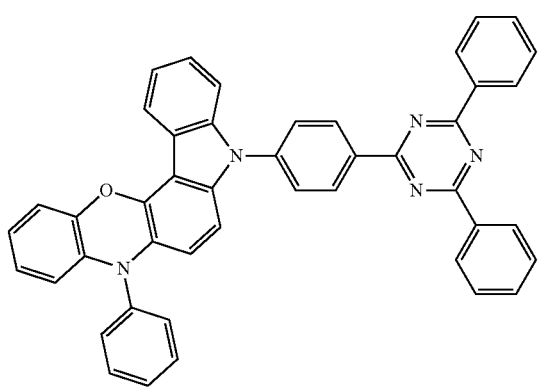
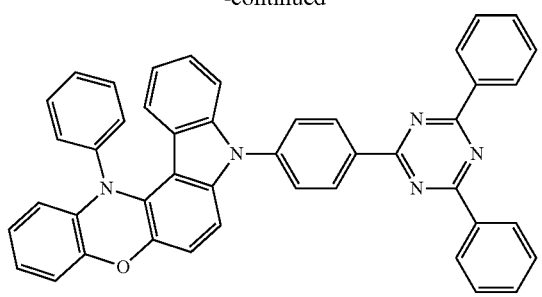
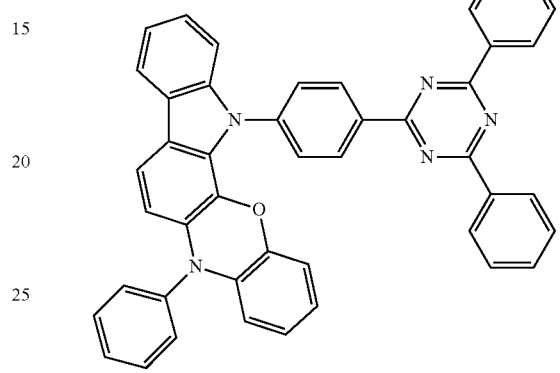
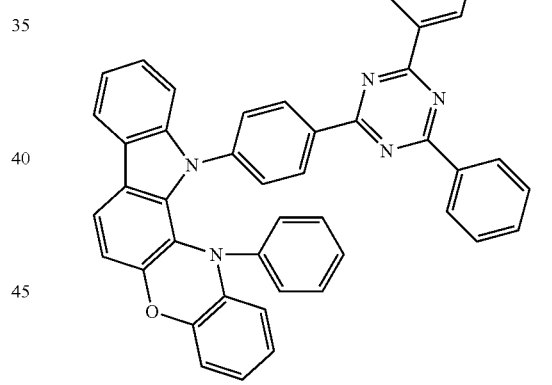
[Formula 135]
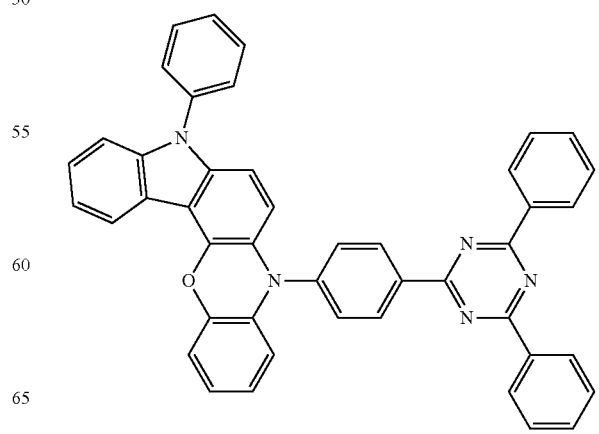

-continued

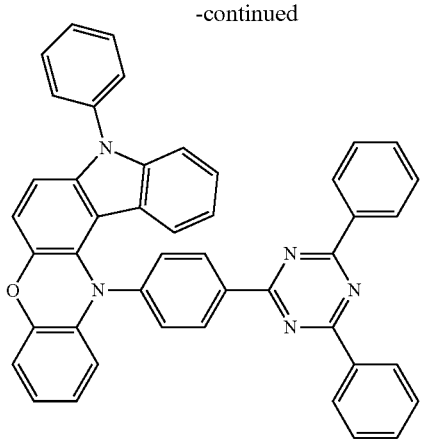

It is preferable that the organic EL device according to the exemplary embodiment does not contain a metal complex. The metal complex is exemplified by a phosphorescent organic metal complex. In other words, it is preferable that the emitting layer does not contain a phosphorescent material.

The compound represented by the formula (1) and the compound represented by the formula (2) can be synthesized by a known synthetic method.

By containing the compound represented by the formula (1) and the compound represented by the formula (2) in the emitting layer, the drive voltage of the organic EL device can be reduced and the luminous efficiency thereof can be improved. Moreover, such an organic EL device can emit light with a high efficiency in a low current density area of approximately 0.01 mA/cm$^2$. Further, even in a high current density area approximately from 1 mA/cm$^2$ to 10 mA/cm$^2$, reduction of the luminous efficiency can be inhibited.

A film thickness of the emitting layer is preferably in a range of 5 nm to 50 nm, more preferably in a range of 7 nm to 50 nm and most preferably in a range of 10 nm to 50 nm. The thickness of less than 5 nm may cause difficulty in forming the emitting layer and in controlling chromaticity, while the thickness of more than 50 nm may raise drive voltage.

In the emitting layer, a ratio of the host material and the dopant material is preferably in a range of 99:1 to 50:50 at a mass ratio.

Substrate

The organic EL device according to the exemplary embodiment is formed on a light-transmissive substrate. The light-transmissive substrate supports the anode, organic compound layer, cathode and the like of the organic EL device. The light-transmissive substrate is preferably a smoothly-shaped substrate that transmits 50% or more of light in a visible region of 400 nm to 700 nm.

The light-transmissive plate is exemplified by a glass plate and a polymer plate.

The glass plate is particularly formed of soda-lime glass, barium/strontium-containing glass, lead glass, aluminosilicate glass, borosilicate glass, barium borosilicate glass, quartz and the like.

The polymer plate is formed of polycarbonate, acryl, polyethylene terephthalate, polyether sulfide and polysulfone.

Anode and Cathode

The anode of the organic EL device injects holes into the emitting layer, so that it is efficient that the anode has a work function of 4.5 eV or higher.

Exemplary materials for the anode are indium-tin oxide (ITO), tin oxide (NESA), indium zinc oxide, gold, silver, platinum and copper.

When light from the emitting layer is to be emitted through the anode, the anode preferably transmits more than 10% of the light in the visible region. Sheet resistance of the anode is preferably several hundreds Q/sq. or lower. The thickness of the anode is typically in the range of 10 nm to 1 μm, and preferably in the range of 10 nm to 200 nm, though it depends on the material of the anode.

The cathode is preferably formed of a material with smaller work function in order to inject electrons into the emitting layer.

Although a material for the cathode is not particularly limited, examples of the material are indium, aluminium, magnesium, alloy of magnesium and indium, alloy of magnesium and aluminium, alloy of aluminium and lithium, alloy of aluminium, scandium and lithium, and alloy of magnesium and silver.

Like the anode, the cathode may be made by forming a thin film on, for instance, the electron transporting layer and the electron injecting layer by a method such as vapor deposition. In addition, the light from the emitting layer may be emitted through the cathode. When light from the emitting layer is to be emitted through the cathode, the cathode preferably transmits more than 10% of the light in the visible region. Sheet resistance of the cathode is preferably several hundreds Q/sq. or lower. The thickness of the cathode is typically in the range of 10 nm to 1 μm, and preferably in the range of 50 nm to 200 nm, though it depends on the material of the cathode.

Hole Injecting•Transporting Layer

The hole injection/transport layer helps injection of holes to the emitting layer and transport the holes to an emitting region. A compound having a large hole mobility and a small ionization energy is used as the hole injection/transport layer.

A material for forming the hole injecting layer and the hole transporting layer is preferably a material for transporting the holes to the emitting layer at a lower electric field intensity. For instance, an aromatic amine compound is preferably used. The material for the hole injecting layer is preferably a porphyrin compound, an aromatic tertiary amine compound or a styryl amine compound, particularly preferably the aromatic tertiary amine compound such as hexacyanohexaazatriphenylene (HAT).

Electron Injecting•Transporting Layer

The electron injecting•transporting layer helps injection of the electrons into the emitting layer and transports the electrons to an emitting region. A compound having a large electron mobility is used as the electron injecting•transporting layer.

A preferable example of the compound used as the electron injecting•transporting layer is an aromatic heterocyclic compound having at least one heteroatom in a molecule. Particularly, a nitrogen-containing cyclic derivative is preferable. The nitrogen-containing cyclic derivative is preferably a heterocyclic compound having a nitrogen-containing six-membered or five-membered ring skeleton, or a fused aromatic cyclic compound having a nitrogen-containing six-membered or five-membered ring skeleton. Moreover, the electron injecting•transporting layer may contain an alkali metal and the like.

In the organic EL device in the exemplary embodiment, in addition to the aforementioned compounds, any compound selected from compounds to be used in a typical organic El device is usable as a compound for the organic compound layer other than the emitting layer.

Layer Formation Method(s)

A method for forming each layer of the organic EL device in the exemplary embodiment is subject to no limitation except for the above particular description. However, known methods of dry film-forming such as vacuum deposition, sputtering, plasma or ion plating and wet film-forming such as spin coating, dipping, flow coating or ink-jet are applicable.

Thickness

The thickness of each organic layer of the organic EL device in the exemplary embodiment is subject to no limitation except for the thickness particularly described above. However, the thickness is typically preferably in a range of several nanometers to 1 μm because an excessively thin film is likely to entail defects such as a pin hole while an excessively thick film requires high applied voltage and deteriorates efficiency.

Second Exemplary Embodiment

Arrangement(s) of an organic EL device according to a second exemplary embodiment will be described. In the description of the second exemplary embodiment, the same components as those in the first exemplary embodiment are denoted by the same reference signs and names to simplify or omit an explanation of the components. In the second exemplary embodiment, the same materials and compounds as described in the first exemplary embodiment are usable unless particularly described.

The organic EL device in the second exemplary embodiment has the same device arrangement as in the first exemplary embodiment, in which the host material and the dopant material contained in the emitting layer has a specific value of ΔST. Specifically, a difference ΔST(H) between singlet energy EgS(H) of the host material and an energy gap $Eg_{77K}(H)$ at 77K of the host material satisfies a numerical formula (Numerical Formula 1) below. Further, a difference ΔST(D) between singlet energy EgS(D) of the dopant material and an energy gap $Eg_{77K}(D)$ at 77K of the dopant material satisfies a numerical formula (Numerical Formula 2) below.

$$\Delta ST(H)=EgS(H)-Eg_{77K}(H)<0.4 \text{ (eV)} \quad \text{(Numerical Formula 1)}$$

$$\Delta ST(D)=EgS(D)-Eg_{77K}(D)<0.4 \text{ (eV)} \quad \text{(Numerical Formula 2)}$$

ΔST(H) is preferably less than 0.3 eV and ΔST(D) is preferably less than 0.3 eV.

Relationship in Singlet Energy Between Host Material and Dopant Material

In the exemplary embodiment, a compound used as the host material and a compound used as the dopant material satisfy a relationship represented by a numerical formula (3) below in terms of the singlet energy.

$$EgS(H)>EgS(D) \quad \text{(Numerical Formula 3)}$$

When the relationship represented by the numerical formula (3) is satisfied, energy of the singlet excitons initially generated on the host material and the singlet excitons derived from the delayed fluorescence is easily transferred to the dopant material. Consequently, the dopant efficiently emits fluorescence.

In the exemplary embodiment, it is preferable that the compound represented by the formula (1) and satisfying the numerical formula (1) is used as the host material and the compound represented by the formula (2) and satisfying the numerical formula (2) is used as the dopant material, thereby forming the emitting layer.

ΔST will be described herein.

A voltage is more reduced when the compounds each having a small energy gap (ΔST) between the singlet energy EgS and the triplet energy EgT are used as the host material and the dopant material than when the host material having a large ΔST and the dopant material having a small ΔST are used.

From quantum chemical viewpoint, decrease in the energy difference (ΔST) between the singlet energy EgS and the triplet energy EgT can be achieved by a small exchange interaction therebetween. Physical details of the relationship between ΔST and the exchange interaction are described, for instance, in Reference Document 1 and Reference Document 2 below.

Reference Document 1: Organic EL Symposium, proceeding for the tenth meeting edited by Chihaya Adachi et al., S2-5, pp. 11-12

Reference Document 2: Organic Photochemical Reaction Theory edited by Katsumi Tokumaru, Tokyo Kagaku Dojin Co., Ltd. (1973).

Such a material can be synthesized according to molecular design based on quantum calculation. Specifically, the material is a compound in which a LUMO electron orbit and a HOMO electron orbit are localized to avoid overlapping.

Examples of the compound having a small ΔST are compounds in which a donor element is bonded to an acceptor element in a molecule and ΔST is in a range of 0 eV or more and less than 0.3 eV in terms of electrochemical stability (oxidation-reduction stability).

A more preferable compound is such a compound that dipoles formed in the excited state of a molecule interact with each other to form an aggregate having a reduced exchange interaction energy. According to analysis by the inventors, the dipoles are oriented substantially in the same direction in the compound, so that ΔST can be further reduced by the interaction of the molecules. In such a case, ΔST can be extremely small in a range of 0 eV to 0.2 eV. It should be noted that energy may be transferred by Dexter mechanism from the triplet energy level of the host material to the triplet energy level of the dopant material.

TADF Mechanism

As described above, when ΔST of the organic material is small, inverse intersystem crossing from the triplet energy level of the organic material to the singlet energy level thereof is easily caused by heat energy given from the outside. An energy state conversion mechanism to perform spin exchange from the triplet state of electrically excited excitons within the organic EL device to the singlet state by inverse intersystem crossing is referred to as TADF Mechanism.

In the exemplary embodiment, a compound having a small ΔST is preferably used as the host material and the dopant material. By heat energy given from the outside, inverse intersystem crossing from the triplet energy level of the host material to the singlet energy level thereof is easily caused while inverse intersystem crossing from the triplet energy level of the dopant material to the singlet energy level thereof is easily caused.

Figure 2:
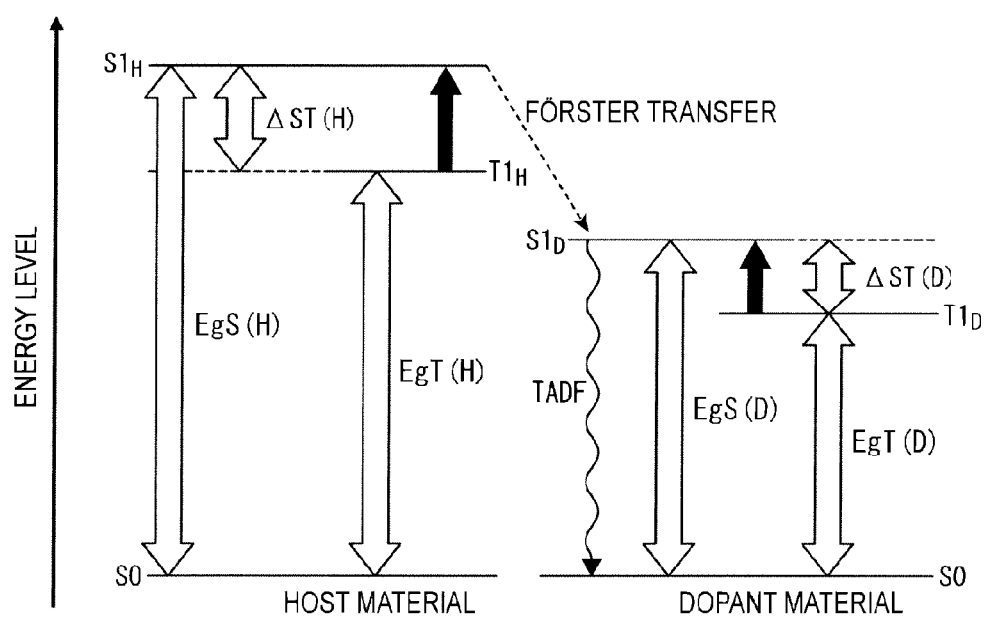
FIG. 2 illustrates a relationship of an energy level between a host material and a dopant material in an emitting layer of an organic electroluminescence device according to a second exemplary embodiment FIG. 3 schematically shows an exemplary arrangement of an organic electroluminescence device according to a modification example of the invention.

FIG. 2 shows a relationship in energy level between the host material and the dopant material in the emitting layer. In FIG. 2, S0 represents a ground state, $S1_H$ represents a lowest singlet state of the host material, $T1_H$ represents a lowest triplet state of the host material, $S1_D$ represents a lowest singlet state of the dopant material, and $T1_D$ represents a lowest triplet state of the dopant material. A dotted-line arrow shows energy transfer between the respective excited states. A bold arrow extending from the triplet state to the singlet state represents inverse intersystem crossing.

In the exemplary embodiment, a compound having a small ΔST(H) is used as the host material. It is speculated that the compound having a small ΔST(H) easily causes inverse intersystem crossing from the triplet excitons generated in the lowest triplet state $T1_H$ to the lowest singlet state $S1_H$ of the host material by heat energy. Due to the small ΔST(H) of the host material, inverse intersystem crossing is easily caused, for instance, even around a room temperature. When the inverse intersystem crossing is thus easily caused, a ratio of energy transfer from the host material to the lowest singlet state $T1_D$ of the dopant material is increased by Förster transfer, resulting in improvement in a luminous efficiency of the organic EL device.

In the exemplary embodiment, the compound having a small ΔST(D) is used as the dopant material. It is speculated that the compound having a small ΔST(D) easily causes inverse intersystem crossing from the triplet excitons generated in the lowest triplet state $T1_D$ to the lowest singlet state $S1_D$ by heat energy. Since the dopant material also has a small ΔST(D) similar to the host material, inverse intersystem crossing is easily caused, for instance, even around a room temperature. Consequently, fluorescent emission from the lowest singlet state $S1_D$ of the dopant material can be observed.

In other words, when the compound having a small ΔST(H) is used as the host material and the compound having a small ΔST(D) is used as the dopant material, emission by the TADF mechanism is increased, so that a delayed fluorescence ratio is increased. When the delayed fluorescence ratio is increased, a higher internal quantum efficiency is achievable. It is speculated that the internal quantum efficiency can be theoretically raised up to 100% by using delayed fluorescence by the TADF mechanism.

Relationship Between EgT and $Eg_{77K}$

The triplet energy EgT of measurement target compounds is measured as follows. Each of the measurement target compounds and a compound TH-2 below are co-deposited on a quartz substrate by vacuum deposition to prepare a sample encapsulated in an NMR tube. Each of the samples was prepared under the following conditions.

quartz substrate/TH-2: measurement target compound (100 nm of thickness, 12 mass % of concentration of a second material)

[Formula 136]

TH-2

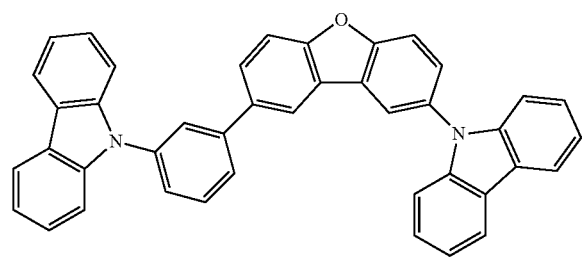

A phosphorescent spectrum (ordinate axis: phosphorescent luminous intensity, abscissa axis: wavelength) of each of the samples was measured at a low temperature (77K). A tangent was drawn to the rise of the phosphorescent spectrum on the short-wavelength side. An energy amount was calculated as the energy gap $Eg_{77K}$ at 77K according to a conversion equation 2 below based on a wavelength value $\lambda_{edge}$ (nm) at an intersection of the tangent and the abscissa axis.

$$Eg_{77K}(eV) = 1239.85/\lambda_{edge} \qquad \text{Conversion Equation 2:}$$

For phosphorescence measurement, a spectrophotofluorometer body F-4500 (manufactured by Hitachi High-Technologies Corporation) was used.

The tangent to the rise of the phosphorescence spectrum on the short-wavelength side is drawn as follows. While moving on a curve of the phosphorescence spectrum from the short-wavelength side to the maximum spectral value closest to the short-wavelength side among the maximum spectral values, a tangent is checked at each point on the curve toward the long-wavelength of the phosphorescence spectrum. An inclination of the tangent is increased as the curve rises (i.e., a value of the ordinate axis is increased). A tangent drawn at a point of the maximum inclination (i.e., a tangent at an inflection point) is defined as the tangent to the rise of the phosphorescence spectrum on the short-wavelength side.

The maximum with peak intensity being 15% or less of the maximum peak intensity of the spectrum is not included in the above-mentioned maximum closest to the short-wavelength side of the spectrum. The tangent drawn at a point of the maximum spectral value being closest to the short-wavelength side and having the maximum inclination is defined as a tangent to the rise of the phosphorescence spectrum on the short-wavelength side.

The material used in the exemplary embodiment is preferably a compound having a small ΔST. When ΔST is small, intersystem crossing and inverse intersystem crossing are likely to occur even at a low temperature (77K), so that the singlet state and the triplet state coexist. As a result, the spectrum to be measured in the same manner as the above includes emission from both the singlet state and the triplet state. Although it is difficult to distinguish the emission from the singlet state from the emission from the triplet state, the value of the triplet energy is basically considered dominant.

Accordingly, in the exemplary embodiment, the spectrum is measured by the same method as that for measuring a typical triplet energy, but an energy value of the spectrum measured in the aforementioned manner is referred to as an energy gap $Eg_{77K}$ in order to differentiate the measured energy from a typical triplet energy in a strict meaning.

The calculation of the singlet energy EgS and the energy gap $Eg_{77K}$ will be described in detail later.

Third Exemplary Embodiment

Arrangements) of an organic EL device according to a third exemplary embodiment will be described. In the description of the third exemplary embodiment, the same components as those in the first exemplary embodiment are denoted by the same reference signs and names to simplify or omit an explanation of the components. In the third exemplary embodiment, the same materials and compounds as described in the above exemplary embodiments are usable unless particularly described.

The organic EL device in the third exemplary embodiment has the same device arrangement as in the first exemplary embodiment, except that the compound represented by the formula (1) is represented by a formula (40) below. The compound represented by the formula (40) below is contained in the emitting layer. As for other points, the organic EL device according to the third exemplary embodiment is the same as the organic EL device according to the above exemplary embodiments.

[Formula 137]

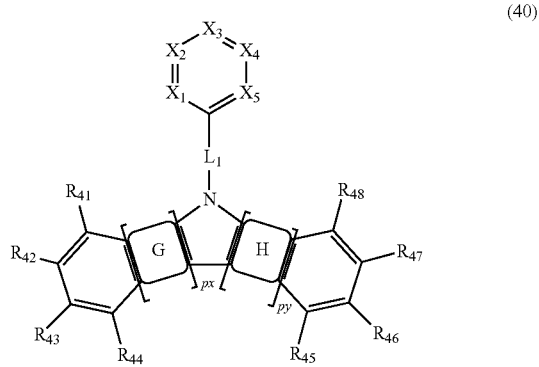

(40)

In the formula (40), $X_1$ to $X_5$ each independently represent $CR_1$ or a nitrogen atom and at least one of $X_1$ to $X_5$ is a nitrogen atom.

In the formula (40), one to three of $X_1$ to $X_5$ are preferably nitrogen atom(s). In the formula (40), adjacent ones of $R_1$ as the substituents for carbon atoms may be bonded to each other to form a cyclic structure.

When one nitrogen atom is provided, $X_1$ or $X_5$ is preferably a nitrogen atom. When two nitrogen atoms are provided, $X_1$ and $X_5$ are preferably nitrogen atoms. When three nitrogen atoms are provided, $X_1$, $X_3$ and $X_5$ are preferably nitrogen atoms. Among the above arrangements, a triazine ring in which $X_1$, $X_3$ and $X_5$ are nitrogen atoms is preferable in the formula (40).

In the formula (40), $L_1$ represents a substituted or unsubstituted divalent aromatic hydrocarbon group.

In the formula (40), $R_1$ and $R_{41}$ to $R_{48}$ are each independently a hydrogen atom, a cyano group, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkylsilyl group having 3 to 30 carbon atoms, a substituted or unsubstituted arylsilyl group having 6 to 60 ring carbon atoms, a substituted or unsubstituted alkoxy group having 1 to 30 carbon atoms, a substituted or unsubstituted aryloxy group having 6 to 30 ring carbon atoms, a substituted or unsubstituted alkylamino group having 2 to 30 carbon atoms, a substituted or unsubstituted arylamino group having 6 to 60 ring carbon atoms, a substituted or unsubstituted alkylthio group having 1 to 30 carbon atoms, or a substituted or unsubstituted arylthio group having 6 to 30 ring carbon atoms.

Each of pairs of $R_{41}$ and $R_{42}$, $R_{42}$ and $R_{43}$, $R_{43}$ and $R_{44}$, $R_{45}$ and $R_{46}$, $R_{46}$ and $R_{47}$, and $R_{47}$ and $R_{48}$ may be mutually bonded to form a cyclic structure.

In the formula (40), G and H each independently represent a cyclic structure represented by a formula (3g) below or a cyclic structure represented by a formula (3h) below. Each of the cyclic structure G and the cyclic structure H is fused to an adjacent cyclic structure at any position.

px and py are each independently an integer of 0 to 4 and respectively represent the number of the cyclic structure G and the number of the cyclic structure H. When px is an integer of 2 to 4, a plurality of cyclic structures G may be mutually the same or different. When py is an integer of 2 to 4, a plurality of cyclic structures H may be mutually the same or different. Accordingly, for instance, when px is 2, the cyclic structures G may be either two cyclic structures represented by the formula (3g) below or two cyclic structures represented by the formula (3h), or alternatively, the cyclic structures G may be a combination of one cyclic structure represented by the formula (3g) and one cyclic structure represented by the formula (3h).

[Formula 138]

(3g)

[Formula 139]

(3h)

In the formula (3g), $R_{20}$ and $R_{21}$ each independently represent the same as $R_1$ described above and may be mutually bonded to form a cyclic structure. $R_{20}$ and $R_{21}$ are respectively bonded to carbon atoms forming the six-membered ring of the formula (3g).

In the formula (3h), $Z_8$ represents $CR_{22}R_{23}$, $NR_{24}$, a sulfur atom, or an oxygen atom. $R_{22}$ to $R_{24}$ each independently represent a cyano group, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkylsilyl group having 3 to 30 carbon atoms, a substituted or unsubstituted arylsilyl group having 6 to 60 ring carbon atoms, a substituted or unsubstituted alkoxy group having 1 to 30 carbon atoms, a substituted or unsubstituted aryloxy group having 6 to 30 ring carbon atoms, a substituted or unsubstituted alkylamino group having 2 to 30 carbon atoms, a substituted or unsubstituted acylamino group having 6 to 60 ring carbon atoms, a substituted or unsubstituted alkylthio group having 1 to 30 carbon atoms, or a substituted or unsubstituted arylthio group having 6 to 30 ring carbon atoms.

$R_{22}$ and $R_{23}$ are each independently preferably a substituted or unsubstituted alkyl group having 1 to 30 carbon atoms or a substituted or unsubstituted aryl group having 6 to 30 ring carbon atoms. Specific examples of $R_{22}$ and $R_{23}$ include a methyl group, ethyl group, n-propyl group, phenyl group, biphenyl group, and terphenyl group. $R_{24}$ is preferably a substituted or unsubstituted aryl group having 6 to 30 ring carbon atoms or a substituted or unsubstituted heterocyclic group having 5 to 30 ring atoms. Specific examples of $R_{24}$ include a phenyl group, biphenyl group, terphenyl group, naphthyl group, phenanthryl group, triphenylenyl group, dibenzofuranyl group, dibenzothiophenyl group, and carbazolyl group. $R_{24}$ is more preferably a substituted or unsubstituted aryl group having 6 to 30 ring carbon atoms. Specific examples of $R_{24}$ include a phenyl group, biphenyl group, terphenyl group, naphthyl group, phenanthryl group and triphenylenyl group.

In the formula (40), at least one of combinations of substituents selected from $R_{41}$ to $R_{48}$ and $R_{20}$ to $R_{24}$ may be mutually bonded to form a cyclic structure.

$L_1$ of the formula (40) preferably has a divalent six-membered ring structure, more preferably a divalent six-membered ring structure represented by a formula (4), (4a) or (4b) below, further preferably a divalent six-membered ring structure represented by the formula (4) below.

[Formula 140]

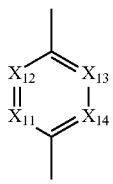

(4)

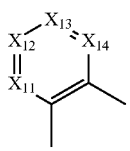

(4a)

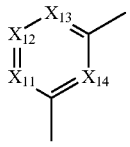

(4b)

In the formulae (4), (4a) and (4b), $X_{11}$ to $X_{14}$ each independently represent $CR_{11}$ or a nitrogen atom, in which $R_{11}$ each independently represents a hydrogen atom, a halogen atom, a cyano group, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkylsilyl group having 3 to 30 carbon atoms, a substituted or unsubstituted arylsilyl group having 6 to 60 ring carbon atoms, a substituted or unsubstituted alkoxy group having 1 to 30 carbon atoms, a substituted or unsubstituted aryloxy group having 6 to 30 ring carbon atoms, a substituted or unsubstituted alkylamino group having 2 to 30 carbon atoms, a substituted or unsubstituted arylamino group having 6 to 60 ring carbon atoms, a substituted or unsubstituted alkylthio group having 1 to 30 carbon atoms, or a substituted or unsubstituted arylthio group having 6 to 30 ring carbon atoms.

$X_{11}$ to $X_{14}$ of the formulae (4), (4a) and (4b) are each independently preferably $CR_{11}$, in which $R_{11}$ is more preferably a hydrogen atom, alkyl group, alkoxy group, aryloxy group, cyano group, halogen atom and silyl group.

Particularly preferably, $L_1$ is represented by the formula (4); $X_{11}$ to $X_{14}$ are each independently $CR_{11}$; $X_1$, $X_3$ and $X_5$ of the formula (40) are nitrogen atoms; and $X_2$ and $X_4$ are $CR_1$. In other words, the compound represented by the formula (1) is preferably provided by a compound in which an electron accepting moiety is a substituted or unsubstituted triazine ring and the triazine ring is connected to an electron donating moiety by a substituted or unsubstituted p-phenylene group. The compound in this arrangement is represented by a formula (41) below.

[Formula 141]

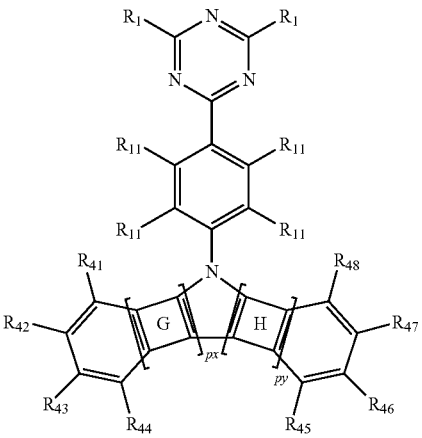

(41)

In the formula (41), $R_1$, $R_{11}$, $R_{41}$ to $R_{48}$, the cyclic structure G, the cyclic structure H, px and py respectively represent the same as $R_1$, $R_{11}$, $R_{41}$ to $R_{48}$, the cyclic structure G, the cyclic structure H, px and py described in the formulae (4) and (40).

In the third exemplary embodiment, px and py are preferably the same integer, among which px and py are preferably 2. In this arrangement, the compound of the formula (40) is represented by a formula (42) below.

[Formula 142]

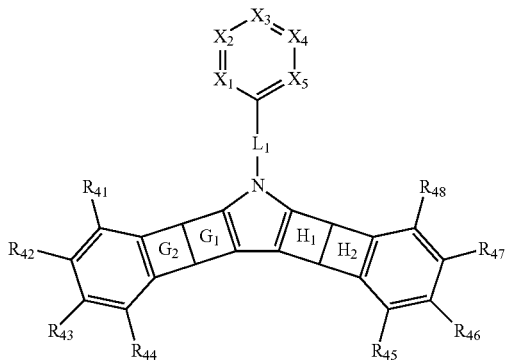

(42)

In the formula (42), $X_1$ to $X_5$, $R_{41}$ to $R_{48}$ and $L_1$ respectively independently represent the same as $X_1$ to $X_5$, $R_{41}$ to $R_{48}$ and $L_1$ of the formula (40).

The cyclic structure $G_1$ and the cyclic structure $G_2$ each independently represent the same as the cyclic structure G described above. The cyclic structure $H_1$ and the cyclic structure $H_2$ each independently represent the same as the cyclic structure H described above.

In the formula (42), the cyclic structure $G_1$ and the cyclic structure $H_1$ are each independently the cyclic structure represented by the formula (3g). The cyclic structure $G_2$ and the cyclic structure $H_2$ are each independently the cyclic structure represented by the formula (3h).

In the third exemplary embodiment, it is also preferable that one of px and py is 0 while the other of px and py is 4. For instance, when px is 4 and py is 0, the compound of the formula (40) is represented by a formula (43) below.

[Formula 143]

(43)

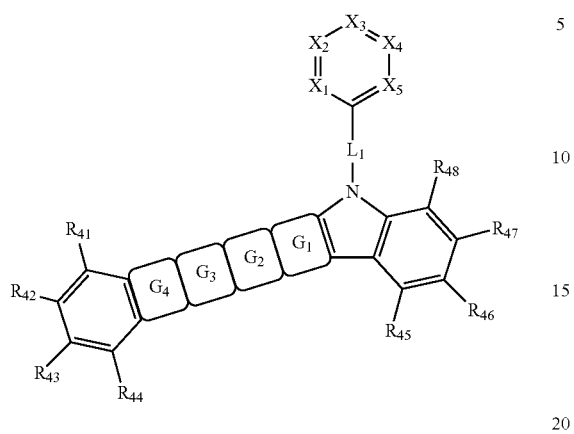

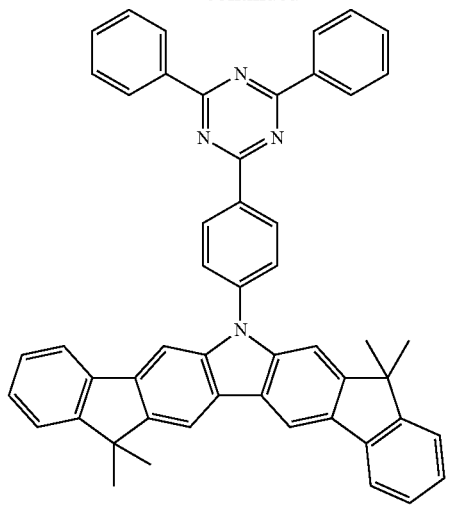

In the formula (43), $X_1$ to $X_5$, $R_{41}$ to $R_{48}$ and $L_1$ respectively independently represent the same as $X_1$ to $X_5$, $R_{41}$ to $R_{48}$ and $L_1$ of the formula (40).

The cyclic structure $G_1$, the cyclic structure $G_2$, a cyclic structure $G_3$, and a cyclic structure $G_4$ each independently represent the same as the cyclic structure G.

In the formula (43), the cyclic structure $G_1$ and the cyclic structure $G_3$ are each independently the cyclic structure represented by the formula (3g). The cyclic structure $G_2$ and the cyclic structure $G_4$ are each independently the cyclic structure represented by the formula (3h).

In the formulae (42) and (43), $X_1$ to $X_5$ and $L_1$ are preferably the above preferable examples of $X_1$ to $X_5$ and $L_1$.

Also in the third exemplary embodiment, it is preferable that a difference ΔST(D1) between singlet energy EgS(D1) and energy gap Eg77K(D1) at 77(K) in the compound represented by the formula (40) satisfies the above numerical formula (1).

Specific examples of the compound represented by the formula (40) in the third exemplary embodiment are shown below, but the invention is not limited thereto.

[Formula 144]

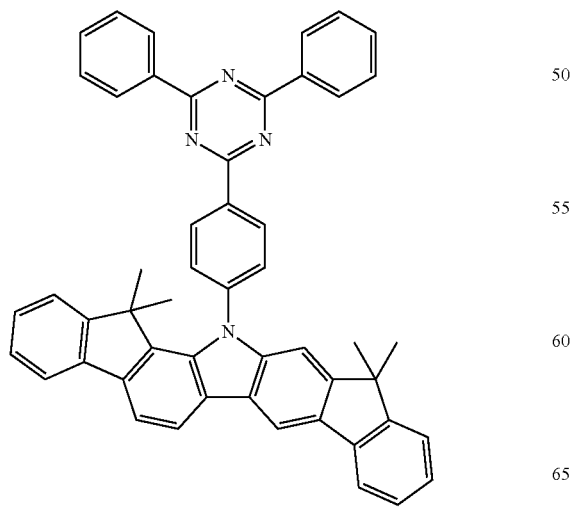

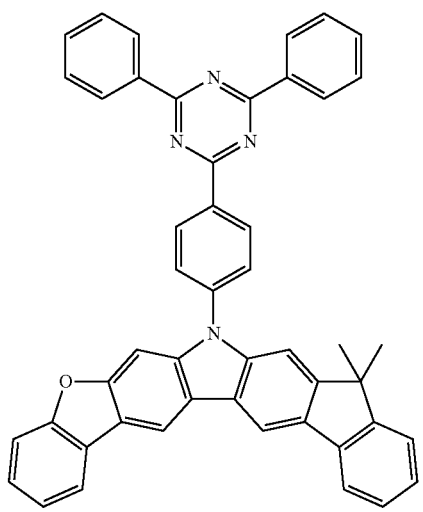

[Formula 145]

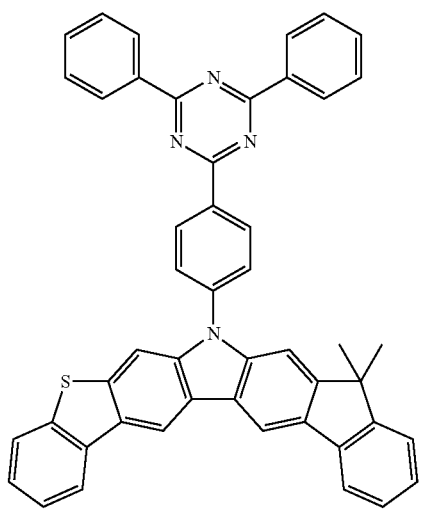

201
-continued
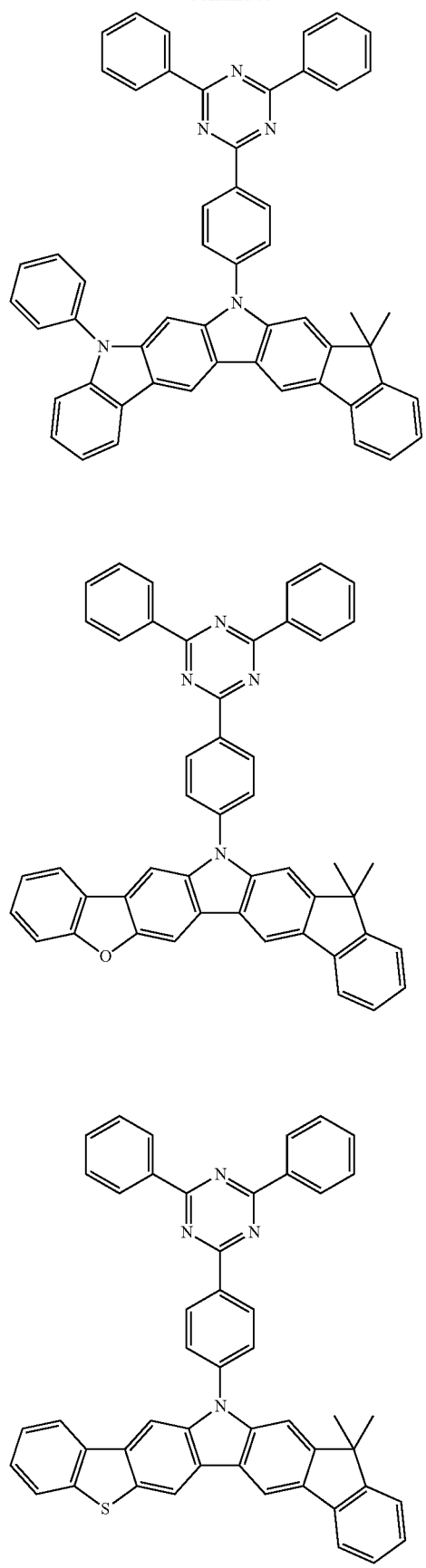
202
-continued
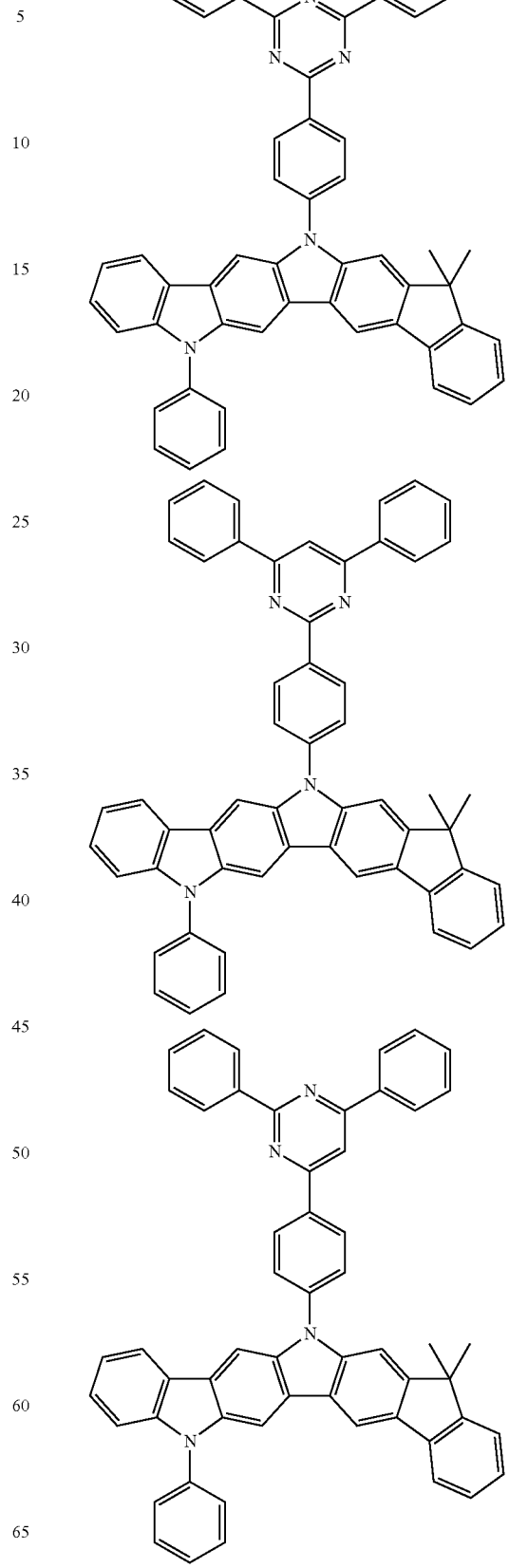

203
-continued
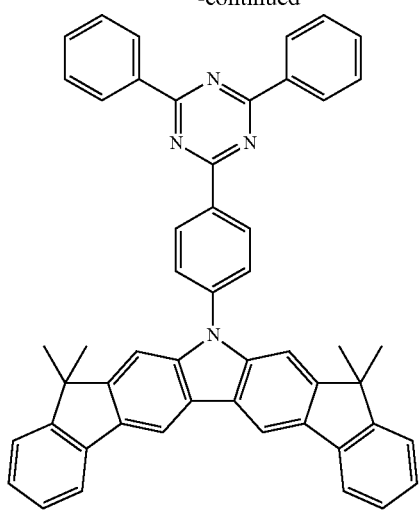
[Formula 146]
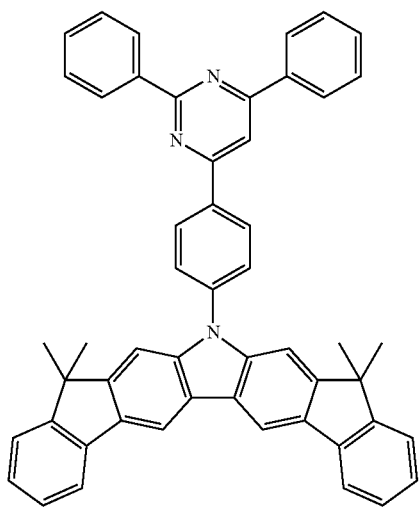
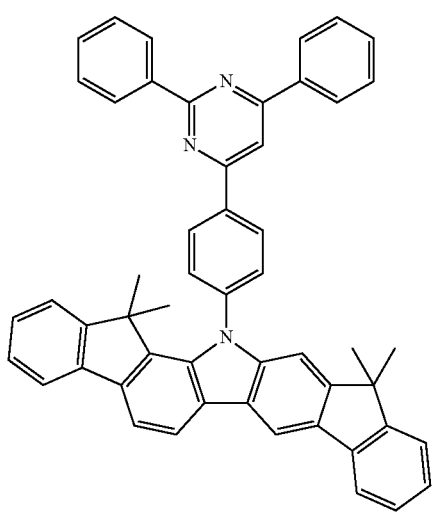
204
-continued
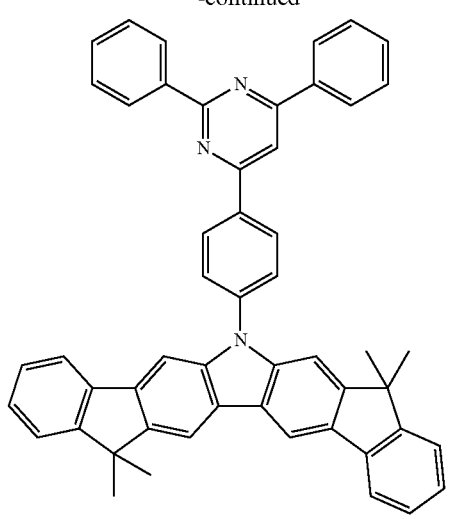
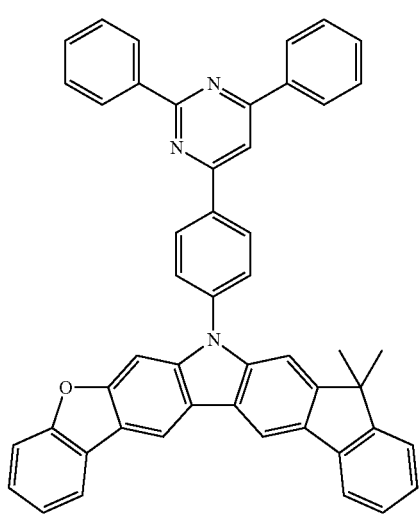
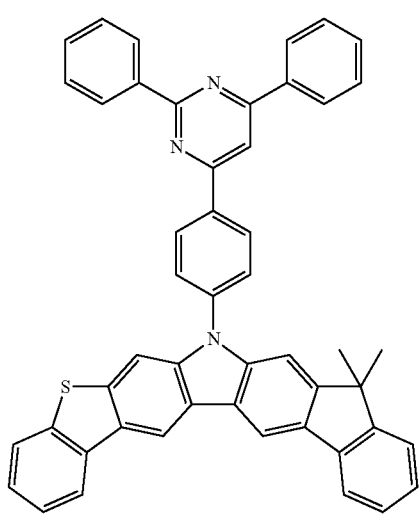

205
-continued
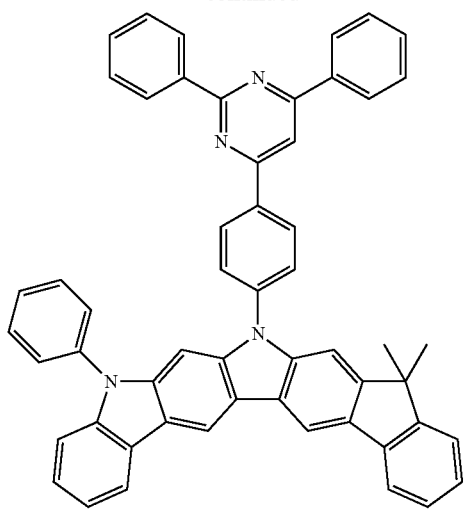
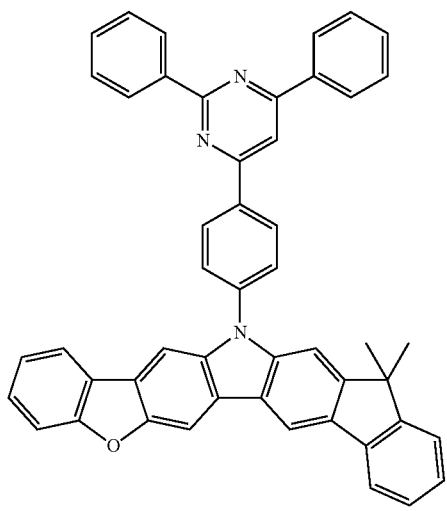
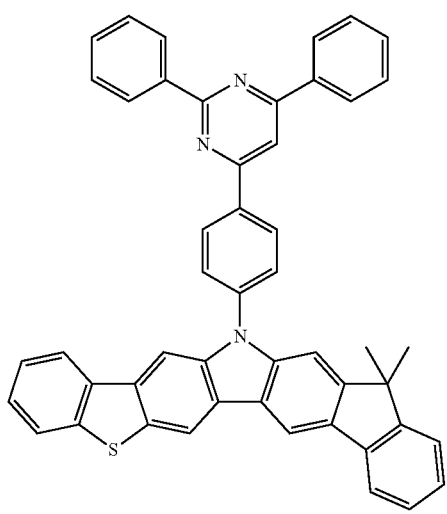
206
-continued
[Formula 147]
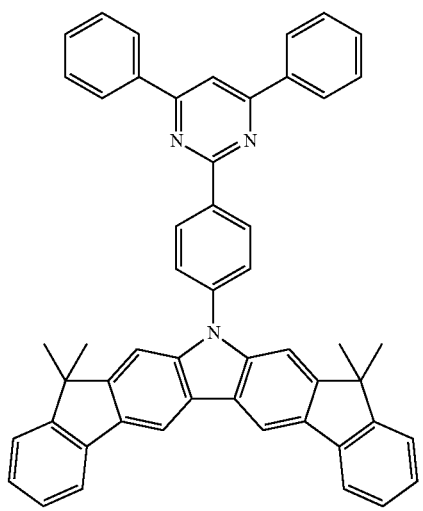
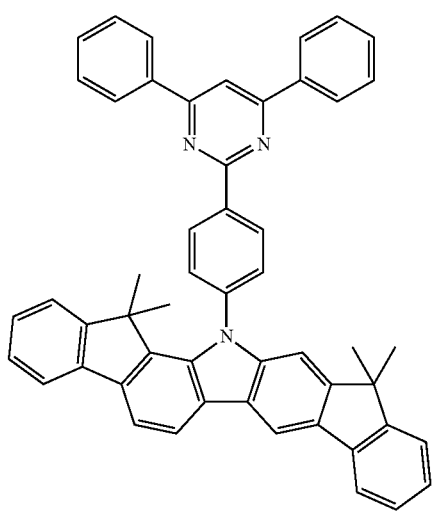
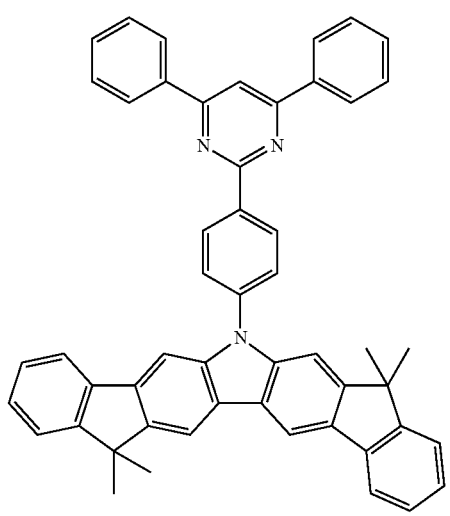

207
-continued
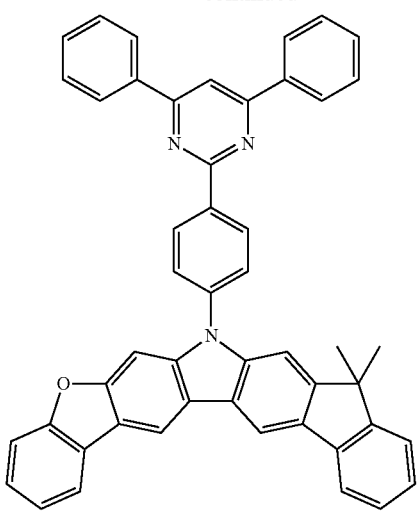
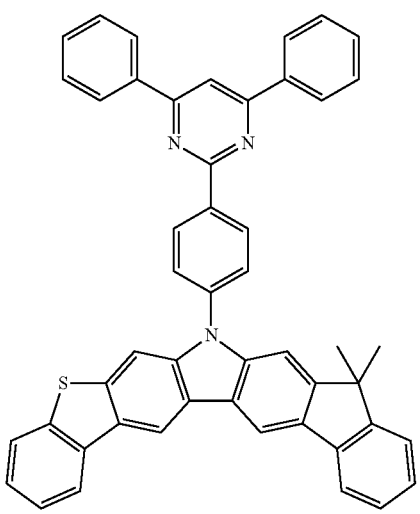
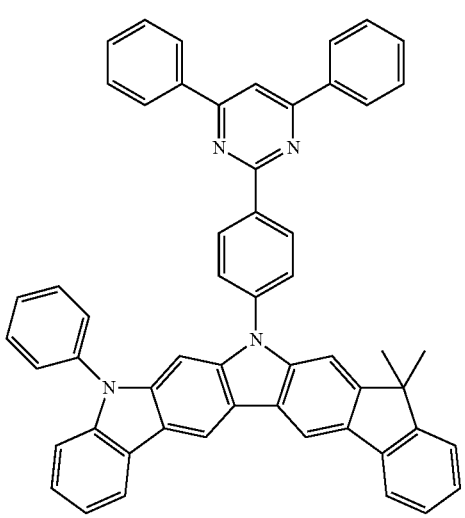
208
-continued
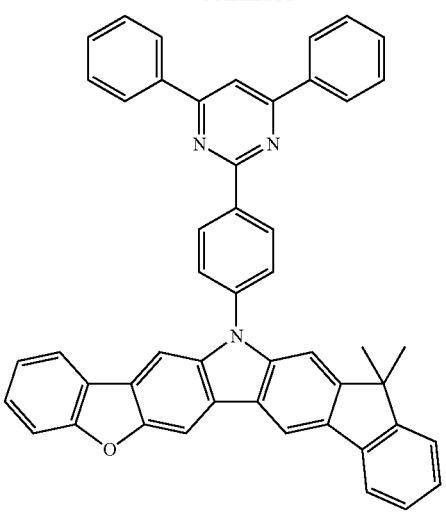
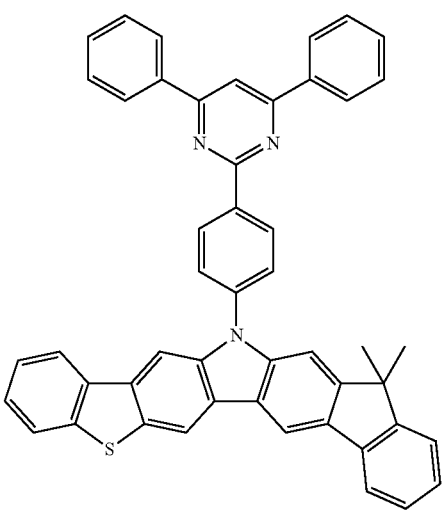
[Formula 148]
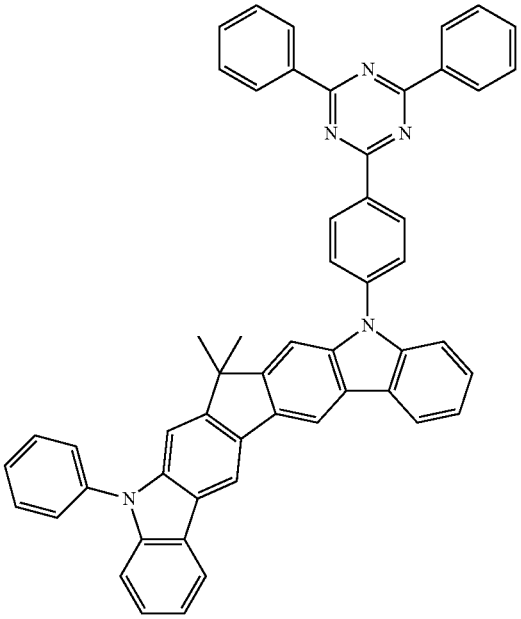

209
-continued
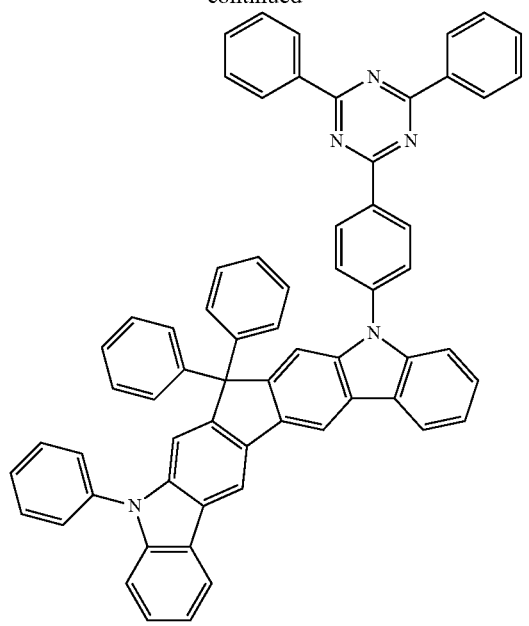
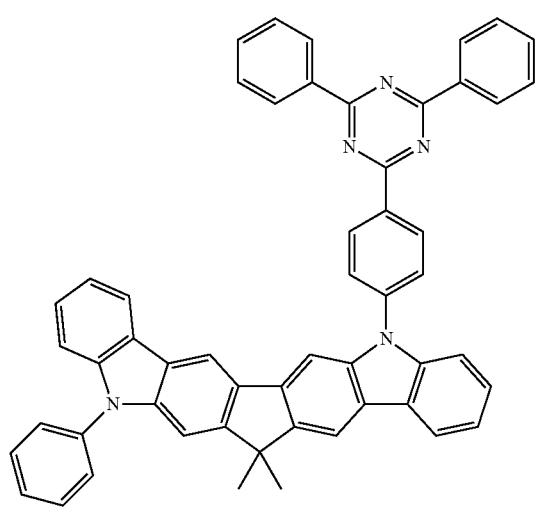
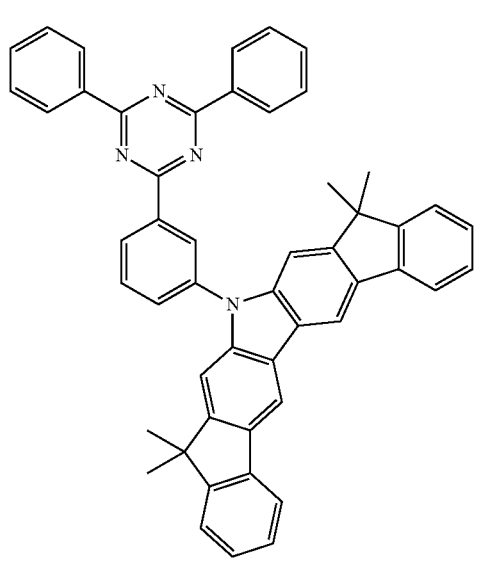
210
-continued
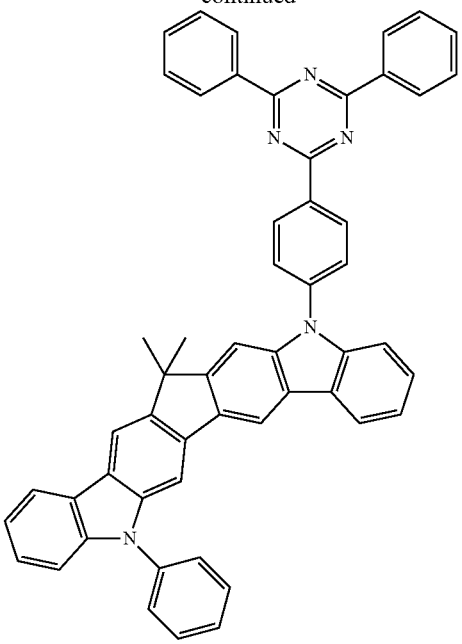
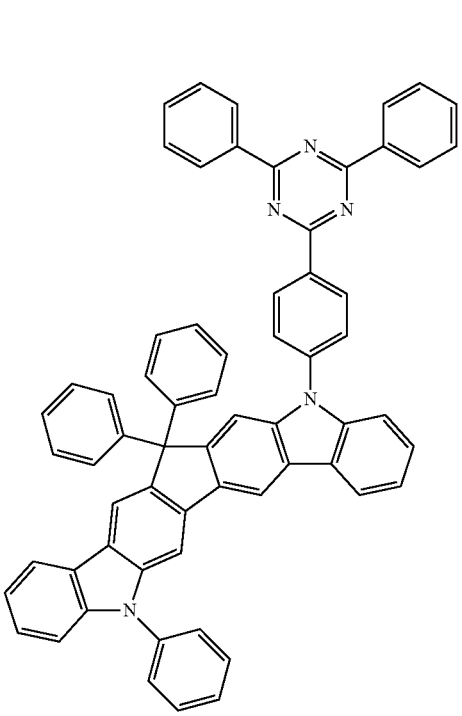

211
-continued
212
-continued
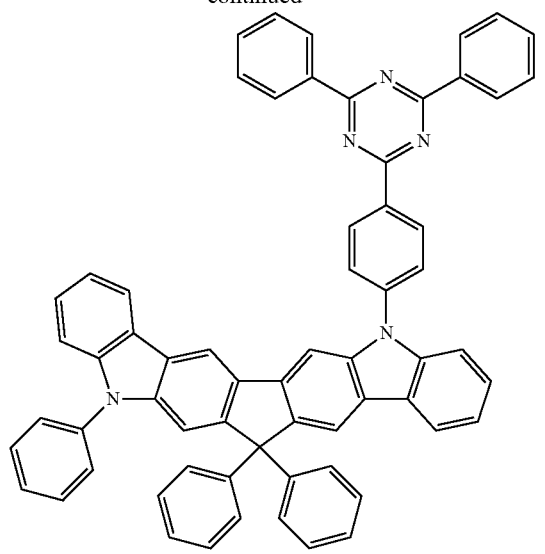
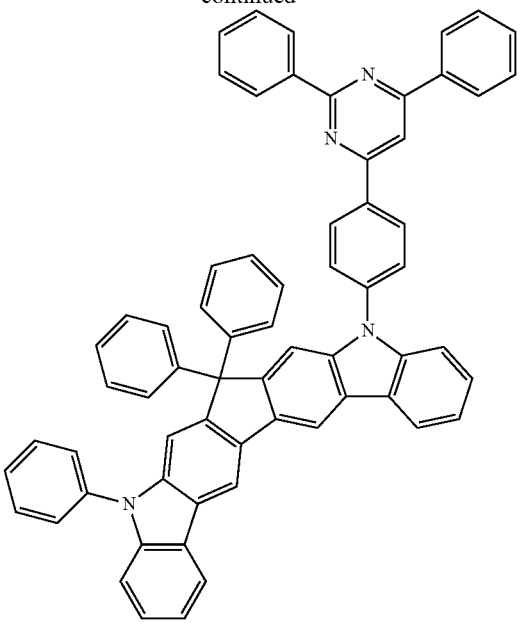
[Formula 149]
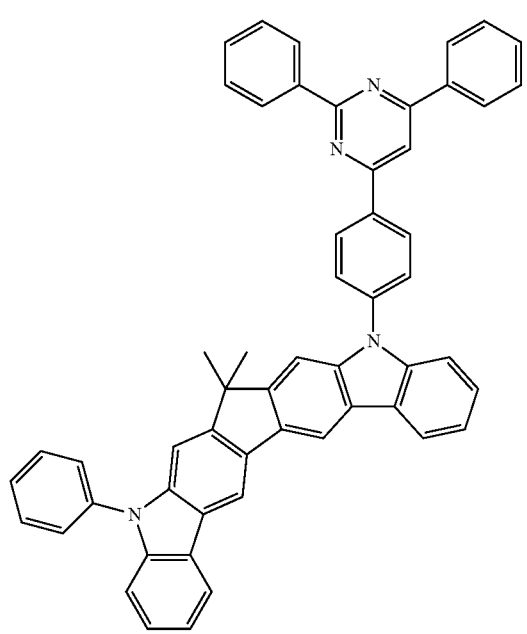

213
-continued
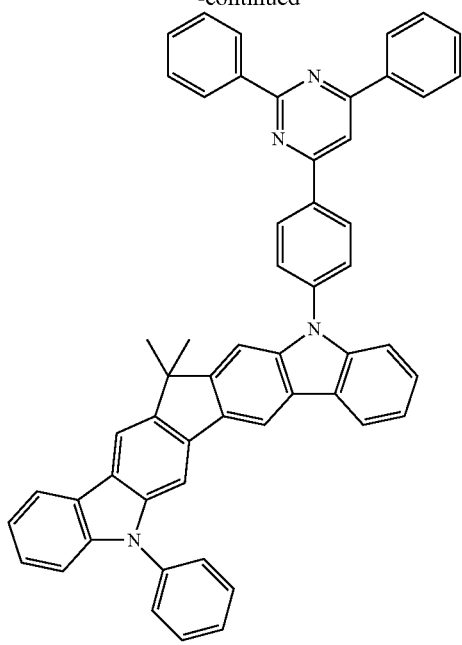
214
-continued
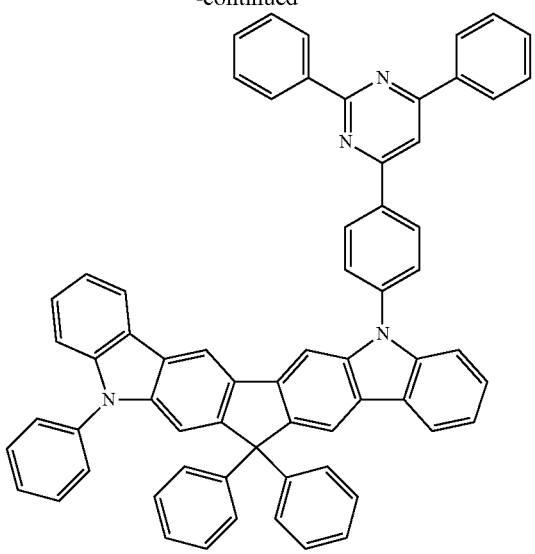
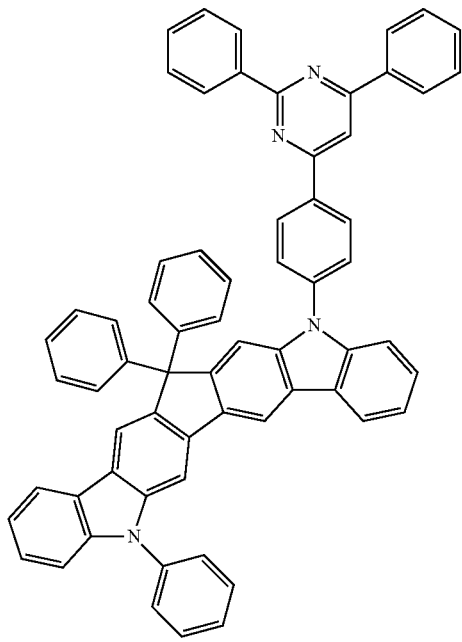
[Formula 150]
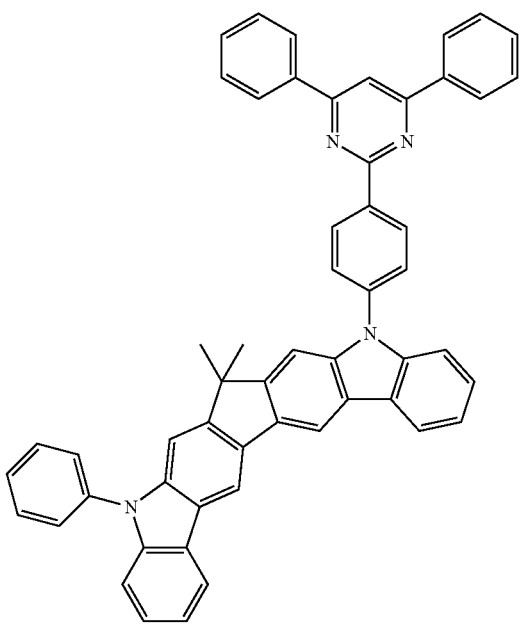

215
-continued
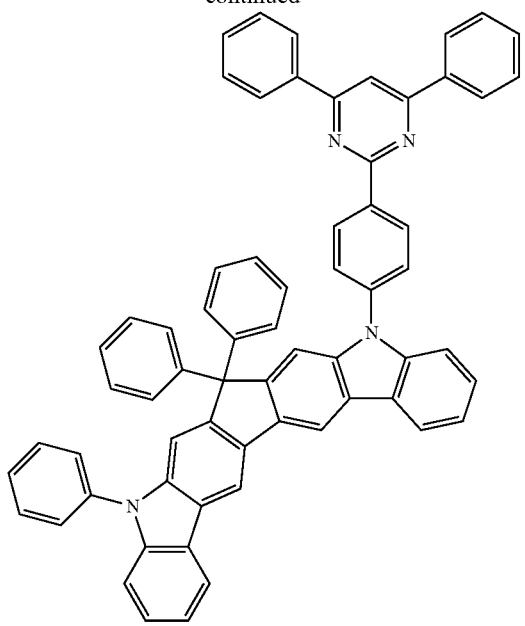
216
-continued
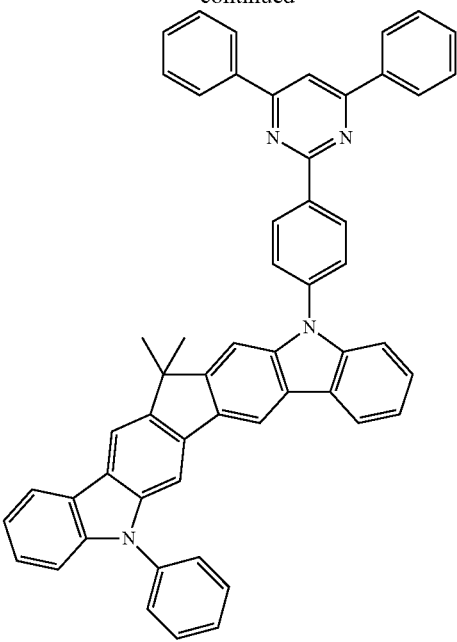
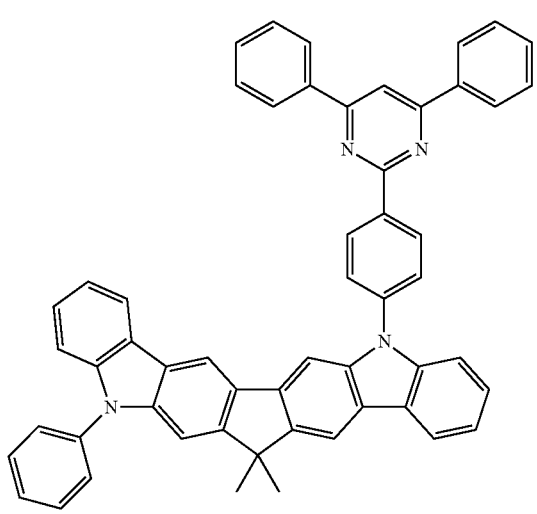
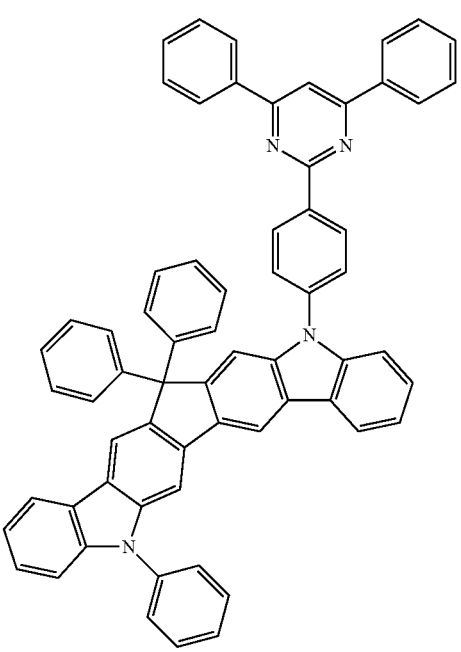

217
-continued
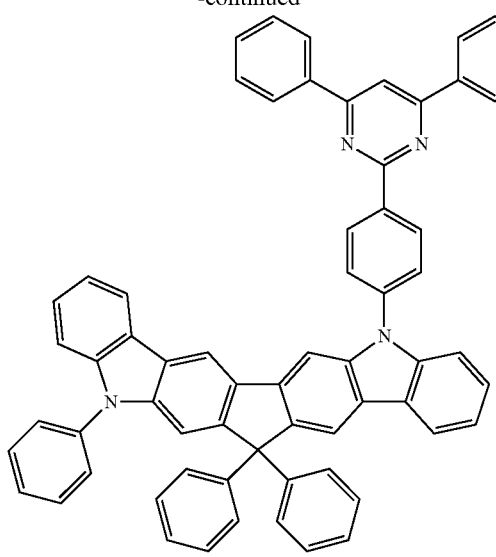
[Formula 151]
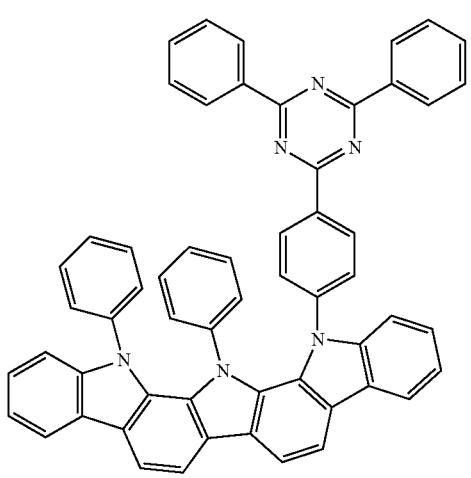
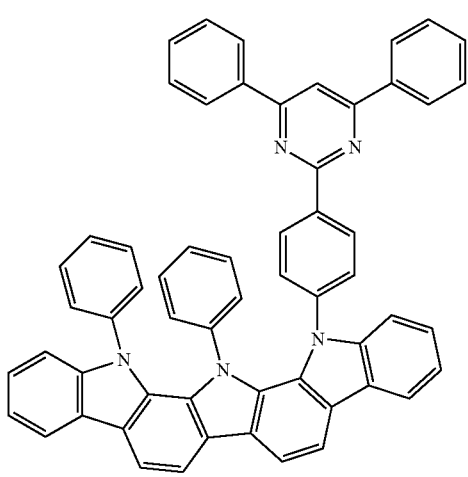
218
-continued
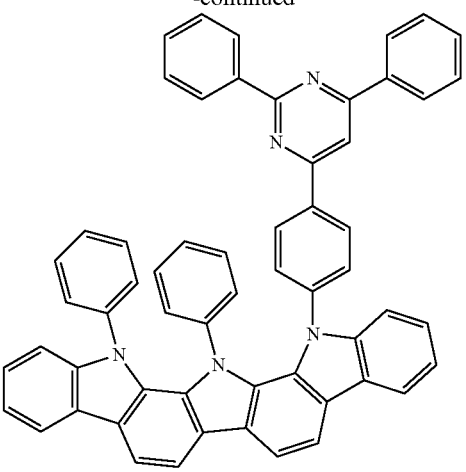
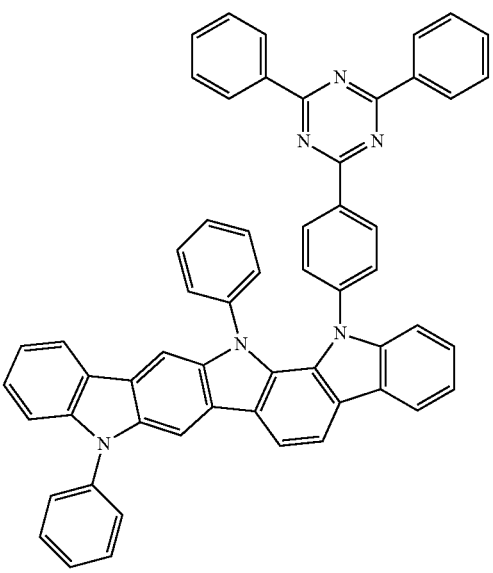
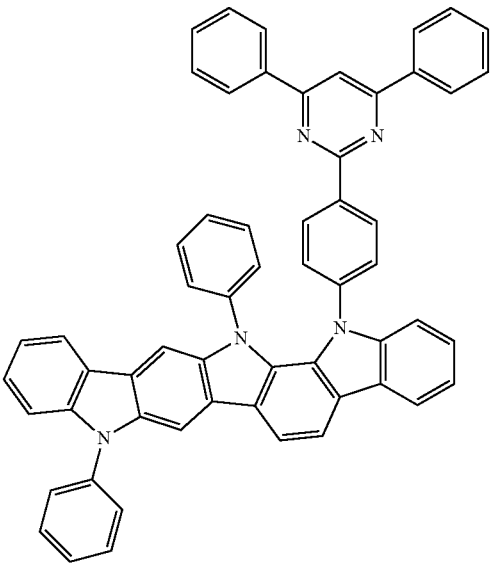

219
-continued
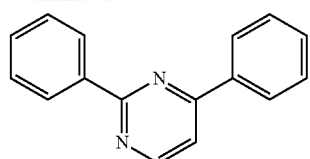
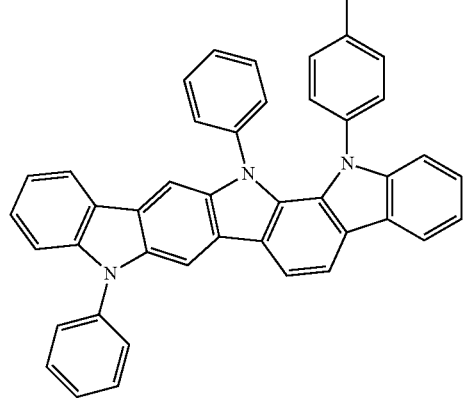
220
-continued
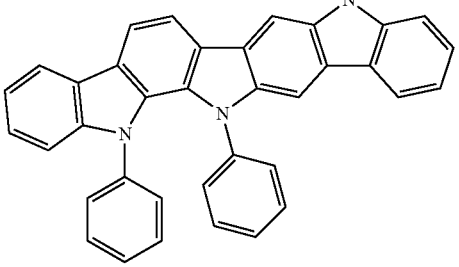
[Formula 152]
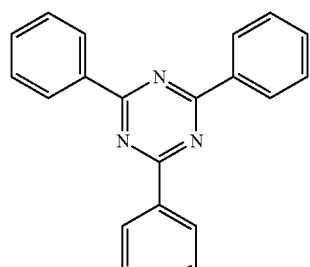
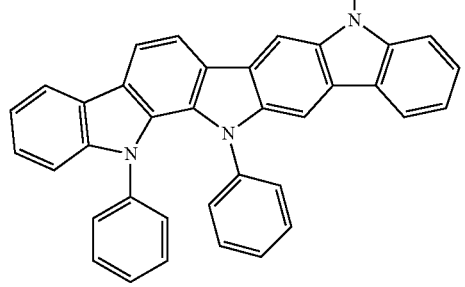
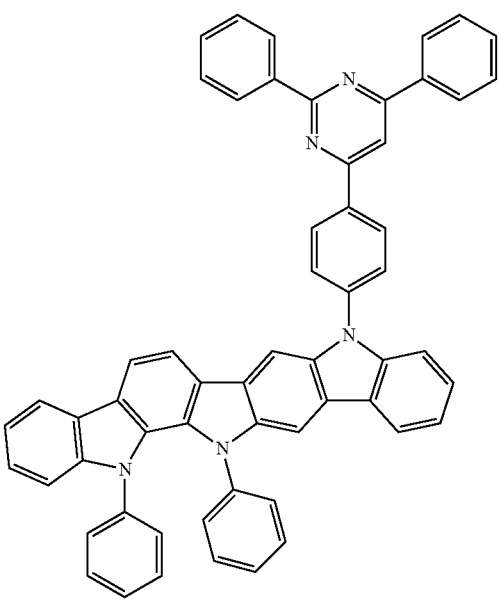

221
-continued
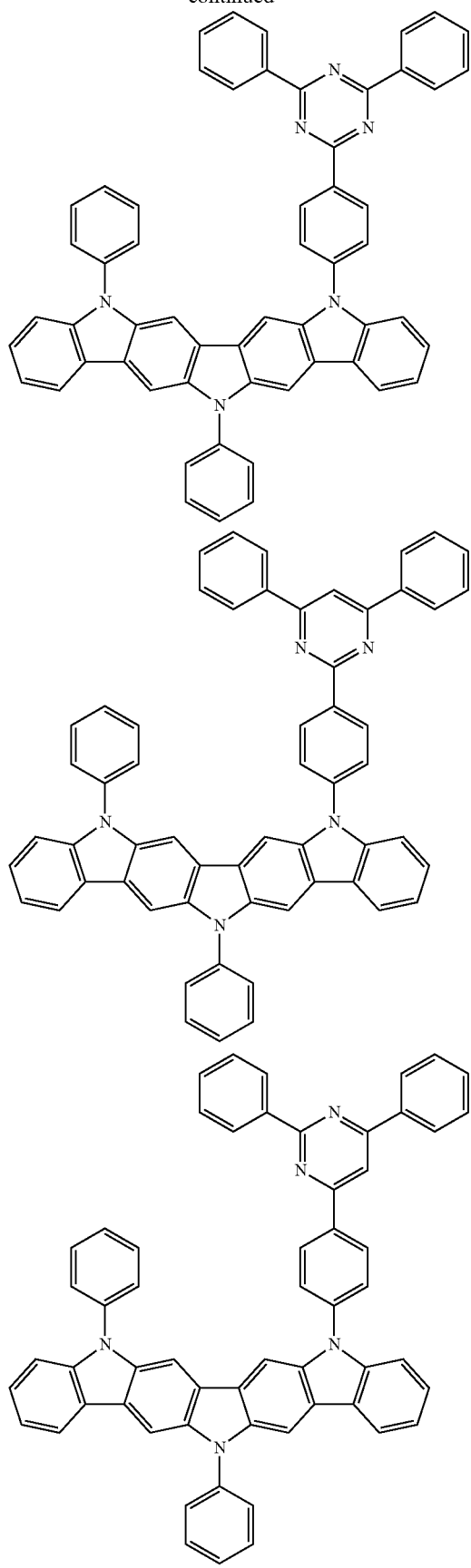
222
-continued
[Formula 153]

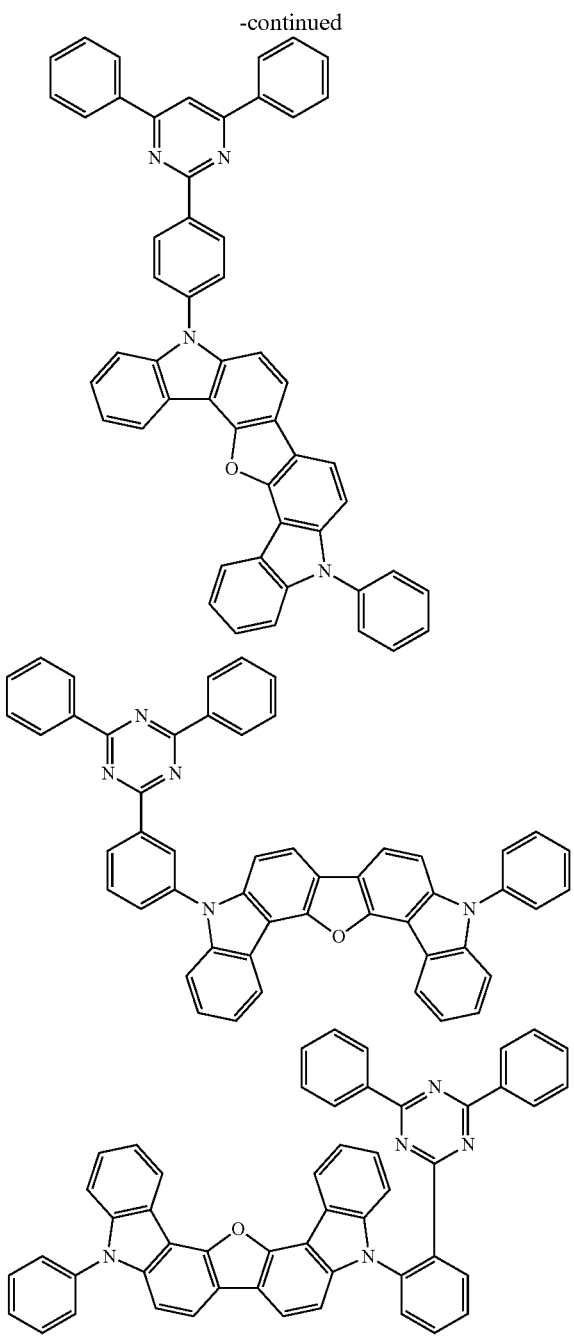

Fourth Exemplary Embodiment

Arrangement(s) of an organic EL device according to a fourth exemplary embodiment will be described. In the description of the fourth exemplary embodiment, the same components as those in the first exemplary embodiment are denoted by the same reference signs and names to simplify or omit an explanation of the components. In the fourth exemplary embodiment, the same materials and compounds as described in the above exemplary embodiments are usable unless particularly described.

The organic EL device of the fourth exemplary embodiment has the same device arrangement as in the first exemplary embodiment and includes the light-transmissive substrate, the anode, the cathode, and the organic layer interposed between the anode and the cathode. The organic layer includes the emitting layer containing the host material and the dopant material. The organic layer also includes hole injecting•transporting layer interposed between the emitting layer and the anode. The organic layer further includes the electron injecting•transporting layer interposed between the emitting layer and the cathode.

The hole injecting•transporting layer in the fourth exemplary embodiment at least includes the hole transporting layer. As for other points, the organic EL device according to the fourth exemplary embodiment is the same as the organic EL device according to the above exemplary embodiments.

The hole transporting layer in the fourth exemplary embodiment is preferably formed of a material for transporting holes to the emitting layer at a lower electric field intensity. In the fourth exemplary embodiment, a compound represented by a formula (111) is used in the hole transporting layer.

[Formula 154]

$$(HAr_{131})\!-\!L_{131}\!-\!(HAr_{132}) \tag{111}$$

In the formula (111), $L_{131}$ represents a single bond or a linking group, in which the linking group is a substituted or unsubstituted divalent aromatic hydrocarbon group having 6 to 30 ring carbon atoms or a substituted or unsubstituted divalent heterocyclic group having 5 to 30 ring atoms.

$HAr_{131}$ and $HAr_{132}$ are each independently a group derived from a structure represented by a formula (111-1) below.

[Formula 155]

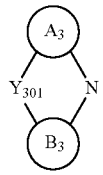

(111-1)

In the formula (111-1), $Y_{301}$ represents a single bond, an oxygen atom, a sulfur atom, a carbonyl group, $NR_{311}$, $CR_{312}R_{313}$, $SiR_{314}R_{315}$ or $GeR_{316}R_{317}$.

$A_3$ and $B_3$ each independently represent a substituted or unsubstituted cyclic structure. When at least one of the cyclic structure $A_3$ and the cyclic structure $B_3$ have a plurality of substituents, adjacent ones of the substituents may form a ring. When at least one of the cyclic structure $A_3$ and the cyclic structure $B_3$ is a substituted or unsubstituted heterocyclic structure, the heterocyclic structure has a partial structure represented by a formula (111-2) below.

$R_{311}$ to $R_{317}$ each represent a hydrogen atom or a substituent. The substituent in $R_{311}$ to $R_{317}$ is selected from the group consisting of a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkylsilyl group having 3 to 30 carbon atoms, a substituted or unsubstituted arylsilyl group having 6 to 60 ring carbon atoms, a substituted or unsubstituted alkoxy group having 1 to 30 carbon atoms, a substituted or unsubstituted aryloxy group having 6 to 30 ring carbon atoms, a substituted or unsubstituted alkylamino group having 2 to 30 carbon atoms, a substituted or unsubstituted arylamino group having 6 to 60 ring carbon atoms, a substituted or unsubstituted alkylthio group having 1 to 30 carbon atoms, and a substituted or unsubstituted arylthio group having 6 to 30 ring carbon atoms.

[Formula 156]

(111-2)

The cyclic structure represented by the formula (111-1) is preferably selected from the group consisting of cyclic structures represented by formulae (111b) to (111i) below.

[Formula 157]

(111b)

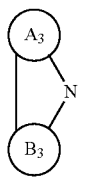

(111c)

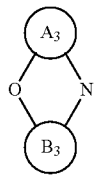

(111d)

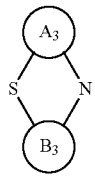

(111e)

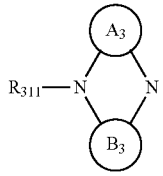

(111f)

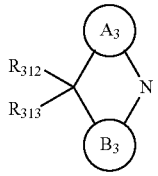

(111g)

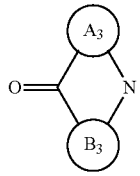

-continued (111h)

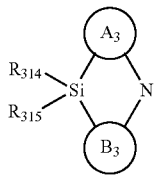

(111i)

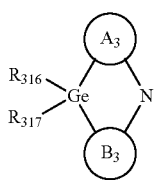

In the formulae (111b) to (111i), the cyclic structure $A_3$, the cyclic structure $B_3$ and $R_{311}$ to $R_{317}$ respectively independently represent the same as the cyclic structure $A_3$, the cyclic structure $B_3$ and $R_{311}$ to $R_{317}$ of the formula (111-1).

In the formula (111), $L_{131}$ represents a single bond or a linking group. When $L_{131}$ is a linking group, $L_{131}$ is bonded to any atom selected from atoms forming the cyclic structure $A_3$ and the cyclic structure $B_3$ and nitrogen atoms in the formula (111-1).

The compound represented by the formula (111) is preferably a compound represented by a formula (101) below.

[Formula 158]

(101)

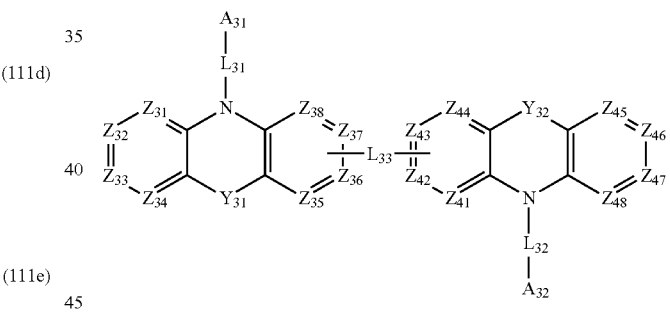

In the formula (101), $Y_{31}$ and $Y_{32}$ each represent a single bond, $CR_{131}R_{132}$ or $SiR_{133}R_{134}$.

$R_{131}$ to $R_{134}$ each independently represent the same as $R_{311}$ to $R_{317}$ in the formula (111-1).

$A_{31}$ and $A_{32}$ are each independently a substituted or unsubstituted aromatic hydrocarbon group having 6 to 30 ring carbon atoms, or a substituted or unsubstituted heterocyclic group having 5 to 30 ring atoms.

$L_{31}$ to $L_{33}$ each independently represent a single bond or a linking group, in which the linking group is a substituted or unsubstituted divalent aromatic hydrocarbon group having 6 to 30 ring carbon atoms or a substituted or unsubstituted divalent heterocyclic group having 5 to 30 ring atoms.

One of $Z_{35}$ to $Z_{38}$ and one of $Z_{41}$ to $Z_{44}$ are bonded to $L_{33}$. The rest of $Z_{35}$ to $Z_{38}$ and the rest of $Z_{41}$ to $Z_{44}$ are each independently $CR_{135}$ or a nitrogen atom.

$R_{135}$ each independently represent the same as $R_{311}$ to $R_{317}$ in the formula (111-1). Adjacent ones of $R_{135}$ may be mutually bonded to form a ring or may be not bonded.

In the formula (101), an arrangement where adjacent ones of $R_{135}$ are mutually bonded to form a ring is exemplified by an arrangement where a fused cyclic skeleton including $Y_{31}$ is represented by any one of formulae (101a) to (101c) below and a fused cyclic skeleton including $Y_{32}$ is represented by any one of formulae (101d) to (101f) below.

[Formula 159]

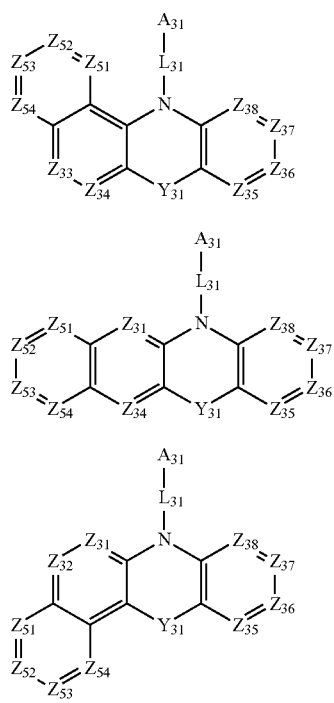

[Formula 160]

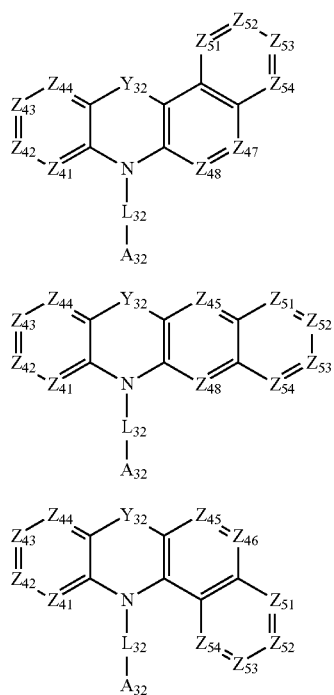

In the formulae (101a) to (101f), $A_{31}$, $A_{32}$, $L_{31}$ to $L_{32}$, $Y_{31}$, $Y_{32}$, $Z_{31}$ to $Z_{38}$ and $Z_{41}$ to $Z_{48}$ respectively represent the same as $A_{31}$, $A_{32}$, $L_{31}$ to $L_{32}$, $Y_{31}$, $Y_{32}$, $Z_{31}$ to $Z_{38}$ and $Z_{41}$ to $Z_{48}$ of the formula (101). $Z_{51}$ to $Z_{54}$ represent the same as $Z_{31}$ to $Z_{38}$ and $Z_{41}$ to $Z_{48}$ of the formula (101).

In the formula (101), when $Y_{31}$ represents a single bond, $CR_{131}R_{132}$ or $SiR_{133}R_{134}$, the fused cyclic skeleton including $Y_{31}$ is represented by one of formulae (101A) to (101C).

In the formula (101), when $Y_{32}$ represents a single bond, $CR_{131}R_{132}$ or $SiR_{133}R_{134}$, the fused cyclic skeleton including $Y_{32}$ is represented by one of formulae (101D) to (101F).

[Formula 161]

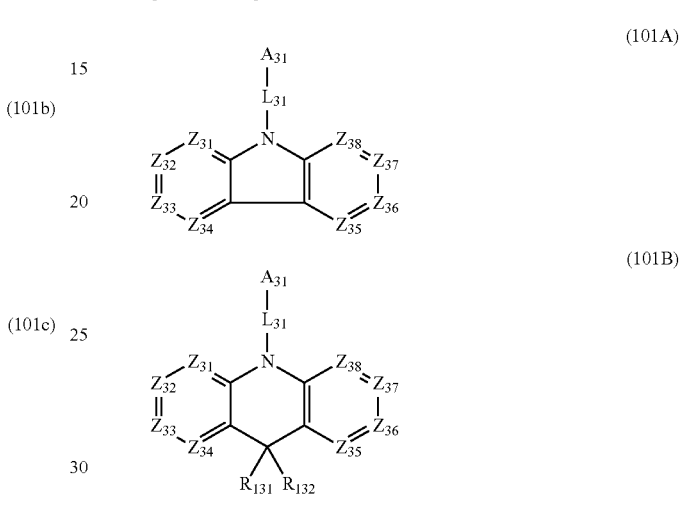

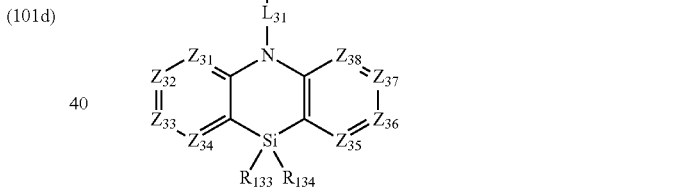

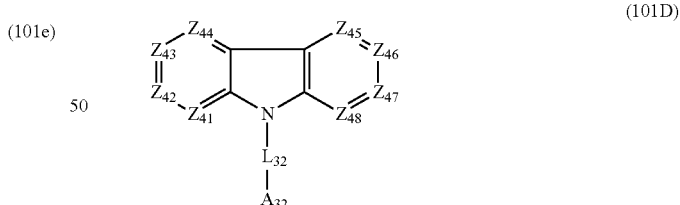

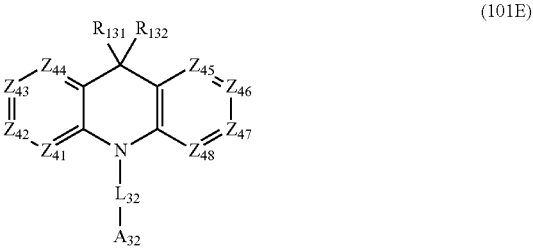

-continued

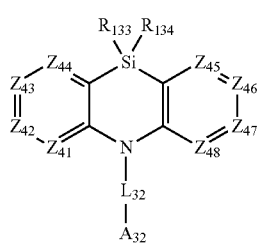

(101F)

In the formulae (101A) to (101F), $A_{31}$, $A_{32}$, $L_{31}$ to $L_{32}$, $Z_{31}$ to $Z_{38}$ and $Z_{41}$ to $Z_{48}$ respectively represent the same as $A_{31}$, $A_{32}$, $L_{31}$ to $L_{32}$, $Z_{31}$ to $Z_{38}$ and $Z_{41}$ to $Z_{48}$ of the formula (101).

Among the above, the fused cyclic skeleton including $Y_{31}$ is preferably represented by the formula (101A) and the fused cyclic skeleton including $Y_{32}$ is preferably represented by the formula (101D) and the formula (101) is preferably represented by a formula (101-1) below.

[Formula 162]

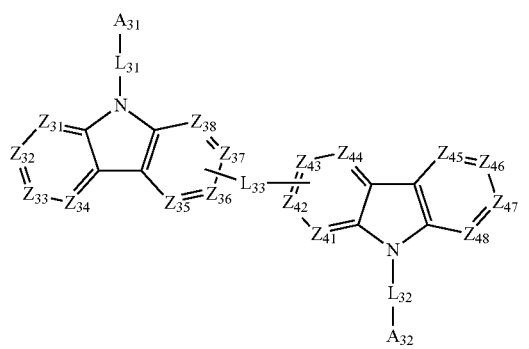

(101-1)

In the formula (101-1), $A_{31}$, $A_{32}$, $L_{31}$ to $L_{33}$, $Z_{31}$ to $Z_{38}$ and $Z_{41}$ to $Z_{48}$ respectively represent the same as $A_{31}$, $A_{32}$, $L_{31}$ to $L_{33}$, $Z_{31}$ to $Z_{38}$ and $Z_{41}$ to $Z_{48}$ of the formula (101).

Moreover, in the formula (101-1), $L_{33}$ is preferably a single bond. The single bond more preferably bonds the respective positions 3 of the carbazolyl groups. Specifically, the formula (101-1) is preferably represented by a formula (101-2) below in which $Z_{36}$ and $Z_{43}$ of the formula (101-1) are carbon atoms and the carbon atoms are bonded by a single bond.

[Formula 163]

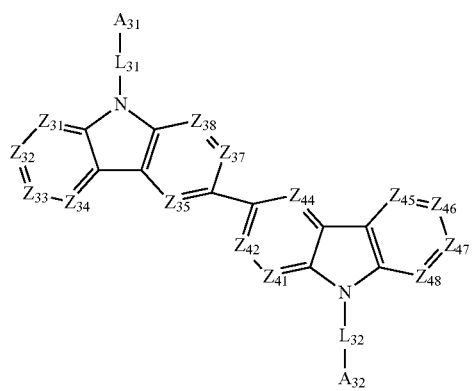

(101-2)

In the formula (101-2), $A_{31}$, $A_{32}$, $L_{31}$ to $L_{32}$, $Z_{31}$ to $Z_{35}$, $Z_{37}$ to $Z_{38}$, $Z_{41}$ to $Z_{42}$, and $Z_{44}$ to $Z_{48}$ respectively represent the same as $A_{31}$, $A_{32}$, $L_{31}$ to $L_{32}$, $Z_{31}$ to $Z_{35}$, $Z_{37}$ to $Z_{38}$, $Z_{41}$ to $Z_{42}$, and $Z_{44}$ to $Z_{48}$ of the formula (101).

Moreover, in the formula (101-1), $L_{33}$ is preferably a single bond. It is also preferable that the single bond bonds a position 2 of the carbazolyl group and the position 3 of the other carbazolyl group. Specifically, the formula (101-1) is preferably represented by a formula (101-3) below in which $Z_{37}$ and $Z_{43}$ of the formula (101-1) are carbon atoms and the carbon atoms are bonded by a single bond. Alternatively, the formula (101-1) is preferably represented by a formula (101-3) below in which $Z_{36}$ and $Z_{42}$ of the formula (101-1) are carbon atoms and the carbon atoms are bonded by a single bond.

[Formula 164]

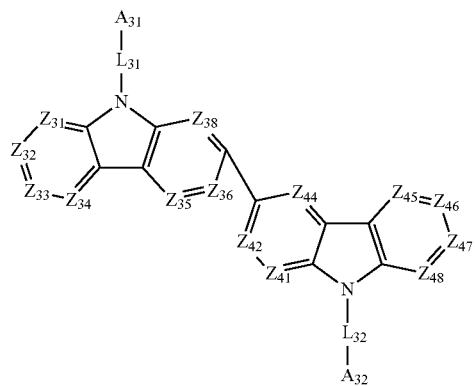

(101-3)

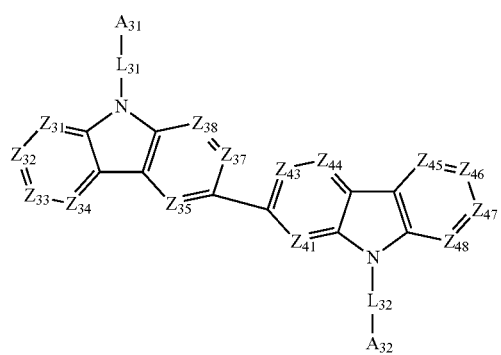

(101-4)

In the formula (101-3), $A_{31}$, $A_{32}$, $L_{31}$ to $L_{32}$, $Z_{31}$ to $Z_{36}$, $Z_{38}$, $Z_{41}$ to $Z_{42}$, and $Z_{44}$ to $Z_{48}$ respectively represent the same as $A_{31}$, $A_{32}$, $L_{31}$ to $L_{32}$, $Z_{31}$ to $Z_{36}$, $Z_{38}$, $Z_{41}$ to $Z_{42}$, and $Z_{44}$ to $Z_{48}$ of the formula (101).

In the formula (101-4), $A_{31}$, $A_{32}$, $L_{31}$ to $L_{32}$, $Z_{31}$ to $Z_{35}$, $Z_{37}$ to $Z_{38}$, $Z_{41}$, and $Z_{43}$ to $Z_{48}$ respectively represent the same as $A_{31}$, $A_{32}$, $L_{31}$ to $L_{32}$, $Z_{31}$ to $Z_{35}$, $Z_{37}$ to $Z_{38}$, $Z_{41}$, and $Z_{43}$ to $Z_{48}$ of the formula (101).

The formulae (101-2) to (101-4) are preferably represented by formulae (101-2a) to (101-4a) in which the rest of $Z_{31}$ to $Z_{38}$ and $Z_{41}$ to $Z_{48}$ except for carbon atoms to be mutually bonded in the formulae (101-2) to (101-4) are each independently $CR_{135}$.

[Formula 165]

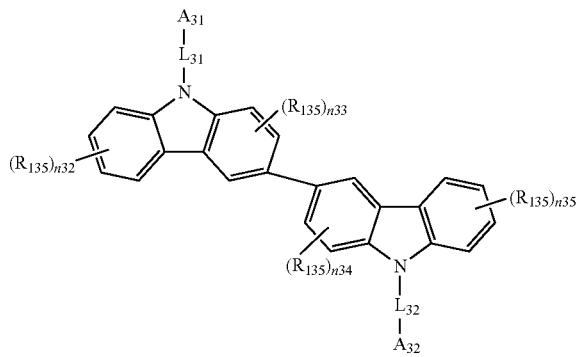

(101-2a)

(101-3a)

(101-4a)

In the formulae (101-2a) to (101-4a), $A_{31}$, $A_{32}$, $L_{31}$, $L_{32}$ and $R_{135}$ represents the same as $A_{31}$, $A_{32}$, $L_{31}$, $L_{32}$ and $R_{135}$ of the formula (101).

n32 and n35 are an integer of 0 to 4. n33 and n34 are an integer of 0 to 3.

A plurality of $R_{135}$ are mutually the same or different.

In the formulae (101), (101-1) to (101-4) and (101-2a) to (101-4a), at least one of $A_{31}$ and $A_{32}$ is preferably represented by a formula (101-A30) below, more preferably represented by a formula (101-A31) below. Further, in the formula (101-A31), $Y_{33}$ is preferably one of a nitrogen atom, an oxygen atom and a sulfur atom. In other words, at least one of $A_{31}$ and $A_{32}$ is preferably a substituted or unsubstituted dibenzofuranyl group, a substituted or unsubstituted carbazolyl group, or a substituted or unsubstituted dibenzothiophenyl group.

[Formula 166]

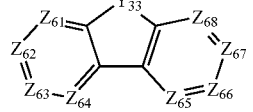

(101-A30)

In the formula (101-A30), $Y_{33}$ represents a nitrogen atom, an oxygen atom or a sulfur atom. $Z_{61}$ to $Z_{68}$ represent the same as $Z_{31}$ to $Z_{38}$ that are not to be bonded to $L_{33}$ in the formula (101).

[Formula 167]

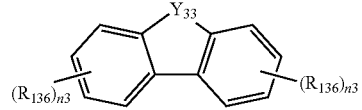

(101-A31)

In the formula (101-A31), $Y_{33}$ represents a nitrogen atom, an oxygen atom or a sulfur atom. $R_{136}$ represents the same as $R_{135}$ of the formula (101). n3 is an integer of 0 to 4.

At least one of $A_{31}$ and $A_{32}$ is preferably a substituted or unsubstituted dibenzofuranyl group or a substituted or unsubstituted dibenzothiophenyl group.

When $A_{31}$ is a substituted or unsubstituted dibenzofuranyl group or a substituted or unsubstituted dibenzothiophenyl group, a position 1 or position 4 of $A_{31}$ is preferably bonded to $L_{31}$.

When $A_{32}$ is a substituted or unsubstituted dibenzofuranyl group or a substituted or unsubstituted dibenzothiophenyl group, a position 1 or position 4 of $A_{32}$ is preferably bonded to $L_{32}$.

In the formulae (101), (101-1) to (101-4) and (101-2a) to (101-4a), $L_{31}$ and $L_{32}$ are preferably a single bond or a substituted or unsubstituted divalent aromatic hydrocarbon group having 6 to 30 ring carbon atoms.

More preferably, $A_{31}$ is represented by the formula (101-A31) and $L_{31}$ is a substituted or unsubstituted divalent aromatic hydrocarbon group having 6 to 30 ring carbon atoms. Further preferably, $A_{32}$ is a substituted or unsubstituted aromatic hydrocarbon group having 6 to 30 ring carbon atoms and $L_{32}$ is a single bond. At this time, the substituted or unsubstituted divalent aromatic hydrocarbon group having 6 to 30 ring carbon atoms in $L_{31}$ is more preferably a substituted or unsubstituted phenylene group. The substituted or unsubstituted aromatic hydrocarbon group having 6 to 30 ring carbon atoms in $A_{32}$ is more preferably a substituted or unsubstituted phenyl group. Such a compound in the formula (101-1) is represented by a formula (101-5) below.

[Formula 168]

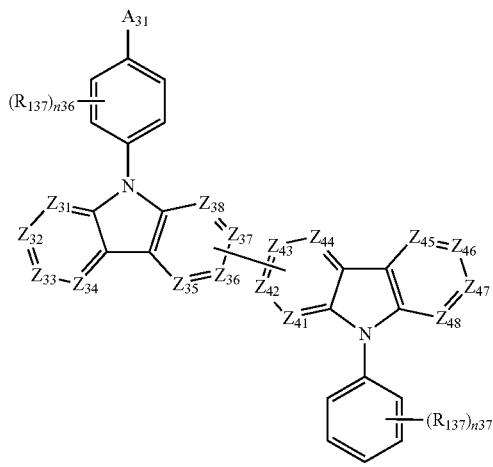

(101-5)

In the formula (101-5), $Z_{31}$ to $Z_{38}$ and $Z_{41}$ to $Z_{48}$ respectively represent the same as $Z_{31}$ to $Z_{38}$ and $Z_{41}$ to $Z_{48}$ of the formula (1). $A_{31}$ is represented by the formula (101-A31). $R_{137}$ represents the same as $R_{135}$ of the formula (1). n36 is an integer of 0 to 4. n37 is an integer of 0 to 5. A plurality of $R_{137}$ are mutually the same or different.

The formula (101-5) is more preferably represented by a formula (101-6) below.

[Formula 169]

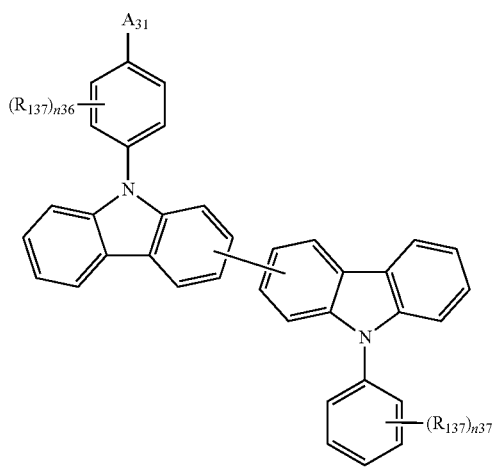

(101-6)

In the formula (101-6), $A_{31}$, $R_{137}$, n36 and n37 represent the same as $A_{31}$, $R_{137}$, n36 and n37 of the formula (101-4).

It is also preferable that $HAr_{131}$ and $HAr_{132}$ of the formula (111) are each independently a group derived from a structure represented by a formula (111-3) below.

[Formula 170]

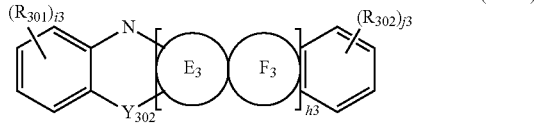

(111-3)

In the formula (111-3), $Y_{302}$ represents the same as $Y_{301}$ of the formula (111-1).

$R_{301}$ and $R_{302}$ each independently represent the same as $R_{301}$ and $R_{302}$ in the formula (111-1).

i3 and j3 are 4.

$E_3$ represents a cyclic structure represented by a formula (111-3a) below and $F_3$ represents a cyclic structure represented by a formula (111-3b) or (111-3c) below. Each of the cyclic structure $E_3$ and the cyclic structure $F_3$ is fused to an adjacent cyclic structure at any position. In the formula (111-3), h is an integer of 0 to 4. h is a repeating unit of a linking cyclic structure in which the cyclic structure $E_3$ and the cyclic structure $F_3$ are fused to each other. When h is 2 or more, a plurality of cyclic structures $F_3$ may be the same or different.

[Formula 171]

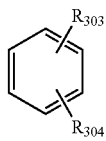

(111-3a)

In the formula (111-3a), $R_{303}$ and $R_{304}$ represent the same as $R_{311}$ to $R_{317}$ of the formula (111-1). In the formula (111-3a), when $R_{303}$ and $R_{304}$ are substituents at adjacent positions, $R_{303}$ and $R_{304}$ may form a ring.

[Formula 172]

(111-3b)

(111-3c)

$Y_{311}$ in the formula (111-3b) and $Y_{312}$ in the formula (111-3c) represent $NR_{318}$, $CR_{319}R_{320}$, a sulfur atom, an oxygen atom or a nitrogen atom to be bonded to $L_{131}$.

In the formula (111-3c), $Y_{313}$ represents the same as $Y_{301}$ of the formula (111-1). However, $Y_{313}$ is not a single bond.

$R_{318}$ to $R_{320}$ represent the same as $R_{311}$ to $R_{317}$ of the formula (111-1).

In the formula (111-3), when h3 is 1 and the cyclic structure $F_3$ is represented by the formula (111-3b), the structure of the formula (111-3) is represented by any one of formulae (111-3A) to (111-3F).

[Formula 173]

(111-3A)
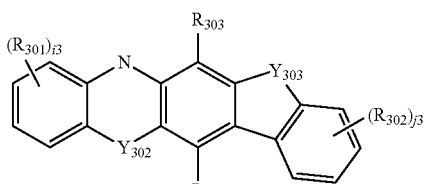

(111-3B)
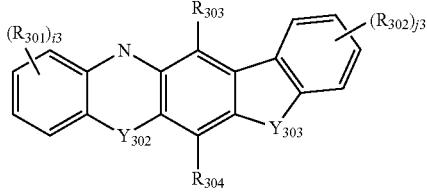

(111-3C)
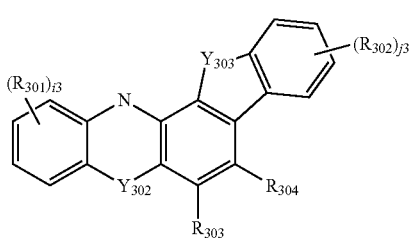

(111-3D)
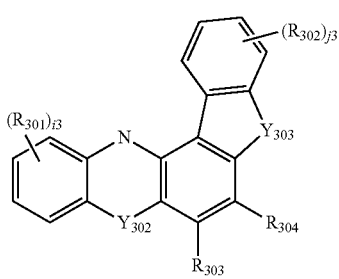

(111-3E)
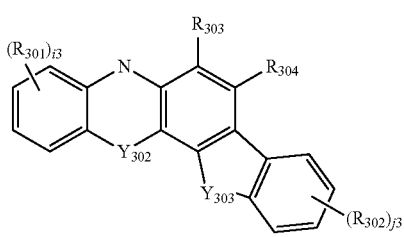

(111-3F)
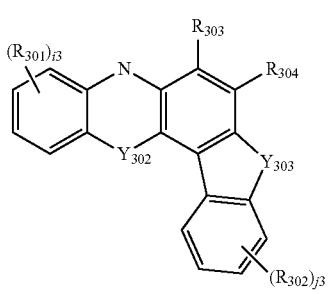

In the formulae (111-3A) to (111-3F), $Y_{302}$ represents the same as $Y_{302}$ of the formula (111-3).

$R_{301}$ to $R_{304}$ each independently represent the same as $R_{311}$ to $R_{317}$ in the formula (111-1). Adjacent ones of $R_{301}$ may form a ring. Adjacent ones of $R_{302}$ may form a ring. Adjacent $R_{303}$ and $R_{304}$ may form a ring.

$Y_{303}$ represents the same as $Y_{311}$ of the formula (111-3b).

i3 and j3 are 4.

Each of the substituents described in the formulae (101), (101-1) to (101-6), (101-2a) to (101-3a), (101-A30), (101-A31), (111), (111b) to (111i), (111-1) to (111-3), (111-3A) to (111-3F), and (111-3a) to (111-3c) will be described below.

Specific examples of the compound represented by the formulae (101), (101-1) to (101-6), (101-2a) to (101-3a), (101-A30), (101-A31), (111), (111b) to (111i), (111-1) to (111-3), (111-3A) to (111-3F), and (111-3a) to (111-3c) are shown below, but the invention is not limited thereto.

[Formula 174]

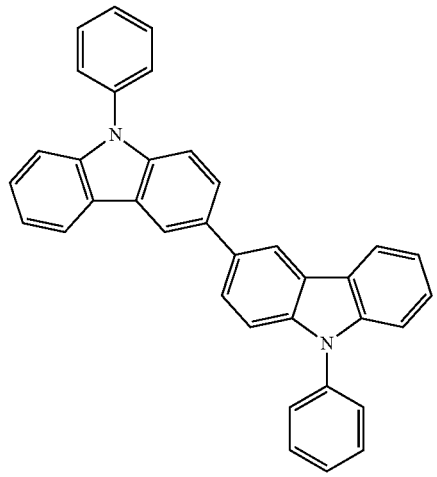

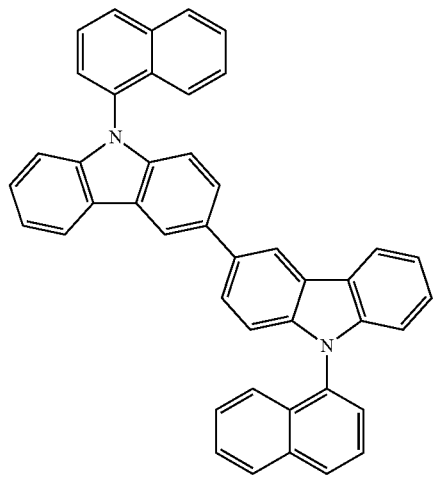

237
-continued
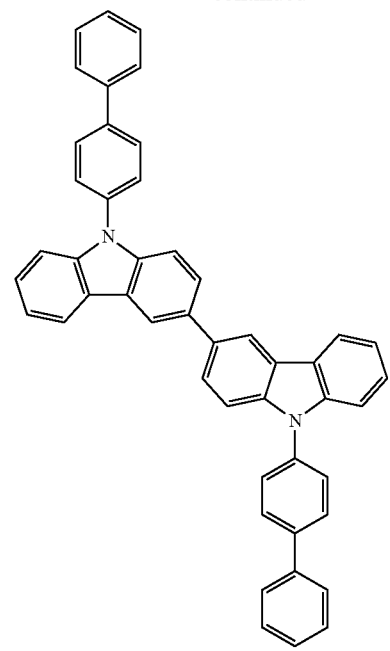
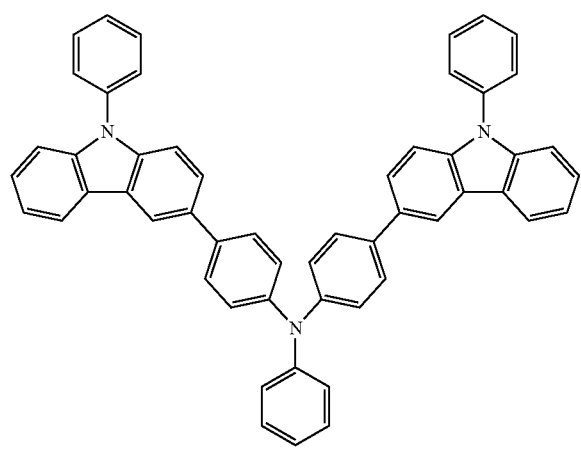
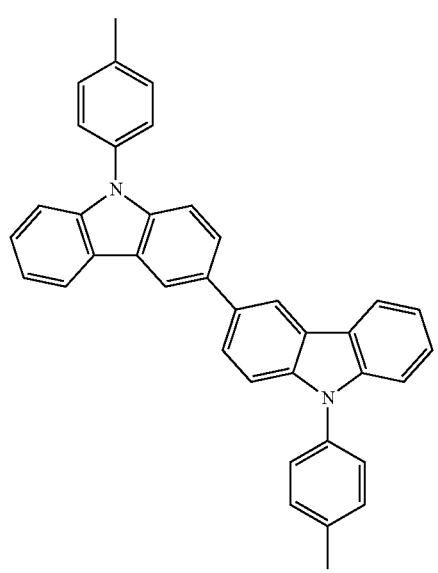
238
-continued
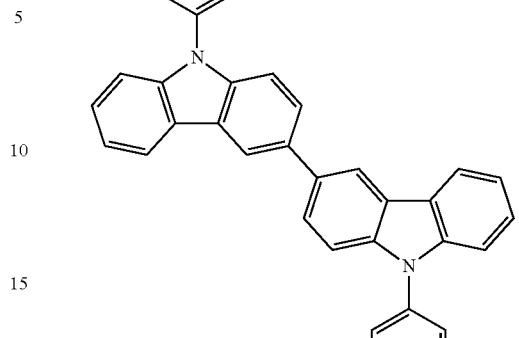
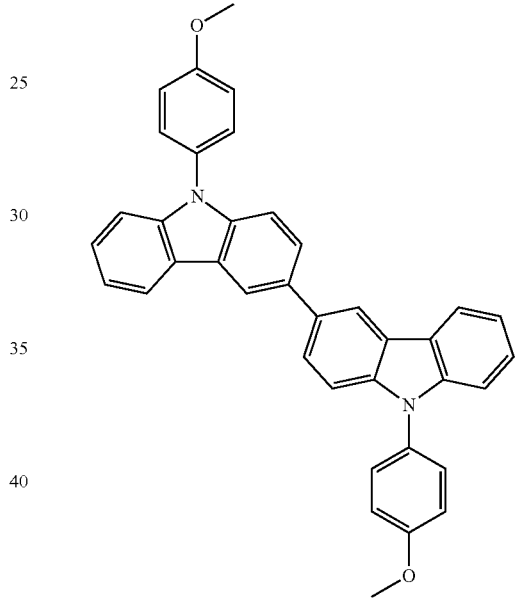
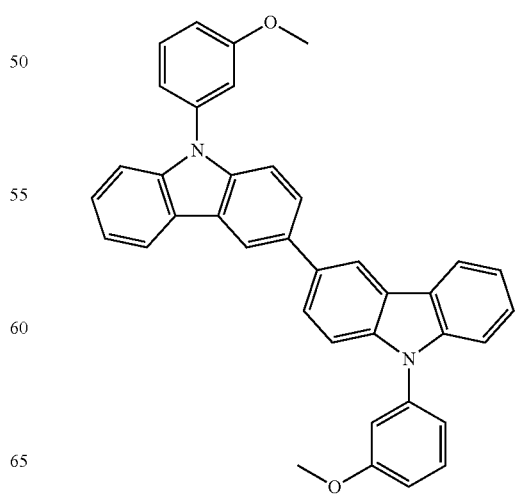

239
-continued
[Formula 175]
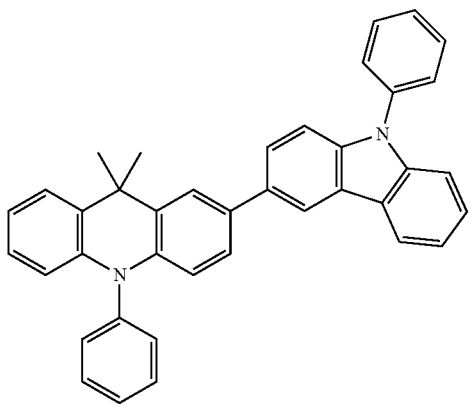
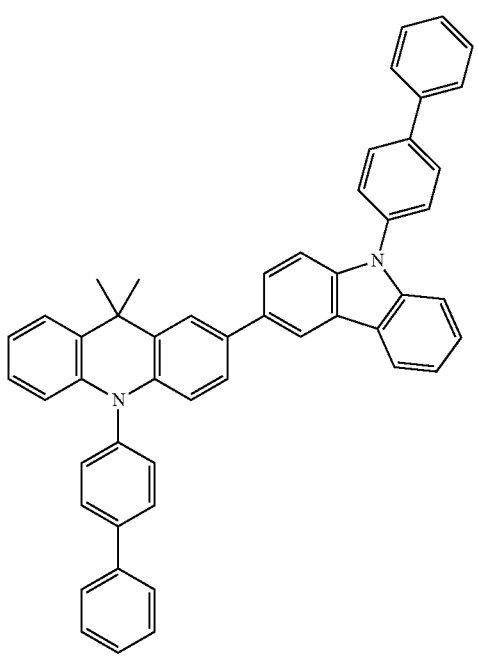
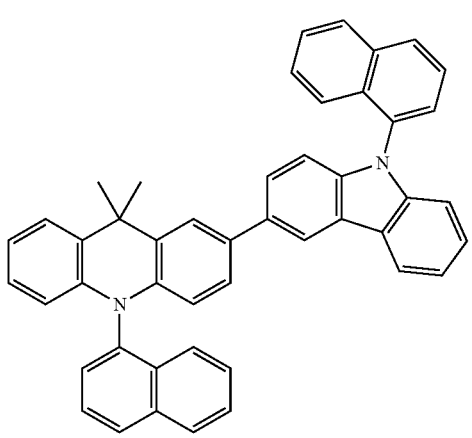
240
-continued
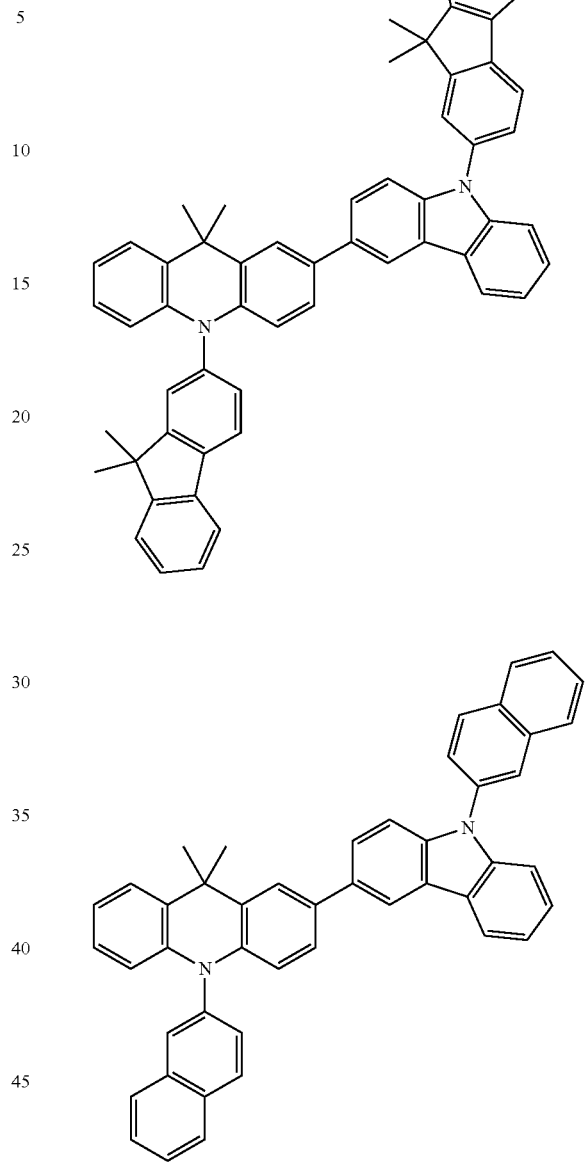
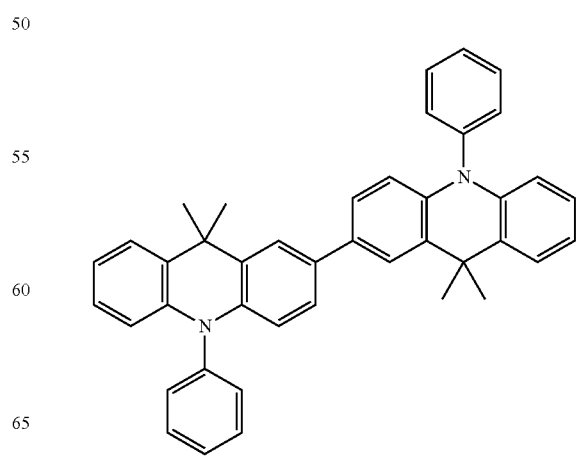

241
-continued
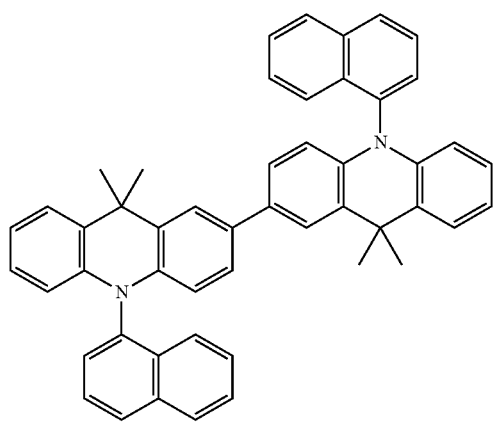
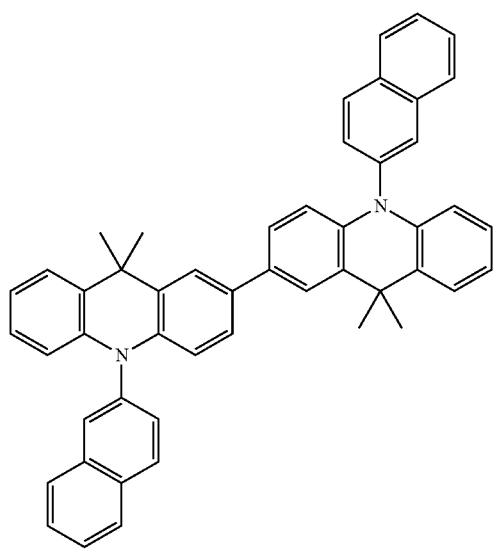
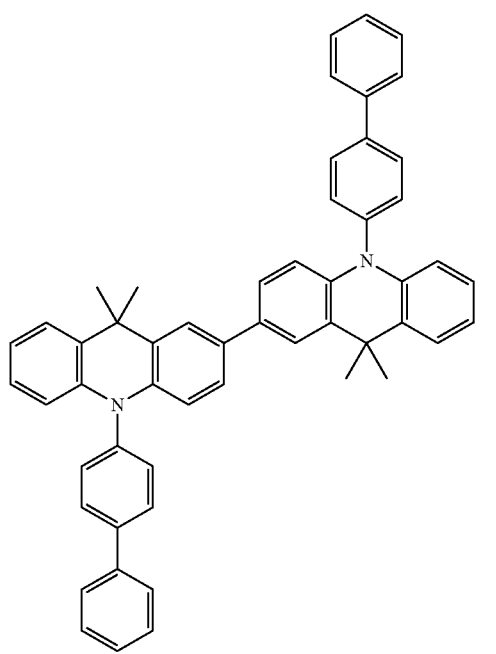
242
-continued
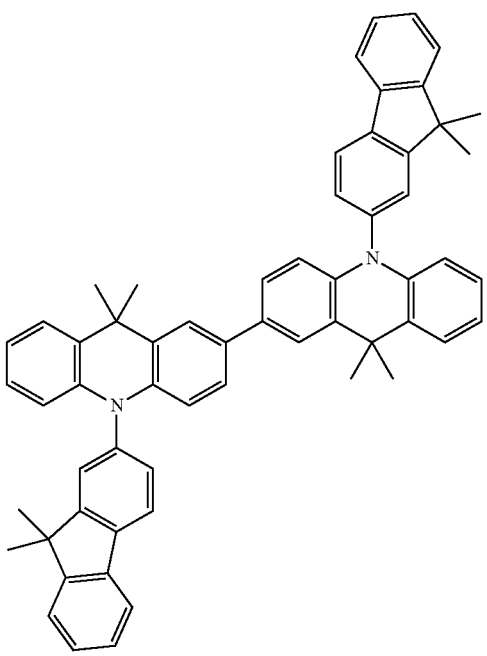
[Formula 176]
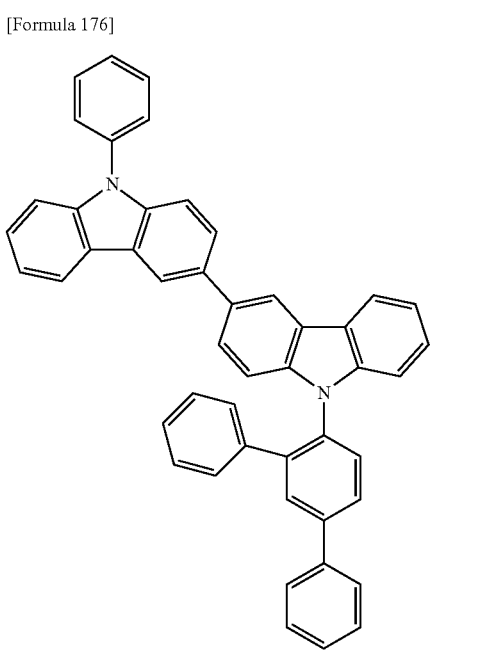

243
-continued
244
-continued
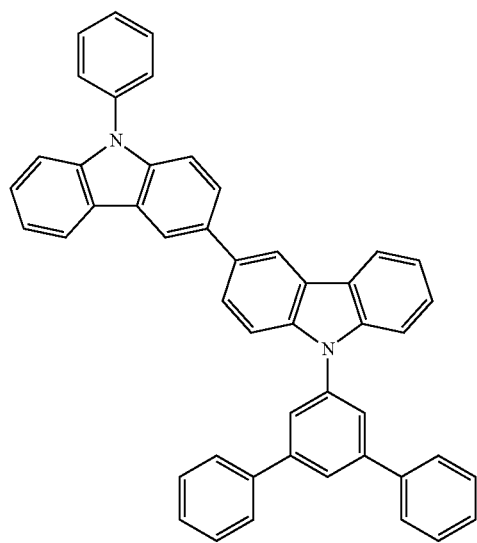
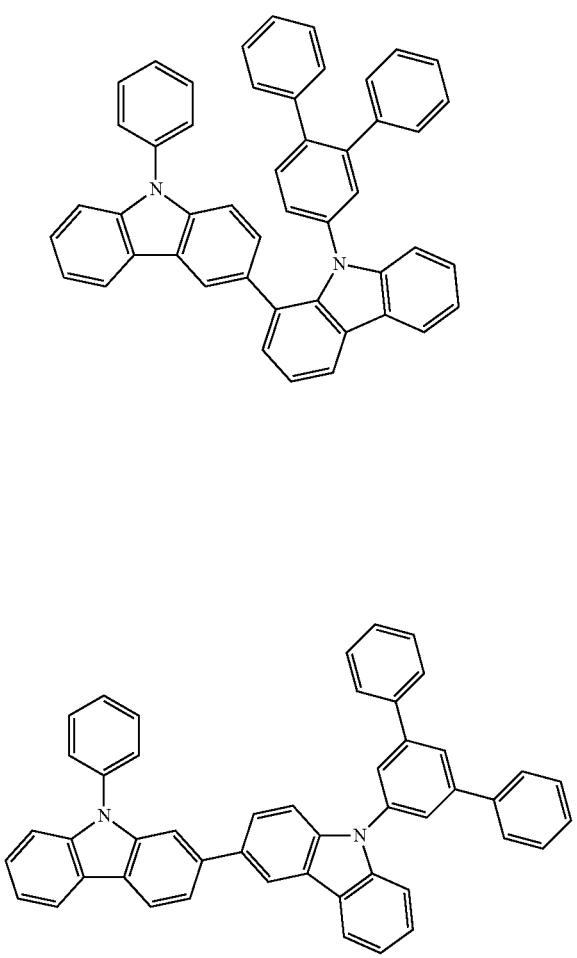
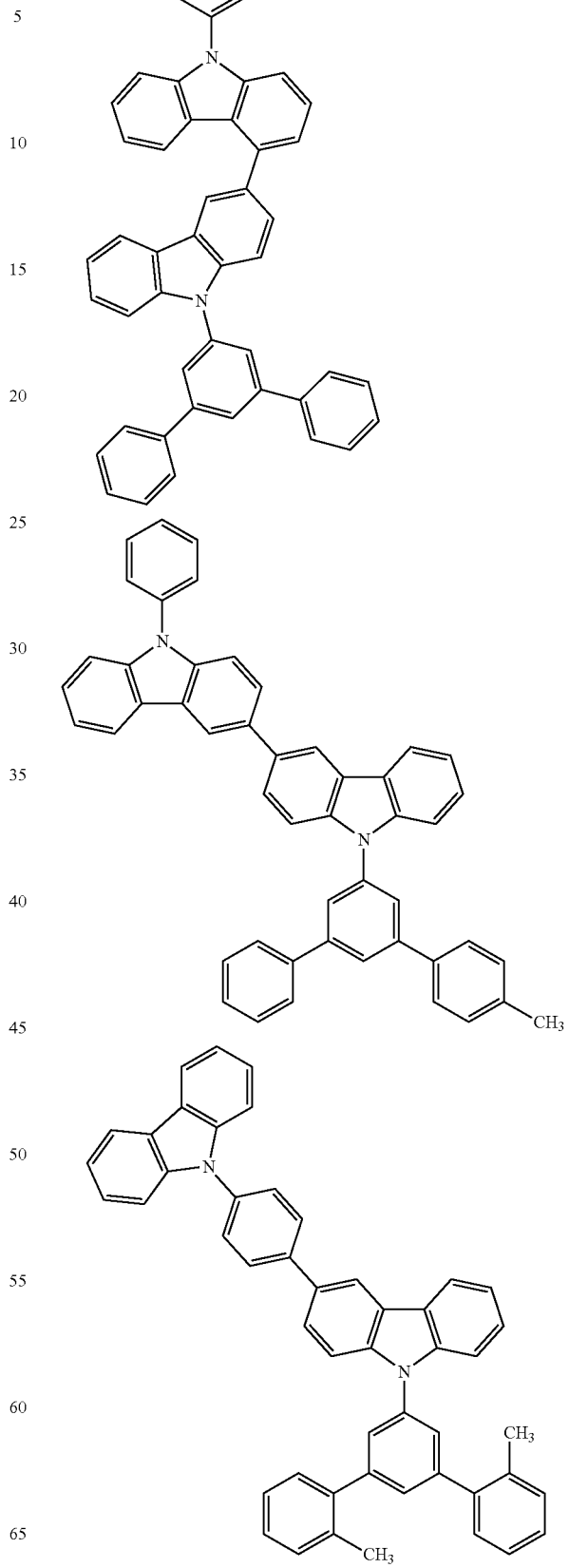

-continued
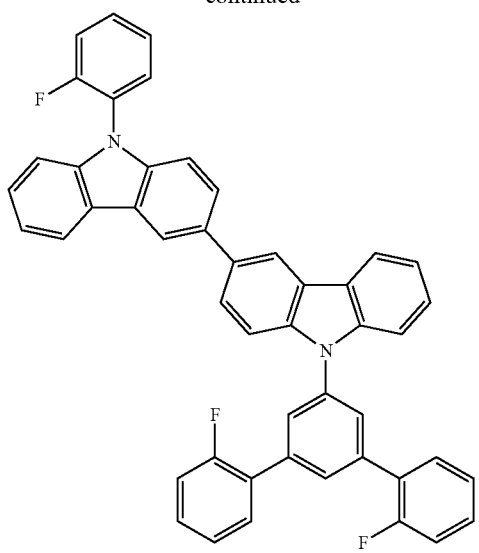
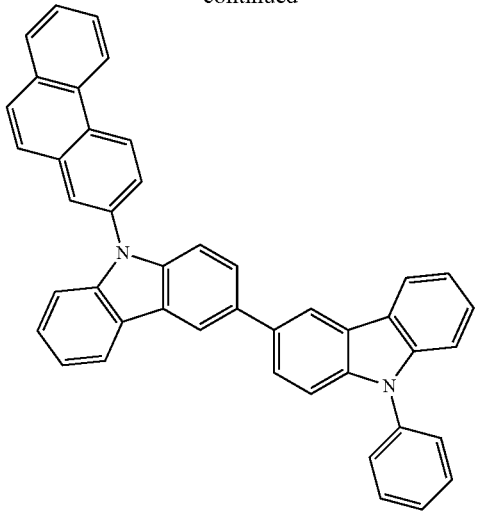
[Formula 178]
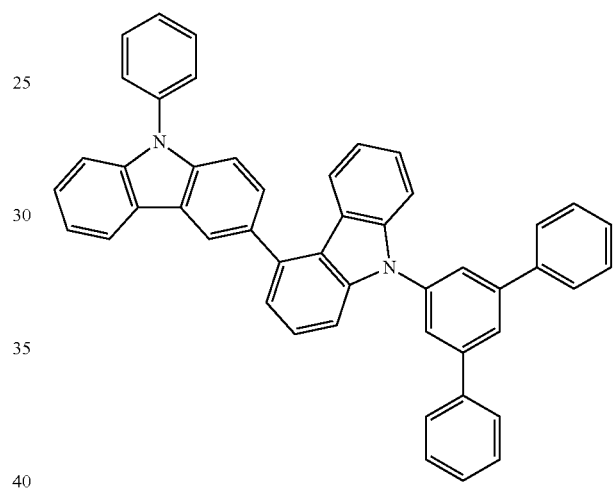
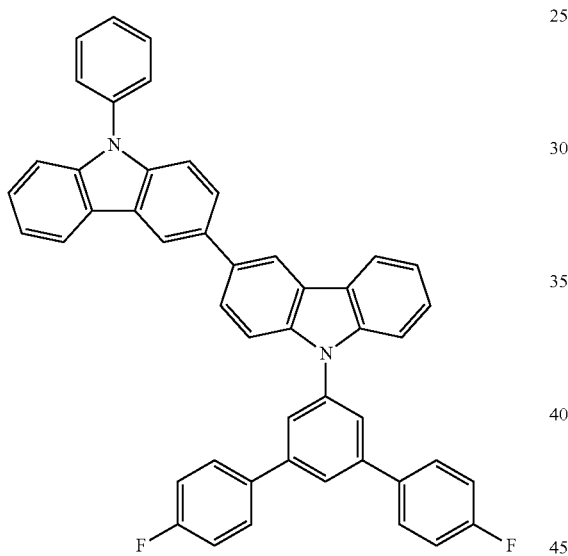
[Formula 177]
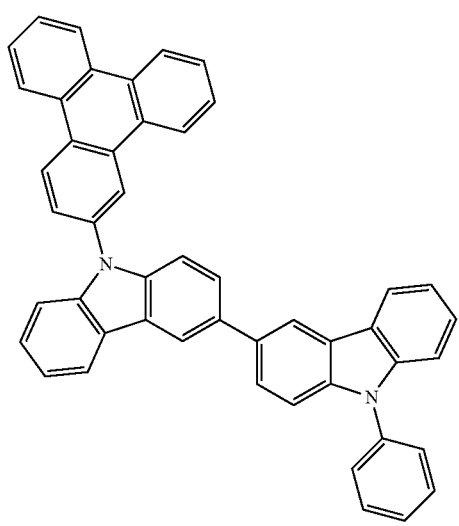
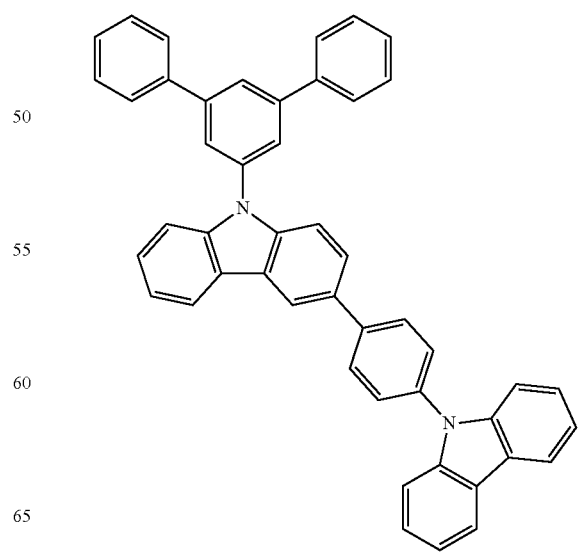

247
-continued
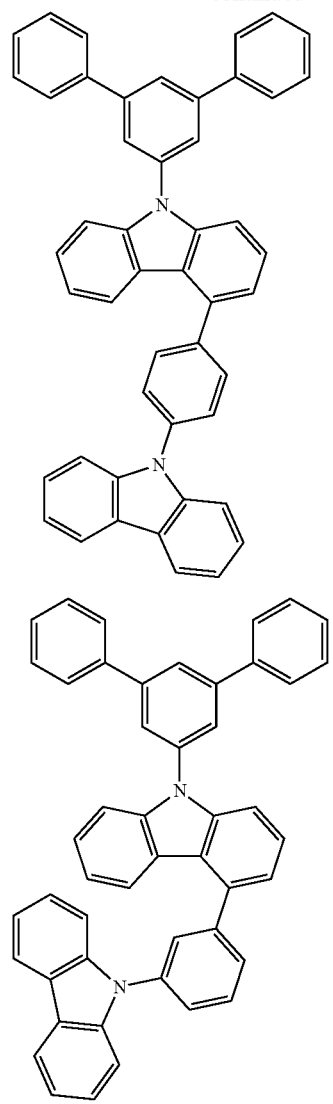
248
-continued
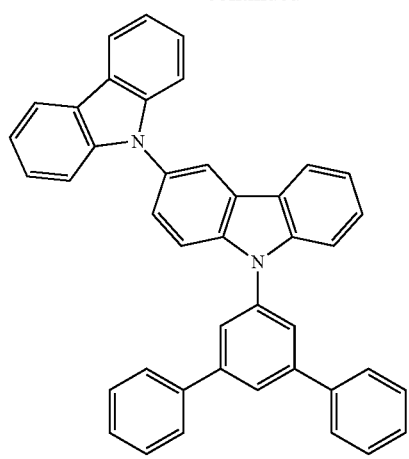
[Formula 179]
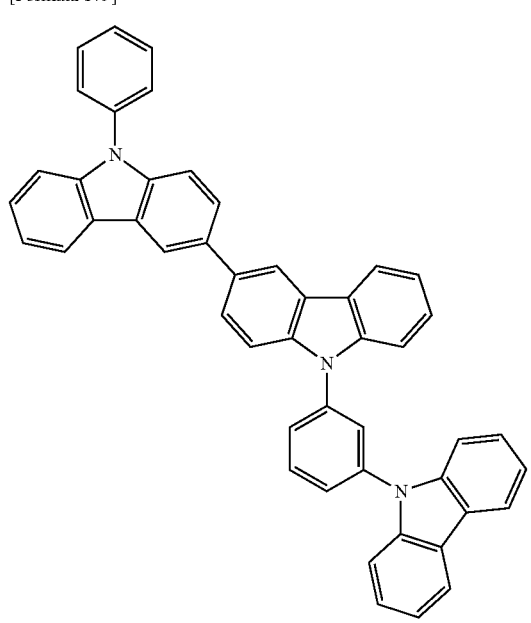

249
-continued
250
-continued
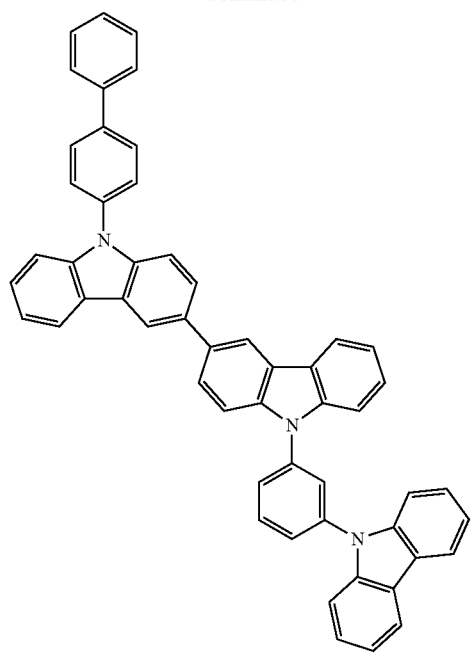
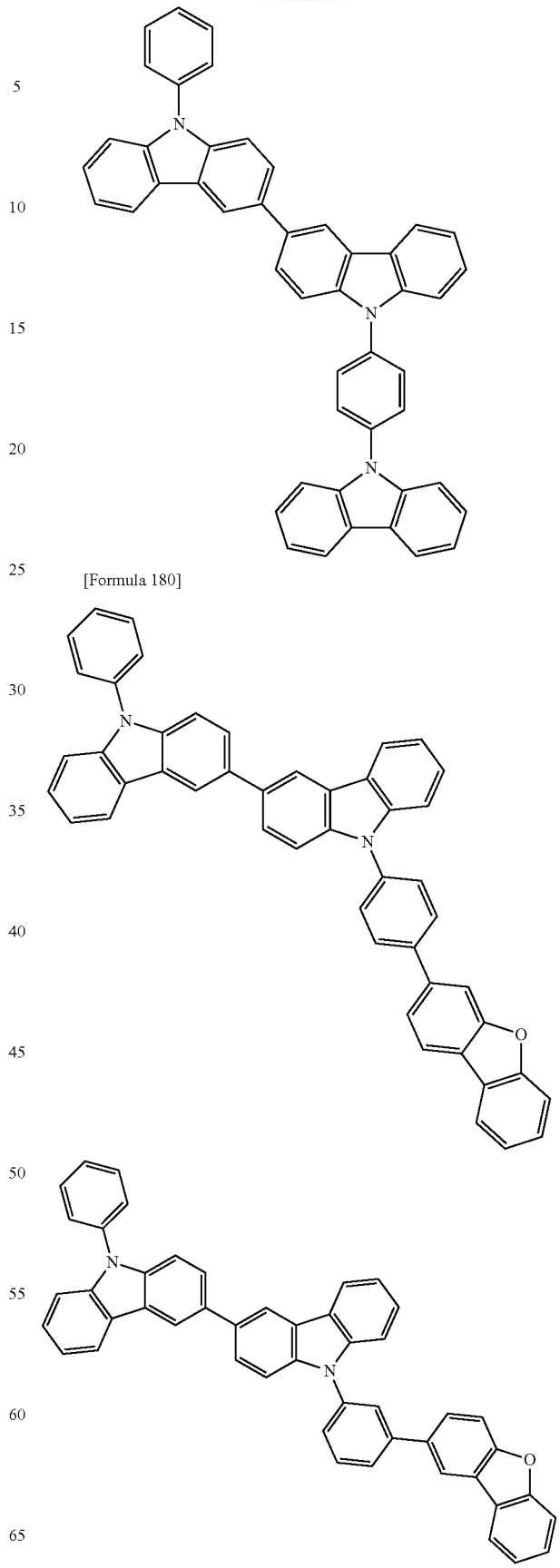
[Formula 180]

251
-continued
252
-continued
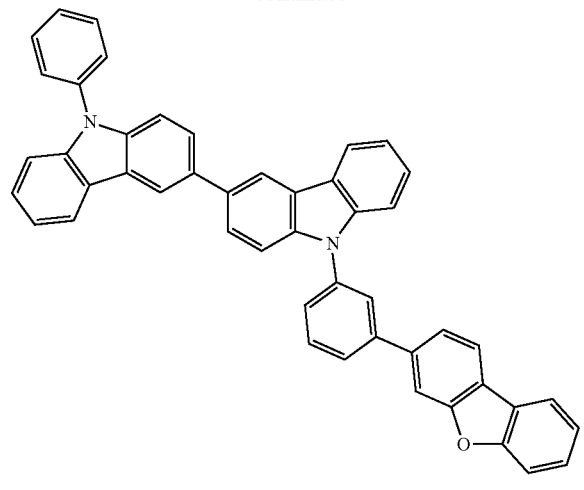
[Formula 181]
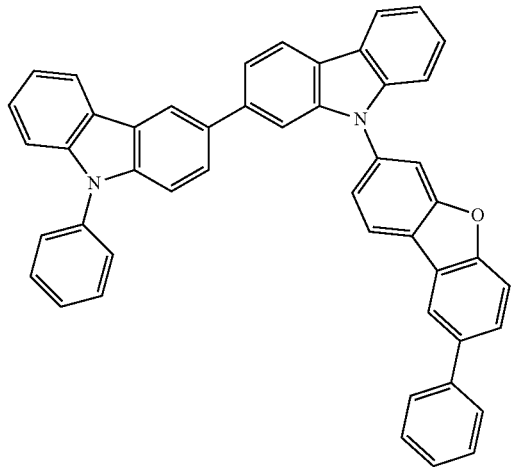
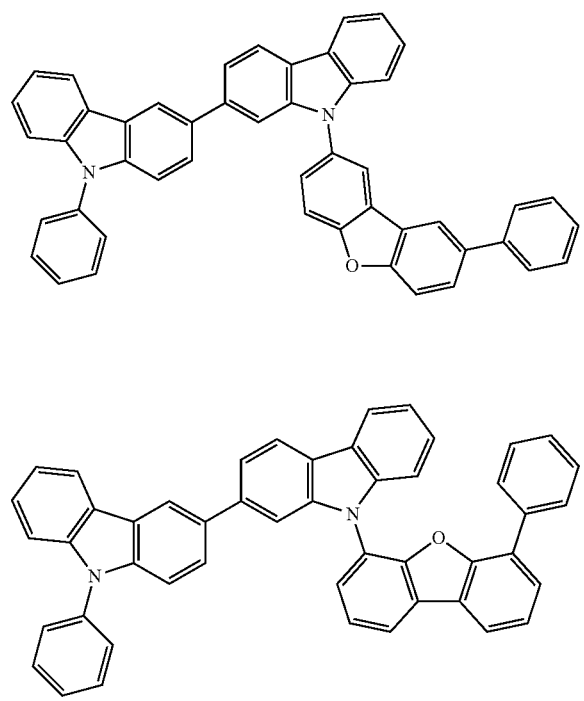

-continued
[Formula 182]
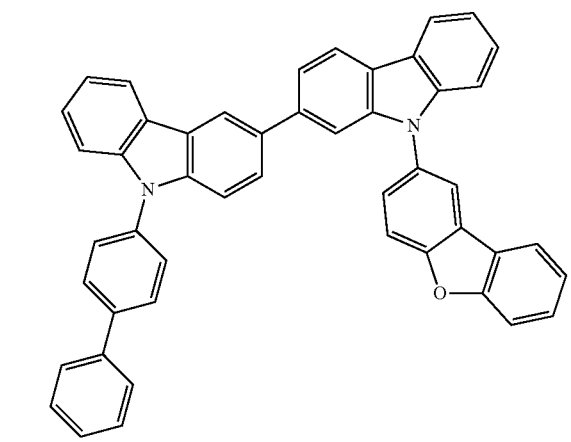
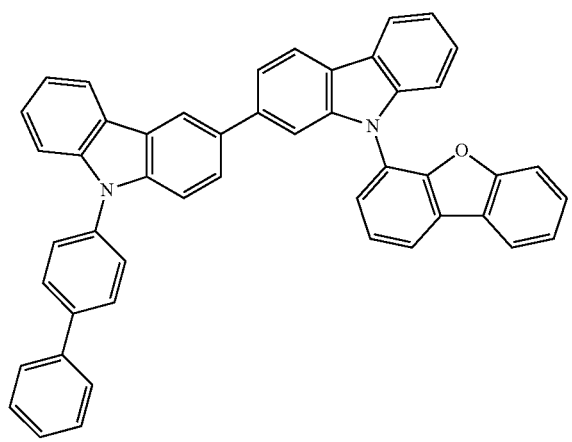
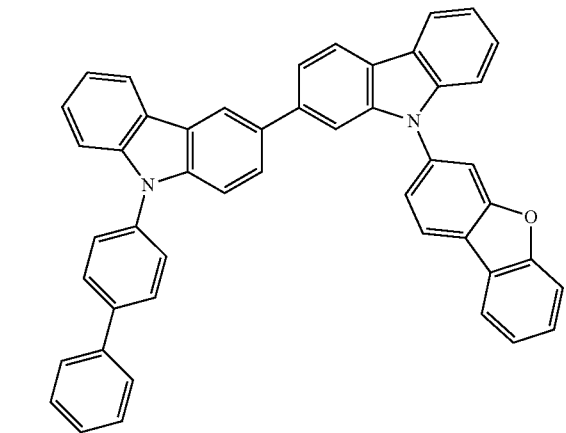
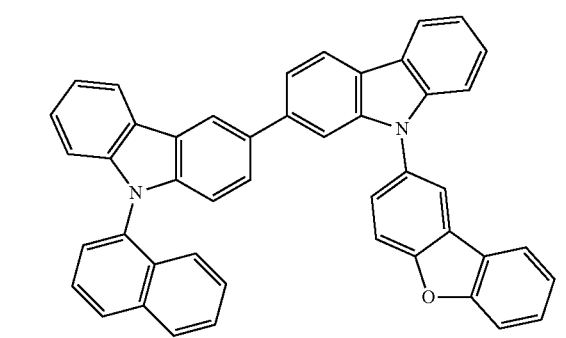
-continued
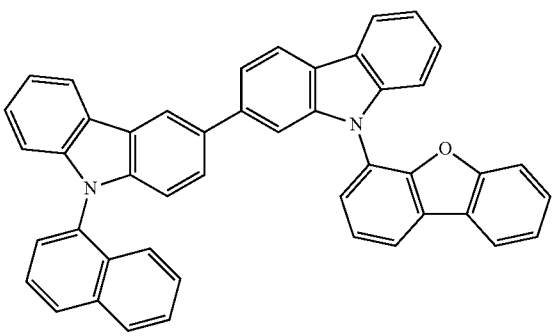
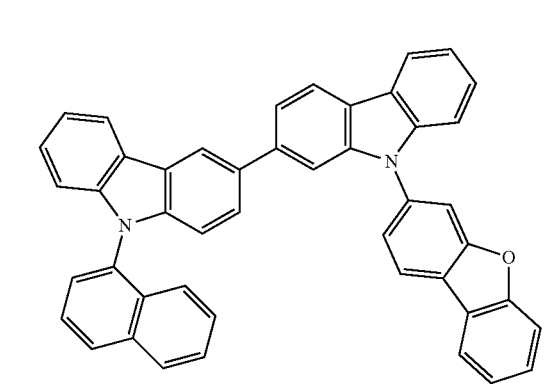
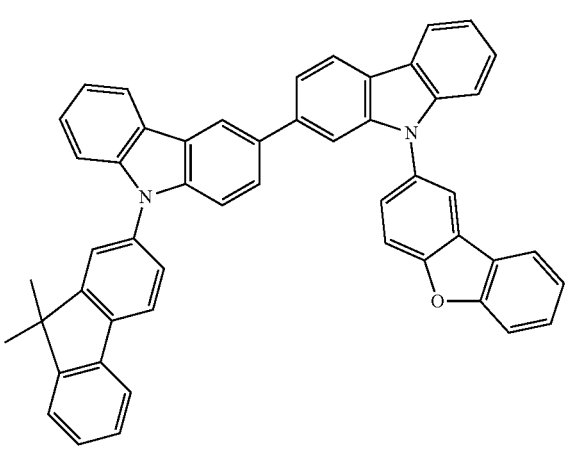
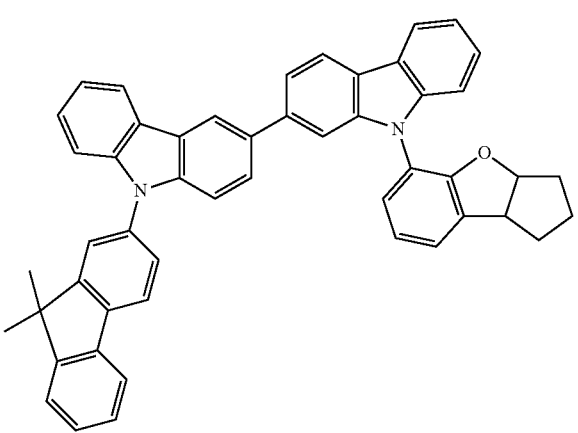

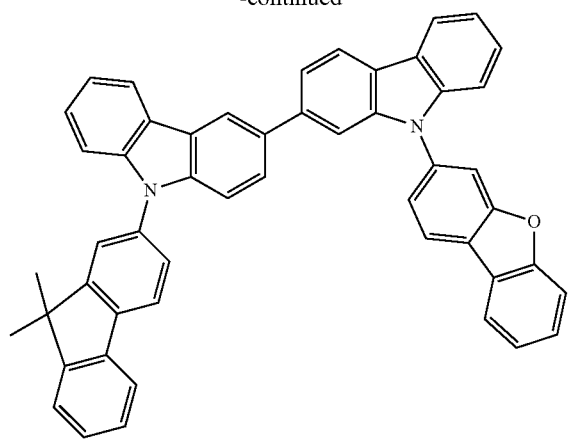
[Formula 183]
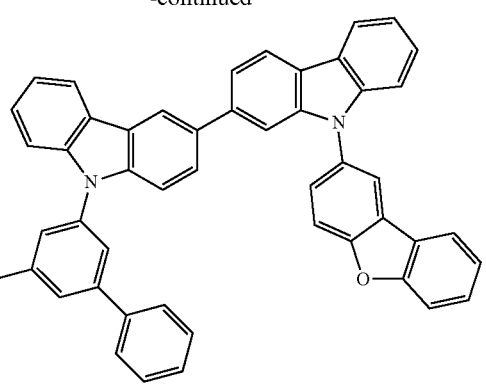
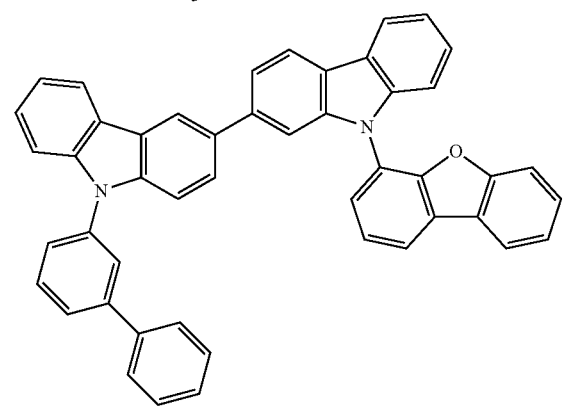
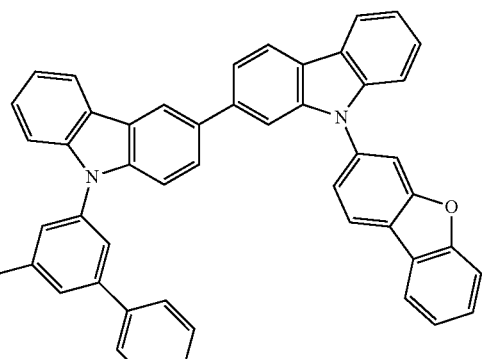
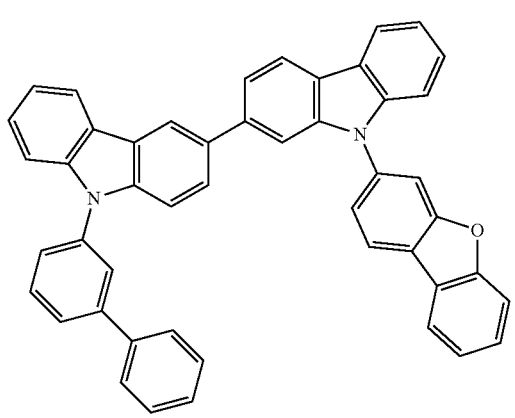
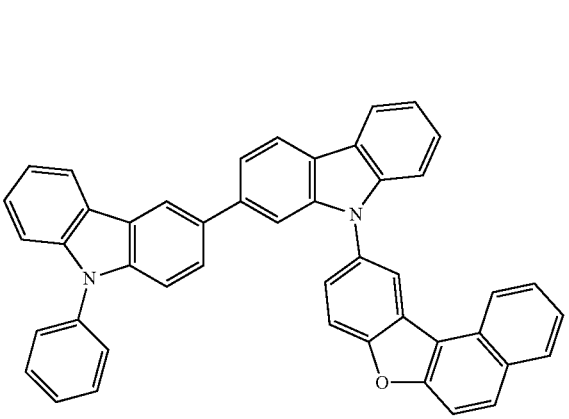

-continued

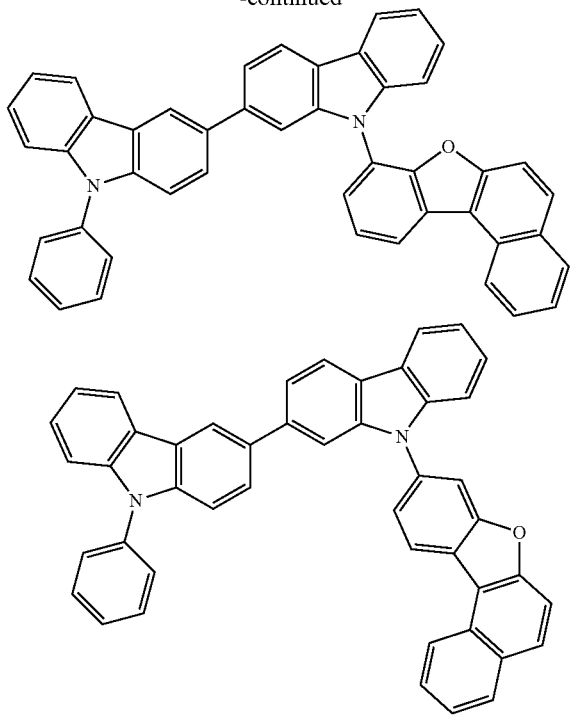

In the exemplary embodiment, the hole transporting layer containing the compound represented by the formula (111) is preferably provided adjacent to the emitting layer and is preferably bonded to the emitting layer.

A plurality of hole transporting layers may be provided. In such an arrangement, the hole transporting layer containing the compound represented by the formula (111) is preferably provided adjacent to the emitting layer and is preferably bonded to the emitting layer.

When the emitting layer and the hole transporting layer are mutually adjacent or bonded, the compound represented by the formula (111) is preferably different from the dopant material contained in the emitting layer.

Since the compound represented by the formula (111) has a large triplet energy, the drive voltage of the organic EL device can be reduced and the luminous efficiency thereof can be improved by including the hole transporting layer containing the compound represented by the formula (101). This advantage is outstanding when the organic EL device includes the emitting layer containing a hole-trapping dopant material such as the compound represented by the formula (2).

In the exemplary embodiment, when the hole injecting layer is provided, a material for forming the hole injecting layer is preferably a material for transporting holes to the emitting layer at a lower electric field intensity. For instance, an aromatic amine compound is preferably used. The material for the hole injecting layer is preferably a porphyrin compound, an aromatic tertiary amine compound or a styryl amine compound, particularly preferably the aromatic tertiary amine compound such as hexacyanohexaazatriphenylene (HAT).

Modifications of Embodiment(s)

It should be noted that the invention is not limited to the above exemplary embodiments but may include any modification and improvement as long as such modification and improvement are compatible with the invention.

The emitting layer is not limited to a single layer, but may be provided as laminate by a plurality of emitting layers. When the organic EL device includes the plurality of emitting layers, it is only required that at least one of the emitting layers includes the compound represented by the formula (1) and the compound represented by the formula (2). The rest of the emitting layers may be a fluorescent emitting layer or a phosphorescent emitting layer.

When the organic EL device includes the plurality of emitting layers, the plurality of emitting layers may be adjacent to each other, or may be laminated on each other via an intermediate layer (a so-called tandem organic EL device).

Figure 3:
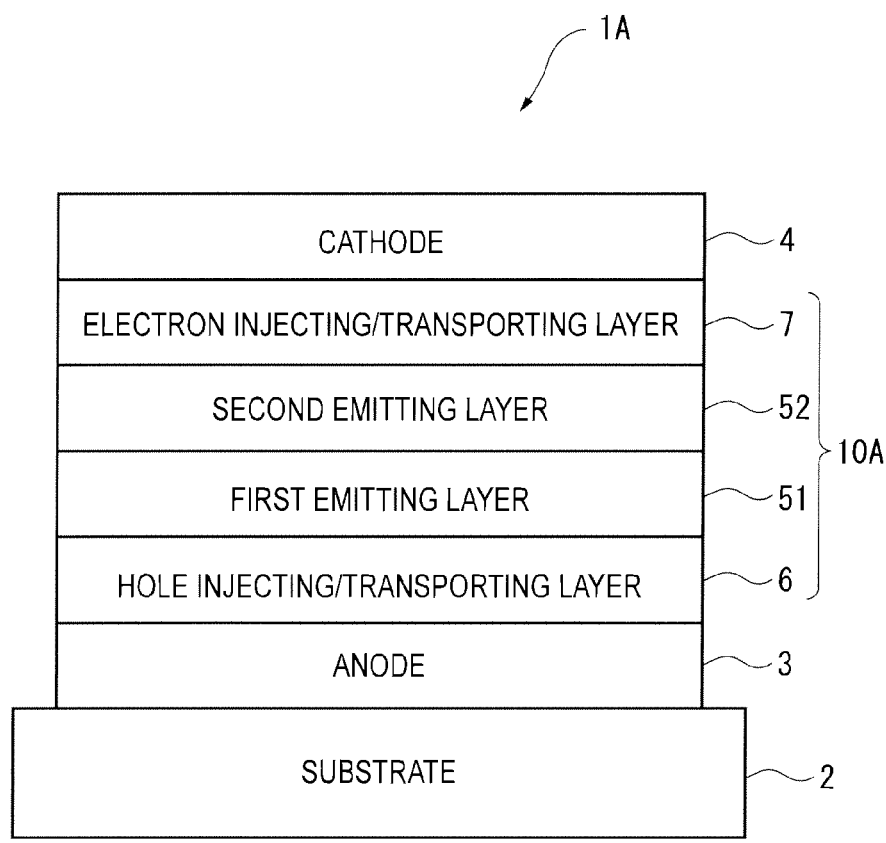

When the plurality of emitting layers are laminated, an organic EL device 1A is exemplarily shown in FIG. 3. The organic EL device 1A includes an organic layer 10A. The organic EL device 1A is different from organic EL device 1 shown in FIG. 1 in that the organic layer 10A has a first emitting layer 51 and a second emitting layer 52 between the hole injecting/transporting layer 6 and the electron injecting/transporting layer 7. At least one of the first emitting layer 51 and the second emitting layer 52 contains the compound represented by the formula (1) and the compound represented by the formula (2). As for other points, the organic EL device 1A is formed in the same manner as the organic EL device 1.

The electron blocking layer may be provided to the emitting layer adjacent to the anode while the hole blocking layer may be provided adjacent to the emitting layer near the cathode. With this arrangement, the electrons and the holes can be trapped in the emitting layer, thereby enhancing probability of exciton generation in the emitting layer.

Further, the specific arrangement and disposition for practicing the invention may be altered to other arrangements and dispositions as long as such other arrangements and dispositions are compatible with the invention.

EXAMPLES

Examples of the invention will be described below. However, the invention is not limited by these Examples.

Compounds used in Examples for preparing the organic EL device will be shown as follows.

[Formula 184]

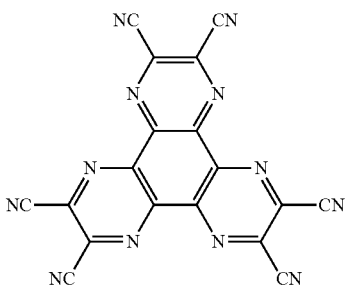

HI

-continued
HT-1
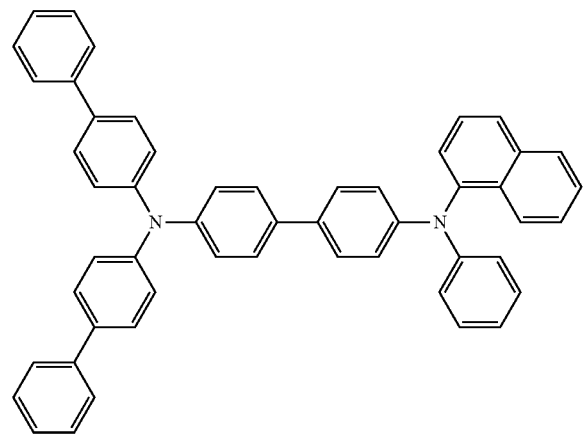
-continued
[Formula 185]
H1
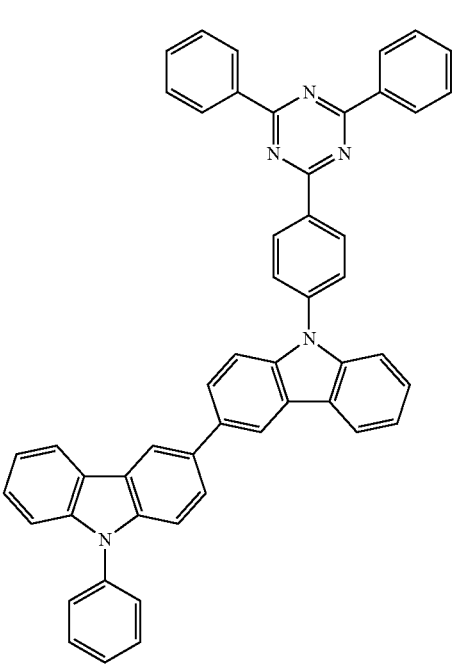
HT-2
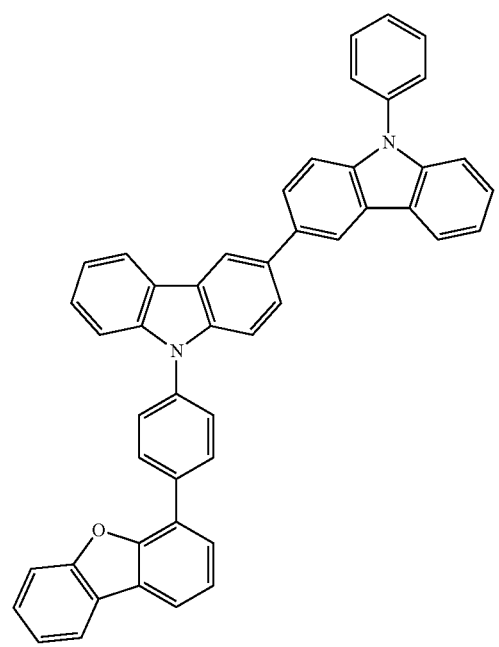

-continued

[Formula 186]

Comparative Host 1

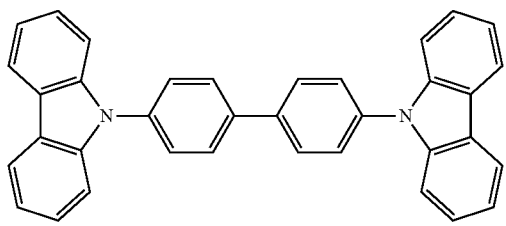

[Formula 187]

D1

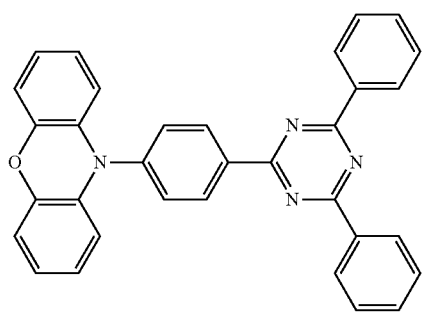

ET-1

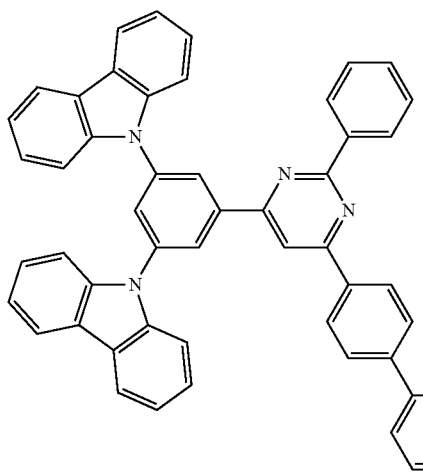

ET-2

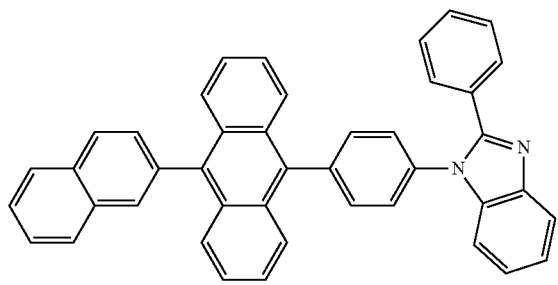

Evaluation of Compounds

Next, properties of the compounds used in Example were measured. The measurement target compounds are a compound H1, a compound H3 and a compound D1. A measurement method or a calculation method is described below. Measurement results or calculation results are shown in Table 1.

(Measurement 1) Singlet Energy EgS

Singlet Energy EgS was obtained according to the following method.

A 100 nm thick film of each of the compounds was formed on a quartz substrate by vacuum deposition to provide a measurement sample. Emission spectrum of each sample was measured at a room temperature (300K). The emission spectrum was expressed in coordinates of which ordinate axis indicated the luminous intensity and of which abscissa axis indicated the wavelength. A tangent was drawn to the rise of the emission spectrum on the short-wavelength side, and a wavelength value λedge (nm) at an intersection of the tangent and the abscissa axis was obtained. The wavelength value was converted to an energy value by the following conversion equation. The energy value was defined as EgS.

$$EgS(eV)=1239.85/\lambda edge$$   Conversion Equation:

For the emission spectrum measurement, a spectrophoto-fluorometer body F-7000 (manufactured by Hitachi High-Technologies Corporation) was used.

The tangent to the rise of the emission spectrum on the short-wavelength side was drawn as follows. While moving on a curve of the emission spectrum from the short-wavelength side to the maximum spectral value closest to the short-wavelength side among the maximum spectral values, a tangent is checked at each point on the curve toward the long-wavelength of the emission spectrum. An inclination of the tangent is increased as the curve rises (i.e., a value of the ordinate axis is increased). A tangent drawn at a point of the maximum inclination was defined as the tangent to the rise of the phosphorescence spectrum on the short-wavelength side.

The maximum with peak intensity being 10% or less of the maximum peak intensity of the spectrum is not included in the above-mentioned maximum closest to the short-wavelength side of the spectrum. The tangent drawn at a point of the maximum spectral value being closest to the short-wavelength side and having the maximum inclination is defined as a tangent to the rise of the emission spectrum on the short-wavelength side.

(Measurement 2) Energy Gap $Eg_{77K}$ $Eg_{77K}$ was obtained by the following method.

Each of the measurement target compounds and a compound TH-2 below were co-deposited on the quartz substrate by vacuum deposition to prepare a sample encapsulated in an NMR tube. The samples were prepared under the following conditions.

quartz substrate/TH-2:measurement target compound (100 nm of thickness, 12 mass % of concentration of a second material)

[Formula 188]

TH-2

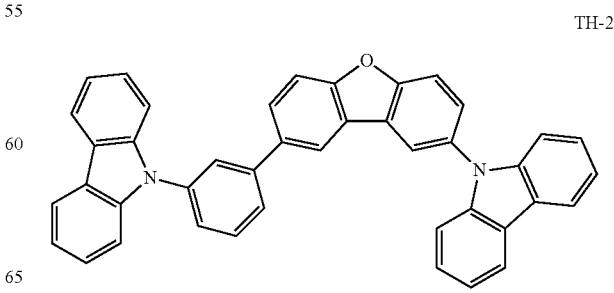

A phosphorescent spectrum (ordinate axis: phosphorescent luminous intensity, abscissa axis: wavelength) of each of the samples was measured at a low temperature (77K). A tangent was drawn to the rise of the phosphorescent spectrum on the short-wavelength side. An energy amount was calculated as the energy gap $Eg_{77K}$ at 77K according to a conversion equation 2 below based on a wavelength value $\lambda_{edge}$ (nm) at an intersection of the tangent and the abscissa axis.

$$Eg_{77K}(eV)=1239.85/\lambda_{edge} \qquad \text{Conversion Equation 2:}$$

For phosphorescence measurement, a spectrophotofluorometer body F-4500 (manufactured by Hitachi High-Technologies Corporation) was used.

The tangent to the rise of the phosphorescence spectrum on the short-wavelength side is drawn as follows. While moving on a curve of the phosphorescence spectrum from the short-wavelength side to the maximum spectral value closest to the short-wavelength side among the maximum spectral values, a tangent is checked at each point on the curve toward the long-wavelength of the phosphorescence spectrum. An inclination of the tangent is increased as the curve rises (i.e., a value of the ordinate axis is increased). A tangent drawn at a point of the maximum inclination (i.e., a tangent at an inflection point) is defined as the tangent to the rise of the phosphorescence spectrum on the short-wavelength side.

The maximum with peak intensity being 15% or less of the maximum peak intensity of the spectrum is not included in the above-mentioned maximum closest to the short-wavelength side of the spectrum. The tangent drawn at a point of the maximum spectral value being closest to the short-wavelength side and having the maximum inclination is defined as a tangent to the rise of the phosphorescence spectrum on the short-wavelength side.

(Measurement 3) ΔST

ΔST was obtained as a difference between EgS and $Eg_{77K}$ respectively measured in the above (Measurement 1) and (Measurement 2) (see the above numerical formula (2)). The results are shown in Table 1.

TABLE 1

| Host Material | EgS (eV) | $Eg_{77K}$ (eV) | ΔST (eV) |
|---|---|---|---|
| Compound H1 | 2.85 | 2.72 | 0.13 |
| Compound H3 | 2.95 | 2.70 | 0.25 |
| Compound D1 | 2.67 | 2.46 | 0.21 |

Preparation and Evaluation of Organic EL Device

The organic EL device was prepared and evaluated as follows.

Example 1

A glass substrate (size: 25 mm×75 mm×1.1 mm thick, manufactured by Geomatec Co., Ltd.) having an ITO transparent electrode (anode) was ultrasonic-cleaned in isopropyl alcohol for five minutes, and then UV/ozone-cleaned for 30 minutes. A film of ITO was 130 nm thick.

After the glass substrate having the transparent electrode line was cleaned, the glass substrate was mounted on a substrate holder of a vacuum evaporation apparatus. Initially, a compound HI was evaporated on a surface of the glass substrate where the transparent electrode line was provided in a manner to cover the transparent electrode, thereby forming a 5-nm thick film of the compound HI. The HI film serves as a hole injecting layer.

After the film formation of the HI film, a compound HT-1 was deposited on the HI film to form a 160 nm thick HT-1 film. The HT-1 film serves as a first hole transporting layer.

A compound HT-2 was further deposited on the HT-1 film to form a 10 nm thick HT-2 film. The HT-2 film serves as a second hole transporting layer.

The compound H1 (the host material) and the compound D1 (TADF dopant material) were co-deposited on the HT-2 film to form a 35 nm thick emitting layer. The concentration of the dopant material was set at 6 mass %.

A compound ET-1 was deposited on the emitting layer to form a 5 nm thick ET-1 film. The ET-1 film serves as a first electron transporting layer.

A compound ET-2 was deposited on the ET-1 film to form a 25 nm thick ET-2 film. The ET-2 film serves as a second electron transporting layer.

LiF was deposited on the ET-2 film to form a 1-nm thick LiF film.

A metal Al was deposited on the LiF film to form an 80 nm thick metal cathode.

A device arrangement of the organic EL device in Example 1 is simply shown as follows.

ITO(130)/HI(5)/HT-1(160)/HT-2(10)/H1:D1(35.6%)/ET-1(5)/ET-2(25)/LiF(1)/Al(80)

Numerals in parentheses represent a film thickness (unit: nm). Numerals represented by percentage in the same parentheses represent a ratio (mass %) of an added component such as the dopant material in the emitting layer.

Example 2

An organic EL device in Example 2 was manufactured in the same manner as in Example 1 except that the concentration of the dopant material in the emitting layer of the organic EL device in Example 1 was changed to 12 mass %.

A device arrangement of the organic EL device in Example 2 is simply shown as follows.

ITO(130)/HI(5)/HT-1(160)/HT-2(10)/H1:D1(35.12%)/ET-1(5)/ET-2(25)/LiF(1)/Al(80)

Numerals in parentheses represent a film thickness (unit: nm). Numerals represented by percentage in the same parentheses represent a ratio (mass %) of an added component such as the dopant material in the emitting layer.

Example 3

An organic EL device in Example 3 was manufactured in the same manner as in Example 1 except that the host material in the emitting layer of the organic EL device in Example 1 was replaced by the compound H2.

A device arrangement of the organic EL device in Example 3 is simply shown as follows.

ITO(130)/HI(5)/HT-1(160)/HT-2(10)/H2:D1(35.6%)/ET-1(5)/ET-2(25)/LiF(1)/Al(80)

Numerals in parentheses represent a film thickness (unit: nm). Numerals represented by percentage in the same parentheses represent a ratio (mass %) of an added component such as the dopant material in the emitting layer.

Example 4

An organic EL device in Example 4 was manufactured in the same manner as in Example 1 except that the host material was replaced by the compound H2 and the concentration of the dopant material was changed to 12 mass % in the emitting layer of the organic EL device in Example 1.

A device arrangement of the organic EL device in Example 4 is simply shown as follows.

ITO(130)/HI(5)/HT-1(160)/HT-2(10)/H2:D1(35,12%)/ET-1(5)/ET-2(25)/LiF(1)/Al(80)

Numerals in parentheses represent a film thickness (unit: nm). Numerals represented by percentage in the same parentheses represent a ratio (mass %) of an added component such as the dopant material in the emitting layer.

Example 5

An organic EL device in Example 5 was manufactured in the same manner as in Example 1 except that the host material in the emitting layer of the organic EL device in Example 1 was replaced by a compound H3.

A device arrangement of the organic EL device in Example 5 is simply shown as follows.

ITO(130)/HI(5)/HT-1(160)/HT-2(10)/H3:D1(35,6%)/ET-1(5)/ET-2(25)/LiF(1)/Al(80)

Numerals in parentheses represent a film thickness (unit: nm). Numerals represented by percentage in the same parentheses represent a ratio (mass %) of an added component such as the dopant material in the emitting layer.

Example 6

An organic EL device in Example 6 was manufactured in the same manner as in Example 1 except that the host material was replaced by the compound H3 and the concentration of the dopant material was changed to 12 mass % in the emitting layer of the organic EL device in Example 1.

A device arrangement of the organic EL device in Example 6 is simply shown as follows.

ITO(130)/HI(5)/HT-1(160)/HT-2(10)/H3:D1(35,12%)/ET-1(5)/ET-2(25)/LiF(1)/Al(80)

Numerals in parentheses represent a film thickness (unit: nm). Numerals represented by percentage in the same parentheses represent a ratio (mass %) of an added component such as the dopant material in the emitting layer.

Comparative 1

An organic EL device in Comparative 1 was manufactured in the same manner as in Example 1 except that the host material in the emitting layer of the organic EL device in Example 1 was replaced by a comparative host 1. The comparative host 1 was CBP.

A device arrangement of the organic EL device in Comparative 1 is simply shown as follows.

ITO(130)/HI(5)/HT-1(160)/HT-2(10)/Comparative Host 1:D1(35, 6%)/ET-1(5)/ET-2(25)/LiF(1)/Al(80)

Numerals in parentheses represent a film thickness (unit: nm). Numerals represented by percentage in the same parentheses represent a ratio (mass %) of an added component such as the dopant material in the emitting layer.

Comparative 2

An organic EL device in Comparative 2 was manufactured in the same manner as in Example 1 except that the host material was replaced by the comparative host 1 and the concentration of the dopant material was changed to 12 mass % in the emitting layer of the organic EL device in Example 1. The comparative host 1 was CBP.

A device arrangement of the organic EL device in Comparative 2 is simply shown as follows.

ITO(130)/HI(5)/HT-1(160)/HT-2(10)/Comparative Host 1: D1(35, 12%)/ET-1(5)/ET-2(25)/LiF(1)/Al(80)

Numerals in parentheses represent a film thickness (unit: nm). Numerals represented by percentage in the same parentheses represent a ratio (mass %) of an added component such as the dopant material in the emitting layer.

Evaluation of Organic EL Devices

The prepared organic EL devices of Examples 1 to 6 and Comparatives 1 to 2 were evaluated as follows. The evaluation results of the organic EL devices in Examples 1 to 6 are shown in Table 2. The evaluation results of Comparatives 1 to 2 are shown in Table 3.

Drive Voltage

Voltage was applied between the ITO transparent electrode and the metal Al cathode such that the current density was 0.1 mA/cm², 1 mA/cm² or 10 mA/cm², where voltage (unit: V) was measured.

Luminance and CIE1931 Chromaticity

Voltage was applied on each of the organic EL devices such that the current density was 0.1 mA/cm², 1 mA/cm² or 10 mA/cm², where luminance and CIE1931 chromaticity coordinates (x, y) were measured using a spectroradiometer CS-1000 (manufactured by Konica Minolta, Inc.).

Current Efficiency L/J and Power Efficiency η

Voltage was applied on each of the organic EL devices such that the current density was 0.1 mA/cm², 1.00 mA/cm² or 10.00 mA/cm², where spectral radiance spectra were measured by the aforementioned spectroradiometer. Based on the obtained spectral radiance spectra, the current efficiency (unit: cd/A) and the power efficiency η (unit: lm/W) were calculated.

Main Peak Wavelength $\lambda_p$

A main peak wavelength $\lambda_p$ was calculated based on the obtained spectral-radiance spectra.

External Quantum Efficiency EQE

Voltage was applied on each of the organic EL devices such that the current density was 0.1 mA/cm², 1 mA/cm² or 10 mA/cm², where spectral-radiance spectra were measured using a spectroradiometer CS-1000 (manufactured by Konica Minolta, Inc.).

The external quantum efficiency EQE (unit: %) was calculated based on the obtained spectral-radiance spectra, assuming that the spectra were provided under a Lambertian radiation.

TABLE 2

|  | Current Density [mA/cm²] | Voltage [V] | Luminance [cd/m²] | L/J [cd/A] | η [l/W] | Chromaticity x | Chromaticity y | $\lambda_p$ [nm] | EQE [%] |
| --- | --- | --- | --- | --- | --- | --- | --- | --- | --- |
| Example 1 | 0.10 | 2.50 | 67.5 | 67.51 | 84.98 | 0.382 | 0.579 | 543 | 19.93 |
|  | 1.00 | 2.85 | 688.6 | 68.86 | 76.00 | 0.378 | 0.579 | 542 | 20.33 |
|  | 10 | 3.73 | 5883.2 | 58.83 | 49.58 | 0.373 | 0.579 | 541 | 17.41 |

TABLE 2-continued

|  | Current Density [mA/cm$^2$] | Voltage [V] | Luminance [cd/m$^2$] | L/J [cd/A] | η [l/W] | Chromaticity x | Chromaticity y | λ$_p$ [nm] | EQE [%] |
|---|---|---|---|---|---|---|---|---|---|
| Example 2 | 0.10 | 2.48 | 67.5 | 67.55 | 85.59 | 0.392 | 0.577 | 545 | 19.89 |
|  | 1.00 | 2.83 | 693.9 | 69.39 | 76.91 | 0.388 | 0.578 | 545 | 20.39 |
|  | 10 | 3.74 | 5981.7 | 59.82 | 50.21 | 0.384 | 0.579 | 545 | 17.59 |
| Example 3 | 0.10 | 2.61 | 62.9 | 62.91 | 75.71 | 0.398 | 0.571 | 546 | 18.78 |
|  | 1.00 | 2.95 | 605.0 | 60.50 | 64.32 | 0.392 | 0.573 | 546 | 18.04 |
|  | 10 | 3.85 | 5065.4 | 50.65 | 41.35 | 0.387 | 0.574 | 545 | 15.11 |
| Example 4 | 0.10 | 2.60 | 61.5 | 61.53 | 74.26 | 0.410 | 0.565 | 550 | 18.43 |
|  | 1.00 | 2.95 | 609.8 | 60.98 | 64.84 | 0.405 | 0.567 | 551 | 18.21 |
|  | 10 | 3.87 | 5328.4 | 53.28 | 43.25 | 0.401 | 0.569 | 549 | 15.89 |
| Example 5 | 0.10 | 2.70 | 64.6 | 64.61 | 75.30 | 0.382 | 0.575 | 545 | 19.19 |
|  | 1.00 | 3.09 | 627.5 | 62.75 | 63.86 | 0.377 | 0.575 | 544 | 18.63 |
|  | 10 | 3.93 | 4917.7 | 49.18 | 39.34 | 0.372 | 0.574 | 544 | 14.64 |
| Example 6 | 0.10 | 2.68 | 63.7 | 63.66 | 74.75 | 0.395 | 0.572 | 547 | 19.00 |
|  | 1.00 | 3.04 | 642.7 | 64.27 | 66.47 | 0.389 | 0.574 | 545 | 19.12 |
|  | 10 | 3.89 | 5163.1 | 51.63 | 41.68 | 0.384 | 0.575 | 545 | 15.36 |

TABLE 3

|  | Current Density [mA/cm$^2$] | Voltage [V] | Luminance [cd/m$^2$] | L/J [cd/A] | η [l/W] | Chromaticity x | Chromaticity y | λ$_p$ [nm] | EQE [%] |
|---|---|---|---|---|---|---|---|---|---|
| Comparative 1 | 0.10 | 3.88 | 56.7 | 56.71 | 45.86 | 0.371 | 0.577 | 542 | 16.82 |
|  | 1.00 | 4.77 | 541.3 | 54.13 | 35.68 | 0.368 | 0.578 | 543 | 16.03 |
|  | 10 | 6.70 | 4452.6 | 44.52 | 20.87 | 0.363 | 0.578 | 543 | 13.22 |
| Comparative 2 | 0.10 | 3.47 | 61.5 | 61.48 | 55.61 | 0.384 | 0.576 | 543 | 18.32 |
|  | 1.00 | 4.13 | 589.9 | 58.99 | 44.91 | 0.383 | 0.576 | 543 | 17.55 |
|  | 10 | 5.77 | 5067.6 | 50.68 | 27.61 | 0.381 | 0.577 | 544 | 15.07 |

As shown in Tables 2 and 3, it was found that the organic EL devices of Examples 1 to 6 including the emitting layer containing the compound represented by the formula (1) and the compound represented by the formula (2) emitted light at a lower drive voltage with a higher efficiency than the drive voltage and the efficiency of the organic EL devices of Comparatives 1 to 2 containing CBP as the host material. It was also found that the drive voltage of each of the organic EL devices of Comparatives 1 to 2 was more significantly increased in a high current density area of 1 mA/cm$^2$ and 10 mA/cm$^2$ than the drive voltage of each of the organic EL devices of Examples 1 to 6.

Preparation and Evaluation of Organic EL Device

Example 7

An organic EL device according to Example 7 was manufactured as follows.

A glass substrate (size: 25 mm×75 mm×1.1 mm thick, manufactured by Geomatec Co., Ltd.) having an ITO transparent electrode (anode) was ultrasonic-cleaned in isopropyl alcohol for five minutes, and then UV/ozone-cleaned for 30 minutes. A film of ITO was 130 nm thick.

After the glass substrate having the transparent electrode line was cleaned, the glass substrate was mounted on a substrate holder of a vacuum evaporation apparatus. Initially, a compound HI was evaporated on a surface of the glass substrate where the transparent electrode line was provided in a manner to cover the transparent electrode, thereby forming a 5 nm thick film of the compound HI. The HI film serves as a hole injecting layer.

After the film formation of the HI film, the compound HT-1 was deposited on the HI film to form a 95 nm thick HT-1 film. The HT-1 film serves as the first hole transporting layer.

The compound HT-2 was further deposited on the HT-1 film to form a 10 nm thick HT-2 film. The HT-2 film serves as the second hole transporting layer.

The compound H1 and a compound H4 were co-deposited on the HT-2 film to form a 30 nm thick emitting layer. The respective concentrations of the compound H1 and the compound H4 in the emitting layer were set at 88 mass % and 12 mass %.

The compound ET-1 was deposited on the emitting layer to form a 5 nm thick ET-1 film. The ET-1 film serves as the first electron transporting layer.

The compound ET-2 was deposited on the ET-1 film to form a 25 nm thick ET-2 film. The ET-2 film serves as the second electron transporting layer.

LiF was deposited on the ET-2 film to form a 1 nm thick LiF film.

A metal Al was deposited on the LiF film to form an 80 nm thick metal cathode.

A device arrangement of the organic EL device in Example 7 is simply shown as follows.

ITO(130)/HI(5)/HT-1(95)/HT-2(10)/H1:H4(30.88%: 12%)/ET-1(5)/ET-2(25)/LiF(1)/Al(80)

Numerals in parentheses represent a film thickness (unit: nm). The numerals represented by percentage in parentheses indicate a ratio (mass percentage) of the compounds in the emitting layer.

Example 8

An organic EL device in Example 8 was manufactured in the same manner as in Example 7 except that the respective ratio of the compound H1 and the compound H4 in the emitting layer of the organic EL device in Example 7 were changed to 76% and 24%.

A device arrangement of the organic EL device in Example 8 is simply shown as follows.

ITO(130)/HI(5)/HT-1(95)/HT-2(10)/H1:H4(30.76%: 24%)/ET-1(5)/ET-2(25)/LiF(1)/Al(80)

Numerals in parentheses represent a film thickness (unit: nm). The numerals represented by percentage in parentheses indicate a ratio (mass percentage) of the compounds in the emitting layer.

[Formula 189]

H4

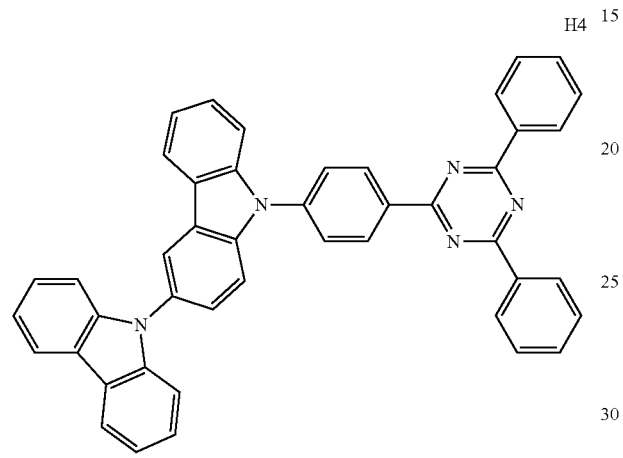

Evaluation of Compounds

Next, properties of the compounds used in Examples 7 and 8 were measured. The measurement target compound is the compound H4. The measurement method or the calculation method is the same as described above. The results are shown in Table 4.

TABLE 4

| Measurement Target Compound | EgS (eV) | Eg$_{77K}$ (eV) | ΔST (eV) |
|---|---|---|---|
| Compound H4 | 3.00 | 2.75 | 0.25 |

Evaluation of Organic EL Devices

The organic EL devices of Examples 7 and 8 were evaluated in terms of drive voltage, luminance, CIE1931 chromaticity, current efficiency L/J, power efficiency η, main peak wavelength $\lambda_p$ and external quantum efficiency EQE in the same manner as described above. The results are shown in Table 5.

Further, a lifetime of each of the organic EL devices of Examples 7 and 8 was measured according to the following method.

Lifetime LT50

Voltage was applied to the devices and a time until an initial luminance (1000 cd/m$^2$) was decreased in half was defined as the lifetime (unit: h).

As a result, the lifetime LT50 of the organic EL device in Example 7 was 186 hours. The lifetime LT50 of the organic EL device in Example 8 was 176 hours.

The invention claimed is:

1. An organic electroluminescence device, comprising:
   an anode;
   a cathode; and
   a single-layer or multi-layer organic layer interposed between the anode and the cathode;
   wherein:
   the organic layer comprises an emitting layer;
   the emitting layer comprises a compound according to formula (1) and a compound according to formula (2);
   the emitting layer does not comprise a metal complex;
   formula (1) is:

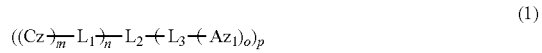

(1)

where:
   each Cz is a group according to formula (10b):

(10b)

where:
   each of A and B is independently a substituted or unsubstituted cyclic structure;
   when at least one of the cyclic structure A and the cyclic structure B has a plurality of substituents, adjacent ones of the substituents optionally form a ring; and
   at least one of the cyclic structure A and the cyclic structure B has a partial structure according to formula (11):

TABLE 5

| | Current Density [mA/cm$^2$] | Voltage [V] | Luminance [cd/m$^2$] | Chromaticity x | Chromaticity y | L/J [cd/A] | η [l/W] | EQE [%] | $\lambda_p$ [nm] |
|---|---|---|---|---|---|---|---|---|---|
| Example 7 | 0.10 | 2.76 | 26.9 | 0.216 | 0.455 | 26.95 | 30.66 | 10.44 | 499 |
| | 1.00 | 3.16 | 272.0 | 0.208 | 0.446 | 27.20 | 27.01 | 10.69 | 499 |
| | 10 | 3.85 | 1981.7 | 0.199 | 0.429 | 19.82 | 16.16 | 8.01 | 497 |
| Example 8 | 0.10 | 2.77 | 24.6 | 0.211 | 0.442 | 24.58 | 27.90 | 9.73 | 497 |
| | 1.00 | 3.18 | 249.8 | 0.203 | 0.432 | 24.98 | 24.71 | 10.04 | 497 |
| | 10 | 3.87 | 1834.4 | 0.194 | 0.414 | 18.34 | 14.90 | 7.60 | 495 |

(11)

$L_1$ is a single bond, a substituted or unsubstituted (m+1)-valent aromatic hydrocarbon group, or a substituted or unsubstituted (m+1)-valent heterocyclic group;

$L_2$ is a single bond, a substituted or unsubstituted (n+p)-valent aromatic hydrocarbon group, or a substituted or unsubstituted (n+p)-valent heterocyclic group;

$L_3$ represents a single bond, a substituted or unsubstituted (o+1)-valent aromatic hydrocarbon group, or a substituted or unsubstituted (o+1)-valent heterocyclic group;

m is an integer of 1 to 6;
n and p are each independently an integer of 1 to 6;
o is an integer of 1 to 6; and
$Az_1$ is a group according to formula (12);

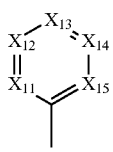
(12)

where:
each of $X_{11}$ to $X_{15}$ is independently $CR_8$ or a nitrogen atom;
at least one of $X_{11}$ to $X_{15}$ is a nitrogen atom; and
adjacent ones of $R_8$ optionally form a ring;
formula (2) is:

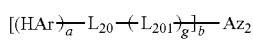
(2)

where:
$L_{20}$ is a substituted or unsubstituted (a+g)-valent aromatic hydrocarbon group or a substituted or unsubstituted (a+g)-valent heterocyclic group;
$L_{201}$ is a substituted or unsubstituted divalent aromatic hydrocarbon group or a substituted or unsubstituted divalent heterocyclic group;
a is an integer of 1 to 6;
b is an integer of 1 to 6;
g is an integer of 0 to 2; and
HAr is a group derived from a structure according to formula (20);

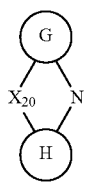
(20)

where:
$X_{20}$ represents a single bond, an oxygen atom, a sulfur atom, a carbonyl group, $NR_9$, $CR_{10}R_{11}$, $SiR_{12}R_{13}$, or $GeR_{14}R_{15}$;

each of G and H is independently a substituted or unsubstituted cyclic structure;

when at least one of the cyclic structure G and the cyclic structure H has a plurality of substituents, adjacent ones of the substituents optionally form a ring; and when at least one of the cyclic structure G and the cyclic structure H is a substituted or unsubstituted heterocyclic structure, the heterocyclic structure has a partial structure according to formula (20-2):

(20-2)

and
$Az_2$ is a group according to formula (2d):

(2d)

where:
each of $X_{21}$ to $X_{26}$ is independently $CR_{16}$ or a nitrogen atom;
at least one of $X_{21}$ to $X_{26}$ is a nitrogen atom and b of $X_{21}$ to $X_{26}$ is a carbon atom to be bonded to $L_{20}$ or $L_{201}$; and
adjacent ones of $R_{16}$ optionally form a ring; and
each of $R_8$ to $R_{16}$ is independently a hydrogen atom, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkylsilyl group having 3 to 30 carbon atoms, a substituted or unsubstituted arylsilyl group having 6 to 60 ring carbon atoms, a substituted or unsubstituted alkoxy group having 1 to 30 carbon atoms, a substituted or unsubstituted aryloxy group having 6 to 30 ring carbon atoms, a substituted or unsubstituted alkylamino group having 2 to 30 carbon atoms, a substituted or unsubstituted arylamino group having 6 to 60 ring carbon atoms, a substituted or unsubstituted alkylthio group having 1 to 30 carbon atoms, or a substituted or unsubstituted arylthio group having 6 to 30 ring carbon atoms.

2. The organic electroluminescence device according to claim 1, wherein
the compound according to formula (1) is a compound according to formula (13):

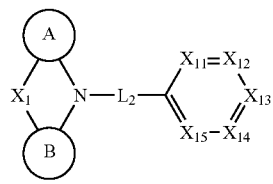
(13)

where:
X₁ is a single bond;
the cyclic structure A and the cyclic structure B are as defined in formula (10b);
L₂ is as defined in formula (1); and
X₁ to X₁₅ are as defined in formula (12).

3. The organic electroluminescence device according to claim 1, wherein
each of the cyclic structure A and the cyclic structure B of formula (10b) is a six-membered ring having the partial structure according to formula (11).

4. The organic electroluminescence device according to claim 1, wherein L₂ has a divalent six-membered ring structure according to formula (3):

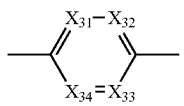
(3)

where:
each of X₃₁ to X₃₄ is independently CR₅₁; and
each R₅₁ is independently as R₈ to R₁₆ are defined.

5. The organic electroluminescence device according to claim 1, wherein HAr of formula (2) is a group derived from a structure according to formula (2B):

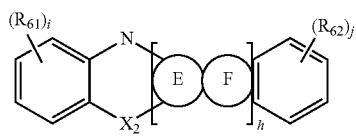
(2B)

where:
X₂ is the same as X₂₀ of formula (20);
each of R₆₁ to R₆₂ is independently as R₈ to R₁₆ are defined;
i and j are 4;
E is a cyclic structure according to formula (2h);
F is a cyclic structure according to formula (2i) or (2j);
each of the cyclic structure E and the cyclic structure F is fused to an adjacent cyclic structure at any position;
h is 0 or 1;

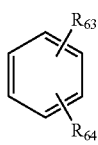
(2h)

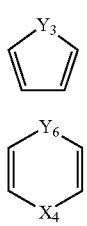
(2i)

(2j)

in formula (2h), when R₆₃ and R₆₄ are substituents at adjacent positions, R₆₃ and R₆₄ optionally form a ring;
each of Y₃ of formula (2i) and Y₆ of formula (2j) is independently CR₆₅R₆₆, NR₆₇, a sulfur atom, an oxygen atom, or a nitrogen atom to be bonded to L₂₀;
X₄ of formula (2j) is the same as X₂₀ of formula (20); and
each of R₆₃ to R₆₇ is independently as R₈ to R₁₆ are defined.

6. The organic electroluminescence device according to claim 5, wherein HAr is a group according to formula (2b) or a group according to formula (2bx):

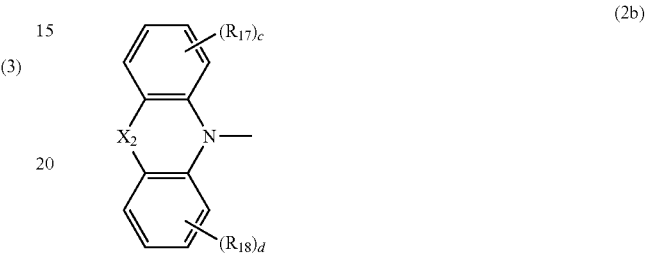
(2b)

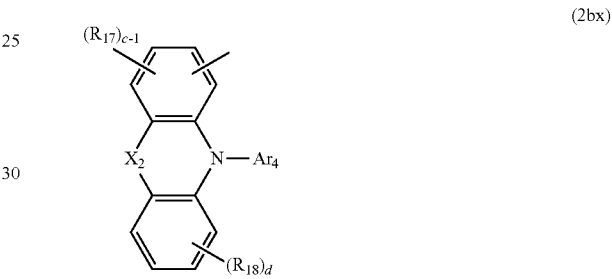
(2bx)

where:
X₂ is as defined in formula (2B);
each of R₁₇, R₁₈, and Ar₄ is independently as R₈ to R₁₆ are defined;
c and d are 4; and
adjacent ones of R₁₇ optionally form a ring and adjacent ones of R₁₈ optionally form a ring.

7. The organic electroluminescence device according to claim 1, wherein at least one of L₂₀ and L₂₀₁ of formula (2) has a divalent six-membered ring structure according to formula (2e):

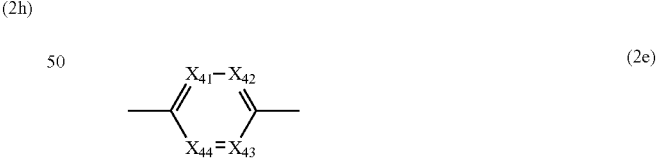
(2e)

where:
each X₄₁ to X₄₄ is independently; and
each R₅₂ is independently as R₈ to R₁₆ are defined.

8. The organic electroluminescence device according to claim 1, wherein the compound according to formula (2) is a compound emitting a delayed fluorescence.

9. An organic electroluminescence device, comprising:
an anode;
a cathode; and
a single-layer or multi-layer organic layer interposed between the anode and the cathode;

wherein:

the organic layer comprises an emitting layer;

the emitting layer comprises a compound according to formula (1) and a compound according to formula (2);

the emitting layer does not comprise a metal complex;

formula (1) is:

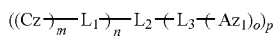
(1)

where:

each Cz is a group selected from the group consisting of groups according to formulae (110) to (115):

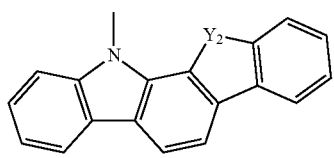
(110)

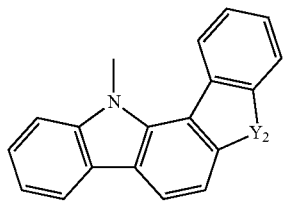
(111)

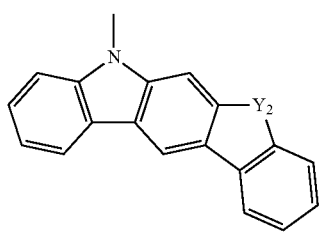
(112)

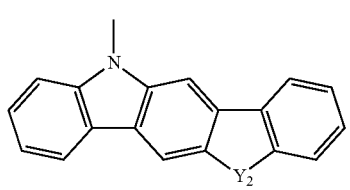
(113)

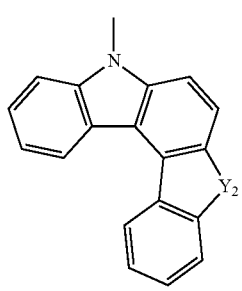
(114)

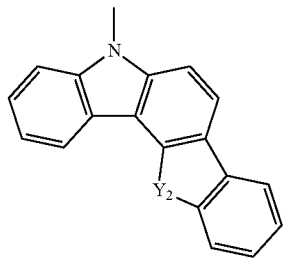
(115)

where $Y_2$ is an oxygen atom;

$L_1$ is a single bond, a substituted or unsubstituted (m+1)-valent aromatic hydrocarbon group, or a substituted or unsubstituted (m+1)-valent heterocyclic group;

$L_2$ is a single bond, a substituted or unsubstituted (n+p)-valent aromatic hydrocarbon group, or a substituted or unsubstituted (n+p)-valent heterocyclic group;

$L_3$ represents a single bond, a substituted or unsubstituted (o+1)-valent aromatic hydrocarbon group, or a substituted or unsubstituted (o+1)-valent heterocyclic group;

m is an integer of 1 to 6;

n and p are each independently an integer of 1 to 6;

o is an integer of 1 to 6; and $Az_1$ is a group according to formula (12):

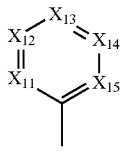
(12)

where:

each of $X_{11}$ to $X_{15}$ is independently $CR_8$ or a nitrogen atom;

at least one of $X_{11}$ to $X_{15}$ is a nitrogen atom; and adjacent ones of $R_8$ optionally form a ring;

formula (2) is:

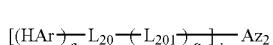
(2)

where:

$L_{20}$ is a substituted or unsubstituted (a+g)-valent aromatic hydrocarbon group or a substituted or unsubstituted (a+g)-valent heterocyclic group;

$L_{201}$ is a substituted or unsubstituted divalent aromatic hydrocarbon group or a substituted or unsubstituted divalent heterocyclic group;

a is an integer of 1 to 6;

b is an integer of 1 to 6;

g is an integer of 0 to 2; and

HAr is a group derived from a structure according to formula (20):

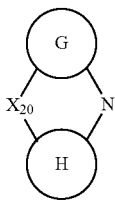

(20)

where:
X$_{20}$ is a single bond, an oxygen atom, a sulfur atom, a carbonyl group, NR$_9$, CR$_{10}$R$_{11}$, SiR$_{12}$R$_{13}$, or GeR$_{14}$R$_{15}$;
each of G and H is independently a substituted or unsubstituted cyclic structure;
when at least one of the cyclic structure G and the cyclic structure H has a plurality of substituents, adjacent ones of the substituents optionally form a ring; and
when at least one of the cyclic structure G and the cyclic structure H is a substituted or unsubstituted heterocyclic structure, the heterocyclic structure has a partial structure represented by a formula (20-2):

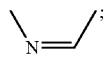

(20-2)

and
Az$_2$ is a group according to formula (2d):

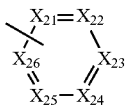

(2d)

where:
each of X$_{21}$ to X$_{26}$ is independently CR$_{16}$ or a nitrogen atom;
at least one of X$_{21}$ to X$_{26}$ is a nitrogen atom and b of X$_{21}$ to X$_{26}$ is a carbon atom to be bonded to L$_{20}$ or L$_{201}$; and adjacent ones of R$_{16}$ optionally form a ring; and
each of R$_8$ to R$_{16}$ is independently a hydrogen atom, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkylsilyl group having 3 to 30 carbon atoms, a substituted or unsubstituted arylsilyl group having 6 to 60 ring carbon atoms, a substituted or unsubstituted alkoxy group having 1 to 30 carbon atoms, a substituted or unsubstituted aryloxy group having 6 to 30 ring carbon atoms, a substituted or unsubstituted alkylamino group having 2 to 30 carbon atoms, a substituted or unsubstituted arylamino group having 6 to 60 ring carbon atoms, a substituted or unsubstituted alkylthio group having 1 to 30 carbon atoms, or a substituted or unsubstituted arylthio group having 6 to 30 ring carbon atoms.

10. The organic electroluminescence device according to claim 9, wherein, in the compound according to formula (1):
m is 1;
L$_1$ is a single bond;
n is 1;
L$_3$ is a single bond;
o is 1; and
p is 1.

11. The organic electroluminescence device according to claim 9, wherein, in the compound according to formula (1):
L$_1$ is a single bond;
n is 1;
L$_3$ is a single bond;
o is 1; and
p is 1.

12. The organic electroluminescence device according to claim 9, wherein L$_2$ has a divalent six-membered ring structure according to formula (3):

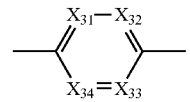

(3)

where:
each of X$_{31}$ to X$_{34}$ is independently CR$_{51}$ or a nitrogen atom; and
each R$_{51}$ is independently as R$_8$ to R$_{16}$ are defined.

13. The organic electroluminescence device according to claim 12, wherein each of X$_{31}$ to X$_{34}$ of formula (3) is independently CR$_{51}$.

14. The organic electroluminescence device according to claim 9, wherein X$_{20}$ of formula (20) is an oxygen atom, a sulfur atom, a carbonyl group, NR$_9$, CR$_{10}$R$_{11}$, SiR$_{12}$R$_{13}$, or GeR$_{14}$R$_{15}$.

15. The organic electroluminescence device according to claim 9, wherein each HAr of formula (2) is a group derived from a structure according to formula (2B):

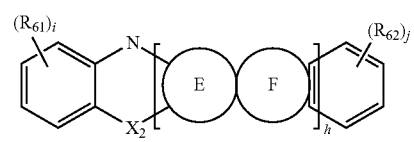

(2B)

where:
X$_2$ is the same as X$_{20}$ of formula (20);
each of R$_{61}$ and R$_{62}$ is independently as R$_8$ to R$_{16}$ are defined;
i and j are 4;
E is a cyclic structure according to formula (2h);
F is a cyclic structure according to formula (2i) or (2j);
each of the cyclic structure E and the cyclic structure F is fused to an adjacent cyclic structure at any position;
h is an integer of 0 to 4;
h is a repeating unit of a linking cyclic structure in which the cyclic structure E and the cyclic structure F are fused to each other; and
when h is 2 or more, a plurality of cyclic structures F are optionally the same or different:

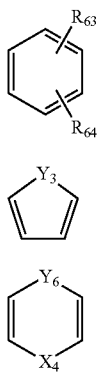

(2h)

(2i)

(2j)

in formula (2h), when $R_{63}$ and $R_{64}$ are substituents at adjacent positions, $R_{63}$ and $R_{64}$ optionally form a ring; each of $Y_3$ of formula (2i) and $Y_6$ of formula (2j) is independently $CR_{65}R_{66}$, $NR_{67}$, a sulfur atom, an oxygen atom, or a nitrogen atom to be bonded to $L_{20}$; $X_4$ of formula (2j) is the same as $X_{20}$ of formula (20); and each of $R_{63}$ to $R_{67}$ is independently as $R_3$ to $R_{16}$ are defined.

16. The organic electroluminescence device according to claim 15, wherein h is 0 or 1.

17. The organic electroluminescence device according to claim 16, wherein HAr is a group according to formula (2b) or formula (2bx):

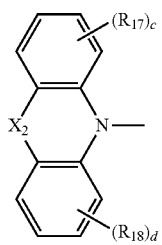

(2b)

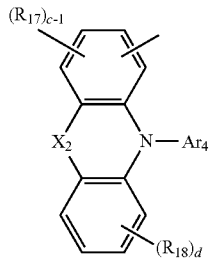

(2bx)

where:

$X_2$ is the same as $X_2$ of formula (2B);

each of $R_{17}$, $R_{18}$, and $Ar_4$ is independently as $R_8$ to $R_{16}$ are defined;

c and d are 4; and adjacent ones of $R_{17}$ optionally form a ring and adjacent ones of $R_{18}$ optionally form a ring.

18. The organic electroluminescence device according to claim 17, wherein:

a is 1 or 2;

g is 0; and $X_2$ of formula (2b) or (2bx) is an oxygen atom.

19. The organic electroluminescence device according to claim 9, wherein at least one of $L_{20}$ and $L_{201}$ of formula (2) has a divalent six-membered ring structure according to formula (2e):

(2e)

where:

each of $X_{41}$ to $X_{44}$ is independently $CR_{52}$ or a nitrogen atom;

each of $R_{52}$ is independently as $R_8$ to $R_{16}$ are defined.

20. The organic electroluminescence device according to claim 19, wherein each of $X_{41}$ to $X_{44}$ of formula (2e) is independently $CR_{52}$.

21. The organic electroluminescence device according to claim 9, wherein:

the compound according to formula (1) is a host material; and the compound according to formula (2) is a dopant material.

22. The organic electroluminescence device according to claim 9, wherein a maximum emission component of an emission from the organic electroluminescence device is an emission from the compound according to formula (2).

23. The organic electroluminescence device according to claim 9, wherein the compound according to formula (2) is a compound emitting a delayed fluorescence.

* * * * *

UNITED STATES PATENT AND TRADEMARK OFFICE
CERTIFICATE OF CORRECTION

PATENT NO. : 9,882,144 B2
APPLICATION NO. : 14/655612
DATED : January 30, 2018
INVENTOR(S) : Masahiro Kawamura et al.

Page 1 of 1

It is certified that error appears in the above-identified patent and that said Letters Patent is hereby corrected as shown below:

Claim 1, Column 272, Line 10:

and  (20-2) should read

-- 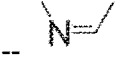 (20-2) ; and--

Claim 2, Column 273, Line 6, "$X_1$ to $X_{15}$ are as defined in formula (12)." should read --$X_{11}$ to $X_{15}$ are as defined in formula (12).--

Claim 7, Column 274, Line 10 from the bottom, "each $X_{41}$ to $X_{44}$ is independently; and" should read -- each $X_{41}$ to $X_{44}$ is independently $CR_{52}$; and--

Claim 9, Column 277, Line 26:

and 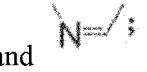 (20-2) should read

-- 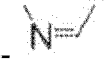 (20-2) ; and--

Claim 15, Column 279, Line 25, "each of $R_{63}$ to $R_{67}$ is independently as $R_3$ to $R_{16}$ are defined." should read --each of $R_{63}$ to $R_{67}$ is independently as $R_8$ to $R_{16}$ are defined.--

Signed and Sealed this
Twenty-first Day of August, 2018

Andrei Iancu
*Director of the United States Patent and Trademark Office*